(12) United States Patent
Hashimoto et al.

(10) Patent No.: US 7,932,394 B2
(45) Date of Patent: Apr. 26, 2011

(54) ARYLOXY-SUBSTITUTED BENZIMIDAZOLE DERIVATIVES

(75) Inventors: Noriaki Hashimoto, Ibaraki (JP); Keiji Takahashi, Ibaraki (JP); Chisato Nakama, Ibaraki (JP); Yoshio Ogino, Ibaraki (JP); Fumiko Sakai, Hokkaido (JP); Teruyuki Nishimura, Ibaraki (JP); Jun-ichi Eiki, Ibaraki (JP)

(73) Assignee: MSD K.K., Chiyoda-Ku (JP)

( * ) Notice: Subject to any disclaimer, the term of this patent is extended or adjusted under 35 U.S.C. 154(b) by 930 days.

(21) Appl. No.: 11/666,555

(22) PCT Filed: Nov. 1, 2005

(86) PCT No.: PCT/JP2005/020483
§ 371 (c)(1),
(2), (4) Date: Jun. 18, 2007

(87) PCT Pub. No.: WO2006/049304
PCT Pub. Date: May 11, 2006

(65) Prior Publication Data
US 2008/0125429 A1    May 29, 2008

(30) Foreign Application Priority Data

Nov. 2, 2004  (JP) ................................. 2004-319339
Jun. 17, 2005 (JP) ................................. 2005-178628

(51) Int. Cl.
*C07D 401/00* (2006.01)
*A61K 31/445* (2006.01)
(52) U.S. Cl. ..................................... 546/273.4; 514/323
(58) Field of Classification Search ............... 546/273.4; 514/323
See application file for complete search history.

(56) References Cited

U.S. PATENT DOCUMENTS

| | | | |
|---|---|---|---|
| 4,766,133 A * | 8/1988 | Fischli et al. ................. | 514/338 |
| 5,243,054 A | 9/1993 | Naka et al. | |
| 6,162,804 A * | 12/2000 | Bilodeau et al. ............ | 514/234.5 |
| 6,433,188 B1 | 8/2002 | Corbett et al. | |
| 6,441,184 B1 | 8/2002 | Corbett et al. | |
| 6,448,399 B1 | 9/2002 | Corbett et al. | |
| 6,545,155 B2 | 4/2003 | Corbett et al. | |
| 2002/0032330 A1 | 3/2002 | Nomura et al. | |
| 2002/0103199 A1 | 8/2002 | Corbett et al. | |
| 2002/0103241 A1 | 8/2002 | Corbett et al. | |
| 2002/0107396 A1 | 8/2002 | Corbett et al. | |
| 2002/0111372 A1 | 8/2002 | Corbett et al. | |

FOREIGN PATENT DOCUMENTS

| | | |
|---|---|---|
| JP | 10-306076 | 11/1998 |
| JP | 2004-067629 | 3/2004 |
| JP | 2004-123711 | 4/2004 |
| JP | 2004-517087 | 6/2004 |
| WO | 2004/013109 A1 | 2/2004 |
| WO | WO 2005/063738 | 7/2005 |

OTHER PUBLICATIONS

Votocek et al., CA 27:38557, 1933.*

* cited by examiner

*Primary Examiner* — Janet L. Andres
*Assistant Examiner* — Raymond Covington
(74) *Attorney, Agent, or Firm* — Richard C. Billups; Heidi M. Struse; John C. Todaro

(57) ABSTRACT

A glucokinase activator is provided; and a treatment and/or a preventive for diabetes, or a treatment and/or a preventive for diabetes such as retinopathy, nephropathy, neurosis, ischemic cardiopathy, arteriosclerosis, and further a treatment and/or a preventive for obesity are provided.
The invention relates to a compound of a formula (I):

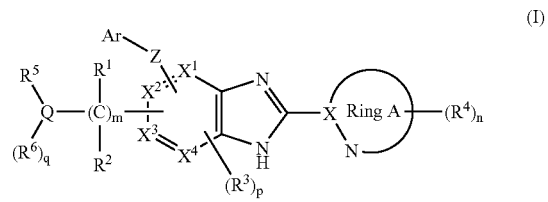

[wherein $R^1$ and $R^2$ represent a hydrogen, etc.; $R^3$ represents a hydrogen atom, a halogen atom, etc.; $R^4$ each independently represents a hydrogen atom, a lower alkyl group, etc.; Q represents a carbon atom, a nitrogen atom or a sulfur atom (the sulfur atom may be mono- or di-substituted with an oxo group); $R^5$ and $R^6$ each represent a hydrogen atom, a lower alkyl group, etc.; $X^1$, $X^2$, $X^3$ and $X^4$ each independently represent a carbon atom or a nitrogen atom; Z represents an oxygen atom, a sulfur atom or a nitrogen atom; Ar represents an aryl or heteroaryl group optionally mono to tri-substituted with a group selected from the substituent group β; ring A represents a 5- or 6-membered nitrogen-containing heteroaromatic group; m indicates an integer of from 1 to 6; n indicates an integer of from 0 to 3; p indicates an integer of from 0 to 2 (provided that at least two of $X^1$ to $X^4$ are carbon atoms); q indicates 0 or 1] or its pharmaceutically-acceptable salt, which has an effect of glucokinase activation and is useful as a treatment for diabetes.

14 Claims, No Drawings

US 7,932,394 B2

ARYLOXY-SUBSTITUTED BENZIMIDAZOLE DERIVATIVES

TECHNICAL FIELD

The present invention relates to a glucokinase activator comprising, as the active ingredient thereof, an aryloxy-substituted benzimidazole derivative and useful in the field of medicines. Further, it relates to a novel aryloxy-substituted benzimidazole derivative.

BACKGROUND ART

Glucokinase (GK) (ATP: D-hexose 6-phosphotransferase, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver beta cells and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood-sugar level. Therefore, in accordance with the blood-sugar level change from a normal blood-sugar level (5 mM) to an increased blood-sugar level after meals (10 to 15 mM), intercellular glucose metabolism is accelerated via glucokinase.

Since ten years ago, a hypothesis that glucokinase may act as a glucose sensor in pancreas beta cells and liver has been proposed (for example, see Garfinkel D. et al., Computer modeling identifies glucokinase as glucose sensor of pancreatic beta-cells; American Journal Physiology, Vol. 247 (3Pt2), 1984, pp. 527-536).

A result of recent glucokinase gene-manipulated mice has confirmed that glucokinase actually plays an important role in systemic glucose homeostasis. Mice in which the glucokinase gene was disrupted die soon after their birth (for example, see Grupe A. et al., Transgenic knockouts reveal a critical requirement for pancreatic beta cell glucokinase in maintaining glucose homeostasis; Cell, Vol. 83, 1995, pp. 69-78); but on the other hand, normal or diabetic mice in which glucokinase was excessively expressed have a lowered blood-sugar level (for example, see Ferre T. et al., Correction of diabetic alterations by glucokinase; Proceedings of the National Academy of Sciences of the U.S.A., Vol. 93, 1996, pp. 7225-7230).

With the increase in glucose concentration therein, the reaction of pancreas beta cells and that of liver cells are both toward the reduction in a blood-sugar level, though differing from each other. Pancreas beta cells come to secrete more insulin, and liver takes up sugar to store it as glycogen therein and simultaneously reduces sugar release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-sugar level increase (for example, see Vionnet N. et al., Nonsense mutation in the glucokinase gene causes early-onset non-insulin-dependent diabetes mellitus; Nature Genetics, Vol. 356, 1992, pp. 721-722).

On the other hand, a pedigree having mutation of increasing glucokinase activity has been found, and those of the family line show low blood-sugar level symptoms (for example, see Glaser B. et al., Familial hyperinsulinism caused by an activating glucokinase mutation; New England Journal Medicine, Vol. 338, 1998, pp. 226-230).

From these, glucokinase acts as a glucose sensor and plays an important role in glucose homeostasis also in humans. On the other hand, blood-sugar level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a treatment for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VHM, a glucose-mediated mechanism is anticipated like the insulin secretion in pancreas beta cells. Accordingly, there may be a possibility that a substance for glucokinase activation in VHM, in addition to liver and pancreas beta cells, may be effective not only for blood-sugar level correction but also for solution of obesity that is problematic in many type-II diabetes patients.

This indicates that compounds having glucokinase-activating effects are useful as therapeutic and/or prophylactic agents for diabetes, as therapeutic and/or prophylactic agents for diabetes complications such as retinopathy, nephropathy, neurosis, ischemic cardiopathy, arteriosclerosis and the like, and as therapeutic and/or prophylactic agents for obesity.

For benzimidazole derivatives, for example, a compound of the following formula is described (for example, O2002/032872):

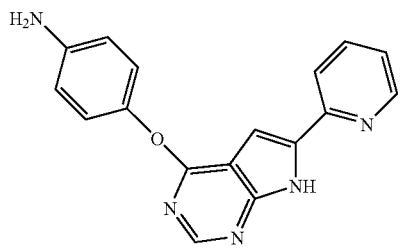

The compound of the above formula is similar to the compound of the present invention in that they have a 2-pyridinyl group at the 6-position of the 7H-pyrrolo[2,3-d]pyrimidinyl skeleton thereof have a phenoxy group at the 4-position thereof, but the two differ structurally in that the former has one substituent on the 7H-pyrrolo[2,3-d]pyrimidinyl group and that, in the former, the substituent on the phenoxy group is an amino group.

Further, the above compound is an intermediate for angiogenesis-inhibiting compounds, and there is given neither description indicating that the compound may be useful for treatment and/or prevention of specific diabetes and obesity nor description suggesting it.

DISCLOSURE OF THE INVENTION

Problems that the Invention is to Solve

An object of the present invention is to provide a novel aryloxy-substituted imidazole derivative and a glucokinase activator comprising it, especially providing therapeutic and/or prophyractic agents for diabetes and obesity.

We, the present inventors have assiduously studied so as to develop a novel medicine for diabetes, which has a pharmaceutical potency over that of the above-mentioned already-existing medicines for diabetes owing to its effect different from that of the already-existing medicines and which has an additional pharmaceutical potency, and, as a result, have found that a novel aryloxy-substituted benzimidazole derivative has a glucokinase-activating effect and have completed the present invention.

Specifically, the invention relates to:
(1) A compound of a formula (I):

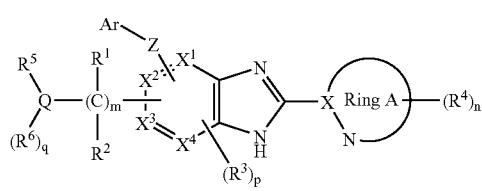

or a pharmaceutically acceptable salt thereof, wherein:
$R^1$ and $R^2$ each independently represent a hydrogen atom, a halogen atom, a lower alkyl group, a hydroxyl group, a cyano group or a lower alkoxy group;
$R^3$ independently represents a hydrogen atom, a halogen atom, a lower alkyl group, a lower alkoxy group, a hydroxyalkyl group, a trifluoromethyl group, a lower alkenyl group or a cyano group;
$R^4$ independently represents a hydrogen atom, a lower alkyl group, a lower alkoxy group, a halogen atom, a trifluoromethyl group, a hydroxyalkyl group optionally substituted with a lower alkyl group, an aminoalkyl group optionally substituted with a lower alkyl group, an alkanoyl group, a carboxyl group, a lower alkoxycarbonyl group or a cyano group;
Q represents a carbon atom, a nitrogen atom or a sulfur atom optionally substituted with one or two oxo groups;
$R^5$ and $R^6$ each independently represent a hydrogen atom, a lower alkyl group, a halogen atom, a lower alkyl group, a lower alkylsulfonyl group, a lower alkylsulfinyl group, an alkanoyl group, a formyl group, an aryl group, a mono- or di-lower alkylcarbamoyl group or a mono- or di-lower alkylsulfamoyl group; or taken together, Q, $R^5$ and $R^6$ may form the following:
(A) a 5- or 6-membered aliphatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms;
said heterocyclid group may have one or two double bonds;
(B) a 5- or 6-membered aromatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms, or
(C) a phenyl group,
and the aliphatic nitrogen-containing heterocyclic group, the aromatic nitrogen-containing heterocyclic group or the phenyl group may have from 1 to 3 groups selected from the following substituent group α, and/or may have, as the substituent thereof, a 3- to 6-membered ring formed through bonding to each other of the bondable groups selected from the substituent group a, and/or may be condensed with a group of a formula (A):

(A)

wherein ═══ represents a single bond or a double bond;
$X^1$, $X^2$, $X^3$ and $X^4$ each independently represent a carbon atom or a nitrogen atom;
Z represents an oxygen atom, a sulfur atom or a nitrogen atom;
Ar represents an aryl or heteroaryl group optionally substituted with from 1 to 3 groups selected from the following substituent group β;
ring A represents a 5- or 6-membered nitrogen-containing heteroaromatic group of a formula (III):

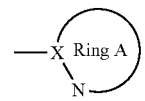

(III)

wherein X represents a carbon atom;
m indicates an integer of from 1 to 6;
n indicates an integer of from 0 to 3;
p indicates an integer of from 0 to 2; provided that at least two of $X^1$ to $X^4$ are hydrogen atoms;
q indicates 0 or 1;
Substituent Group α:
an oxo group, a thioxo group, a lower alkyl group, a lower alkoxy group, an alkanoyl group, a formyl group, a hydroxy group, a carboxyl group, a trifluoromethyl group, a hydroxyalkyl group optionally substituted with a lower alkyl group, a cyano group, a mono- or di-lower alkylcarbamoyl group, a lower alkylsulfinyl group, a lower alkylsulfonyl group and a halogen atom;
Substituent Group β:
a lower alkyl group, a lower alkoxy group, a halogen atom, a trifluoromethyl group, a hydroxyalkyl group optionally substituted with a lower alkyl group, a lower alkylsulfonyl group, a lower alkylsulfanyl group, a lower alkylsulfinyl group, an aminoalkyl group optionally substituted with a lower alkyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, and a heteroaryl group, having in the ring thereof, from 1 to 3 hetero atoms selected from the group consisting of a nitrogen atom, an oxygen atom and a sulfur atom;

said aryl group and heteroaryl group may have one or two groups selected from the following substituent group γ;

Substituent Group γ:

a lower alkyl group, a lower alkoxy group, a halogen atom, a hydroxyl group, a lower alkylsulfonyl group, a lower alkylsulfinyl group, an alkanoyl group, a cyano group, a mono- or di-lower alkylcarbamoyl group;

(2) The compound or a pharmaceutically acceptable salt of above (1), wherein the ring A is a thiazolyl group, an imidazolyl group, an isothiazolyl group, a thiadiazolyl group, a triazolyl group, an oxazolyl group, an isoxazolyl group, a pyrazinyl group, a pyridyl group, a pyridazinyl group, a pyrazolyl group or a pyrimidinyl group;

(3) The compound or a pharmaceutically acceptable salt of claims, wherein the ring A is a thiazolyl group, an imidazolyl group, an isothiazolyl group, a thiadiazolyl group, a triazolyl group, an oxazolyl group, an isoxazolyl group, a pyrazinyl group, a pyridyl group, a pyridazinyl group, a pyrazolyl group or a pyrimidinyl group, and the formula (I) is represented by the following formula (I-1):

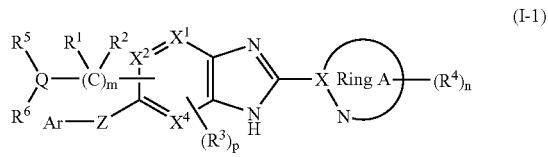

wherein the symbols have the same meanings as above;

(4) The compound or a pharmaceutically acceptable salt of above (1), wherein the ring A is a thiazolyl group, an imidazolyl group, an isothiazolyl group, a thiadiazolyl group, a triazolyl group, an oxazolyl group, an isoxazolyl group, a pyrazinyl group, a pyridyl group, a pyridazinyl group, a pyrazolyl group or a pyrimidinyl group, and the formula (I) is represented by the formula (I-2):

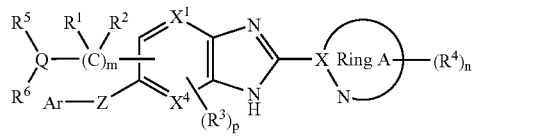

wherein the symbols have the same meanings as above;

(5) The compound or a pharmaceutically acceptable salt of above (1), wherein the ring A is a thiazolyl group, an imidazolyl group, an isothiazolyl group, a thiadiazolyl group, a triazolyl group, an oxazolyl group, an isoxazolyl group, a pyrazinyl group, a pyridyl group, a pyridazinyl group, a pyrazolyl group or a pyrimidinyl group, and the formula (I) is represented by the formula (I-3):

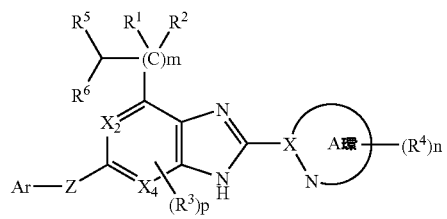

wherein the symbols have the same meanings as above;

(6) The compound or a pharmaceutically acceptable salt of above (3), wherein m is from 1 to 4;

(7) The compound or a pharmaceutically acceptable salt of above (3), wherein Z is an oxygen atom or a sulfur atom;

(8) The compound or a pharmaceutically acceptable salt of above (3), wherein Ar is a phenyl group, a furyl group, a thienyl group, a pyrrolyl group, an imidazolyl group, a triazolyl group, a pyrazolyl group, a thiazolyl group, a thiadiazolyl group, an isothiazolyl group, an oxazolyl group, an isoxazolyl group, a pyridyl group, a pyrimidinyl group, a pyridazinyl group or a pyrazinyl group, which may be substituted with a group selected from the substituent group β;

(9) The compound or a pharmaceutically acceptable salt of above (3), wherein $R^1$ and $R^6$ each independently represent a hydrogen atom, a lower alkyl group, a halogen atom, a lower alkyl group, a lower alkylsulfonyl group, a lower alkylsulfinyl group, an alkanoyl group or a formyl group;

(10) The compound or a pharmaceutically acceptable salt of above (3), wherein Q is a nitrogen atom;

(11) The compound or a pharmaceutically acceptable salt of above (3), wherein Q is a carbon atom;

(12) The compound or a pharmaceutically acceptable salt of above (3), wherein the group of a formula (I-A):

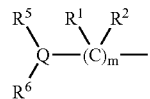

in the formula (I-1) is a group of the following formula:

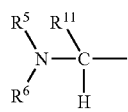

wherein: $R^{11}$ represents a hydrogen atom or a lower alkyl group; and the other symbols have the same meanings as above;

(13) The compound or a pharmaceutically acceptable salt of above (3), wherein:

Q is a nitrogen atom;

$R^5$ and $R^6$, taken together with the nitrogen atom, form a 5- or 6-membered aliphatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms;

said 5- or 6-membered aliphatic nitrogen-containing heterocyclic group may have one or two double bonds, an may be mono- or di-substituted with the same or different groups selected from the following substituent group α1;

m is 1;

Z is an oxygen atom;

Ar is a phenyl or a pyridyl group optionally mono- or di-substituted with the same or different groups selected from the following substituent group β1;

$R^1$ and $R^2$ are independently a hydrogen atom or a lower alkyl group,

Substituent Group α1:

an oxo group, a thioxo group, a lower alkyl group, a lower alkoxy group, an alkanoyl group, a halogen atom, a cyano group, a mono- or di-lower alkylcarbamoyl group;

Substituent Group β1:

a lower alkyl group, a lower alkoxy group, a halogen atom, a trifluoromethyl group, a hydroxyalkyl group optionally substituted with a lower alkyl group, a lower alkylsulfonyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, or a heteroaryl group having, in the ring thereof, 2 or 3 hetero atoms selected from the group consisting of a nitrogen atom, an oxygen atom and a sulfur atom;

said aryl group and the heteroaryl group may have one or two groups selected from the substituent group γ;

(14) The compound or a pharmaceutically acceptable salt of above (3), wherein: Q, $R^5$ and $R^6$, taken together, form a 5- or 6-membered aromatic nitrogen-containing heterocyclic group having at least one nitrogen atom, optionally having in the ring from 1 to 3 hetero atoms selected from the group consisting of a nitrogen atom, an oxygen atom and a sulfur atom in addition to that nitrogen atom, or a phenyl group;

said aromatic heterocyclic group or the phenyl group may have from 1 to 3 groups selected from the following substituent group α2;

Z is an oxygen atom;

Ar is a phenyl group or a pyridyl group optionally mono- or di-substituted with the same or different groups selected from the following substituent group β1;

$R^1$ and $R^2$ are independently a hydrogen atom or a lower alkyl group;

Substituent Group α2:

a hydroxyl group, a lower alkyl group, a lower alkoxy group, an alkanoyl group, a halogen atom, a cyano group and a mono- or di-lower alkylcarbamoyl group;

Substituent Group β1:

a lower alkyl group, a lower alkoxy group, a halogen atom, a trifluoromethyl group, a hydroxyalkyl group optionally substituted with a lower alkyl group, a lower alkylsulfonyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, or a heteroaryl group having, in the ring thereof, 2 or 3 hetero atoms selected from the group consisting of a nitrogen atom, an oxygen atom and a sulfur atom;

said aryl group and the heteroaryl group may have one or two groups selected from the substituent group γ;

(15) The compound or a pharmaceutically acceptable salt thereof of above (1), wherein: the formula (I) is:

1-{[5-[4-(methylsulfonyl)phenoxy]-2-(2-pyridinyl)-1H-benzimidazol-6-yl]methyl}-5-thioxo-2-pyrrolidinone, 4-{[5-[4-(methylsulfonyl)phenoxy]-2-(2-pyridinyl)-1H-benzimidazol-6-yl]methyl}morpholine-3,5-dione, 3-{[5-[4-(methylsulfonyl)phenoxy]-2-(2-pyridinyl)-1H-benzimidazol-6-yl]methyl}-1,3-thiazolane-2,4-dione, 3-{[5-[4-(methylsulfonyl)phenoxy]-2-(2-pyridinyl)-1H-benzimidazol-6-yl]methyl}-1,3-thiazolan-2-one, 1-{[5-[4-(ethylsulfonyl)phenoxy]-2-(2-pyridinyl)-1H-benzimidazol-6-yl]methyl}pyrrolidine-2,5-dione, 1-{[5-[4-(ethylsulfonyl)phenoxy]-2-(2-pyridinyl)-1H-benzimidazol-6-yl]methyl}-3-methyl-imidazolidine-2,5-dione, 2-{[5-[4-(ethylsulfonyl)phenoxy]-2-(2-pyridinyl)-1H-benzimidazol-6-yl]methyl}isothiazolidine-1,1-dioxide, 3-{[5-[4-(ethylsulfonyl)phenoxy]-2-(2-pyrazinyl)-1H-benzimidazol-6-yl]methyl}-2-oxazolidinone, 1-{[5-{[6-(ethylsulfonyl)-3-pyridinyl]oxy}-2-(2-pyridinyl)-1H-benzimidazol-6-yl]methyl}pyrrolidine-2,5-dione, 1-[(5-{[6-(5-methyl-1,2,4-oxadiazol-3-yl)-3-pyridinyl]oxy}-2-(2-pyridinyl)-1H-benzimidazol-6-yl)methyl]-2-pyrrolidinone, N-({5-[4-(ethylsulfonyl)phenoxy]-2-(2-pyridinyl)-1H-benzimidazol-6-yl}methyl)-N-methylacetamide, 3-{[5-[4-(5-methyl-1,2,4-oxadiazol-3-yl)phenoxy]-2-(2-pyridinyl)-1H-benzimidazol-6-yl]methyl}-1,3-oxazolidine-2,4-dione, 5-[4-(ethylsulfonyl)phenoxy]-6-((2-methyl-2H-tetrazol-5-yl)methyl)-2-(2-pyridinyl)-1H-benzimidazole, 5-[4-(ethylsulfonyl)phenoxy]-6-(1-(1-methyl-1H-tetrazol-5-yl)ethyl)-2-(2-pyridinyl)-1H-benzimidazole, 1-[(6-{[6-(ethylsulfonyl)pyridin-3-yl]oxy}-2-pyridin-2-yl-1H-benzimidazol-4-yl)methyl]pyrrolidin-2-one, or 4-(2,6-difluorobenzyl)-6-{[6-(ethylsulfonyl)pyridin-3-yl]oxy}-2-pyrazin-2-yl-1H-benzimidazole;

(16) The compound or a pharmaceutically acceptable salt of above (1), wherein the formula (I) is 1-{[5-[4-(methylsulfonyl)phenoxy]-2-(2-pyridinyl)-1H-benzimidazol-6-yl]methyl}-5-thioxo-2-pyrrolidinone;

(17) The compound or a pharmaceutically acceptable salt of above (1), wherein the formula (I) is 4-{[5-[4-(methylsulfonyl)phenoxy]-2-(2-pyridinyl)-1H-benzimidazol-6-yl]methyl}morpholine-3,5-dione;

(18) The compound or a pharmaceutically acceptable salt of above (1), wherein the formula (I) is 3-{[5-[4-(methylsulfonyl)phenoxy]-2-(2-pyridinyl)-1H-benzimidazol-6-yl]methyl}-1,3-thiazolane-2,4-dione;

(19) The compound or a pharmaceutically acceptable salt of above (1), wherein the formula (I) is 3-{[5-[4-(methylsulfonyl)phenoxy]-2-(2-pyridinyl)-1H-benzimidazol-6-yl]methyl}-1,3-thiazolan-2-one;

(20) The compound or a pharmaceutically acceptable salt of above (1), wherein the formula (I) is 1-{[5-[4-(ethylsulfonyl)phenoxy]-2-(2-pyridinyl)-1H-benzimidazol-6-yl]methyl}pyrrolidine-2,5-dione;

(21) The compound or a pharmaceutically acceptable salt of above (1), wherein the formula (I) is 1-{[5-[4-(ethylsulfonyl)phenoxy]-2-(2-pyridinyl)-1H-benzimidazol-6-yl]methyl}-3-methyl-imidazolidine-2,5-dione;

(22) The compound or a pharmaceutically acceptable salt of above (1), wherein the formula (I) is 2-{[5-[4-(ethylsulfonyl)phenoxy]-2-(2-pyridinyl)-1H-benzimidazol-6-yl]methyl}isothiazolidine-1,1-dioxide;

(23) The compound or a pharmaceutically acceptable salt of above (1), wherein the formula (I) is 3-{[5-[4-(ethylsulfonyl)phenoxy]-2-(2-pyrazinyl)-1H-benzimidazol-6-yl]methyl}-2-oxazolidinone;

(24) The compound or a pharmaceutically acceptable salt of above (1), wherein the formula (I) is 1-{[5-{[6-(ethylsulfonyl)-3-pyridinyl]oxy}-2-(2-pyridinyl)-1H-benzimidazol-6-yl]methyl}pyrrolidine-2,5-dione;

(25) The compound or a pharmaceutically acceptable salt of above (1), wherein the formula (I) is 1-[(5-{[6-(5-methyl- 1,2,4-oxadiazol-3-yl)-3-pyridinyl]oxy}-2-(2-pyridinyl)-1H-benzimidazol-6-yl)methyl]-2-pyrrolidinone;

(26) The compound or a pharmaceutically acceptable salt of above (1), wherein the formula (I) is N-({5-[4-(ethylsulfonyl)phenoxy]-2-(2-pyridinyl)-1H-benzimidazol-6-yl}methyl)-N-methylacetamide;

(27) The compound or a pharmaceutically acceptable salt of above (1), wherein the formula (I) is 3-{[5-[4-(5-methyl-1,2,4-oxadiazol-3-yl)phenoxy]-2-(2-pyridinyl)-1H-benzimidazol-6-yl]methyl}-1,3-oxazolidine-2,4-dione;

(28) The compound or a pharmaceutically acceptable salt of above (1), wherein the formula (I) is 5-[4-(ethylsulfonyl)phenoxy]-6-((2-methyl-2H-tetrazol-5-yl)methyl)-2-(2-pyridinyl)-1H-benzimidazole;

(29) The compound or a pharmaceutically acceptable salt of above (1), wherein the formula (I) is 5-[4-(ethylsulfonyl)phenoxy]-6-(1-(1-methyl-1H-tetrazol-5-yl)ethyl)-2-(2-pyridinyl)-1H-benzimidazole;

(30) The compound or a pharmaceutically acceptable salt of above (1), wherein the formula (I) is 1-[(6-{[6-(ethylsulfonyl)pyridin-3-yl]oxy}-2-pyridin-2-yl-1H-benzimidazol-4-yl)methyl]pyrrolidin-2-one;

(31) The compound or a pharmaceutically acceptable salt of above (1), wherein the formula (I) is 4-(2,6-difluorobenzyl)-6-{[6-(ethylsulfonyl)pyridin-3-yl]oxy}-2-pyrazin-2-yl-1H-benzimidazole;

(32) A pharmaceutical composition comprising the following (1) to (3), which is used for treatment, prevention and/or delay onset of type-II diabetes:
(1) a compound or its pharmaceutically-acceptable salt of above (1) to (31),
(2) one or more compounds selected from the following groups (a) to (h):
(a) any other glucokinase activator,
(b) a bis-guanide,
(c) a PPAR agonist,
(d) an insulin,
(e) a somatostatin,
(f) an α-glucosidase inhibitor,
(g) an insulin secretion promoter, and
(h) a DP-IV inhibitor (dipeptidyl peptidase IV inhibitor),
(3) a pharmaceutically-acceptable carrier;

(33) A glucokinase activator comprising a compound or a pharmaceutically acceptable salt of any one of above (1) to (31), as the active ingredient thereof;

(34) A therapeutic and/or prophyractic agents for diabetes, comprising a compound or a pharmaceutically acceptable salt of any one of above (1) to (31), as the active ingredient thereof;

(35) A therapeutic and/or prophyractic agents for diabetes, comprising a compound or a pharmaceutically acceptable salt of any one of above (1) to (31), as the active ingredient thereof.

BEST MODE FOR CARRYING OUT THE INVENTION

The meanings of the terms used in this description are described below, and the compounds of the invention are described in more detail hereinunder.

Unless otherwise specifically indicated in this description, the following groups have the meanings described below.

"Halogen atom" includes, for example, a fluorine atom, a chlorine atom, a bromine atom, an iodine atom.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Lower alkoxy group" means a hydroxyl group of which the hydrogen atom is substituted with the above-mentioned lower alkyl group, and includes, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Hydroxyalkyl group" means the above-mentioned lower alkyl group substituted with a hydroxyl group, and includes, for example, a hydroxymethyl group, a 2-hydroxyethyl group, a 1-hydroxyethyl group.

"Lower alkenyl group" means a linear or branched lower alkenyl group having from 2 to 6 carbon atoms, and includes, for example, a vinyl group, an allyl group, a 1-butenyl group, a 2-butenyl group, a 1-pentenyl group.

"Aminoalkyl group" means the above-mentioned alkyl group of which one hydrogen atom is substituted with an amino group, and includes, for example, an aminomethyl group, an aminoethyl group, an aminopropyl group.

"Alkanoyl group" means the above-mentioned alkyl group bonding to a carbonyl group, and includes, for example, a methylcarbonyl group, an ethylcarbonyl group, a propylcarbonyl group, an isopropylcarbonyl group.

"Lower alkoxycarbonyl group" means a carboxyl group of which the hydrogen atom is substituted with the above-mentioned lower alkyl group, and includes, for example, a methoxycarbonyl group, an ethoxycarbonyl group, a propylcarbonyl group, an isopropylcarbonyl group.

"Lower alkylsulfonyl group" means the above-mentioned lower alkyl group bonding to a sulfonyl group and includes, for example, a methylsulfonyl group, an ethylsulfonyl group, an isopropylsulfonyl group, an n-propylsulfonyl group.

"Lower alkylsulfinyl group" means the above-mentioned lower alkyl group bonding to a sulfinyl group and includes, for example, a methylsulfinyl group, an ethylsulfinyl group, an isopropylsulfinyl group.

"Lower alkylsulfanyl group" means the above-mentioned lower alkyl group bonding to a sulfanyl group and includes, for example, a methylsulfanyl group, an ethylsulfanyl group, an isopropylsulfanyl group.

"Mono-lower alkylcarbamoyl group" means a carbamoyl group mono-substituted with the above-mentioned lower alkyl group, and includes, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group.

"Di-lower alkylcarbamoyl group" means a carbamoyl group di-substituted with the same or different, above-mentioned lower alkyl groups, and includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

"Mono-lower alkylsulfamoyl group" means a sulfamoyl group mono-substituted with the above-mentioned lower alkyl group and includes, for example, a methylsulfamoyl group, an ethylsulfamoyl group, a propylsulfamoyl group, an isopropylsulfamoyl group.

"Di-lower alkylsulfamoyl group" means a sulfamoyl group di-substituted with the same or different, above-mentioned lower alkyl groups and includes, for example, a dimethylsulfamoyl group, a diethylsulfamoyl group, an ethylmethylsulfamoyl group, an isopropylmethylsulfamoyl group.

For more concretely disclosing the compounds of the invention of the following formula (I):

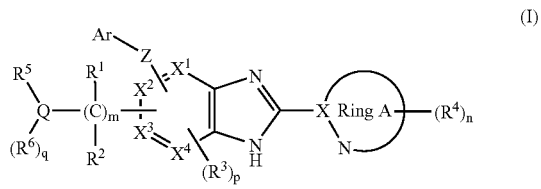

(I)

[wherein the symbols have the same meanings as above], symbols used in that formula (I) are described with reference to their concrete examples.

$R^1$ and $R^2$ each independently represent a hydrogen atom, a halogen atom, a lower alkyl group, a hydroxyl group, a cyano group or a lower alkoxy group.

"Halogen atom", "lower alkyl group" and "lower alkoxy group" for $R^1$ and $R^2$ have the same meanings as those defined in the above.

Preferably, one of $R^1$ and $R^2$ is a hydrogen atom and the other is a lower alkyl group, or the two are both hydrogen atoms. More preferably, the two are both hydrogen atoms.

$R^3$ independently represents a hydrogen atom, a halogen atom, a lower alkyl group, a lower alkoxy group, a hydroxyalkyl group, a trifluoromethyl group, a lower alkenyl group or a cyano group.

"Halogen atom", "lower alkyl group", "lower alkoxy group", "hydroxyalkyl group" and "lower alkenyl group" for $R^3$ have the same meanings as those defined in the above.

Preferably, $R^3$ is a hydrogen atom.

$R^4$ independently represents a hydrogen atom, a lower alkyl group, a lower alkoxy group, a halogen atom, a trifluoromethyl group, a hydroxyalkyl group (the hydrogen atom of the hydroxyl group in the hydroxyalkyl group may be substituted with a lower alkyl group), an aminoalkyl group (the amino group may be substituted with a lower alkyl group), an alkanoyl group, a carboxyl group, a lower alkoxycarbonyl group or a cyano group.

"Lower alkyl group", "lower alkoxy group", "halogen atom", "alkanoyl group" and "lower alkoxycarbonyl group" for $R^4$ have the same meanings as those defined in the above.

"Hydroxyalkyl group" for $R^4$ includes those where the hydrogen atom of the hydroxyl group is substituted with a lower alkyl group, in addition to the above-defined "hydroxyalkyl group".

"Hydroxyalkyl group" for $R^4$ includes, for example, a hydroxymethyl group, a 2-hydroxyethyl group, a 1-hydroxyethyl group, a methoxymethyl group, a methoxyethyl group, an ethoxyethyl group.

$R^4$ is preferably a hydrogen atom, a lower alkyl group, a halogen atom, a trifluoromethyl group or a hydroxyalkyl group (the hydrogen atom of the hydroxyl group in the hydroxyalkyl group may be substituted with a lower alkyl group); more preferably a hydrogen atom, a lower alkyl group, a halogen atom, or a trifluoromethyl group.

Q represents a carbon atom, a nitrogen atom or a sulfur atom (the sulfur atom may be substituted with one or two oxo groups). Q is preferably a carbon atom or a nitrogen atom.

$R^5$ and $R^6$ each independently represent a hydrogen atom, a lower alkyl group, a halogen atom, a lower alkyl group, a lower alkylsulfonyl group, a lower alkylsulfinyl group, an alkanoyl group, a formyl group, an aryl group, a mono- or di-lower alkylcarbamoyl group or a mono- or di-lower alkylsulfamoyl group; or taken together, Q, $R^5$ and $R^6$ in the following formula (II):

(II)

may form a 5- or 6-membered aliphatic nitrogen-containing heterocyclic group (the group may have one or two double bonds) or aromatic nitrogen-containing heterocyclic group optionally having, in the ring thereof, from 1 to 4 hetero atoms selected from the group consisting of a nitrogen atom, a sulfur atom and an oxygen atom, or a phenyl group.

The aliphatic nitrogen-containing heterocyclic group, the aromatic nitrogen-containing heterocyclic group or the phenyl group may have from 1 to 3 groups selected from the following substituent group a, and/or may have, as the substituent thereof, a 3- to 6-membered ring formed through bonding to each other of the bondable groups selected from the substituent group α, and/or may be condensed with a group of a formula (A):

(A)

(wherein ===== represents a single bond or a double bond).

"Lower alkyl group", "halogen atom", "lower alkyl group", "lower alkylsulfonyl group", "lower alkylsulfinyl group" and "alkanoyl group" for $R^5$ and $R^6$ may have the same meanings as those defined in the above.

The group of the following formula (II):

(II)

in which Q is a carbon atom, a nitrogen atom or a sulfur atom, and $R^5$ and $R^6$ are independently a hydrogen atom, a lower alkyl group, a halogen atom, a lower alkyl group, a lower alkylsulfonyl group, a lower alkylsulfinyl group, an alkanoyl group, a formyl group, an aryl group, a mono- or di-lower alkylcarbamoyl group or a mono- or di-lower alkylsulfamoyl group, includes, for example, an acetylamino group, a methanesulfonylamino group, a benzenesulfonyl group, a benzenesulfinyl group, a methanesulfonyl group. Of those, preferred is an acetylamino group, an acetylaminomethyl group, a methanesulfonylamino group.

The 5- or 6-membered aliphatic nitrogen-containing heterocyclic group (the group may have one or two double bonds) or aromatic nitrogen-containing heterocyclic group optionally having, in the ring, from 1 to 4 hetero atoms selected from the group consisting of a nitrogen atom, a sulfur atom and an oxygen atom, or the phenyl group to be formed by Q, $R^5$ and $R^6$, taken together, is preferably a 5- or 6-membered aliphatic nitrogen-containing heterocyclic group (the group may have one or two double bonds) having, in the ring, one or two hetero atoms selected from the group consisting of a nitrogen atom, a sulfur atom and an oxygen atom, or a 5- or 6-membered aromatic nitrogen-containing heterocyclic group optionally having from 1 to 4 hetero atoms selected from the group consisting of a nitrogen atom, a sulfur atom and an oxygen atom, or a phenyl group to be formed by Q, $R^5$ and $R^6$, taken together.

The substituent that the 5- or 6-membered aliphatic nitrogen-containing heterocyclic group (the group may have one or two double bonds) may have is preferably an oxo group, a thioxo group, a lower alkyl group, a lower alkoxy group, an alkanoyl group, a halogen atom, a cyano group, a mono- or di-lower alkylcarbamoyl group, selected from the substituent group α.

The substituent that the 5- or 6-membered aromatic nitrogen-containing heterocyclic group or the phenyl group may have is preferably a hydroxyl group, a lower alkyl group, a lower alkoxy group, an alkanoyl group, a halogen atom, a cyano group, a mono- or di-lower alkylcarbamoyl group, selected from the substituent group α.

Concretely, the 5- or 6-membered aliphatic nitrogen-containing heterocyclic group of formula (II) includes, for example, the following groups (II-1):

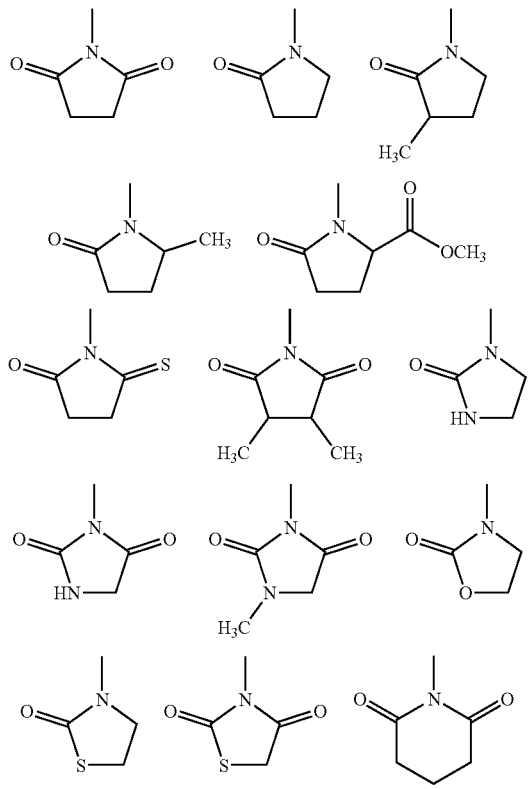

(II-1)

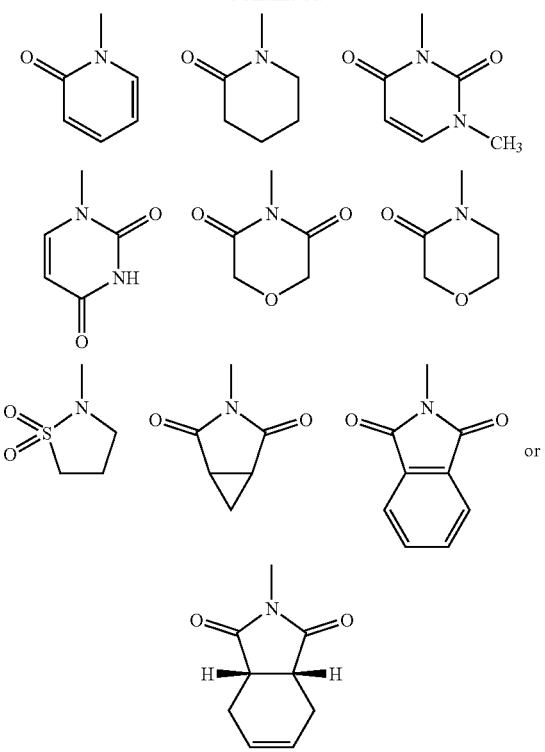

Of those, preferred are groups of the following formula (II-2):

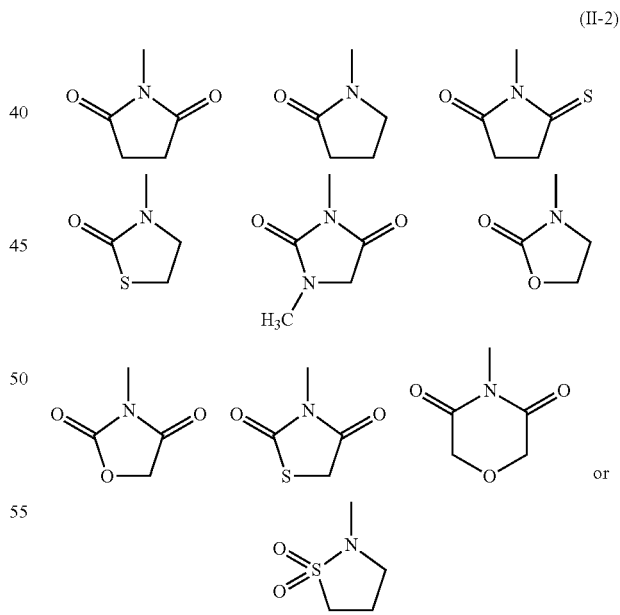

(II-2)

Concretely, the 5- or 6-membered aromatic nitrogen-containing heterocyclic group and the phenyl group of formula (II) include, for example, groups of the following formula (II-2):

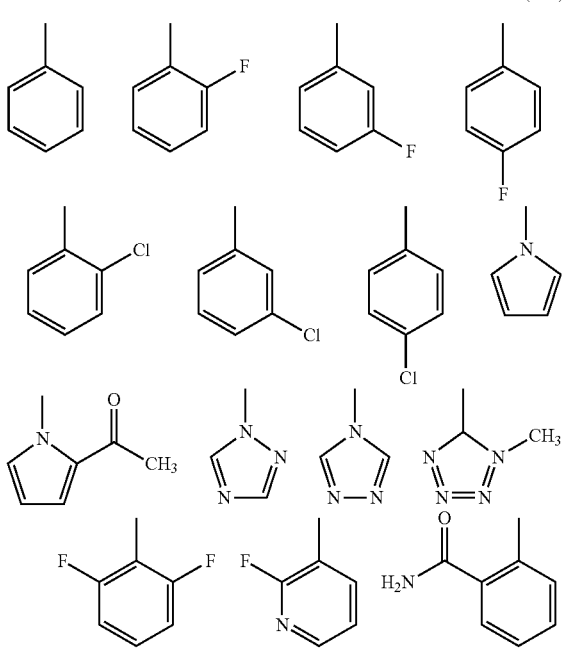

(II-2)

$X^1$, $X^2$, $X^3$ and $X^4$ each independently represent a carbon atom or a nitrogen atom. Preferably, all of $X^1$ to $X^4$ are carbon atoms.

Z represents an oxygen atom, a sulfur atom or a nitrogen atom, preferably an oxygen atom or a sulfur atom, more preferably an oxygen atom.

Ar represents an aryl or heteroaryl group optionally substituted with from 1 to 3 groups selected from the substituent group β.

"Aryl group" for Ar includes a phenyl group and a naphthyl group, and is preferably a phenyl group.

"Heteroaryl group" for Ar means a 5- or 6-membered monocyclic ring having, in the ring, from 1 to 3 hetero atoms selected from the group consisting of a nitrogen atom, a sulfur atom and an oxygen atom.

Concretely, the heteroaryl group includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group. Of those, preferred is a pyridyl group.

The substituent that Ar may have includes the groups selected from the above-mentioned substituent group β. Of those, preferred are a lower alkyl group, a lower alkoxy group, a halogen atom, a trifluoromethyl group, a hydroxyalkyl group (the hydrogen atom of the hydroxyl group in the hydroxyalkyl group may be substituted with a lower alkyl group), a lower alkylsulfonyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, and a heteroaryl group having, in the ring, 2 or 3 hetero atoms selected from the group consisting of a nitrogen atom, an oxygen atom and a sulfur atom (the aryl group and the heteroaryl group may have one or two groups selected from the substituent group γ).

The substituent group γ includes a lower alkyl group, a lower alkoxy group, a halogen atom, a hydroxyl group, a lower alkylsulfonyl group, a lower alkylsulfinyl group, an alkanoyl group, a cyano group, and a mono- or di-lower alkylcarbamoyl group. Of those, preferred are a lower alkylsulfonyl group, a cyano group and a halogen atom.

The ring A means a nitrogen-containing heteroaryl group of a formula (III):

(III)

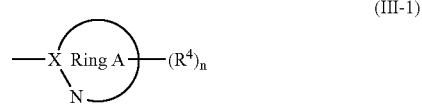

(wherein the symbols have the same meanings as above). The ring A may have, in the ring, one or two hetero atoms selected from the group consisting of a nitrogen atom, a sulfur atom and an oxygen atom, in addition to at least one nitrogen atom.

The group of formula (III) concretely includes, for example, a thiazolyl group, an imidazolyl group, an isothiazolyl group, a thiadiazolyl group, a triazolyl group, an oxazolyl group, an isoxazolyl group, a pyrazinyl group, a pyridyl group, a pyridazinyl group, a pyrazolyl group and a pyrimidinyl group. Of those, preferred are a pyridyl group, a thiazolyl group, a pyrazolyl group, a pyrazinyl group and a thiadiazolyl group.

n indicates an integer of from 0 to 3, preferably from 0 to 2.

The lower alkyl group for $R^4$ is, for example, preferably a methyl group, an ethyl group, a propyl group.

The lower alkoxy group for $R^4$ is, for example, preferably a methoxy group, an ethoxy group, a propoxy group, an isopropoxy group.

The halogen atom for $R^4$ is, for example, preferably a fluorine atom, a chlorine atom, a bromine atom.

The hydroxyalkyl group for $R^4$ is, for example, preferably a hydroxymethyl group, a 2-hydroxyethyl group, a 1-hydroxyethyl group, a 2-hydroxy-1-methylethyl group. The hydrogen atom of the hydroxyl group in the hydroxyalkyl group may be substituted with a lower alkyl group. The lower alkyl group-substituted hydroxyalkyl group includes, for example, a methoxymethyl group, an ethoxymethyl group.

The aminoalkyl group for $R^4$ includes, for example, a methylamino group, an ethylamino group, an isopropylamino group.

The amino group of the aminoalkyl group may be substituted with a lower alkyl group.

The aminoalkanoyl group for $R^4$ includes, for example, an acetylamino group, an ethylcarbonylamino group, a propylcarbonylamino group, an isopropylcarbonylamino group.

The lower alkoxycarbonyl group for $R^4$ includes, for example, a methoxycarbonyl group, an ethoxycarbonyl group, an isopropylcarbonyl group.

From the above, the group of a formula (III-1):

(III-1)

[wherein the symbols have the same meanings as above] concretely includes, for example, a thiazol-2-yl group, a 5-chloro-thiazol-2-yl group, a 4-methyl-thiazol-2-yl group, a 5-methyl-thiazol-2-yl group, a 4-hydroxymethylthiazol-2-yl group, a 4-methoxycarbonyl-thiazol-2-yl group, a 4-methoxymethyl-thiazol-2-yl group, a 4-cyano-thiazol-2-yl group, a 4-fluoro-thiazol-2-yl group, an imidazol-2-yl group, a 4-methyl-imidazol-2-yl group, a 4-methoxycarbonyl-imidazol-2-yl group, a 4-acetyl-imidazol-2-yl group, a 5-hydroxymethyl-imidazol-2-yl group, an isothiazol-3-yl group, a 4-hydroxymethyl-isothiazol-3-yl group, a 5-acetyl-[1,3,4]thiadiazol-2-yl group, a [1,3,4]thiadiazol-2-yl group, a 5-methyl-[1,3,4]thiadiazol-2-yl group, a 5-fluoro-[1,3,4]thiadiazol-2-yl group, a [1,2,4]thiadiazol-5-yl group, a 3-methyl-[1,2,4]thiadiazol-5-yl group, a [1,2,4]triazol-3-yl group, a 5-hydroxymethyl-[1,2,4]triazol-3-yl group, a 5-acetyl-[1,2,4]triazol-3-yl group, an oxazol-2-yl group, an isoxazol-3-yl group, a pyrazin-2-yl group, a 5-methyl-pyrazin-2-yl group, a pyridin-2-yl group, a 4-methyl-pyridin-2-yl group, a pyridazin-3-yl group, a 6-methyl-pyridazin-3-yl group, a 1H-pyrazol-3-yl group, a 1-methyl-1H-pyrazol-3-yl group, a pyrimidin-2-yl group, a pyrimidin-4-yl group.

m indicates an integer of from 1 to 6, preferably from 1 to 4, more preferably 1 or 2, even more preferably 1.

p indicates an integer of from 0 to 2, preferably 0 or 1.

q indicates 0 or 1, preferably q is 1.

Of the compounds of formula (I) of the invention, preferred are those and their pharmaceutically-acceptable salts of a formula (I-11):

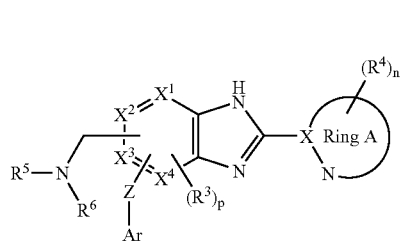

(I-11)

or a formula (I-1):

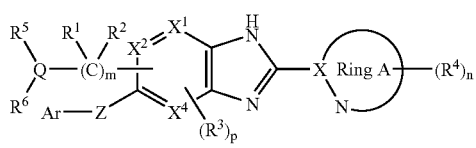

(I-1)

[wherein the symbols have the same meanings as above]; and of the compounds of formula (I-1), more preferred are compounds of a formula (I-2):

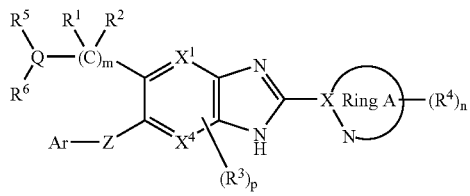

(I-2)

[wherein the symbols have the same meanings as above], and compounds of a formula (I-3):

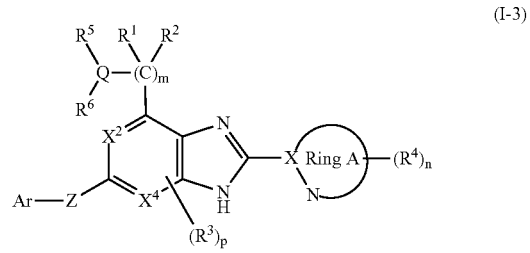

(I-3)

In formula (I-1), the following formula (I-A):

(I-A)

is preferably a group of the following formula:

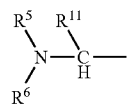

[wherein $R^{11}$ represents a hydrogen atom or a lower alkyl group; and the other symbols have the same meanings as above].

The compounds of formula (I) include, for example, the following compounds and their pharmaceutically-acceptable salts:

1-{[5-[4-(methylsulfonyl)phenoxy]-2-(2-pyridinyl)-1H-benzimidazol-6-yl]methyl}-5-thioxo-2-pyrrolidinone, 4-{[5-[4-(methylsulfonyl)phenoxy]-2-(2-pyridinyl)-1H-benzimidazol-6-yl]methyl}morpholine-3,5-dione, 3-{[5-[4-(methylsulfonyl)phenoxy]-2-(2-pyridinyl)-1H-benzimidazol-6-yl]methyl}-1,3-thiazolane-2,4-dione, 3-{[5-[4-(methylsulfonyl)phenoxy]-2-(2-pyridinyl)-1H-benzimidazol-6-yl]methyl}-1,3-thiazolan-2-one, 1-{[5-[4-(ethylsulfonyl)phenoxy]-2-(2-pyridinyl)-1H-benzimidazol-6-yl]methyl}pyrrolidine-2,5-dione, 1-{[5-[4-(ethylsulfonyl)phenoxy]-2-(2-pyridinyl)-1H-benzimidazol-6-yl]methyl}-3-methyl-imidazolidine-2,5-dione, 2-{[5-[4-(ethylsulfonyl)phenoxy]-2-(2-pyridinyl)-1H-benzimidazol-6-yl]methyl}isothiazolidine-1,1-dioxide, 3-{[5-[4-(ethylsulfonyl)phenoxy]-2-(2-pyrazinyl)-1H-benzimidazol-6-yl]methyl}-2-oxazolidinone, 1-{[5-{[6-(ethylsulfonyl)-3-pyridinyl]oxy}-2-(2-pyridinyl)-1H-benzimidazol-6-yl]methyl}pyrrolidine-2,5-dione, 1-[(5-{[6-(5-methyl-1,2,4-oxadiazol-3-yl)-3-pyridinyl]oxy}-2-(2-pyridinyl)-1H-benzimidazol-6-yl)methyl]-2-pyrrolidinone, N-({5-[4-(ethylsulfonyl)phenoxy]-2-(2-pyridinyl)-1H-benzimidazol-6-yl}methyl)-N-methylacetamide, 3-{[5-[4-(5-methyl-1,2,4-oxadiazol-3-yl)phenoxy]-2-(2-pyridinyl)-1H-benzimidazol-6-yl]methyl}-1,3-oxazolidine-2,4-dione, 5-[4-(ethylsulfonyl)phenoxy]-6-((2-methyl-2H-tetrazol-5-yl)methyl)-2-(2-pyridinyl)-H-benzimidazole, 5-[4-(ethylsulfonyl)phenoxy]-6-(1-(1-methyl-1H-tetrazol-5-yl)ethyl)-2-(2-pyridinyl)-1H-benzimidazole, 1-[(6-{[6-(ethylsulfonyl)pyridin-3-yl]oxy}-2-pyridin-2-yl-1H-benzimidazol-4-yl)methyl]pyrrolidin-2-one, or 4-(2,6-difluorobenzyl)-6-{[6-(ethylsulfonyl)pyridin-3-yl]oxy}-2-pyrazin-2-yl-1H-benzimidazole;

Production methods for the compounds of the invention are described.

Of the compounds of formula (I) of the invention, those of a formula (I-11):

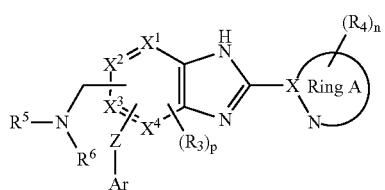
(I-11)

or a formula (I-21):

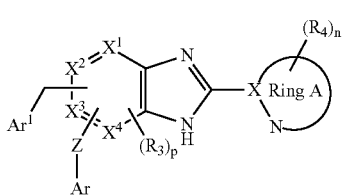
(I-21)

[wherein Ar¹ has the same meaning as the above Ar; and the other symbols have the same meanings as above] may be produced, for example, according to the following process:

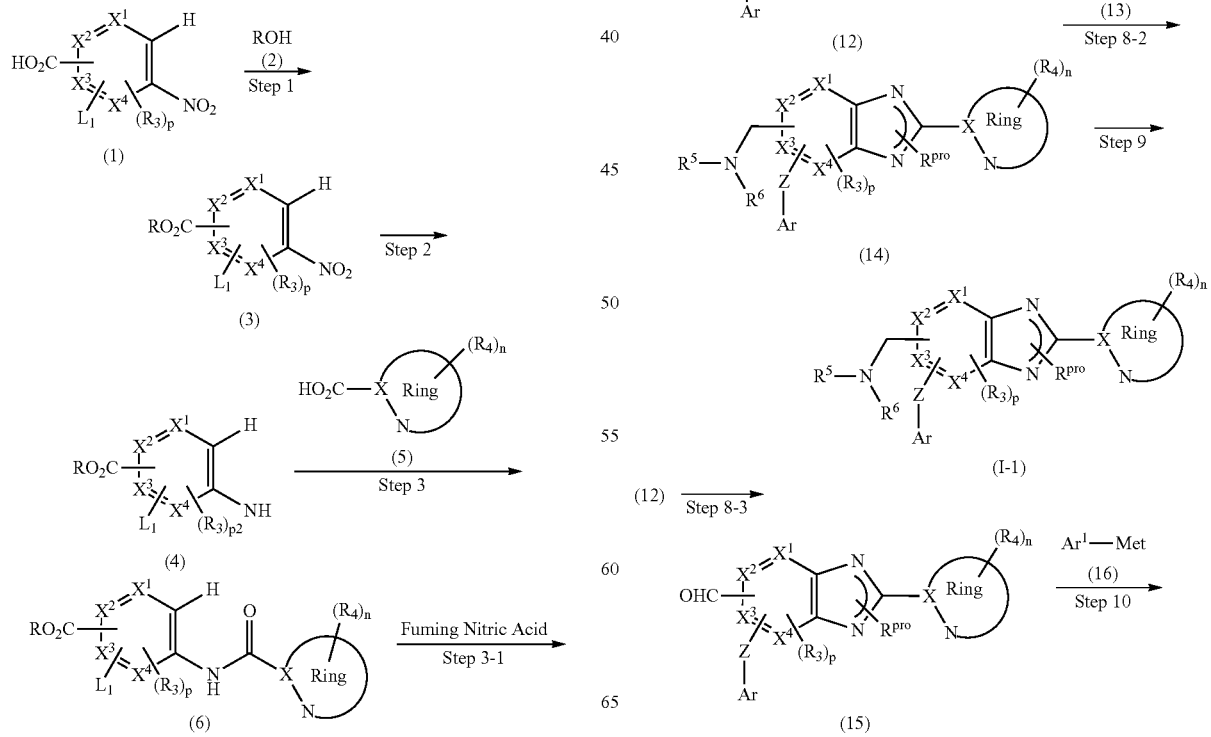

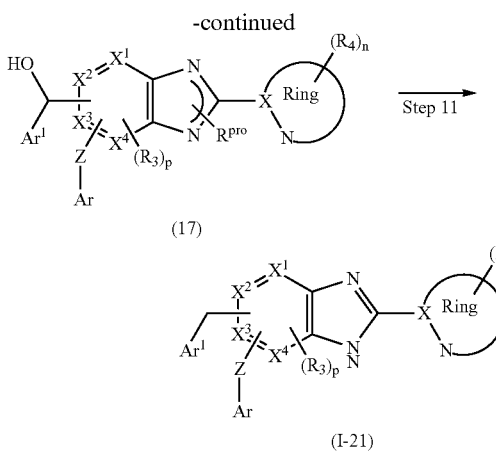

('R represents a lower alkyl group; $R^{pro}$ represents a protective group of an aromatic group; $L_1$ and $L_2$ each represent a leaving group; Met represents a metal group; and the other symbols have the same meanings as above.)

(Step 1)

This step is a method of reacting a compound (1) with a compound (2) in the presence of an acid catalyst to produce a compound (3).

$L_1$ may be any one capable of producing a compound (8) though reaction of a compound (7) with Ar-ZH in the step 4, including, for example, a fluorine atom, a chlorine atom and a bromine atom. Of those, preferred is a fluorine atom.

The acid catalyst to be used in this step includes, for example, a sulfuric acid, p-toluenesulfonic acid, methanesulfonic acid, hydrochloric acid, thionyl chloride.

The amount of the acid catalyst to be used may be generally from 0.01 to 10 equivalents relative to one equivalent of the compound (1), preferably from 0.1 to 1 equivalent.

The compound (1) to be used includes, for example, 2-fluoro-4-nitrobenzoic acid, 2-fluoro-5-nitrobenzoic acid, 5-fluoro-2-nitrobenzoic acid, 3-fluoro-5-nitrobenzoic acid.

The lower alkyl group for R is the same group as the above-defined lower alkyl group.

The compound (2) may serve also as a reaction solvent, including, for example, methanol, ethanol.

The amount of the compound (2) to be used may be generally a solvent amount relative to one equivalent of the compound (1).

The reaction temperature may be generally from room temperature to the reflux temperature of the reaction solvent, preferably from 60° C. to the reflux temperature of the reaction solvent. The reaction time may be generally from 1 to 120 hours, preferably from 24 to 72 hours.

The reaction solvent for use in this step includes, for example, methanol, ethanol, toluene, tetrahydrofuran, dimethylformamide.

The compound (3) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 2)

This step is a method of reducing the nitro group of the compound (3) obtained in the above step 1, thereby producing a compound (4).

For the reduction in this step, employable is a method well known to those skilled in the art.

The reduction in this step concretely includes, for example, catalytic reduction using hydrogen, formic acid, ammonium formate or hydrazine hydrate, and a palladium, platinum or nickel catalyst; reduction using hydrochloric acid or ammonium chloride, and iron; and reduction using methanol and tin chloride.

The amount of the reducing agent to be used for the reduction varies depending on the type of the compound and the solvent used, but may be generally from 1 to 50 equivalents, preferably from 2 to 20 equivalents relative to one equivalent of the compound (3).

The reaction temperature may be generally from −10 to 100° C., preferably from 0 to 50° C.

The reaction time may be generally from 1 to 20 hours, preferably from 1 to 5 hours.

The reaction solvent to be used is not specifically defined so far as it does not interfere with the reaction. For it, for example, herein employable are methanol, N,N-dimethylformamide, ethyl acetate, tetrahydrofuran and their mixed solvents.

The compound (4) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 3)

This step is a method of reacting the compound (4) obtained in the above step 2 with a compound (5), thereby producing a compound (6).

The amide bond-forming reaction in this step may be effected by the use of a carboxylic acid of compound (5) or its reactive derivative.

The compound (5) to be used includes, for example, pyridine-2-carboxylic acid, pyrazine-2-carboxylic acid, pyrimidine-4-carboxylic acid, pyrimidine-2-carboxylic acid, thiazole-2-carboxylic acid, isoxazole-3-carboxylic acid, 5-methyl-isoxazole-3-carboxylic acid, 1-methyl-1H-imidazole-4-carboxylic acid, imidazole-2-carboxylic acid, 1-methyl-1H-imidazole-2-carboxylic acid, imidazole-1-carboxylic acid, [1,2,4]triazole-1-carboxylic acid, [1,2,4]triazole-3-carboxylic acid, [1,2,3]triazole-4-carboxylic acid, 3-methyl-[1,2,4]thiadiazole-5-carboxylic acid, [1,2,5]thiadiazole-3-carboxylic acid, [1,2,3]oxadiazole-3-carboxylic acid, pyrazole-2-carboxylic acid.

The amount of the compound (5) or its reactive derivative to be used may be generally from 0.1 to 100 equivalents, preferably from 0.1 to 20 equivalents, more preferably from 0.1 to 3 equivalents relative to one equivalent of the compound (4).

The reactive derivative of the compound (5) includes, for example, mixed acid anhydrides, active esters, active amides. These can be obtained, for example, according to the method described in WO98/05641.

In the above reaction, when a carboxylic acid of the compound (5) is used, then, for example, the reaction is preferably effected in the presence of a condensing agent such as carbonyldiimidazole, N,N'-dicyclohexylcarbodiimide, 1-ethyl-3-(3-dimethylaminopropyl)carbodiimide, diphenylphosphorylazide, dipyridyl disulfide-triphenyl phosphine, more preferably carbonyldiimidazole.

Not strictly defined, the amount of the condensing agent to be used may be generally from 0.1 to 100 equivalents, preferably from 1 to 10 equivalents relative to the compound (5).

The reaction may be effected generally in an inert solvent. The inert solvent includes, for example, tetrahydrofuran, N,N-dimethylformamide, 1,4-dioxane, benzene, toluene, methylene chloride, chloroform, carbon tetrachloride, 1,2-dichloroethane, pyridine, and their mixtures.

The reaction temperature may be generally from 0° C. to the reflux temperature of the reaction solvent, preferably from room temperature to the reflux temperature of the reaction solvent.

The reaction time may be generally from 0.1 hours to 72 hours, preferably from 0.5 hours to 24 hours.

For smoothly promoting it, the reaction may be effected in the presence of a base and a condensation promoter.

The base includes 4-dimethylaminopyridine, triethylamine.

The amount of the base to be used may be generally from 0.1 to 100 equivalents, preferably from 0.1 to 1 equivalent relative to one mol of a carboxylic acid of the compound (5) or its reactive derivative.

The condensation promoter includes N-hydroxybenzotriazole hydrate, N-hydroxysuccinimide.

The amount of the condensation promoter may be generally from 1 to 100 equivalents, preferably from 1 to 5 equivalents relative to one mol of a carboxylic acid of the compound (5) or its reactive derivative.

In the above reaction, when the reactant has an amino group or an imino group not participating in the reaction, then it is desirable that the amino group or the imino group is suitably protected with a protective group for an amino group or an imino group and the protective group is removed after the reaction.

The compound (6) thus obtained may be subjected to the next step, after isolated and purified in any known manner for separation and purification, for example, through concentration, concentration under reduced pressure, solvent extraction, crystallization, reprecipitation, chromatography, or not after isolated and purified.

(Step 3-1)

This step is a method of reacting the compound (6) obtained in the above step 3 with fuming nitric acid, thereby producing a compound (6-1).

The amount of fuming nitric acid to be used in this step may be generally from 1 to 100 equivalents, preferably from 2 to 20 equivalents relative to one equivalent of the compound (6).

The reaction temperature may be generally from 0 to 100° C., preferably from 10 to 50° C.

The reaction time may be generally from 0.1 to 48 hours, preferably from 0.5 to 12 hours.

The compound (6-1) may also be produced by reacting the compound (6) with potassium nitrate in the presence of an acid.

The amount of potassium nitrate to be used may be generally from 1 to 100 equivalents, preferably from 1 to 5 equivalents relative to one equivalent of the compound (6).

The acid to be used includes, for example, trifluoroacetic acid, hydrochloric acid, sulfuric acid, nitric acid.

The amount of the acid to be used may be generally from 1 equivalent to the solvent amount, preferably from 1 to 100 equivalents relative to one equivalent of the compound (6). The reaction temperature may be generally from 0° C. to the reflux temperature of the solvent, preferably from room temperature to 100° C.

The reaction time may be generally from 0.1 to 72 hours, preferably from 0.5 to 12 hours.

The reaction solvent may be any one not interfering with the reaction, including, for example, chloroform, dichloromethane.

The compound (7) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 4)

This step is a method of reacting the compound (6-1) obtained in the above step 3-1 with a compound (7) in the presence of a base, thereby producing a compound (8).

The amount of the compound (7) to be used may be generally from 0.1 to 20 equivalents, preferably from 0.5 to 5 equivalents relative to 1 equivalent of the compound (6-1).

The compound (7) to be used includes, for example, 4-methanesulfonylphenol, 4-ethanesulfonylphenol, 3-chloro-4-methanesulfonylphenol, 6-methanesulfonyl-pyridin-3-ol, 6-ethanesulfonyl-pyridin-3-ol, 4-cyanophenyl, 6-(5-methyl-[1,2,4]thiadiazol-3-yl)-pyridin-3-ol, 6-(5-methyl-1,2,4-oxadiazol-3-yl)-3-pyridinol, 4-(5-methyl-1,2,4-oxadiazol-3-yl)phenol. These compounds may be commercially available, or may be produced in a method well known to those skilled in the art or according to a method similar to it or according to a method combined with it, starting from commercially-available compounds.

The amount of the base to be used may be generally from 0.1 to 20 equivalents, preferably from 0.5 to 5 equivalents relative to 1 equivalent of the compound (6-1).

The base to be used may be any one capable of producing the compound (8) through reaction of the compound (6-1) with the compound (7) in this step, including, for example, sodium hydride, cesium carbonate, sodium carbonate, potassium carbonate, potassium phosphate, potassium acetate, potassium tert-butyrate, triethylamine. Of those, preferred are potassium carbonate, cesium carbonate. When the compound (7) is a primary or secondary amine, then the reaction of this step may be effected in the absence of a base.

The reaction temperature may be generally from 0° C. to the reflux temperature of the reaction solvent, preferably from room temperature to the reflux temperature of the reaction solvent.

The reaction time may be generally from 0.1 to 72 hours, preferably from 0.5 to 5 hours.

Not specifically defined, the reaction solvent may be any inert solvent not interfering with the reaction, and concretely includes, for example, pyridine, toluene, tetrahydrofuran, 1,4-dioxane, N,N-dimethylformamide, N,N-dimethylacetamide, dimethyl sulfoxide, 1-methyl-2-pyrrolidinone.

The compound (8) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 5)

This step is a method of reducing the nitro group of the compound (8) obtained in the above step 4 and simultaneously dehydrating and cyclizing the compound in the presence of an acid catalyst, thereby producing a compound (9).

The reaction condition in this step may be the same as that in the step 2 or may be similar to it or may be a combination of an ordinary method with it.

The compound (9) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 6)

This step is a method of reacting the compound (9) obtained in the above step 8 with a compound (10) "in the presence of a base", thereby producing a compound (11).

The reaction in this step is a method of introducing a protective group into the aromatic amino group, and it may be effected according to a method described in references (e.g., Protective Groups in Organic Synthesis, T. W. Green, 2nd Ed., John Wiley & Sons, 1991) or according to a method similar to it or according to a method combined with it.

$L^2$ in the compound (10) is, for example, a halogen atom, preferably a chlorine atom or a bromine atom.

The compound (10) to be used includes 2-(trimethylsilyl) ethoxymethyl chloride (SEMCl), methoxymethyl chloride (MOMCl).

The amount of the compound (10) to be used may be generally from 1 to 10 equivalents, preferably from 1 to 3 equivalents relative to 1 equivalent of the compound (9).

The base to be used is, for example, sodium hydride.

The amount of the base to be used may be generally from 1 to 10 equivalents, preferably from 1 to 3 equivalents.

The reaction temperature may be generally from −20 to 50° C., preferably from 0° C. to room temperature.

The reaction time may be generally from 0.1 to 12 hours, preferably from 0.1 to 3 hours.

The reaction solvent may be any one not interfering with the reaction, including, for example, N,N-dimethylformamide, tetrahydrofuran, methylene chloride.

The compound (11) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 7)

This step is a method of reducing the ester group of the compound (11) obtained in the above step 6, thereby producing the compound (12).

The reducing agent to be used in this step includes lithium aluminium hydride ($LiAlH_4$), lithium borohydride, sodium borohydride. After the ester form of the compound (11) has been hydrolyzed into a carboxylic acid, and it may be processed into the compound (12) according to a method described in references (e.g., SYNLETT, 1995, Vol. 8, pp. 839-840) or according to a method similar to it or according to a method combined with it.

The amount of the reducing agent to be used may be generally from 1 to 20 equivalents, preferably from 1 to 3 equivalents relative to 1 equivalent of the compound (11).

The reaction temperature may be generally from 0 to 80° C., preferably from 0.1 to room temperature The reaction time may be generally from 0.1 to 24 hours, preferably from 0.1 to 3 hours.

Not specifically defined, the reaction solvent may be any one not interfering with the reaction, and includes, for example, methanol, N,N-dimethylformamide, ethyl acetate, tetrahydrofuran, their mixed solvents.

The compound (12) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 8)

This step is a method of reacting the compound (12) obtained in the previous step 7 with a compound (13), thereby producing the compound 13.

The reaction in this step may be a step (8-1) of Mitsunobu reaction, or a step (8-2) of nucleating reaction to be effected in the presence of a base.

(Step 8-1)

The reaction in this step is so-called Mitsunobu reaction, which may be effected in the presence of a phosphine compound and an azo compound, according to a method described in references (e.g., "The use of diethyl azodicarboxylate and triphenylphosphine in synthesis and transformation of natural products", by Mitsunobu O.; Synthesis, Vol. 1, 1981, pp. 1-28), or according to a method similar to it, or according to an ordinary method combined with it.

The compound (13) to be used includes, for example, succinimide, morpholine-3,5-dione, phthalimide, 1-methylhydantoin, 1-methyluracil.

The amount of the compound (13) to be used may be generally from 0.5 to 10 equivalents, preferably from 1 to 3 equivalents relative to 1 equivalent of the compound (12).

The phosphine compound to be used is generally, for example, triphenyl phosphine, triethyl phosphine.

The amount of the phosphine compound to be used may be generally from 0.5 to 10 equivalents, preferably from 1 to 3 equivalents relative to 1 equivalent of the compound (12).

The azo compound to be used includes, for example, diethyl azodicarboxylate, diisopropyl azodicarboxylate.

The amount of the azo compound to be used may be generally from 0.5 to 10 equivalents, preferably from 1 to 3 equivalents relative to 1 equivalent of the compound (12).

The reaction time in this step may be generally from 1 to 48 hours, preferably from 4 to 12 hours.

The reaction temperature in this step may be generally from 0° C. to the reflux temperature of the reaction solvent, preferably from 15 to 30° C.

Not specifically defined, the reaction solvent to be used in this step may be any one not interfering with the reaction, and includes, for example, tetrahydrofuran, toluene.

The compound (14) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 8-2)

This step is a method of reacting the compound (12) with a compound (13) in the presence of a base, thereby producing a compound (14).

The base to be used includes, for example, sodium hydride, butyllithium, lithium diisopropylamide.

The amount of the base to be used may be generally from 0.5 to 10 equivalents, preferably from 1 to 3 equivalents relative to 1 equivalent of the compound (12).

The compound (13) to be used includes concretely, for example, those listed in the above step 8-1, and pyrrolidone, oxazolidone, 3-methyluracil, 1-methylimidazolidinone.

The reaction temperature may be generally from −78 to 50° C., preferably from 0° C. to room temperature.

The reaction time may be generally from 0.1 to 24 hours, preferably from 0.1 to 6 hours.

The reaction solvent may be any one not interfering with the reaction, including, for example, N,N-dimethylformamide, tetrahydrofuran, methylene chloride.

The compound (14) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 8-3)

This step is a method of oxidizing the hydroxyl group of the compound (12) obtained in the above step 7, thereby producing a compound (15).

The reaction in this step may be effected according to a method described in references (e.g., Journal of the American Chemical Society, 1967, Vol. 89, pp. 5505-5507), or according to a method similar to it, or according to an ordinary method combined with it.

The compound (15) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 9)

This step is a method of removing the amino-protective group $R^{pro}$ from the compound (14) obtained in the above step 8-1 or 8-2, thereby producing a compound (I-1) of the invention.

The removal of the protective group may be attained in the same manner as in the method described in references (for example, Protective Groups in Organic Synthesis, by T. W. Green, 2nd Ed., John Wiley & Sons, 1991), or in accordance with it, or by combining it with an ordinary method. For example, when the protective group is SEM, then the compound (14) may be reacted with trifluoroacetic acid to remove the group SEM.

The compound (I-1) thus obtained may be isolated and purified in any known manner for separation and purification, for example, through concentration, concentration under reduced pressure, crystallization, solvent extraction, reprecipitation, chromatography.

(Step 10)

This step is a method of reacting the compound (15) obtained in the above step 8-3 with a compound (16), thereby producing a compound (17).

$Ar^1$ in the compound (16) and the compound (17) has the same meaning as the above Ar.

The compound (16) to be used includes, for example, 4-fluorophenylmagnesium bromide, 2-fluorophenylmagnesium bromide, 3-lithio-2-fluoropyridine.

The amount of the compound (16) to be used may be generally from 1 to 5 equivalents, preferably from 1 to 10 equivalents relative to 1 equivalent of the compound (15).

The reaction temperature may be generally from −78 to 50° C., preferably from −78° C. to room temperature.

The reaction time may be generally from 0.1 to 24 hours, preferably from 0.1 to 12 hours.

The reaction solvent may be any one not interfering with the reaction, and includes, for example, tetrahydrofuran, diethyl ether.

The compound (17) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 11)

This step is a method of removing the protective group from the compound (17) obtained in the above step 10, thereby producing a compound (1-2) of the invention.

The reaction in this step may be attained in the same manner as in the above step 9, or in accordance with it, or by combining it with an ordinary method.

The compound (I-2) of the invention thus obtained may be isolated and purified in any known manner for separation and purification, for example, through concentration, concentration under reduced pressure, crystallization, solvent extraction, reprecipitation, chromatography.

The compound (12) may also be produced according to the following process:

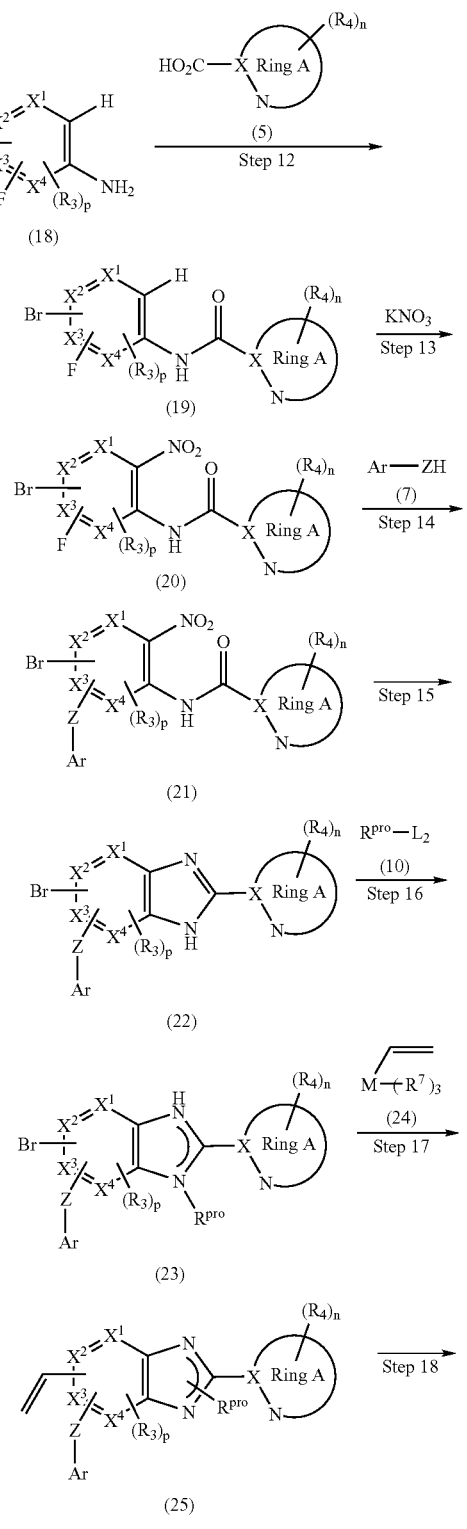

-continued

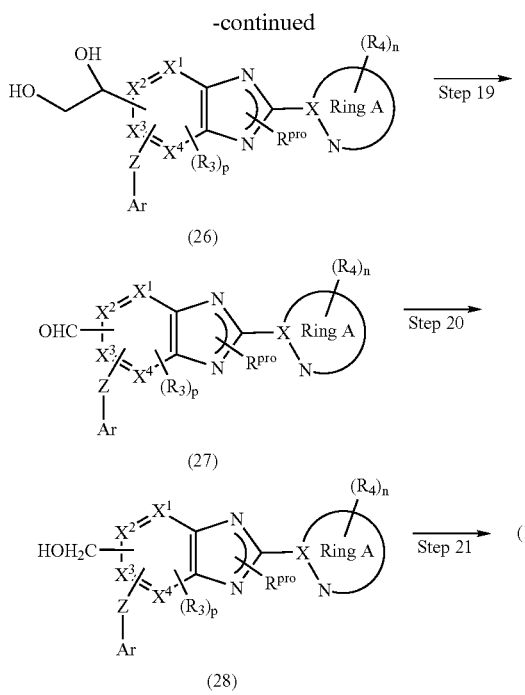

(26)

(27)

(28)

[wherein R[7] represents a lower alkyl group; M represents a metal atom; and the other symbols have the same meanings as above.]

(Step 12)

This step is a method of reacting a compound (18) with the above compound (5), thereby producing a compound (19).

The reaction in this step may be attained in the same manner as in the above step 3, or in accordance with it, or by combining it with an ordinary method.

The compound (18) to be used includes, for example, 4-bromo-3-fluoroaniline, 3-bromo-5-fluoroaniline.

The compound (19) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 13)

This step is a method of reacting the compound (19) obtained in the above step 12 with potassium nitrate in the presence of an acid, thereby producing a compound (20).

The amount of potassium nitrate to be used may be generally from 1 to 100 equivalents, preferably from 1 to 5 equivalents relative to 1 equivalent of the compound (19).

The acid to be used includes, for example, trifluoroacetic acid, hydrochloric acid, sulfuric acid, nitric acid.

The amount of the acid to be used may be generally from 1 equivalent to the solvent amount, preferably from 1 to 100 equivalents relative to 1 equivalent of the compound (19).

The reaction temperature may be generally from 0° C. to the reflux temperature of the reaction solvent, preferably from room temperature to 100° C.

The reaction time may be generally from 0.1 to 72 hours, preferably from 0.5 to 12 hours.

The reaction solvent may be any one not interfering with the reaction, including, for example, chloroform, dichloromethane.

The compound (20) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 14)

This step is a method of reacting the compound (20) obtained in the above step 13 with a compound (7), thereby producing a compound (21).

The reaction in this step may be attained in the same manner as in the above step 4, or in accordance with it, or by combining it with an ordinary method.

The compound (21) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 15)

This step is a method of reducing the nitro group of the compound (21) obtained in the above step 14, thereby producing a compound (22).

The reaction in this step may be attained in the same manner as in the above step 2 or 5, or in accordance with it, or by combining it with an ordinary method.

The compound (22) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 16)

This step is a method of reacting the compound (22) obtained in the above step 15 with a compound (10), thereby producing a compound (23).

The reaction in this step may be attained in the same manner as in the above step 6, or in accordance with it, or by combining it with an ordinary method.

The compound (23) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 17)

This step is a method of reacting the compound (23) obtained in the above step 16 with a compound (24) in the presence of a metal catalyst, thereby producing a compound (25).

The compound (24) to be used includes, for example, tributyl(vinyl)tin, or potassium vinyltrifluoroborate described in a reference (Organic Letters, 2002, Vol. 4, No. 1, pp. 107-109).

The amount of the compound (24) to be used may be generally from 1 to 10 equivalents, preferably from 1 to 3 equivalents relative to 1 equivalent of the compound (23).

The metal catalyst to be used includes, for example, tetrakistriphenylphosphine palladium, dichlorobistriphenylphosphine palladium, dichloro(1,1'-bis(diphenylphosphino)ferrocene) palladium.

The amount of the metal catalyst to be used may be generally from 0.01 to 10 equivalents, preferably from 0.05 to 5 equivalents.

The reaction solvent to be used in this step may be any one not interfering with the reaction, and is not specifically defined. For example, it includes ethylene glycol dimethyl ether, water, toluene, tetrahydrofuran, N,N-dimethylformamide, 1,4-dioxane, benzene, acetone, isopropanol.

The reaction temperature in this step may be generally from 0° C. to the reflux temperature of the reaction solvent, preferably from room temperature to 150° C. The reaction time in this step may be generally from 0.1 hours to 72 hours, preferably from 0.5 hours to 12 hours.

The compound (25) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 18)

this step is a method of oxidizing the compound (25) obtained in the above step 17, thereby producing a diol compound (26).

The reaction in this step comprises reacting the compound (25) with osmium oxide.

The reaction system may contain 4-methylmorpholine-N-oxide.

The amount of osmium oxide to be used may be generally from 0.001 to 3 equivalents, preferably from 0.01 to 0.5 equivalents relative to 1 equivalent of the compound (25).

The amount of 4-methylmorpholine-N-oxide to be used may be generally from 1 to 50 equivalents, preferably from 1 to 5 equivalents relative to 1 equivalent of the compound (25).

The reaction temperature may be generally from 0 to 70° C., preferably from 0° C. to room temperature.

The reaction time may be generally from 0.5 to 72 hours, preferably from 6 to 48 hours.

The reaction solvent may be any one not interfering with the reaction, including, for example, tetrahydrofuran, water, acetone, ethylene glycol dimethyl ether, N,N-dimethylformamide, 1,4-dioxane, isopropanol.

The compound (26) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 19)

This step is a method of oxidizing the compound (26) obtained in the above step 18, thereby producing a compound (27).

The reaction in this step comprises reacting the compound (26) with sodium periodate.

The amount of sodium periodate to be used may be generally from 1 to 100 equivalents, preferably from 1 to 10 equivalents relative to 1 equivalent of the compound (26).

The reaction temperature may be generally from 0 to 80° C., preferably from room temperature to 50° C.

The reaction time may be generally from 0.5 to 72 hours, preferably from 12 to 48 hours.

The reaction solvent may be any one not interfering with the reaction, including, for example, water, tetrahydrofuran, acetone, ethylene glycol dimethyl ether, N,N-dimethylformamide, 1,4-dioxane, isopropanol.

The compound (27) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 20)

This step is a method of reducing the compound (27) obtained in the above step 19, thereby producing a compound (12).

The reaction in this step comprises reacting the compound (27) with a reducing agent.

The reducing agent to be used includes, for example, sodium borohydride, sodium triacetoxyborohydride.

The amount of the reducing agent to be used may be generally from 1 to 50 equivalents, preferably from 1 to 10 equivalents, relative to 1 equivalent of the compound (27).

The reaction temperature may be generally from 0 to 100° C., preferably from 0 to 50° C.

The reaction time may be generally from 0.1 to 72 hours, preferably from 0.5 to 24 hours.

The reaction solvent may be any one not interfering with the reaction, including, for example, methanol, tetrahydrofuran, 1,4-dioxane, isopropanol.

The compound (12) thus obtained may be used in the above step 8, after isolated and purified in any known manner for separation and purification, for example, through concentration, concentration under reduced pressure, crystallization, solvent extraction, reprecipitation, chromatography, or not after isolated and purified.

A compound (12-1) which is within the scope of the compound (12) may also be produced according to the following process:

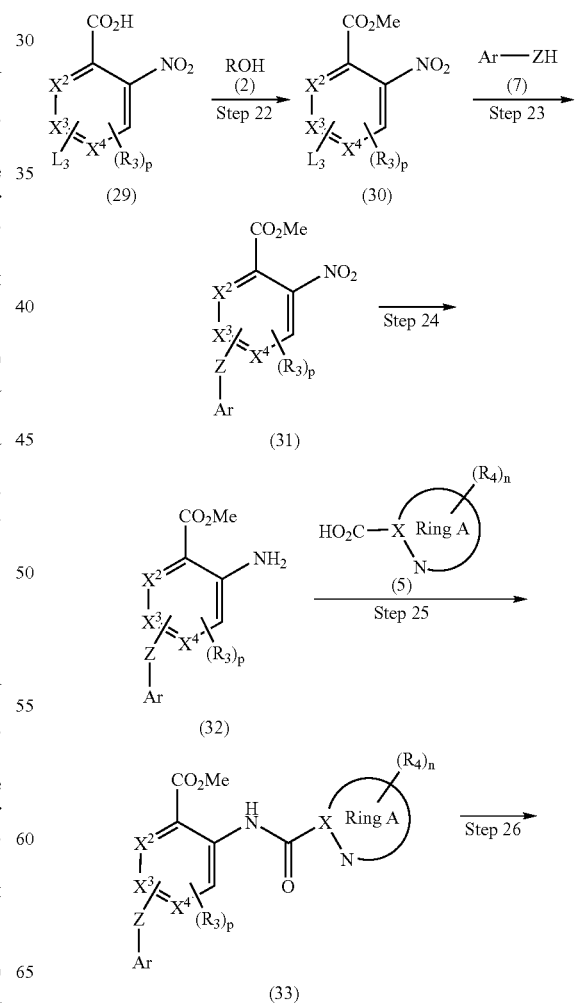

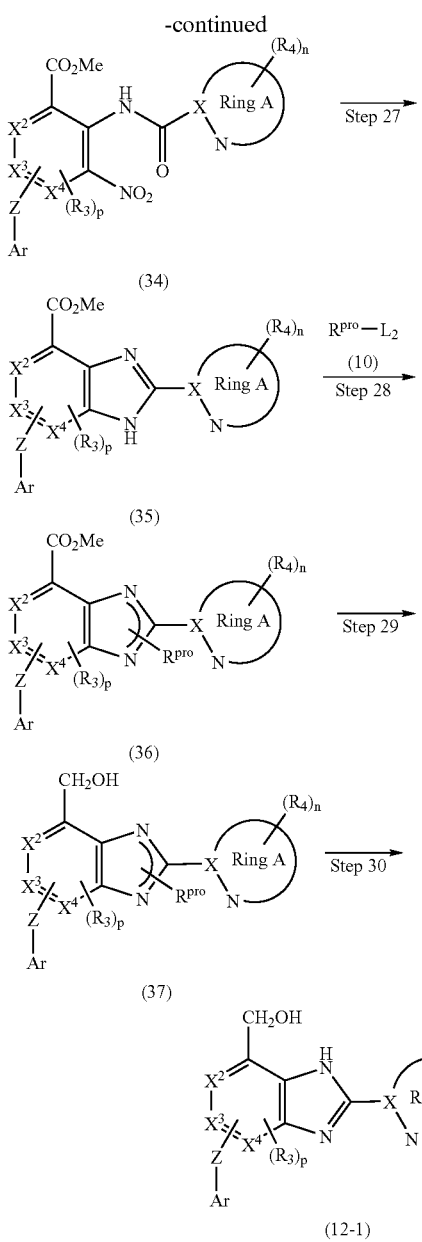

[wherein $L_3$ represents a leaving group; $R^{PRO}$ represents a protective group of an aromatic amino group; and the other symbols have the same meanings as above.]

(Step 22)

This step is a method of reacting a compound (29) with a compound (2) in the presence of an acid catalyst, thereby producing a compound (30).

The compound (29) to be used is, for example, 5-fluoro-2-nitrobenzoic acid.

The reaction in this step may be attained in the same manner as in the above step 1, or in accordance with it, or by combining it with an ordinary method.

The compound (30) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 23)

This step is a method of reacting the compound (30) obtained in the above step 22 with a compound (7), thereby producing a compound (31).

The reaction in this step may be attained in the same manner as in the above step 4, or in accordance with it, or by combining it with an ordinary method.

The compound (31) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 24)

This step is a method of reducing the nitro group of the compound (31) obtained in the above step 23, thereby producing a compound (32).

The reaction in this step may be attained in the same manner as in the above step 2, or in accordance with it, or by combining it with an ordinary method.

The compound (32) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 25)

This step is a method of reacting the compound (32) obtained in the above step 24 with a compound (5), thereby producing a compound (33).

The reaction in this step may be attained in the same manner as in the above step 3, or in accordance with it, or by combining it with an ordinary method.

The compound (33) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 26)

This step is a method of reacting the compound (33) obtained in the above step 25 with potassium nitrite in the presence of an acid, thereby producing a compound (34).

The reaction in this step may be attained in the same manner as in the above step 13, or in accordance with it, or by combining it with an ordinary method.

The compound (34) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 27)

This step is a method of reducing the nitro group of the compound (34) obtained in the above step 26, thereby producing a compound (35).

The reaction in this step may be attained in the same manner as in the above step 5, or in accordance with it, or by combining it with an ordinary method.

The compound (35) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 28)

This step is a method of reacting the compound (35) obtained in the above step 27 with a compound (10), thereby producing a compound (36).

The reaction in this step may be attained in the same manner as in the above step 6, or in accordance with it, or by combining it with an ordinary method.

The compound (36) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 29)

This step is a method of reducing the compound (36) obtained in the above step 28, thereby producing a compound (37).

The reaction in this step may be attained in the same manner as in the above step 7, or in accordance with it, or by combining it with an ordinary method.

The compound (37) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 30)

This step is a method of removing the aromatic amino-protective group $R^{pro}$ from the compound (37) obtained in the above step 29, thereby producing a compound (12-1).

The reaction in this step may be attained in the same manner as in the above step 9, or in accordance with it, or by combining it with an ordinary method.

The compound (12-1) thus obtained may be subjected to the next step, after isolated and purified in any known manner for separation and purification, for example, through concentration, concentration under reduced pressure, crystallization, solvent extraction, reprecipitation, chromatography, or not after isolated and purified.

A compound (I-1-1) or its pharmaceutically-acceptable salt of the invention of a formula:

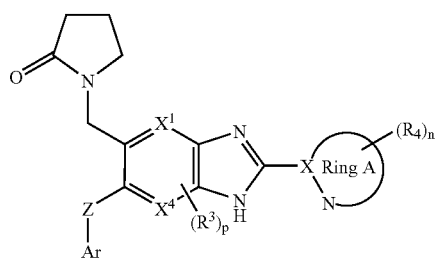

(I-1-1)

[wherein the symbols have the same meanings as above] may be produced, for example, according to the following process:

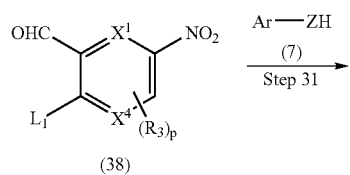

(38)

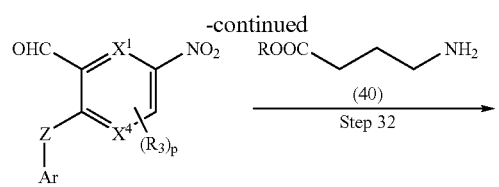

(39)

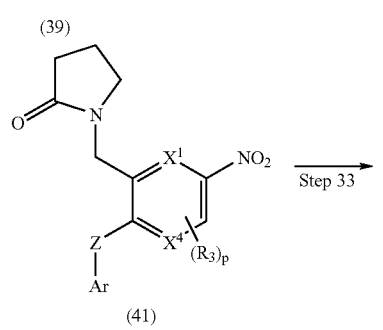

(41)

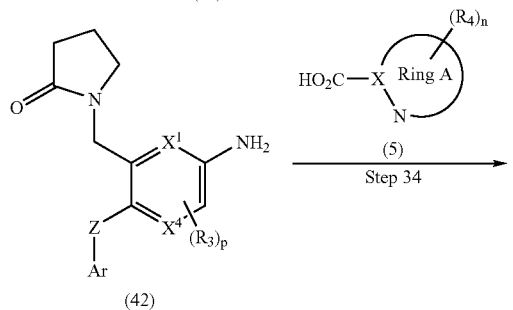

(42)

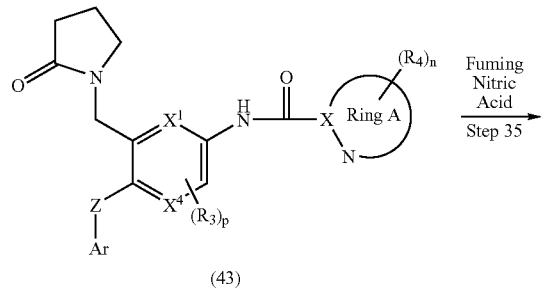

(43)

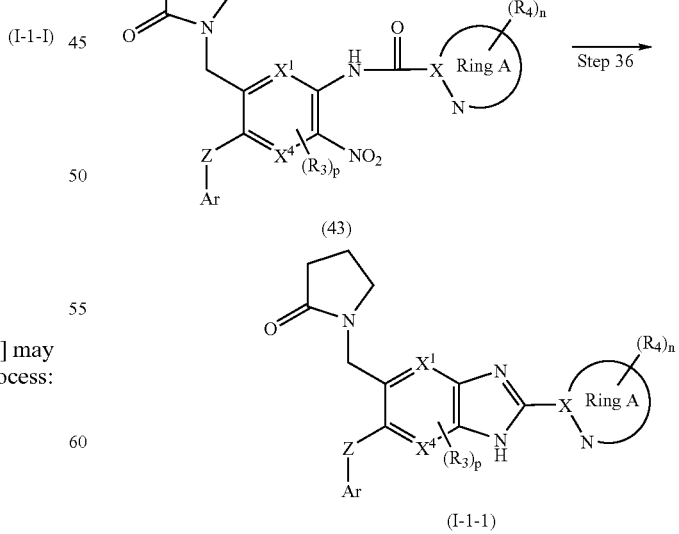

(I-1-1)

[wherein the symbols have the same meanings as above.]

(Step 31)

This step is a method of reacting a compound (38) with a compound (7) in the presence of a base, thereby producing a compound (39).

The compound (38) to be used in this step may be commercially available, or may be produced in a method well known to those skilled in the art or according to a method similar to it or according to a method combined with it, starting from a commercially-available compound. Concretely, it is, for example, 2-chloro-5-nitrobenzaldehyde.

The amount of the compound (7) to be used in this step may be generally from 0.1 to 20 equivalents, preferably from 0.5 to 5 equivalents relative to 1 equivalent of the compound (38).

The compound (7) to be used includes those mentioned in the above step 4.

The amount of the base to be used may be generally from 0.1 to 20 equivalents, preferably from 0.5 to 5 equivalents relative to 1 equivalent of the compound (38).

The base to be used may be any one capable of producing a compound (39) in this step comprising reacting a compound (38) with a compound (7), and it includes, for example, sodium hydride, cesium carbonate, sodium carbonate, potassium carbonate, potassium phosphate, potassium acetate, potassium tert-butyrate, triethylamine. Of those, preferred are potassium carbonate, cesium carbonate.

The reaction temperature may be generally from 0° C. to the reflux temperature of the reaction solvent, preferably from room temperature to the reflux temperature of the reaction solvent.

The reaction time may be generally from 0.1 to 72 hours, preferably from 0.5 to 5 hours.

The reaction solvent may be an inert solvent and is not specifically defined so far as it does not interfere with the reaction. Concretely, it includes, for example, pyridine, toluene, tetrahydrofuran, 1,4-dioxane, N,N-dimethylformamide, N,N-dimethylacetamide, dimethylsulfoxide, 1-methyl-2-pyrrolidinone.

The compound (39) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 32)

This step is a method of reacting the compound (39) with a compound (40), thereby producing a compound (41).

The compound (40) to be used in this step is, for example, a compound where R is a methyl group or an ethyl group.

The compound (40) may also be in the form of an acid-addition salt such as a hydrochloride. In case where an acid-addition salt of the compound (40) is used, then a base such as triethylamine may be added to the reaction system.

The amount of the compound (40) to be used may be generally from 0.5 to 20 equivalents, preferably from 1 to 5 equivalents relative to 1 equivalent of the compound (39).

The amount of the base to be used may be a nearly equimolar amount relative to 1 equivalent of the compound (40).

The reducing agent to be used in this step includes, for example, triacetoxyborohydride, sodium cyanoborohydride, sodium triacetoxyborohydride.

The amount of the hydride reagent to be used may be generally from 1 to 10 equivalents, preferably from 1 to 3 equivalents relative to 1 equivalent of the compound (39).

Not interfering with the reaction, the reaction solvent is not specifically defined, and it includes, for example, methanol, ethanol, acetic acid, tetrahydrofuran, dichloromethane; and their mixed solvents. Of those, preferred are, for example, methanol, ethanol, tetrahydrofuran and their mixed solvents.

The reaction time may be generally from 1 hour to 8 hours, preferably from 1 hour to 24 hours.

The reaction temperature may be generally from 0 to 100° C., preferably from 0 to 40° C.

The compound (41) of the invention thus obtained may be isolated and purified in any known manner for separation and purification, for example, through concentration, concentration under reduced pressure, crystallization, solvent extraction, reprecipitation, chromatography.

(Step 33)

This step is a method of reducing the nitro group of the compound (41), thereby producing a compound (42).

The reduction in this step may be, for example, catalytic reduction with a catalyst such as Raney nickel in a hydrogen atmosphere.

The amount of the Raney nickel to be used in this step may be from 0.001 to 5 equivalents, preferably from 0.01 to 1 equivalent relative to 1 equivalent of the compound (41).

The reaction temperature may be generally from 0 to 80° C., preferably from 20 to 50° C.

The reaction time may be generally from 1 to 24 hours, preferably from 1 to 10 hours.

The compound (42) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 34)

This step is a method of reacting a carboxylic acid derivative (5) or its reactive derivative with a compound (42), thereby producing a compound (3).

This reaction may be ordinary amidation to be attained according to a method described in references (e.g., Bases and Experiments of Peptide Synthesis, Nobuo Izumiya, et al., Maruzen, 1983; Comprehensive Organic Synthesis, Fol. 6, Pergamon Press, 1991), or according to a method is similar to it, or according to an ordinary method combined with it. Specifically, a condensing agent well known to those skilled in the art is used; or an ester activation method, a mixed acid anhydride method, an acid chloride method or a carbodiimide method available to those skilled in the art may be employed. The amidation reagent includes, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazol-1-yloxy-tris(dimethylamino)phosphonium hexafluorophosphate. Of those, for example, preferred are thionyl chloride, 1-ethyl-3-(3-dimethylaminopropyl)carbodiimide hydrochloride, N,N-dicyclohexylcarbodiimide, benzotriazol-1-yloxytris(dimethylamino)phosphonium hexafluorophosphate. In the amidation, a base and a condensation promoter may be used along with the above amidation reagent.

The base to be used includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN); aromatic amines such as pyridine, 4-dimethylaminopyridine, picoline, lutidine, quinoline, isoquinoline. Of those, for example, preferred are tertiary aliphatic amines, and more preferred are, for example, triethylamine, N,N-diisopropylethylamine.

The condensation promoter to be used includes, for example, N-hydroxybenzotriazole hydrate, N-hydroxysuccinimide, N-hydroxy-5-norbornene-2,3-dicarboximide, 3-hydroxy-3,4-dihydro-4-oxo-1,2,3-benzotriazole. Of those, for example, preferred is N-hydroxybenzotriazole.

The amount of the compound (42) to be used may vary, depending on the type of the compound and the solvent used and on the other reaction conditions, and, for example, it may be generally from 0.1 to 10 equivalents, preferably from 0.5 to 3 equivalents relative to 1 equivalent of the carboxylic acid derivative (5) or its reactive derivative.

The amount of the amidation reagent to be used may also vary depending on the type of the compound and the solvent used and on the other reaction conditions, and, for example, it may be generally from 1 to 10 equivalents, preferably from 1 to 3 equivalents relative to 1 equivalent of the carboxylic acid derivative (5) or its reactive derivative.

The amount of the condensation promoter to be used may also vary depending on the type of the compound and the solvent used and on the other reaction conditions, and, for example, it may be generally from 1 to 10 equivalents, preferably from 1 to 3 equivalents relative to 1 equivalent of the carboxylic acid derivative (5) or its reactive derivative.

The amount of the base to be used may also vary depending on the type of the compound and the solvent used and on the other reaction conditions, and, for example, it may be generally from 0.1 to 10 equivalents, preferably from 1 to 5 equivalents relative to 1 equivalent of the compound (42).

The reaction solvent to be used in this step is, for example, an inert solvent, which is not specifically defined so far as it does not interfere with the reaction. Concretely, for example, it includes methylene chloride, chloroform, 1,2-dichloroethane, N,N-dimethylformamide, ethyl acetate, methyl acetate, acetonitrile, benzene, xylene, toluene, 1,4-dioxane, tetrahydrofuran, dimethoxyethane, and their mixed solvents. For ensuring the preferred reaction temperature, for example, preferred are methylene chloride, chloroform, 1,2-dichloroethane, acetonitrile, N,N-dimethylformamide.

The reaction temperature in this step may be generally from −78° C. to the boiling point of the solvent, preferably from 0 to 30° C.

The reaction time in this step may be generally from 0.5 to 96 hours, preferably from 3 to 24 hours.

The base, the amidation reagent and the condensation promoter to be used in this step may be one or more different types of compounds for them either singly or as combined.

The compound (43) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 35)

This step is a method of reacting the compound (43) with a fuming nitric acid, thereby producing a compound (44).

The amount of fuming nitric acid to be used in this step may be generally from 1 to 100 equivalents, preferably from 2 to 20 equivalents relative to 1 equivalent of the compound (43).

The reaction temperature may be generally from 0 to 100° C., preferably from 10 to 50° C.

The reaction time may be generally from 0.1 to 48 hours, preferably from 0.5 to 12 hours.

The compound (44) may also be produced by reacting the compound (43) with potassium nitrate in the presence of an acid.

The amount of potassium nitrate to be used may be generally from 1 to 100 equivalents, preferably from 1 to 5 equivalents relative to 1 equivalent of the compound (6).

The acid to be used includes, for example, trifluoroacetic acid, hydrochloric acid, sulfuric acid, nitric acid.

The amount of the acid to be used may be generally from 1 equivalent to the solvent amount, preferably from 1 to 100 equivalents relative to 1 equivalent of the compound (6). The reaction temperature may be generally from 0° C. to the reflux temperature of the solvent, preferably from room temperature to 100° C.

The reaction time may be generally from 0.1 to 72 hours, preferably from 0.5 to 12 hours.

The reaction solvent may be any one not interfering with the reaction, including, for example, chloroform, dichloromethane.

The compound (44) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 45)

This step is a method of reducing the nitro group of the compound (44) followed by cyclizing it, thereby producing a compound (I-1-1) of the invention.

The reducing agent to be used in this step is, for example, tin chloride ($SnCl_2$). The reducing agent may also be its hydrate.

The amount of the reducing agent to be used in this step may be generally from 1 to 20 equivalents, preferably from 1 to 10 equivalents relative to 1 equivalent of the compound (44).

The base to be used in this step is, for example, triethylamine.

The amount of the base to be used may be generally from 1 to 10 equivalents, preferably from 1 to 5 equivalents relative to 1 equivalent of the compound (44).

The reaction temperature may be generally from 0 to 100° C., preferably from 20 to 80° C.

The reaction time may be generally from 0.5 to 20 hours, preferably from 1 to 5 hours.

Not specifically defined, the reaction solvent may be any one not interfering with the reaction, and includes, for example, methanol, chloroform, N,N-dimethylformamide, ethyl acetate, tetrahydrofuran, and their mixed solvents.

The compound (I-1-1) thus obtained may be isolated and purified in any known manner for separation and purification, for example, through concentration, concentration under reduced pressure, crystallization, solvent extraction, reprecipitation, chromatography.

The aryloxy-substituted benzimidazole derivatives that the invention provides may be in the form of their pharmaceutically-acceptable salts. The salts may be produced in any ordinary method from the compounds of the above formulae (I-1) and (I-2) that are within the scope of the compounds (1) of the invention.

Concretely, when the compounds of formula (I-1) or (I-2) have a basic group derived from, for example, an amino group or a pyridyl group in the molecule, then the compounds may be processed with acid so as to convert them into the corresponding pharmaceutically-acceptable salts.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

In producing medicines for prevention and treatment of type II diabetes or diseases or symptoms associated with it, the compounds of formula (I) of the invention may be combined with carrier substances.

The dose of the compounds of formula (I) of the invention for prevention or treatment of diseases naturally varies, depending on the property of the symptom to be treated, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 g. More preferably, the daily dose is from about 10 mg to 100 mg for one-time administration a day.

For intravenous administration or oral administration, a typical dose of the compound (I) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for treatment and prevention of type II diabetes and for delay of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

Suspension for Injection (I.M.)

|  | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 |
| water for injection is added to make 1.0 ml. | |

TABLE 2

Tablets

| | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

Capsules

| | mg/capsule |
|---|---|
| compound of formula (I) | 25 |
| lactose powder | 573.5 |
| magnesium stearate | 1.5 |
| total | 600 mg |

TABLE 4

Aerosol

| | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other medicines usable not only for type II diabetes-associated diseases or symptoms but also for treatment/prevention/delay of the onset of type II diabetes. The additional medicines may be administered in any administration route and dose generally employed in the art, simultaneously with or separately from the compound of formula (I).

In case where the compound of formula (I) is used along with one or more other medicines, then a pharmaceutical composition comprising the compound of formula (I) and the additional medicines is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.
(a) other glucokinase activators,
(b) bis-guanides (e.g., buformin, metoformin, fenformin),
(c) PPAR agonists (e.g., triglytazon, pioglytazon, nosiglytazon),
(d) insulin,
(e) somatostatin,
(f) α-glucosidase inhibitors (e.g., boglybose, miglytol, acarbose),
(g) insulin secretion promoters (e.g., acetohexamide, calbutamide, chlorpropamide, glybomlide, glycrazide, glymerpide, glypidide, glyquidine, glysoxepide, glyburide, glyhexamide, glypinamide, fenbutamide, trazamide, tolbutamide, tolcyclamide, nateglynide, repaglynide), and
(h) DPP-IV (dipeptidyl peptidase IV) inhibitors).

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual ingredients should be in the combination.

The glucokinase-activating potency of the compounds of formula (I) of the invention and a test method for it are described below.

The excellent glucokinase-activating effect of the compounds of formula (I) may be determined by a method described in references (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the degree of glucokinase activity of the compound tested may be determined.

In this assay, used was a recombinant human liver GK, which was expressed by *E. coli* as a FLAG fusion protein therein and was purified by ANTIFLAG M2 AFFINITY GEL (Sigma).

Using a flat-bottomed 96-well plate, the assay was carried out at 30° C. 69 μl of an assay buffer (25 mM Hepes Buffer/ pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 μl of an enzyme mixture (FLAG-GK, 20 U/ml G6PDH) cooled in ice was added to it, and 10 μl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for evaluating the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (μM) were computed and used as the index of the GK-activating potency of the compound.

The GK-activating potency of the compounds of the invention was measured according to the method as above, and the results are shown in Table 5 below.

TABLE 5

(GK-Activating Potency of Compounds of the Invention)

| Compound No. | Emax (%) | EC50 (μM) |
|---|---|---|
| Example 1 | 1090 | 0.12 |
| Example 31 | 982 | 0.49 |
| Example 65 | 805 | 0.36 |

Accordingly, the compounds of the invention have an excellent GK-activating potency indicated by Emax and EC50.

EXAMPLES

The invention is described more concretely with reference to the following Examples, by which, however, the invention should not be limited at all.

Preparation Example 1

10 parts of the compound of Production Example 1, 15 parts of heavy magnesium oxide and 75 parts of lactose are uniformly mixed to give a powdery or particulate preparation of at most 350 μm in size. The preparation is encapsulated to prepare capsules.

Preparation Example 2

45 parts of the compound of Production Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 μm in diameter.

Preparation Example 3

Granules are prepared in the same manner as in Preparation Example 2. 3 parts of calcium stearate is added to 96 parts of the granules, and shaped under compression to give tablets having a diameter of 10 mm.

Preparation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

In the following, the invention is described more concretely with reference to Preparation Examples, Production Examples and Reference Examples, by which, however, the invention should not be limited at all.

In the thin-layer chromatography in Examples, Silicagel 60F$_{245}$ (Merck) was used for the plate, and a UV detector was used for detection. For the column silica gel, used was Wakogel™ C-300 (Wako Pure Chemical); and for the reversed-phase column silica gel, used was LC-SORB™ SP-B-ODS (Chemco) or YMC-GEL™ ODS-AQ 120-S50 (Yamamura Chemical Laboratory).

The meanings of the abbreviations in the following Examples are shown below.
i-Bu: isobutyl
n-Bu: n-butyl
t-Bu: t-butyl
Me: methyl
Et: ethyl
Ph: phenyl
i-Pr: isopropyl
n-Pr: n-propyl
CDCl$_3$: heavy chloroform
CD$_3$OD: heavy methanol
DMSO-d$_6$: heavy dimethylsulfoxide
The meanings of the abbreviations in the following nuclear magnetic resonance spectra are shown below.
s: singlet
d: doublet
dd: double-doublet
t: triplet
m: multiplet
br: broad
q: quartet
J: coupling constant
Hz: hertz

Example 1

1-{[5-[4-(Methylsulfonyl)phenoxy]-2-(2-pyridinyl)-1H-benzimidazol-6-yl]methyl}pyrrolidine-2,5-dione (Step 1) Production of N-(4-bromo-3-fluorophenyl)-2-pyridinecarboxamide 2.9 ml of triethylamine and 1.87 g of picolinic acid chloride hydrochloride were added to a chloroform (30 ml) solution of 1 g of 4-bromo-3-fluoroaniline, and stirred at room temperature for 4 hours. The reaction liquid was diluted with chloroform, washed with aqueous saturated sodium bicarbonate solution and saturated saline water, and dried with anhydrous magnesium sulfate. The solvent was evaporated away, and the residue was purified through silica gel column chromatography (developing solvent: hexane/ethyl acetate=4/1) to obtain 1.44 g of the entitled compound as a pale yellow crystal.

(Step 2) Production of N-(4-bromo-5-fluoro-2-nitrophenyl)-2-pyridinecarboxamide 1.71 g of potassium sulfite was added to 10 ml of N-(4-bromo-3-fluorophenyl)-2-pyridinecarboxamide, and stirred overnight at 70° C. The solvent was evaporated away, the residue was diluted with chloroform, and washed with aqueous saturated sodium bicarbonate solution and saturated saline water. This was dried with anhydrous magnesium sulfate, and the solvent was evaporated away to obtain 1.17 g of the entitled compound as a yellow crystal.

(Step 3) Production of N-{4-bromo-5-(4-(methylsulfonyl)phenoxy]-2-nitrophenyl}-2-pyridinecarboxamide 100 ml of N-(4-bromo-5-fluoro-2-nitrophenyl)-2-pyridinecarboxamide, 55 mg of 4-(methylsulfonyl)phenol obtained in Reference Example 1, and 88 mg of potassium carbonate were suspended in 2 ml of dimethylformamide, and stirred at 70° C. for 30 minutes. The reaction liquid was restored to room temperature, then water was added thereto, and the resulting crystal was taken out through filtration to obtain 145 mg of the entitled compound as a pale yellow crystal.

(Step 4) Production of 6-bromo-5-[4-(methylsulfonyl)phenoxy]-2-(2-pyridinyl)-1H-benzimidazole 145 ml of N-{4-bromo-5-(4-(methylsulfonyl)phenoxy]-2-nitrophenyl}-2-pyridinecarboxamide was suspended in 1 ml of dimethylformamide, 1 ml of methanol and 0.5 ml of concentrated hydrochloric acid, and 327 mg of tin(II) chloride dihydrate was added thereto and stirred at 70° C. for 30 minutes. The reaction liquid was neutralized with aqueous sodium bicarbonate solution, and diluted with chloroform. The insoluble matter was taken out through filtration, the filtrate was washed with saturated saline water, and dried with anhydrous magnesium sulfate. The solvent was evaporated away to obtain 121 mg of the entitled compound as a pale yellow crystal.

(Step 5) Production of 6-bromo-5-[4-(methylsulfonyl)phenoxy]-2-(2-pyridinyl)-1-{[2-(trimethylsilyl)ethoxy]methyl}-1H-benzimidazole and 5-bromo-6-[4-(methylsulfonyl)phenoxy]-2-(2-pyridinyl)-1-{[2-(trimethylsilyl)ethoxy]methyl}-1H-benzimidazole 6.50 g of 6-bromo-5-[4-(methylsulfonyl)phenoxy]-2-(2-pyridinyl)-1H-benzimidazole was dissolved in 65 ml of dimethylformamide, and with cooling with ice, 0.71 g of sodium hydride (with 30% liquid paraffin added thereto) was added to it. This was stirred for 15 minutes, and then 3.9 ml of 2-trimethylsilyl-ethoxymethyl chloride was added to it and further stirred for 30 minutes. Aqueous saturated ammonium chloride solution was added to it, diluted with ethyl acetate, then the organic layer was washed with water and saturated saline water and dried with anhydrous sodium sulfate. The solvent was evaporated away, and the residue was purified through silica gel column chromatography (developing solvent: hexane/ethyl acetate=9/1 to 6/4) to obtain 7.39 g of the entitled compound as a pale yellow crystal.

(Step 6) Production of 5-[4-(methylsulfonyl)phenoxy]-2-(2-pyridinyl)-1-{[2-(trimethylsilyl)ethoxy]methyl}-6-vinyl-1H-benzimidazole and 6-[4-(methylsulfonyl)phenoxy]-2-(2-pyridinyl)-1-{[2-(trimethylsilyl)ethoxy]methyl}-5-vinyl-1H-benzimidazole One g of the crystal obtained in the step 5 was dissolved in 10 ml of toluene, and 0.83 g of tributyl(vinyl)tin and 0.1 g of tetrakis(triphenylphosphine)palladium were added thereto, purged with nitrogen, and stirred at 110° C. for 3 hours. This was purified through silica gel column chromatography (developing solvent: hexane/ethyl acetate=9/1 to 3/1) to obtain 0.69 g of the entitled compound as a white amorphous substance.

(Step 7) Production of 1-(5-[4-(methylsulfonyl)phenoxy]-2-(2-pyridinyl)-1-{[2-(trimethylsilyl)ethoxy]methyl}-1H-benzimidazol-6-yl)-1,2-ethanediol and 1-(6-[4-(methylsulfonyl)phenoxy]-2-(2-pyridinyl)-1-{[2-(trimethylsilyl)ethoxy]methyl}-1H-benzimidazol-5-yl)-1,2-ethanediol 0.69 g of the vinyl compound obtained in the step 6 was dissolved in 7 ml of tetrahydrofuran and 1 ml of water, and 0.23 g of 4-methylmorpholine N-oxide and 17 mg of osmium (VIII) oxide were added thereto and stirred overnight at room temperature. Aqueous sodium thiosulfate solution was added to it, diluted with ethyl acetate, and the organic layer was washed with saturated saline water. This was dried with anhydrous magnesium sulfate, the solvent was evaporated away, and the residue was purified through silica gel column chromatography (developing solvent: chloroform to chloroform/methanol=98/2) to obtain 0.57 g of the entitled compound as a white amorphous substance.

(Step 8) Production of 5-[4-(methylsulfonyl)phenoxy]-2-(2-pyridinyl)-1-{[2-(trimethylsilyl)ethoxy]methyl}-1H-benzimidazole-6-carbaldehyde and 6-[4-(methylsulfonyl)phenoxy]-2-(2-pyridinyl)-1-{[2-(trimethylsilyl)ethoxy]methyl}-1H-benzimidazole-5-carbaldehyde 1.7 g of the diol compound obtained in the step 7 was dissolved in 16 ml of chloroform, and 11 ml of water and 0.84 g of sodium periodate were added thereto and stirred at room temperature for 3 hours. The reaction liquid was diluted with chloroform, and washed with saturated saline water. This was dried with anhydrous magnesium sulfate, the solvent was evaporated away, and the residue was purified through silica gel column chromatography (developing solvent: hexane/ethyl acetate=9/1 to 3/1 to 1/1) to obtain 1.2 g of the entitled compound as a white amorphous substance.

(Step 9) Production of (5-[4-(methylsulfonyl)phenoxy]-2-(2-pyridinyl)-1-{[2-(trimethylsilyl)ethoxy]methyl}-1H-benzimidazol-6-yl)methanol or (6-[4-(methylsulfonyl)phenoxy]-2-(2-pyridinyl)-1-{[2-(trimethylsilyl)ethoxy]methyl}-1H-benzimidazol-5-yl)methanol 100 mg of the aldehyde compound obtained in the step 8 was dissolved in 1 ml of methanol, and 15 mg of sodium borohydride was added thereto and stirred at room temperature for 1 hour. The reaction liquid was diluted with ethyl acetate, and washed with saturated saline water. This was dried with anhydrous magnesium sulfate, the solvent was evaporated away, and the residue was purified through silica gel column chromatography (developing solvent: chloroform to chloroform/methanol=98/2) to obtain 94 mg of the entitled compound as a white amorphous substance.

(Step 10) Production of 1-{[5-[4-(ethylsulfonyl)phenoxy]-2-(2-pyridinyl)-1H-benzimidazol-6-yl]methyl}pyrrolidine-2,5-dione 50 mg of the alcohol compound obtained in the step 9, 47.5 mg of succinimide and 127 mg of triphenyl phosphine were dissolved in 1 ml of tetrahydrofuran, and with cooling with ice, 0.21 ml of diethylazodicarboxylate (40% toluene solution) was added to it, and stirred at room temperature for 2 hours. The reaction solvent was evaporated away, and the residue was purified through silica gel column chromatography (developing solvent: hexane/ethyl acetate=9/1 to 5/5 to 8/2) to obtain 52.3 mg of a yellow oil.

52.3 mg of the obtained oil was dissolved in 1 ml of trifluoroacetic acid, and stirred at room temperature for 2 hours. The solvent was evaporated away, the residue was neutralized with triethylamine, and then purified through partitioning thin-layer chromatography (Kieselgel™ 60F$_{254}$, Art 5744 (by Merck), chloroform/methanol=10/1) to obtain 11.2 mg of the entitled compound as a white solid.

$^1$HNMR (CDCl$_3$) δ: 2.56 (2H, m), 2.66 (2H, m), 3.06 (3H, s), 4.79 (2H, s), 7.02-7.20 (2H+1/2H, m), 7.40 (1H, m), 7.44 (1/2H, m), 7.65 (1/2H, m), 7.76 (1/2H, m), 7.85-7.90 (3H, m), 8.35 (m, 1H), 8.64 (m, 1H), 10.5 (br, 1H).

ESI-MASS (m/e): 477 [M+H].

Example 2

1-{[5-[4-(Methylsulfonyl)phenoxy]-2-(2-pyridinyl)-1H-benzimidazol-6-yl]methyl}-2-pyrrolidinone With cooling with ice, 22 μl of methanesulfonyl chloride was added to a tetrahydrofuran (0.75 ml) solution of 75 mg of the alcohol compound obtained in Example 1 (step 9) and 40 μl of triethylamine, and stirred for 30 minutes. Water was added to it, extracted with ethyl acetate, and the organic layer was washed with saturated saline water. This was dried, and the solvent was evaporated away under reduced pressure to obtain 62 mg of a pale yellow amorphous substance.

With cooling with ice, 22 mg of sodium hydride (with 30% liquid paraffin added thereto) was added to a dimethylformamide (0.5 ml) solution of 62 mg of the obtained amorphous substance and 46 mg of 2-pyrrolidone, and stirred at room temperature for 40 minutes. With cooling with ice, aqueous saturated ammonium chloride solution was added to it, extracted with ethyl acetate, and the organic layer was washed with water and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 22.1 mg of a colorless oil.

22.1 mg of the obtained colorless oil was dissolved in 1 ml of trifluoroacetic acid, and stirred at room temperature for 1 hour. The solvent was evaporated away, the residue was neutralized with triethylamine and purified through partitioning thin-layer chromatography (Kieselgel™ 60F$_{254}$, Art 5744 (by Merck), chloroform/methanol=10/1) to obtain 9.3 mg of the entitled compound as a pale yellow amorphous substance.

$^1$HNMR (CDCl$_3$) δ: 1.85-2.00 (2H, m), 2.30-2.38 (2H, m), 3.06 (3H, s), 3.25-3.35 (2H, m), 4.54 (2H, m), 7.04-7.10 (2H, m), 7.19 (1/2H, s), 7.40 (1H, m), 7.49 (1/2H, s), 7.57 (1/2H, s), 7.77 (1/2H, s), 7.85-7.92 (3H, m), 8.40 (1H, m), 8.65 (1H, m), 10.7 (1/2H, brs), 10.8 (1/2H, brs).

ESI-MS (m/e): 463 [M+H].

Example 3

3-{[5-[4-(Methylsulfonyl)phenoxy]-2-(2-pyridinyl)-1H-benzimidazol-6-yl]methyl}-2-oxazolidinone Using 2-oxazolidone, the entitled compound was obtained in the same method as in Example 2 or in accordance with the method or by combining it with an ordinary method.

$^1$HNMR (CDCl$_3$) δ: 3.06 (3H, s), 3.42-3.60 (2H, m), 4.22-4.28 (2H, m), 4.52 (2H, m), 7.09 (2H, m), 7.21 (1/2H, s), 7.41 (1H, m), 7.51 (1/2H, s), 7.65 (1/2H, s), 7.82-7.95 (3H+1/2H, m), 8.40 (1H, m), 6.67 (1H, m), 10.7 (br, 1H).

ESI-MS (m/e): 465 [M+H].

Example 4

1-{[5-[4-(Methylsulfonyl)phenoxy]-2-(2-pyridinyl)-1H-benzimidazol-6-yl]methyl}piperidine-2,6-dione Using glutarimide, the entitled compound was obtained in the same method as in Example 1 (step 10) or in accordance with the method or by combining it with an ordinary method.

$^1$HNMR (CD$_3$OD) δ: 0.93 (1H, m), 1.29 (1H, s), 1.85-1.92 (2H, m), 2.66 (2H, m), 3.11 (3H, s), 5.02 (2H, s), 7.14 (m, 2H), 7.29 (s, 1H), 7.49 (m, 2H), 7.87-7.98 (3H, m), 8.26 (1H, m), 8.71 (1H, m).

ESI-MASS (m/e): 491 (M+H).

Example 5

1-{[5-[4-(Methylsulfonyl)phenoxy]-2-(2-pyridinyl)-1H-benzimidazol-6-yl]methyl}-2(1H)-pyridinone Using 2-hydroxypyridine, the entitled compound was obtained in the same method as in Example 2 or in accordance with the method or by combining it with an ordinary method.

$^1$HNMR (CDCl$_3$) δ: 3.05 (3H, s), 5.21 (2H, s), 6.08 (1H, m), 6.56 (1H, m), 7.07 (2H, m), 7.26 (1H, m), 7.37 (2H, m), 7.42 (1H, s), 7.74 (1H, s), 7.87 (3H, m), 8.35 (1H, m), 8.62 (1H, m).

ESI-MASS (m/e): 473 (M+H).

Example 6

1-{[5-[4-(Methylsulfonyl)phenoxy]-2-(2-pyridinyl)-1H-benzimidazol-6-yl]methyl}-piperidinone Using δ-valerolactone, the entitled compound was obtained in the same method as in Example 2 or in accordance with the method or by combining it with an ordinary method.

$^1$HNMR (CDCl$_3$) δ: 0.91 (2H, m), 1.75 (2H, m), 2.37 (2H, m), 3.04 (3H, s), 3.24 (2H, m), 4.66 (2H, s), 7.06 (2H, m), 7.37-7.40 (1H, m), 7.53 (1H, m), 7.68 (1H, m), 7.86 (3H, m), 8.38 (1H, m), 8.64 (1H, m).

ESI-MASS (m/e): 477.

Example 7

2-{[5-[4-(Methylsulfonyl)phenoxy]-2-(2-pyridinyl)-1H-benzimidazol-6-yl]methyl}-1H-isoindole-1,3(2H)-dione Using phthalimide, the entitled compound was obtained in the same method as in Example 1 (step 10) or in accordance with the method or by combining it with an ordinary method.

$^1$HNMR (CDCl$_3$) δ: 3.03 (3H, s), 4.99 (2H, s), 7.05 (3H, m), 7.40 (1H, m), 7.80 (8H, m), 8.38 (11H, d, J=7.8 Hz), 8.64 (1H, d, J=3.9 Hz), 10.79 (1H, brs).

ESI-MASS (m/e): 525 (M+H).

Example 8

2-{[5-[4-(Methylsulfonyl)phenoxy]-2-(2-pyridinyl)-1H-benzimidazol-6-yl]methyl}-cis-3a,4,7,7a-tetrahydro-1H-isoindol-1,3(2H)-dione Using cis-1,2,3,6-tetrahydrophthalimide, the entitled compound was obtained in the same method as in Example 1 (step 10) or in accordance with the method or by combining it with an ordinary method.

$^1$HNMR (CDCl$_3$) δ: 2.21 (2H, m), 2.59 (2H, m), 2.99 (2H, m), 3.05 (3H, m), 4.73 (2H, s), 5.91 (2H, m), 7.09 (2H, m), 7.29 (1H, m), 7.39 (1H, m), 7.51 (1H, m), 7.86 (3H, m), 8.37 (1H, m), 8.62 (1H, m).

ESI-MASS (m/e): 529 (M+H).

Example 9

5-Methyl-1-{[5-[4-(methylsulfonyl)phenoxy]-2-(2-pyridinyl)-1H-benzimidazol-6-yl]methyl}-2-pyrrolidinone Using 5-methyl-2-pyrrolidinone, the entitled compound was obtained in the same method as in Example 2 or in accordance with the method or by combining it with an ordinary method.

$^1$HNMR (CDCl$_3$) δ: 0.89 (1H, m), 1.16 (3H, m), 2.11 (1H, m), 2.25-2.33 (1H, m), 2.46 (1H, m), 3.07 (3H, d, J=3.5 Hz), 3.62 (1H, m), 4.17 (1H, d, J=15.2 Hz), 4.95 (2H, d, J=15.2 Hz), 7.08 (2H, m), 7.35 (1H, s), 7.42 (1H, m), 7.69 (1H, s), 7.89 (3H, m), 8.41 (1H, m), 8.66 (1H, m).

ESI-MASS (m/e): 477 (M+H).

Example 10

3-Methyl-1-{[5-[4-(methylsulfonyl)phenoxy]-2-(2-pyridinyl)-1H-benzimidazol-6-yl]methyl}-2-pyrrolidinone Using 3-methyl-2-pyrrolidinone, the entitled compound was obtained in the same method as in Example 2 or in accordance with the method or by combining it with an ordinary method.

$^1$HNMR (CDCl$_3$) δ: 0.87 (1H, s), 1.10-1.15 (3H, m), 1.51 (1H, m), 2.41 (1H, m), 3.04 (3H, m), 3.21 (2H, m), 4.44-4.61 (2H, m), 7.01-7.06 (2H, m), 7.38-7.40 (1H, m), 7.50 (1H, d, J=19.2 Hz), 7.74 (1H, s), 7.85-7.90 (3H, m), 8.36-8.41 (1H, m), 8.63-8.64 (1H, m), 10.91 (1H, brs).

ESI-MASS (m/e): 477 (M+H).

Example 11

Methyl 1-{[5-[4-(methylsulfonyl)phenoxy]-2-(2-pyridinyl)-1H-benzimidazol-6-yl]methyl}-5-oxo-2-pyrrolidinecarboxylate (Step 1) Production of methyl pyroglutamate 1 g of dl-pyroglutamic acid was dissolved in a mixed solvent of 25 ml of methanol and 15 ml of chloroform, and 7.7 ml of trimethylsilyldiazomethane (2 M hexane solution) was added to it at room temperature, and then stirred for 20 minutes as it was. The solvent was evaporated away under reduced pressure, the residue was dissolved in chloroform, and washed with saturated saline water. After dried, the solvent was removed to obtain 1.03 g of the entitled compound as a pale yellow oil.

(Step 2) Production of methyl 1-{[5-[4-(methylsulfonyl)phenoxy]-2-(2-pyridinyl)-1H-benzimidazol-6-yl]methyl}-5-oxo-2-pyrrolidinecarboxylate Using methyl pyroglutamate, the entitled compound was obtained in the same method as in Example 2 or in accordance with the method or by combining it with an ordinary method.

$^1$HNMR (CDCl$_3$) δ: 2.01 (1H, m), 2.13 (1H, m), 2.24 (1H, m), 2.44-2.50 (1H, m), 3.04 (3H, m), 3.67 (3H, m), 4.03-4.16 (2H, m), 5.01 (1/2H, m), 5.12 (1/2H, m), 7.01-7.09 (2H, m), 7.16 (1/2H, d, J=2.0 Hz), 7.40 (1H, dd, J=5.5, 6.7 Hz), 7.48 (1/2H, d, J=21.5 Hz), 7.60 (1/2H, s), 7.77 (1/2H, d, J=2.3 Hz), 7.87 (3H, m), 8.36-8.39 (1H, m), 8.64-8.65 (1H, m), 10.65 (1H, d, J=13.7 Hz).

ESI-MASS (m/e): 521 (M+H).

Example 12

1-(1-{[5-[4-(Methylsulfonyl)phenoxy]-2-(2-pyridinyl)-1H-benzimidazol-6-yl]methyl}-1H-pyrrol-2-yl)-1-ethanone Using 2-acetylpyrrole, the entitled compound was obtained in the same method as in Example 2 or in accordance with the method or by combining it with an ordinary method.

$^1$HNMR (CDCl$_3$) δ: 2.29-2.39 (3H, m), 3.05 (3H, m), 5.64 (2H, s), 6.17 (1H, m), 6.91 (1H, m), 6.98 (1H, m), 7.04-7.20 (3H, m), 7.34-7.37 (2H, m), 7.85 (3H, m), 8.53 (1H, d, J=7.8 Hz), 8.59 (1H, d, J=4.7 Hz).

ESI-MASS (m/e): 487 (M+H).

Example 13

1-{[5-[4-(Methylsulfonyl)phenoxy]-2-(2-pyridinyl)-1H-benzimidazol-6-yl]methyl}-5-thioxo-2-pyrrolidinone (Step 1) Production of 5-thioxo-2-pyrrolidinone 300 mg of succinimide was dissolved in 3 ml of tetrahydrofuran at 60° C., and 606 mg of Lawesson's reagent (Aldrich) was added to it. This was stirred at 60° C. for 1.5 hours, and the solvent was evaporated away. Water was added to it, extracted with ethyl acetate, and the organic layer was washed with saturated saline water. This was dried with anhydrous magnesium sulfate, the solvent was evaporated away, and the residue was purified through silica gel column chromatography (developing solvent: hexane/ethyl acetate=20/1 to 7/3 to 1/1) to obtain 255 mg of the entitled compound as a pale yellow solid.

(Step 2) Production of 1-{[5-[4-(methylsulfonyl)phenoxy]-2-(2-pyridinyl)-1H-benzimidazol-6-yl]methyl}-5-thioxo-2-pyrrolidinone Using 5-thioxo-2-pyrrolidinone, the entitled compound was obtained in the same method as in Example 1 (step 10) or in accordance with the method or by combining it with an ordinary method.

$^1$HNMR (CDCl$_3$) δ: 2.62 (1H, m), 2.72 (1H, m), 3.05 (1H, m), 3.07 (3H, s), 3.12 (1H, m), 5.18 (2H, s), 7.00-7.20 (2H+1/2H, m), 7.39-7.43 (1H, m), 7.44 (1/2H, brs), 7.49 (1/2H, brs), 7.60 (1/2H, brs), 7.82-7.90 (3H, m), 8.36 (1H, d, J=8.0 Hz), 8.63 (1H, brs), 10.6 (1H, br).

ESI-MS (m/e): 493 [M+H].

Example 14

5-[4-(Methylsulfonyl)phenoxy]-2-(2-pyridinyl)-6-(1H-1,2,4-triazol-1-ylmethyl)-1H-benzimidazole Using 1,2,4-triazole, the entitled compound was obtained in the same method as in Example 2 or in accordance with the method or by combining it with an ordinary method.

$^1$HNMR (CDCl$_3$) δ: 3.05-3.10 (3H, m), 5.46 (2H, s), 7.06 (2H, m), 7.36-7.44 (2H, m), 7.83-7.93 (5H, m), 8.05 (1H, s), 8.41 (1H, d, J=7.8 Hz), 8.66 (1H, d, J=4.3 Hz).

ESI-MASS (m/e): 447 (M+H).

Example 15

Cis-3,4-dimethyl-1-{[5-[4-(methylsulfonyl)phenoxy]-2-(2-pyridinyl)-1H-benzimidazol-6-yl]methyl}pyrrolidine-2,5-dione (Step 1) Production of cis-3,4-dimethylpyrrolidine-2,5-dione 2.3 ml of acetyl chloride and 0.24 ml of thionyl chloride were added to 500 mg of meso-2,3-dimethylsuccinic acid, and heated under reflux for 2 hours. The reaction liquid was restored to room temperature, and the solvent was evaporated away under reduced pressure. The residue was recrystallized from toluene and hexane to obtain 398 mg of meso-2,3-dimethylsuccinic anhydride as a white solid.

In a cooling bath, ammonia gas was introduced into a toluene (5 ml) solution of 390 mg of cis-2,3-dimethylsuccinic anhydride for 30 minutes. The solvent was evaporated away under reduced pressure to obtain a white solid. This was dissolved in 10 ml of DMF, and at −78° C., 0.5 ml of thionyl chloride was added to it and stirred at 0° C. for 2 hours. The reaction liquid was restored to room temperature, the solvent was evaporated away under reduced pressure, ethyl acetate was added to the residue, and washed with aqueous saturated sodium hydrogencarbonate solution. After dried, the solvent was removed, and the residue was purified through silica gel column chromatography (developing solvent: hexane/ethyl acetate=7/3 to 0/1) to obtain 269 mg of the entitled compound as a white solid.

(Step 2) Production of cis-3,4-dimethyl-1-{[5-[4-(methylsulfonyl)phenoxy]-2-(2-pyridinyl)-1H-benzimidazol-6-yl]methyl}pyrrolidine-2,5-dione Using cis-3,4-dimethylpyrrolidine-2,5-dione, the entitled compound was obtained in the same method as in Example 1 (step 10) or in accordance with the method or by combining it with an ordinary method.
$^1$HNMR (CDCl$_3$) δ: 1.19 (6H, m), 2.84 (2H, m), 3.04 (3H, m), 4.74 (2H, s), 7.08 (3H, m), 7.38-7.42 (2H, m), 7.84-7.86 (3H, m), 8.37 (1H, d, J=7.4 Hz), 8.61 (1H, s), 10.88 (1H, s).
ESI-MASS (m/e): 505 (M+H).

Example 16

4-{[5-[4-(Methylsulfonyl)phenoxy]-2-(2-pyridinyl)-1H-benzimidazol-6-yl]methyl}morpholine-3,5-dione Using morpholine-3,5-dione, the entitled compound was obtained in the same method as in Example 1 (step 10) or in accordance with the method or by combining it with an ordinary method.
$^1$HNMR (CDCl$_3$) δ: 3.05 (3/2H, s), 3.06 (3/2H, s), 4.27 (2H, s), 4.34 (2H, s), 5.07 (2H, s), 7.05-7.10 (2H+1/2H, m), 7.35-7.42 (1H, m), 7.44 (1/2H, m), 7.53 (1/2H, m), 7.74 (1/2H, m), 7.85-7.92 (3H, m), 8.38 (1H, m), 8.61 (1H, m), 10.9 (1H, br).
ESI-MS (m/e): 493 [M+H].

Example 17

3-{[5-[4-(Methylsulfonyl)phenoxy]-2-(2-pyridinyl)-1H-benzimidazol-6-yl]methyl}1,3-thiazolane-2,4-dione Using 2,4-thiazolidinedione, the entitled compound was obtained in the same method as in Example 1 (step 10) or in accordance with the method or by combining it with an ordinary method.
$^1$HNMR (CDCl$_3$) δ: 3.06 (3/2H, s), 3.07 (3/2H, s), 3.77 (11H, s), 3.87 (1H, s), 4.89 (11H, s), 4.91 (11H, s), 7.02-7.12 (2H+1/2H, m), 7.35-7.44 (1H, m), 7.45 (1/2H, s), 7.62 (1/2H, s), 7.81 (1/2H, s), 7.85-7.92 (3H, m), 8.37 (1H, m), 8.63 (1H, m), 10.7 (1/2H, br), 10.8 (1/2H, br).
ESI-MS (m/e): 495 [M+H].

Example 18

3-{[5-[4-(Methylsulfonyl)phenoxy]-2-(2-pyridinyl)-1H-benzimidazol-6-yl]methyl}1,3-thiazolan-2-one Using 2-oxathiazolidine produced according to the method described in Synthetic communications, 1987, Vol. 17, No. 13, pp. 1577-1785, the entitled compound was obtained in the same method as in Example 2 or in accordance with the method or by combining it with an ordinary method.
$^1$HNMR (CDCl$_3$) δ: 3.06 (3H, s), 3.16 (2H, m), 3.55 (2H, m), 4.55 (1H, s), 4.57 (1H, s), 7.03-7.09 (2H, m), 7.17 (1/2H, s), 7.41 (1H, m), 7.49 (1/2H, s), 7.58 (1/2H, s), 7.83-7.92 (3H+1/2H, m), 8.41 (1H, m), 8.65 (1H, m), 10.95 (1/2H, br), 10.91 (1/2H, br).
ESI-MS (m/e): 481 [M+H].

Example 19

1-{[5-[4-(Ethylsulfonyl)phenoxy]-2-(2-pyridinyl)-1H-benzimidazol-6-yl]methyl}pyrrolidine-2,5-dione (Step 1) Production of methyl 2-fluoro-4-nitrobenzoate 5 ml of concentrated sulfuric acid was added to a methanol (1300 ml) solution of 140 g of 2-fluoro-4-nitrobenzoic acid, and heated under reflux for 48 hours. The solvent was evaporated away under reduced pressure, water was added to the residue, and the formed solid was taken out through filtration. This was dried under reduced pressure to obtain 141 mg of the entitled compound as a yellow solid.

(Step 2) Production of methyl 4-amino-2-fluorobenzoate 141 g of methyl 2-fluoro-4-nitrobenzoate was dissolved in 1000 ml of methanol and 400 ml of tetrahydrofuran, 20 g of Raney nickel was added to it, and stirred overnight in a hydrogen atmosphere. The catalyst was removed through filtration, and the solvent was evaporated away under reduced pressure to obtain 119 g of methyl 4-amino-2-fluorobenzoate.

(Step 3) Production methyl 2-fluoro-4-[(2-pyridinylcarbonyl)amino]benzoate 1-(3-Dimethylaminopropyl)-3-ethylcarbodiimide hydrochloride was added to a pyridine (500 ml) solution of 18.9 g of methyl 4-amino-2-fluorobenzoate and 16.5 g of picolinic acid, and stirred at room temperature for 2 hours. The solvent was evaporated away under reduced pressure, 600 ml of ethyl acetate was added to the residue, the organic layer was washed with aqueous 0.25 N hydrochloric acid solution, aqueous 0.25 N sodium hydroxide solution and saturated saline water, dried, concentrated under reduced pressure, solidified from a mixed solvent of hexane/ethyl acetate, and the solid was taken out through filtration. This was dried under reduced pressure to obtain 28.3 g of the entitled compound as a white solid.

(Step 4) Production of methyl 2-fluoro-5-nitro-4-[(2-pyridinylcarbonyl)amino]benzoate With cooling with ice, 110 ml of fuming nitric acid was gradually added to 27.7 g of methyl 2-fluoro-4-[(2-pyridinylcarbonyl)amino]benzoate, and stirred at room temperature for 1.5 hours. With cooling with ice, the reaction liquid was gradually added to a solution of sodium carbonate (138 g) in water (2000 ml), and the formed solid was taken out through filtration. This was dried under reduced pressure to obtain 27.5 g of the entitled compound as a yellow solid.

(Step 5) Production of methyl 2-[4-(ethylsulfonyl)phenoxy]-5-nitro-4-[(2-pyridinylcarbonyl)amino]benzoate 3.5 g of potassium carbonate was added to a dimethylformamide (110 ml) solution of 6 g of methyl 2-fluoro-5-nitro- 4-[(2-pyridinylcarbonyl)amino]benzoate and 3.48 g of 4-(ethylsulfonyl)phenol obtained in Reference Example 2, and stirred under heat at 80° C. for 30 minutes. The reaction liquid was restored to room temperature, poured into 300 ml of water, and the formed solid was taken out through filtration. This was dried under reduced pressure to obtain 7.46 g of the entitled compound as a yellow solid.

(Step 6) Production of methyl 5-[4-(ethylsulfonyl) phenoxy]-2-(2-pyridinyl)-1-{[2-(trimethylsilyl) ethoxy]methyl}-1H-benzimidazole-6-carboxylate and methyl 6-[4-(ethylsulfonyl)phenoxy]-2-(2-pyridinyl)-1-{[2-(trimethylsilyl)ethoxy]methyl}-1H-benzimidazole-5-carboxylate 7.46 g of methyl 2-[4-(ethylsulfonyl)phenoxy]-5-nitro-4-[(2-pyridinylcarbonyl)amino]benzoate was suspended in 37 ml of dimethylformamide and 37 ml of methanol, and 17.3 g of tin(II) chloride dihydrate and 15 ml of concentrated hydrochloric acid were added thereto, and stirred under heat at 80° C. for 40 minutes. The reaction liquid was restored to room temperature, then aqueous sodium hydrogencarbonate solution was gradually added to it and neutralized. Ethyl acetate was added to it, and stirred at room temperature for 30 minutes, and the formed salt was removed through filtration. The filtrate was washed with water and saturated saline water. After dried, the solvent was evaporated away to obtain 6.9 g of a crude product methyl 5-[4-(ethylsulfonyl)phenoxy]-2-(2-pyridinyl)-1H-benzimidazole-6-carboxylate as a yellow solid.

With cooling with ice, 4 ml of 2-(trimethylsilyl)ethoxymethyl chloride and 0.92 g of sodium hydride (with 30% liquid paraffin added thereto) were added to a dimethylformamide (70 ml) solution of 6.9 g of the crude product, and stirred at room temperature for 30 minutes. With cooling with ice, aqueous saturated ammonium chloride solution was added to it, and extracted with ethyl acetate. The organic layer was washed with water and saturated saline water. After dried, the solvent was evaporated away under reduced pressure, and the residue was purified through silica gel column chromatography (developing solvent: hexane/ethyl acetate=9/1 to 3/2) to obtain 6.43 g of the entitled compound as a yellow oil.

(Step 7) Production of (5-[4-(ethylsulfonyl)phenoxy]-2-(2-pyridinyl)-1-{[2-(trimethylsilyl)ethoxy]methyl}-1H-benzimidazol-6-yl)methanol and (6-[4-(ethylsulfonyl)phenoxy]-2-(2-pyridinyl)-1-{[2-(trimethylsilyl)ethoxy]methyl}-1H-benzimidazol-5-yl)methanol With cooling with ice, a tetrahydrofuran (50 ml) solution of 0.99 g of lithium aluminium hydride and 5.9 g of the above ester was gradually added to 60 ml of tetrahydrofuran. This was stirred at room temperature for 15 minutes, and with cooling with ice, sodium sulfate 10-hydrate was gradually added to it until it foamed no more. Then, ethyl acetate was added to it, and stirred at room temperature for 1 hour. The formed salt was removed through filtration, and the solvent was evaporated away under reduced pressure. The residue was purified through silica gel column chromatography (developing solvent: hexane/ethyl acetate=9/1 to 3/2) to obtain 4.5 g of the entitled compound as a yellow oil.

(Step 8) Production of 1-{[5-[4-(ethylsulfonyl)phenoxy]-2-(2-pyridinyl)-1H-benzimidazol-6-yl] methyl}pyrrolidine-2,5-dione 1.3 g of succinimide and 3.5 g of triphenyl phosphine were added to a tetrahydrofuran (24 ml) solution of 2.4 g of the obtained alcohol compound, and with cooling with ice, 5.8 ml of diethyl azodicarboxylate (40% toluene solution) was added to it, and stirred at room temperature for 1 hour. The reaction solvent was evaporated away under reduced pressure, and the residue was purified through silica gel column chromatography (developing solvent: hexane/ethyl acetate=8/2 to 1/1 to 1/9) to obtain 2.3 g of an yellow oil.

15 ml of trifluoroacetic acid was added to the obtained oil, and stirred for 2 hours. The solvent was evaporated away under reduced pressure, and the residue was purified through silica gel column chromatography (developing solvent: chloroform to chloroform/methanol=99/1) and recrystallized (ethyl acetate) to obtain 1.02 g of the entitled compound as a white crystal.

$^1$HNMR (CDCl$_3$) δ: 1.30 (3H, m), 2.54 (2H, s), 2.65 (2H, s), 3.12 (2H, m), 4.79 (1H, m), 4.80 (1H, s), 7.05-7.12 (2H+1/2H, m), 7.39 (1H, m), 7.44 (1/2H, s), 7.64 (1/2H, s), 7.76 (1/2H, s), 7.81-7.90 (3H, m), 8.38 (1H, m), 8.65 (1H, m), 10.5 (1/2H, br), 10.6 (1/2H, br).

ESI-MASS (m/e): 491 (M+H).

Example 20

1-{[5-[4-(Ethylsulfonyl)phenoxy]-2-(2-pyridinyl)-1H-benzimidazol-6-yl]methyl}-2-pyrrolidinone Using the alcohol compound obtained in Example 19 (step 7), the entitled compound was obtained in the same method as in Example 2 or in accordance with the method or by combining it with an ordinary method.

$^1$HNMR (CDCl$_3$) δ: 1.24-1.30 (3H, m), 1.91 (2H, dt, J=23.7, 7.8 Hz), 2.32 (2H, m), 3.06-3.13 (2H, m), 3.26 (2H, q, J=10.4 Hz), 4.53 (2H, s), 7.05 (2H, m), 7.39 (2H, m), 7.79-7.89 (4H, m), 8.38 (1H, d, J=8.2 Hz), 8.63 (1H, d, J=4.7 Hz).

ESI-MASS (m/e): 477 (M+H).

Example 21

3-{[5-[4-(Ethylsulfonyl)phenoxy]-2-(2-pyridinyl)-1H-benzimidazol-6-yl]methyl}-2-oxazolidinone Using the alcohol compound obtained in Example 19 (step 7) and 2-oxazolidone, the entitled compound was obtained in the same method as in Example 2 or in accordance with the method or by combining it with an ordinary method.

$^1$HNMR (CDCl$_3$) δ: 1.28 (3H, t, J=7.4 Hz), 3.11 (2H, q, J=7.4 Hz), 3.46 (2H, m), 4.23 (2H, t, J=8.2 Hz), 4.51 (2H, s), 7.08 (2H, q, J=9.0 Hz), 7.40 (1H, t, J=6.3 Hz), 7.50 (1H, m), 7.65-7.68 (1H, m), 7.83-7.86 (3H, m), 8.36-8.38 (1H, m), 8.64 (1H, s), 10.63 (1H, s).

ESI-MASS (m/e): 479 (M+H).

Example 22

1-({2-(5-Bromo-2-pyridinyl)-[5-[4-(ethylsulfonyl) phenoxy]-1H-benzimidazol-6-yl}methyl)pyrrolidine-2,5-dione Using 5-bromopicolinic acid in Example 19 (step 3), the entitled compound was obtained in the same method as in Example 19 or in accordance with the method or by combining it with an ordinary method.

$^1$HNMR (CDCl$_3$) δ: 1.29 (3H, m), 2.55 (2H, s), 2.65 (2H, s), 3.12 (2H, s), 4.79 (1H, s), 4.80 (1H, s), 7.05-7.15 (2H+1/2H, m), 7.44 (1/2H, s), 7.65 (1/2H, s), 7.76 (1/2H, s), 7.82-7.90 (2H, m), 8.00 (1H, m), 8.26 (1H, m), 8.70 (1H, m), 10.3 (1/2H, br), 10.4 (1/2H, br).

ESI-MS (m/e): 569, 571 [M+H].

Example 23

1-{[5-[4-(Ethylsulfonyl)phenoxy]-2-(2-pyridinyl)-1H-benzimidazol-6-yl]methyl}-2-imidazolidinone Using the alcohol compound obtained in Example 19 (step 7) and ethyleneurea, the entitled compound was obtained in the same method as in Example 2 or in accordance with the method or by combining it with an ordinary method.

$^1$HNMR (CDCl$_3$, one drop of CD$_3$OD) δ: 1.28 (3H, t, J=7.2 Hz), 3.11 (2H, q, J=7.2 Hz), 3.25-3.28 (4H, m), 4.41 (2H×1/2, s), 4.44 (2H×1/2, s), 4.63 (1H×1/2, s), 4.65 (1H×1/2, s), 7.05 (2H, d, J=8.2 Hz), 7.20 (1H×1/2, s), 7.37-7.41 (1H, m), 7.45 (1H×1/2, s), 7.59 (1H×1/2, s), 7.77 (1H×1/2, s), 7.82 (2H, d, J=8.2 Hz), 7.85-7.90 (1H, m), 8.37 (1H, d, J=7.4 Hz), 8.61-8.65 (1H, m).

ESI-MASS (m/e): ND.

Example 24

1-{[5-[4-(Ethylsulfonyl)phenoxy]-2-(2-pyridinyl)-1H-benzimidazol-6-yl]methyl}imidazolidine-2,5-dione Using the alcohol compound obtained in Example 19 (step 7) and hydantoin, the entitled compound was obtained in the same method as in Example 2 or in accordance with the method or by combining it with an ordinary method.

$^1$HNMR (CDCl$_3$) δ: 1.31 (3H, t, J=7.4 Hz), 3.13 (2H, q, J=7.4 Hz), 3.70-4.00 (2H, m), 4.77-4.89 (3H, m), 7.05-7.90 (8H, m), 8.37-8.42 (1H, m), 8.62-8.67 (1H, m), 10.64-10.95 (1H, m).

ESI-MASS (m/e): 492(M+H).

Example 25

1-{[5-[4-(Ethylsulfonyl)phenoxy]-2-(2-pyridinyl)-1H-benzimidazol-6-yl]methyl}-1H-pyrimidine-2,4-dione Using the alcohol compound obtained in Example 19 (step 7) and uracil, the entitled compound was obtained in the same method as in Example 2 or in accordance with the method or by combining it with an ordinary method.

$^1$HNMR (CDCl$_3$) δ: 1.12 (3H, t, J=7.4 Hz), 3.24 (2H, q, J=7.4 Hz), 4.94 (2H, s), 5.47 (1H, d, J=8.2 Hz), 7.10 (2H, d, J=8.2 Hz), 7.55 (1H, dd, J=7.8, 5.5 Hz), 7.57 (1H, s), 7.59 (1H, s), 7.83 (2H, d, J=8.2 Hz), 8.02 (1H, dd, J=7.8, 7.8 Hz), 8.31 (1H, d, J=7.8 Hz), 8.75 (1H, d, J=5.5 Hz), 11.18 (1H, brs).

ESI-MASS (m/e): 504(M+H).

Example 26

1-{[5-[4-(Ethylsulfonyl)phenoxy]-2-(2-pyridinyl)-1H-benzimidazol-6-yl]methyl}-3-methyl-imidazolidine-2,5-dione Using 1-methylhydantoin, the entitled compound was obtained in the same method as in Example 19 (step 8) or in accordance with the method or by combining it with an ordinary method.

$^1$HNMR (CDCl$_3$) δ: 1.29 (3H, t, J=7.0 Hz), 2.85 (3H×1/2, s), 2.92 (3H×1/2, s), 3.11 (2H, q, J=7.0 Hz), 3.59 (2H×1/2, s), 3.74 (2H×1/2, s), 4.77 (2H×1/2, s), 4.78 (2H×1/2, s), 7.06 (2H, d, J=9.0 Hz), 7.10 (1H×1/2, s), 7.36-7.40 (1H, m), 7.45 (1H×1/2, s), 7.66 (1H×1/2, s), 7.79-7.89 (3H, m), 7.79-7.89 (1H×1/2, m), 8.37 (1H×1/2, d, J=8.2 Hz), 8.40 (1H×1/2, d, J=8.2 Hz), 8.60-8.65 (1H, m), 10.63 (1H×1/2, brs), 10.67 (1H×1/2, brs).

ESI-MASS (m/e): 506(M+H).

Example 27

3-{[5-[4-(Ethylsulfonyl)phenoxy]-2-(2-pyridinyl)-1H-benzimidazol-6-yl]methyl}-1-methyl-1H-pyrimidine-2,4-dione Using 1-methyluracil, the entitled compound was obtained in the same method as in Example 19 (step 8) or in accordance with the method or by combining it with an ordinary method.

$^1$HNMR (CDCl$_3$) δ: 1.28 (3H×1/2, t, J=7.4 Hz), 1.28 (3H×1/2, t, J=7.4 Hz), 3.10 (2H×1/2, q, J=7.4 Hz), 3.10 (2H×1/2, q, J=7.4 Hz), 3.25 (3H×1/2, s), 3.33 (3H×1/2, s), 5.23 (2H×1/2, s), 5.24 (2H×1/2, s), 5.63 (1H×1/2, d, J=7.8 Hz), 5.72 (1H×1/2, d, J=7.8 Hz), 6.99 (1H×1/2, d, J=7.8 Hz), 7.04 (2H×1/2, d, J=9.0 Hz), 7.09 (1H×1/2, s), 7.10 (2H×1/2, d, J=9.0 Hz), 7.10 (1H×1/2, d, J=7.8 Hz), 7.34-7.38 (1H, m), 7.43 (1H×1/2, s), 7.52 (1H×1/2, s), 7.63 (1H×1/2, s), 7.78 (2H×1/2, d, J=9.0 Hz), 7.81-7.87 (1H, m), 7.82 (2H×1/2, d, J=9.0 Hz), 8.35 (1H, d, J=7.8 Hz), 8.60 (1H×1/2, d, J=5.1 Hz), 8.61 (1H×1/2, d, J=5.1 Hz), 10.65 (1H, brs).

ESI-MASS (m/e): 518(M+H).

Example 28

1-{[5-[4-(Ethylsulfonyl)phenoxy]-2-(2-pyridinyl)-1H-benzimidazol-6-yl]methyl}-3-methyl-1H-pyrimidine-2,4-dione Using the alcohol compound obtained in Example 19 (step 7) and 3-methyluracil, the entitled compound was obtained in the same method as in Example 2 or in accordance with the method or by combining it with an ordinary method.

$^1$HNMR (CDCl$_3$) δ: 1.31 (3H, t, J=7.4 Hz), 3.12 (2H, q, J=7.4 Hz), 3.26 (3H×1/2, s), 3.29 (3H×1/2, s), 5.00 (2H×1/2, s), 5.03 (2H×1/2, s), 5.65 (1H×1/2, d, J=7.8 Hz), 5.65 (1H×1/2, d, J=7.8 Hz), 7.05 (2H×1/2, d, J=8.6 Hz), 7.09 (2H×1/2, d, J=8.6 Hz), 7.13 (1H×1/2, s), 7.19 (1H×1/2, d, J=7.8 Hz), 7.27 (1H×1/2, s), 7.38-7.42 (1H, m), 7.43 (1H×1/2, s), 7.70 (1H×1/2, s), 7.83-7.90 (3H, m), 7.83-7.90 (1H×1/2, m), 8.36 (1H, d, J=7.8 Hz), 8.39 (1H, d, J=7.8 Hz), 8.61-8.65 (1H, m), 10.80 (1H, brs).

ESI-MASS (m/e): 518(M+H).

Example 29

1-{[5-[4-(Ethylsulfonyl)phenoxy]-2-(2-pyridinyl)-1H-benzimidazol-6-yl]methyl}-3-methyl-2-imidazolidinone Using the alcohol compound obtained in Example 19 (step 7) and 1-methylimidazolidinone, the entitled compound was obtained in the same method as in Example 2 or in accordance with the method or by combining it with an ordinary method.

$^1$HNMR (CDCl$_3$) δ: 1.28 (3H, t, J=7.4 Hz), 2.73 (3H×1/2, s), 2.75 (3H×1/2, s), 3.10 (2H, q, J=7.4 Hz), 3.16-3.20 (4H, m), 4.43 (2H×1/2, s), 4.43 (2H×1/2, s), 7.03 (2H, d, J=9.0 Hz), 7.06 (1H×1/2, s), 7.16 (1H×1/2, s), 7.37-7.40 (1H, m), 7.47 (1H×1/2, s), 7.61 (1H×1/2, s), 7.80 (2H, d, J=9.0 Hz), 7.84-7.89 (1H, m), 8.37 (1H×1/2, d, J=7.8 Hz), 8.40 (1H×1/2, d,

J=7.8 Hz), 8.62 (1H×1/2, d, J=4.7 Hz), 8.64 (1H×1/2, d, J=4.7 Hz), 10.81 (1H×1/2, brs), 10.84 (1H×1/2, brs).
ESI-MASS (m/e): 492(M+H).

Example 30

3-{[5-[4-(Ethylsulfonyl)phenoxy]-2-(2-pyridinyl)-1H-benzimidazol-6-yl]methyl}-3-azabicyclo[3.1.0]hexane-2,4-dione Using 3-azabicyclo[3.1.0]hexane-2,4-dione, the entitled compound was obtained in the same method as in Example 19 (step 7) or in accordance with the method or by combining it with an ordinary method.
$^1$HNMR (CDCl$_3$) δ: 1.17-1.75 (5H, m), 2.40-2.50 (2H, m), 3.05-3.18 (2H, m), 4.61 (1H, s), 4.63 (1H, s), 7.05-7.13 (2H+1/2H, m), 7.39-7.44 (1H, m), 7.44 (1/2H, s), 7.54 (1/2H, s), 7.73 (1/2H, s), 7.82-7.90 (3H, m), 8.39 (1H, m), 8.63 (1H, m), 10.8 (1/2H, br), 10.9 (1/2H, br).
ESI-MASS (m/e): 503(M+H).

Example 31

N-{[5-[4-(ethylsulfonyl)phenoxy]-2-(2-pyridinyl)-1H-benzimidazol-6-yl]methyl}methanesulfonamide (Step 1) Production of (5-[4-(ethylsulfonyl)phenoxy]-2-(2-pyridinyl)-1-{[2-(trimethylsilyl)ethoxy]methyl}-1H-benzimidazol-6-yl)methylamine or (6-[4-(ethylsulfonyl)phenoxy]-2-(2-pyridinyl)-1-{[2-(trimethylsilyl)ethoxy]methyl}-1H-benzimidazol-5-yl)methylamine With cooling with ice, 74 μl of methanesulfonyl chloride was added to a tetrahydrofuran (2.6 ml) solution of 260 mg of the alcohol compound obtained in Example 19 (step 7) and 134 μl of triethylamine, and stirred for 30 minutes. Water was added to it, extracted with ethyl acetate, and the organic layer was washed with saturated saline water. After dried, the solvent was evaporated away under reduced pressure to obtain a pale yellow oil.
156 mg of sodium azide was added to a dimethylformamide (3 ml) solution of the obtained oil, and stirred at room temperature for 1 hour. Water was added to it, extracted with ethyl acetate, and the organic layer was washed with water and saturated saline water. After dried, the solvent was evaporated away under reduced pressure, and the residue was purified through silica gel column chromatography (developing solvent: hexane/ethyl acetate=9/1 to 3/2) to obtain 177 mg of a yellow oil.
5 mg of copper(II) sulfate pentahydrate and 53 mg of sodium borohydride were added to a methanol (3.2 ml) solution of the obtained oil, and stirred at room temperature for 30 minutes. Aqueous saturated ammonium chloride solution was added to it, neutralized with aqueous saturated sodium bicarbonate, extracted with ethyl acetate, and the organic layer was washed with saturated saline water. After dried, the solvent was evaporated away under reduced pressure, and the residue was purified through silica gel column chromatography (developing solvent: chloroform to chloroform/methanol=20/1) to obtain 141 mg of the entitled compound as a yellow oil.

(Step 2) Production of N-(5-[4-(ethylsulfonyl)phenoxy]-2-(2-pyridinyl)-1-{[2-(trimethylsilyl)ethoxy]methyl}-1H-benzimidazol-6-yl)methanesulfonamide or N-(6-[4-(ethylsulfonyl)phenoxy]-2-(2-pyridinyl)-1-{[2-(trimethylsilyl)ethoxy]methyl}-1H-benzimidazol-5-yl)methanesulfonamide With cooling with ice, 25 μl of triethylamine and 11 μl of methanesulfonyl chloride were added to a chloroform (1 ml) solution of 63 mg of the obtained amine compound. After stirred for 30 minutes, aqueous saturated sodium bicarbonate solution was added to it, extracted with ethyl acetate, and the organic layer was washed with saturated saline water. After dried, the solvent was evaporated away, and the residue was purified through silica gel column chromatography (developing solvent: chloroform to chloroform/methanol=20/1) to obtain 77 mg of the entitled compound as a yellow oil.

(Step 3) Production of N-{[5-[4-(ethylsulfonyl)phenoxy]-2-(2-pyridinyl)-1H-benzimidazol-6-yl]methyl}methanesulfonamide 0.5 ml of trifluoroacetic acid was added to 77 mg of the obtained yellow soil, and stirred at room temperature for 2 hours. The solvent was evaporated away, and the residue was neutralized with triethylamine and purified through partitioning thin-layer chromatography (Kieselgel™ 60F$_{254}$, Art 5744 (by Merck), chloroform/methanol=10/1) to obtain 9.4 mg of the entitled compound as a white amorphous substance.
$^1$HNMR (CDCl$_3$) δ: 1.30 (3H, t, J=7.3 Hz), 2.84 and 2.86 (total 3H, s), 3.14 (2H, q, J=7.3 Hz), 4.41 (2H, m), 4.93 (1H, m), 7.07-7.13 (2H+1/2H, m), 7.41 (1H, m), 7.45 (1/2H, s), 7.67 (1/2H, s), 7.87 (3H, m), 7.93 (1/2H, s), 8.40 (1H, m), 8.65 (1H, m), 10.7 and 10.8 (total 1H, br).
ESI-MASS (m/e): 487(M+H).

Example 32

N-{[5-[4-(ethylsulfonyl)phenoxy]-2-(2-pyridinyl)-1H-benzimidazol-6-yl]methyl}-N-methylmethanesulfonamide With cooling with ice, 14 μl of methyl iodide and 5.3 mg of sodium hydride (with 30% liquid paraffin added thereto) were added to a dimethylformamide (0.6 ml) solution of 60 mg of the sulfonamide compound obtained in Example 31 (step 2). This was stirred at room temperature for 30 minutes, then aqueous saturated ammonium chloride solution was added to it, extracted with ethyl acetate, and the organic layer was washed with water and saturated saline water. After dried, the solvent was evaporated away under reduced pressure to obtain a yellow oil.
0.5 ml of trifluoroacetic acid was added to the obtained yellow oil, and stirred at room temperature for 2 hours. The solvent was evaporated away, the residue was neutralized with triethylamine and purified through partitioning thin-layer chromatography (Kieselgel™ 60F$_{254}$, Art 5744 (by Merck), chloroform/methanol=10/1) to obtain 38.4 mg of the entitled compound as a white amorphous substance.
$^1$HNMR (CDCl$_3$) δ: 1.30 (3H, t, J=7.4 Hz), 2.83 (6H, m), 3.12 (2H, q, J=7.4 Hz), 4.40 and 4.42 (total 2H, s), 7.00-7.10 (2H, m), 7.14 (1/2H, s), 7.41 (1H, m), 7.48 (1/2H, s), 7.72 (1/2H, s), 7.83-7.95 (3H, m), 7.97 (1/2H, s), 8.41 (11H, m), 8.65 (1H, m), 11.0 (1H, br).
ESI-MASS (m/e): 501(M+H).

Example 33

2-{[5-[4-(Ethylsulfonyl)phenoxy]-2-(2-pyridinyl)-1H-benzimidazol-6-yl]methyl}isothiazolidine-1,1-dioxide Using the alcohol compound obtained in Example 19 (step 7) and isothiazolidine-1,1-dioxide produced according to the method described in Organic letters, 2003, Vol. 5, No. 22, pp. 4175-4277, the entitled compound was obtained in the same method as in Example 2 or in accordance with the method or by combining it with an ordinary method.

$^1$HNMR (CDCl$_3$) δ: 1.30 (3H, t, J=7.5 Hz), 2.20-2.30 (2H, m), 3.05-3.20 (6H, m), 4.28 (2H, brs), 7.08 (2H, d, J=8.9 Hz), 7.19 (1/2H, brs), 7.41 (1H, m), 7.50 (1/2H, brs), 7.71 (1/2H, brs), 7.84 (2H, d, J=8.9 Hz), 7.89 (1H, m), 7.96 (1/2H, brs), 8.41 (1H, m), 8.65 (1H, m), 10.7 (1H, br).

ESI-MASS (m/e): 513(M+H).

Example 34

1-{[5-[4-(Methylsulfonyl)phenoxy]-2-(2-pyrazinyl)-1H-benzimidazol-6-yl]methyl}pyrrolidine-2,5-dione (Step 1) Production of methyl 2-fluoro-5-nitro-4-[(2-pyrazinylcarbonyl)amino]benzoate Using methyl 4-amino-2-fluorobenzoate obtained in Example 19 (step 2) and pyrazine-2-carboxylic acid, the entitled compound was obtained in the same method as in Example 19 (step 3, step 4) or in accordance with the method or by combining it with an ordinary method.

(Step 2) Production of methyl 5-[4-(methylsulfonyl)phenoxy]-2-(2-pyrazinyl)-1-{[2-(trimethylsilyl)ethoxy]methyl}-1H-benzimidazole-6-carboxylate and methyl 6-[4-(methylsulfonyl)phenoxy]-2-(2-pyrazinyl)-1-{[2-(trimethylsilyl)ethoxy]methyl}-1H-benzimidazole-5-carboxylate Using methyl 2-fluoro-5-nitro-4-[(2-pyrazinylcarbonyl)amino]benzoate obtained in the above and 4-(methylsulfonyl)phenol obtained in Reference Example 1, the entitled compound was obtained in the same method as in Example 19 (step 5, step 6) or in accordance with the method or by combining it with an ordinary method.

(Step 3) Production of (5-[4-(methylsulfonyl)phenoxy]-2-(2-pyrazinyl)-1-{[2-(trimethylsilyl)ethoxy]methyl}-1H-benzimidazol-6-yl)methanol and (6-[4-(methylsulfonyl)phenoxy]-2-(2-pyrazinyl)-1-{[2-(trimethylsilyl)ethoxy]methyl}-1H-benzimidazol-5-yl)methanol 570 mg of the obtained methyl ester compound was dissolved in 4 ml of methanol and 1 ml of tetrahydrofuran, then 1 ml of aqueous 5 N sodium hydroxide solution was added to it, and stirred at room temperature for 2 hours. This was controlled to have a pH of 3 with aqueous 10% citric acid solution, then extracted with ethyl acetate, and the organic layer was washed with saturated saline water. After dried, the solvent was evaporated away under reduced pressure to obtain 447 mg of a pale yellow solid.

201 mg of 1,1'-carbodiimidazole was added to a tetrahydrofuran (5 ml) solution of the obtained yellow solid, and stirred for 12 hours.

The reaction liquid was added to a solution of 157 mg of sodium borohydride in water (5 ml), and stirred at room temperature for 30 minutes. Aqueous 10% citric acid solution was added to it, extracted with ethyl acetate, the organic layer was washed with saturated saline water. After dried, the solvent was evaporated away under reduced pressure, and the residue was purified through silica gel column chromatography (developing solvent: hexane/ethyl acetate=9/1 to 1/9) to obtain 234 mg of the entitled compound as yellow oil.

(Step 4) Production of 1-{[5-[4-(methylsulfonyl)phenoxy]-2-(2-pyrazinyl)-1H-benzimidazol-6-yl]methyl}pyrrolidine-2,5-dione Using the obtained alcohol compound, the entitled compound was obtained in the same method as in Example 19 (step 8) or in accordance with the method or by combining it with an ordinary method.

$^1$HNMR (CDCl$_3$) δ: 1.71 (3H, s), 2.57 (2H, s), 2.69 (2H, s), 3.06 (3/2H, s), 3.07 (3/2H, s), 4.79 (1H, s), 4.80 (1H, s), 7.05-7.15 (2H+1/2H, m), 7.47 (1/2H, s), 7.68 (1/2H, s), 7.77 (1/2H, s), 7.85-7.95 (2H, m), 8.60 (1H, m), 8.68 (1H, m), 9.61 (1H, dd, J=1.6, 7.0 Hz), 10.59 (1H, br).

ESI-MS (m/e): 478[M+H].

Example 35

1-{[5-[4-(Methylsulfonyl)phenoxy]-2-(2-pyrazinyl)-1H-benzimidazol-6-yl]methyl}-2-pyrrolidinone Using the alcohol compound obtained in Example 34 (step 3), the entitled compound was obtained in the same method as in Example 2 or in accordance with the method or by combining it with an ordinary method.

$^1$HNMR (CDCl$_3$) δ: 1.90-2.02 (2H, m), 2.30-2.45 (2H, m), 3.07 (3H, s), 3.30-3.40 (2H, m), 4.55 (2H, s), 7.00-7.10 (2H, m), 7.18 (3/7H, s), 7.50 (4/7H, s), 7.68 (4/7H, s), 7.78 (3/7H, s), 7.83-7.92 (2H, m), 8.55-8.66 (1H, m), 8.67 (1H, m), 9.62 (1H, m), 11.0 (3/7H, br), 11.5 (4/7H, br).

ESI-MS (m/e): 464[M+H].

Example 36

1-{[5-[4-(Ethylsulfonyl)phenoxy]-2-(2-pyrazinyl)-1H-benzimidazol-6-yl]methyl}pyrrolidine-2,5-dione (Step 1) Production of (5-[4-(ethylsulfonyl)phenoxy]-2-(2-pyrazinyl)-1-{[2-(trimethylsilyl)ethoxy]methyl}-1H-benzimidazol-6-yl)methanol and (6-[4-(ethylsulfonyl)phenoxy]-2-(2-pyrazinyl)-1-{[2-(trimethylsilyl)ethoxy]methyl}-1H-benzimidazol-6-yl)methanol Using 4-(ethylsulfonyl)phenol obtained in Reference Example 2, the entitled compound was obtained in the same method as in Example 34 (step 2, step 3) or in accordance with the method or by combining it with an ordinary method.

(Step 2) Production of 1-{[5-[4-(ethylsulfonyl)phenoxy]-2-(2-pyrazinyl)-1H-benzimidazol-6-yl]methyl}pyrrolidine-2,5-dione Using the obtained alcohol, the entitled compound was obtained in the same method as in Example 19 (step 8) or in accordance with the method or by combining it with an ordinary method.

$^1$HNMR (CDCl$_3$) δ: 1.23-1.31 (3H, m), 2.54 (2H, s), 2.67 (2H, s), 3.11 (2H, q, J=14.8 Hz), 4.79 (2H, s), 7.06 (1/2H, s), 7.08-7.11 (2H, m), 7.46 (1/2H, s), 7.67 (1/2H, s), 7.76 (1/2H, s), 7.81-7.87 (2H, m), 8.57-8.60 (1H, m), 8.66 (1H, m), 9.60 (1H, m), 10.48 (1H, d, J=11.7 Hz).

ESI-MASS (m/e): 492(M+H).

Example 37

1-{[5-[4-(Ethylsulfonyl)phenoxy]-2-(2-pyrazinyl)-1H-benzimidazol-6-yl]methyl}-2-pyrrolidinone Using the alcohol compound obtained in Example 36 (step 1), the entitled compound was obtained in the same method as in Example 2 or in accordance with the method or by combining it with an ordinary method.

$^1$HNMR (CDCl$_3$) δ: 1.32 (3H, t, J=7.4 Hz), 1.94-2.01 (2H, m), 2.35-2.41 (2H, m), 3.14 (2H, q, J=7.4 Hz), 3.33-3.36 (2H, m), 4.58 (2H, d, J=3.5 Hz), 7.09 (2H, m), 7.22 (1/2H, m), 7.53 (1/2H, s), 7.66 (1/2H, s), 7.82 (1/2H, s), 7.87 (2H, d, J=8.2 Hz), 8.62 (1H, m), 8.70 (1H, d, J=2.3 Hz), 9.63-9.66 (1H, m), 10.48 (1/2H, s), 10.73 (1/2H, s).

ESI-MASS (m/e): 478(M+H).

Example 38

3-{[5-[4-(Ethylsulfonyl)phenoxy]-2-(2-pyridinyl)-1H-benzimidazol-6-yl]methyl}-2-pyrrolidinone Using the alcohol compound obtained in Example 36 (step 1) and 2-oxazolidone, the entitled compound was obtained in the same method as in Example 2 or in accordance with the method or by combining it with an ordinary method.

$^1$HNMR (CDCl$_3$) δ: 1.29 (3H, t, 7.4 Hz), 3.11 (2H, q, J=7.4 Hz), 3.50 (2H, m), 4.25 (2H, m), 4.53 (2H, s), 7.06-7.09 (3H, m), 7.84-7.86 (3H, m), 8.61 (1H, m), 8.68 (1H, d, J=2.3 Hz), 9.62 (1H, d, J=1.6 Hz).

ESI-MASS (m/e): 480(M+H).

Example 39

1-{[5-[6-(Ethylsulfonyl)-3-pyridinyl]oxy}-2-(2-pyridinyl)-1H-benzimidazol-6-yl]methyl}pyrrolidine-2,5-dione (Step 1) Production of (5-{[6-(ethylsulfonyl)-3-pyridinyl]oxy}-2-(2-pyridinyl)-1-{[2-(trimethylsilyl)ethoxy]methyl}-1H-benzimidazol-6-yl)methanol and (6-{[6-(ethylsulfonyl)-3-pyridinyl]oxy}-2-(2-pyridinyl)-1-{[2-(trimethylsilyl)ethoxy]methyl}-1H-benzimidazol-5-yl)methanol Using 6-(ethylsulfonyl)-3-pyridinol obtained in Reference Example 4, the entitled compound was obtained in the same method as in Example 19 (step 5 to step 7) or in accordance with the method or by combining it with an ordinary method.

(Step 2) Production of 1-{[5-[6-(ethylsulfonyl)-3-pyridinyl]oxy}-2-(2-pyridinyl)-1H-benzimidazol-6-yl]methyl}pyrrolidine-2,5-dione Using the obtained alcohol compound, the entitled compound was obtained in the same method as in Example 19 (step 8) or in accordance with the method or by combining it with an ordinary method.

$^1$HNMR (CDCl$_3$) δ: 1.27-1.37 (3H, m), 2.63 (2H, s), 2.70 (2H, s), 3.30-3.45 (2H, m), 4.77 (1H, 2), 4.79 (1H, s), 7.10 (1/2H, s), 7.35-7.45 (2H, m), 7.45 (1/2H, m), 7.67 (1/2H, s), 7.80 (1/2H, s), 7.88 (1H, m), 8.03 (1H, m), 8.39 (1H, m), 8.49 (1H, m), 8.64 (1H, m), 10.8 (1H, br).

ESI-MS (m/e): 492[M+H].

Example 40

1-{[5-[6-(Ethylsulfonyl)-3-pyridinyl]oxy}-2-(2-pyridinyl)-1H-benzimidazol-6-yl]methyl}-2-pyrrolidinone Using the alcohol compound obtained in Example 39 (step 1), the entitled compound was obtained in the same method as in Example 2 or in accordance with the method or by combining it with an ordinary method.

$^1$HNMR (CDCl$_3$) δ: 1.31 (3H, t, J=7.6 Hz), 1.95 (2H, m), 2.34 (2H, dt, J=8.0, 16 Hz), 3.30 (2H, q, J=7.0 Hz), 3.39 (2H, q, J=7.6 Hz), 4.54 (1H, s), 4.55 (1H, s), 7.17 (1/2H, s), 7.33 (1H, dd, J=2.7, 8.8 Hz), 7.41 (1H, m), 7.48 (1/2H, s), 7.58 (1/2H, s), 7.79 (1/2H, s), 7.91 (1H, m), 8.01 (1H, m), 8.38-8.45 (1H+1/2H, m), 8.47 (1/2H, m), 8.65 (1H, m), 11.0 (1/2H, br), 11.1 (1/2H, br).

ESI-MS (m/e): 478[M+H].

Example 41

3-{[5-{[6-(Ethylsulfonyl)-3-pyridinyl]oxy}-2-(2-pyridinyl)-1H-benzimidazol-6-yl]methyl}-2-pyrrolidinone Using the alcohol compound obtained in Example 39 (step 1) and 2-oxazolidone, the entitled compound was obtained in the same method as in Example 2 or in accordance with the method or by combining it with an ordinary method.

$^1$HNMR (CDCl$_3$) δ: 1.31 (3H, t, J=7.6 Hz), 3.34-3.42 (2H, q, J=7.6 Hz), 3.43-3.53 (2H, m), 4.25 (2H, q, J=8.0 Hz), 4.52 (1H, s), 4.54 (1H, s), 7.20 (1/2H, m), 7.32-7.37 (1H, m), 7.38-7.45 (1H, m), 7.50 (1/2H, s), 7.63 (1/2H, s), 7.85-7.92 (1H+1/2H, m), 8.01 (1H, d, J=8.6 Hz), 8.37-8.45 (1H+1/2H, m), 8.48 (1/2H, m), 8.65 (1H, m), 11.1 (1H, br).

ESI-MS (m/e): 480[M+H].

Example 42

1-{[5-{[6-Methylsulfonyl)-3-pyridinyl]oxy}-2-(2-pyridinyl)-1H-benzimidazol-6-yl]methyl}pyrrolidine-2,5-dione (Step 1) Production of (5-{[6-(methylsulfonyl)-3-pyridinyl]oxy}-2-(2-pyridinyl)-1-{[2-(trimethylsilyl)ethoxy]methyl}-1H-benzimidazol-6-yl)methanol and (6-{[6-(methylsulfonyl)-3-pyridinyl]oxy}-2-(2-pyridinyl)-1-{[2-(trimethylsilyl)ethoxy]methyl}-1H-benzimidazol-5-yl)methanol Using 6-(methylsulfonyl)-3-pyridinol obtained in Reference Example 3, the entitled compound was obtained in the same method as in Example 19 (step 5 to step 7) or in accordance with the method or by combining it with an ordinary method.

(Step 2) Production of 1-{[5-{[6-methylsulfonyl)-3-pyridinyl]oxy}-2-(2-pyridinyl)-1H-benzimidazol-6-yl]methyl}pyrrolidine-2,5-dione Using the obtained alcohol compound, the entitled compound was obtained in the same method as in Example 19 (step 8) or in accordance with the method or by combining it with an ordinary method.

$^1$HNMR (CDCl$_3$) δ: 2.61 (2H, m), 2.69 (2H, m), 3.24 (3H, m), 4.77 (2H, d, J=9.0 Hz), 7.12 (1/2H, s), 7.35-7.41 (2H, m), 7.44 (1/2H, s), 7.69 (1/2H, s), 7.80 (1/2H, s), 7.87 (1H, m), 8.02 (1H, d, J=13.7, 8.6 Hz), 8.37 (1H, m), 8.48 (1H, m), 8.64 (1H, m), 10.57 (1H, s).

ESI-MASS (m/e): 478(M+H).

Example 43

1-{[5-{[6-Methylsulfonyl)-3-pyridinyl]oxy}-2-(2-pyridinyl)-1H-benzimidazol-6-yl]methyl}-2-pyrrolidinone Using the alcohol compound obtained in Example 42 (step 1), the entitled compound was obtained in the same method as in Example 2 or in accordance with the method or by combining it with an ordinary method.

$^1$HNMR (CDCl$_3$) δ: 1.90-1.98 (2H, m), 2.30-2.35 (2H, m), 3.21 (3H, s), 3.30 (2H, m), 4.53 (2H, d, J=3.9 Hz), 7.19 (1/2H, s), 7.33 (1H, s), 7.40 (1H, m), 7.49 (1/2H, m), 7.57 (1/2H, m), 7.78 (1/2H, m), 7.88 (1H, s), 8.00-8.01 (1H, m), 8.36-8.46 (2H, m), 8.64 (1H, s), 10.65 (1H, s).

ESI-MASS (m/e): 464(M+H).

Example 44

1-{[5-{[3-Chloro-4-(methylsulfonyl)phenoxy]-2-(2-pyridinyl)-1H-benzimidazol-6-yl]methyl}pyrrolidine-2,5-dione (Step 1) Production of (5-[3-chloro-4-(methylsulfonyl)phenoxy]-2-(2-pyridinyl)-1-{[2-(trimethylsilyl)ethoxy]methyl}-1H-benzimidazol-6-yl)methanol and (6-[3-chloro-4-(methylsulfonyl)phenoxy]-2-(2-pyridinyl)-1-{[2-(trimethylsilyl)ethoxy]methyl}-1H-benzimidazol-5-yl)methanol Using 3-chloro-4-(methylsulfonyl)phenol obtained in Reference Example 5, the entitled compound was obtained in the same method as in Example 19 (step 5 to step 7) or in accordance with the method or by combining it with an ordinary method.

(Step 2) Production of 1-{[5-{[3-chloro-4-(methylsulfonyl)phenoxy]-2-(2-pyridinyl)-1H-benzimidazol-6-yl]methyl}pyrrolidine-2,5-dione Using the obtained alcohol compound, the entitled compound was obtained in the same method as in Example 19 (step 8) or in accordance with the method or by combining it with an ordinary method.

$^1$HNMR (CDCl$_3$) δ: 2.63 (4H×1/2, s), 2.71 (4H×1/2, s), 3.28 (3H×1/2, s), 3.28 (3H×1/2, s), 4.77 (2H×1/2, s), 4.78 (2H×1/2, s), 6.99-7.04 (2H×1/2, m), 7.11 (1H×1/2, d, J=2.3 Hz), 7.15 (1H×1/2, d, J=2.3 Hz), 7.15 (1H×1/2, s), 7.40-7.44 (1H, m), 7.47 (1H×1/2, s), 7.69 (1H×1/2, s), 7.81 (1H×1/2, s), 7.86-7.94 (1H, m), 8.08-8.15 (1H, m), 8.38-8.45 (1H, m), 8.64-8.69 (1H, m), 10.62 (1H×1/2, brs), 10.65 (1H×1/2, brs).

ESI-MASS (m/e): 511(M+H).

Example 45

1-{[5-{[3-Chloro-4-(methylsulfonyl)phenoxy]-2-(2-pyridinyl)-1H-benzimidazol-6-yl]methyl}-2-pyrrolidinone Using the alcohol compound obtained in Example 44 (step 1), the entitled compound was obtained in the same method as in Example 2 or in accordance with the method or by combining it with an ordinary method.

$^1$HNMR (CDCl$_3$) δ: 1.93-2.02 (2H, m), 2.33-2.41 (2H, m), 3.27 (3H, s), 3.31-3.34 (2H, m), 4.53 (2H×1/2, s), 4.54 (2H×1/2, s), 6.93-7.03 (1H, m), 7.08-7.10 (1H, m), 7.21 (1H×1/2, s), 7.41-7.44 (1H, m), 7.51 (1H×1/2, s), 7.59 (1H×1/2, s), 7.80 (1H×1/2, s), 7.88-7.93 (1H, m), 8.08 (1H, d, J=9.0 Hz), 8.42 (1H, t, J=8.4 Hz), 8.65-8.69 (1H, m), 10.79 (1H×1/2, brs), 10.85 (1H×1/2, brs).

ESI-MASS (m/e): 497(M+H).

Example 46

3-{[5-{[3-Chloro-4-(methylsulfonyl)phenoxy]-2-(2-pyridinyl)-1H-benzimidazol-6-yl]methyl}-2-oxazolidinone Using the alcohol compound obtained in Example 44 (step 1) and 2-oxazolidone, the entitled compound was obtained in the same method as in Example 2 or in accordance with the method or by combining it with an ordinary method.

$^1$HNMR (CDCl$_3$) δ: 3.25 (3H, s), 3.42-3.51 (2H, m), 4.22-4.29 (2H, m), 4.48 (2H×1/2, s), 4.50 (2H×1/2, s), 6.93-6.99 (1H, m), 7.05-7.10 (1H, m), 7.20 (1H×1/2, s), 7.39-7.44 (1H, m), 7.50 (1H×1/2, s), 7.64 (1H×1/2, s), 7.85-7.90 (1H, m), 7.90 (1H×1/2, s), 8.06 (1H, d, J=8.6 Hz), 8.39 (1H×1/2, d, J=8.6 Hz), 8.41 (1H×1/2, d, J=8.6 Hz), 8.63-8.68 (1H, m), 10.84 (1H, brs).

ESI-MASS (m/e): 499(M+H).

Example 47

4-{[6-[(2,5-Dioxo-1-pyrrolidinyl)methyl]-2-(2-pyridinyl)-1H-benzimidazol-5-yl]oxy}benzonitrile Using 4-cyanophenyl, the entitled compound was obtained in the same method as in Example 19 (step 5 to step 8) or in accordance with the method or by combining it with an ordinary method.

$^1$HNMR (CDCl$_3$) δ: 2.53 (4H×1/2, s), 2.63 (4H×1/2, s), 4.76 (2H×1/2, s), 4.77 (2H×1/2, s), 6.99 (1H, d, J=9.0 Hz), 7.02 (1H, d, J=9.0 Hz), 7.11 (1H×1/2, s), 7.36-7.40 (1H, m), 7.43 (1H×1/2, s), 7.58 (1H, d, J=9.0 Hz), 7.61 (1H, d, J=9.0 Hz), 7.63 (1H×1/2, s), 7.75 (1H×1/2, s), 7.84-7.89 (1H, m), 8.34-8.39 (1H, m), 8.60-8.66 (1H, m), 10.46 (1H×1/2, brs), 10.52 (1H×1/2, brs).

ESI-MASS (m/e): 424(M+H).

Example 48

1-{[5-[(6-Methyl-3-pyridinyl)oxy]-2-(2-pyridinyl)-1H-benzimidazol-6-yl]methyl}pyrrolidine-2,5-dione Using 4-hydroxy-6-methylpyridine, the entitled compound was obtained in the same method as in Example 19 (step 5 to step 8) or in accordance with the method or by combining it with an ordinary method.

$^1$HNMR (CDCl$_3$) δ: 2.53 (3H, d, J=8.2 Hz), 2.60 (2H, s), 2.69 (2H, s), 4.87 (2H, d, J=9.4 Hz), 7.08-7.13 (1H, m), 7.32 (2H, m), 7.52 (1H, m), 7.65 (1/2H, m), 7.83-7.85 (1H, m), 8.26 (1/2H, s), 8.32-8.34 (2H, m), 8.60 (11H, m).

ESI-MASS (m/e): 414(M+H).

Example 49

1-{[5-[6-Methyl-3-pyridinyl)sulfanyl]-2-(2-pyridinyl)-1H-benzimidazol-6-yl]methyl}pyrrolidine-2,5-dione Using 6-methylpyridine-3-thiol produced according to the method described in WO2004/081001, the entitled compound was obtained in the same method as in Example 19

(step 5 to step 8) or in accordance with the method or by combining it with an ordinary method.

$^1$HNMR (CDCl$_3$) δ: 10.59 (brs, 1H), 8.62 (d, 1H, J=4.7 Hz), 8.40-8.37 (m, 2H), 7.85 (m, 1H), 7.56 (d, 1H, J=15.7 Hz), 7.42-7.43 (m, 3H), 7.03 (s, 1H), 4.99 (s, 2H), 2.76 (s, 2H), 2.68 (s, 2H), 2.47 (s, 3H).

ESI-MASS (m/e): 414(M+H).

Example 50

1-{[5-[4-(Methoxymethyl)phenoxy]-2-(2-pyridinyl)-1H-benzimidazol-6-yl]methyl}pyrrolidine-2,5-dione (Step 1) Production of methyl 5-(4-formylphenoxy)-2-(2-pyridinyl)-{[2-(trimethylsilyl)ethoxy]methyl}-1H-benzimidazole-6-carboxylate and methyl 6-(4-formylphenoxy)-2-(2-pyridinyl)-{[2-(trimethylsilyl)ethoxy]methyl}-1H-benzimidazole-5-carboxylate Using 4-hydroxybenzaldehyde, the entitled compound was obtained in the same method as in Example 19 (step 5 to step 6) or in accordance with the method or by combining it with an ordinary method.

(Step 2) Production of methyl 5-[4-(hydroxymethyl)phenoxy]-2-(2-pyridinyl)-{[2-(trimethylsilyl)ethoxy]methyl}-1H-benzimidazole-6-carboxylate and methyl 6-[4-(hydroxymethyl)phenoxy]-2-(2-pyridinyl)-{[2-(trimethylsilyl)ethoxy]methyl}-1H-benzimidazole-5-carboxylate In an ice bath, 54 mg of sodium borohydride was added to a methanol (5 ml) solution of 362 mg of the obtained product, and stirred at room temperature for 20 minutes. Aqueous saturated ammonium chloride solution was added to the reaction liquid, extracted with ethyl acetate, and the organic layer was washed with saturated saline water. After dried, the solvent was removed to obtain 337 mg of a crude product of the entitled compound as a yellow solid.

(Step 3) Production of methyl 5-[4-(methoxymethylmethyl)phenoxy]-2-(2-pyridinyl)-{[2-(trimethylsilyl)ethoxy]methyl}-1H-benzimidazole-6-carboxylate and methyl 6-[4-(methoxymethylmethyl)phenoxy]-2-(2-pyridinyl)-{[2-(trimethylsilyl)ethoxy]methyl}-1H-benzimidazole-5-carboxylate In an ice bath, 89 µl of methyl iodide and 57 mg of sodium hydride (with 30% liquid paraffin added thereto) was added to a DMF (5 ml) solution of 337 mg of the obtained product, and stirred at room temperature for 30 minutes. Aqueous saturated ammonium chloride solution was added to the reaction liquid, extracted with ethyl acetate, and the organic layer was washed with saturated saline water. After dried, the solvent was removed to obtain 346 mg of a crude product of the entitled compound as brown oil.

(Step 4) Production of 1-{[5-[4-(methoxymethyl)phenoxy]-2-(2-pyridinyl)-1H-benzimidazol-6-yl]methyl}pyrrolidine-2,5-dione Using the obtained product, the entitled compound was obtained in the same method as in Example 19 (step 7, step 8) or in accordance with the method or by combining it with an ordinary method.

$^1$HNMR (CDCl$_3$) δ: 2.57 (4H, d, J=24.3 Hz), 3.37 (3H, s), 4.40 (2H, s), 4.85 (2H, s), 6.93 (2H, d, J=8.2 Hz), 7.27 (3H, d, J=8.2 Hz), 7.33-7.37 (1H, m), 7.60 (1H, brs), 7.84 (1H, td, J=7.8, 8.1 Hz), 8.35 (1H, d, J=7.8 Hz), 8.60 (1H, d, J=4.3 Hz).

ESI-MASS (m/e): 443(M+H).

Example 51

1-{5-[4-(2-oxo-1,3-oxozolan-3-yl)phenoxy]-2-(2-pyridinyl)-1H-benzimidazol-6-yl}methyl}pyrrolidine-2,5-dione (Step 1) Production of methyl 5-(4-iodophenoxy)-2-(2-pyridinyl)-{[2-(trimethylsilyl)ethoxy]methyl}-1H-benzimidazole-6-carboxylate and methyl 6-(4-iodophenoxy)-2-(2-pyridinyl)-{[2-(trimethylsilyl)ethoxy]methyl}-1H-benzimidazole-5-carboxylate Using 4-iodophenol, the entitled compound was obtained in the same method as in Example 19 (step 5, step 6) or in accordance with the method or by combining it with an ordinary method.

(Step 2) Production of methyl 5-[4-(2-oxo-1,3-oxazolan-3-yl)]-2-(2-pyridinyl)-1H-benzimidazole-6-carboxylate and methyl 6-[4-(2-oxo-1,3-oxazolan-3-yl)]-2-(2-pyridinyl)-1H-benzimidazole-5-carboxylate 186 mg of 2-oxazolidone, 20 mg of copper(I) iodide and 148 mg of potassium carbonate were added to a DMF (7 ml) solution of 642 mg of the obtained product, and stirred under heat at 150° C. for 28 hours. The reaction liquid was restored to room temperature, then aqueous saturated ammonium chloride solution was added to it, extracted with ethyl acetate, and the organic layer was washed with saturated saline water. After dried, the residue was purified through silica gel column chromatography (developing solvent: chloroform/methanol=10/0 to 100/1) to obtain 427 mg of the entitled compound as a brown oil.

(Step 3) Production of 1-{5-[4-(2-oxo-1,3-oxozolan-3-yl)phenoxy]-2-(2-pyridinyl)-1H-benzimidazol-6-yl}methyl}pyrrolidine-2,5-dione Using the obtained product, the entitled compound was obtained in the same method as in Example 34 (step 3, step 4) or in accordance with the method or by combining it with an ordinary method.

$^1$HNMR (CDCl$_3$) δ: 2.51-2.53 (2H, m), 2.65-2.71 (2H, m), 4.05-4.10 (2H, m), 4.56-4.49 (2H, m), 4.86 (2H, d, J=12.5 Hz), 6.98 (2H, d, J=12.5 Hz), 7.32 (2H, m), 7.49 (2H, m), 7.63 (1H, d, J=9.8 Hz), 7.84 (1H, dd, J=7.8, 5.9 Hz), 8.34-8.36 (1H, m), 8.59-8.61 (1H, m).

ESI-MASS (m/e): 484(M+H).

Example 52

1-[(5-{[6-(5-Methyl-1,2,4-oxadiazol-3-yl)-3-pyridinyl]oxy}-2-(2-pyridinyl)-1H-benzimidazol-6-yl)methyl]pyrrolidine-2,5-dione (Step 1) Production of methyl 5-{[6-(5-methyl-1,2,4-oxadiazol-3-yl)-3-pyridinyl]oxy}-2-(2-pyridinyl)-1-{[2-(trimethylsilyl)ethoxy]methyl}-1H-benzimidazole-6-carboxylate and methyl 6-{[6-(5-methyl-1,2,4-oxadiazol-3-yl)-3-pyridinyl]oxy}-2-(2-pyridinyl)-1-{[2-(trimethylsilyl)ethoxy]methyl}-1H-benzimidazole-5-carboxylate Using 6-(5-methyl-1,2,4-oxadiazol-3-yl)-3-pyridinol obtained from Reference Example 6, the entitled compound was obtained in the same method as in Example 19 (step 5, step 6) or in accordance with the method or by combining it with an ordinary method.

(Step 2) Production of (5-{[6-(5-methyl-1,2,4-oxadiazol-3-yl)-3-pyridinyl]oxy}-2-(2-pyridinyl)-1-[{2-(trimethylsilyl)ethoxy]methyl}-1H-benzimidazol-6-yl)methanol and (6-{[6-(5-methyl-1,2,4-oxadiazol-3-yl)-3-pyridinyl]oxy}-2-(2-pyridinyl)-1-[{2-(trimethylsilyl)ethoxy]methyl}-1H-benzimidazol-5-yl)methanol The entitled compound was obtained in the same method as in Example 34 (step 3) or in accordance with the method or by combining it with an ordinary method.

(Step 3) Production of 1-[(5-{[6-(5-methyl-1,2,4-oxadiazol-3-yl)-3-pyridinyl]oxy}-2-(2-pyridinyl)-1H-benzimidazol-6-yl)methyl]pyrrolidine-2,5-dione Using the obtained alcohol compound, the entitled compound was obtained in the same method as in Example 19 (step 8) or in accordance with the method or by combining it with an ordinary method.

$^1$HNMR (CDCl$_3$) δ: 2.58 (2H, s), 2.67 (2H, s), 2.67 (3H, s), 4.82 (2H×1/2, s), 4.84 (2H×1/2, s), 7.08 (1H×1/2, s), 7.30-7.40 (2H, m), 7.44 (1H×1/2, s), 7.61 (1H×1/2, s), 7.74 (1H× 1/2, s), 7.86 (1H×1/2, t, J=8.2 Hz), 7.86 (1H×1/2, t, J=8.2 Hz), 8.02 (1H×1/2, d, J=8.6 Hz), 8.06 (1H×1/2, d, J=9.4 Hz), 8.35 (1H×1/2, d, J=8.2 Hz), 8.37 (1H×1/2, d, J=8.2 Hz), 8.53 (1H×1/2, d, J=2.3 Hz), 8.57 (1H×1/2, d, J=2.3 Hz), 8.61 (1H×1/2, d, J=4.3 Hz), 8.63 (1H, d×1/2, J=4.3 Hz), 10.60 (1H×1/2, brs), 10.64 (1H×1/2, brs).

ESI-MASS (m/e): 482(M+H).

Example 53

1-[(5-{[6-(5-Methyl-1,2,4-oxadiazol-3-yl)-3-pyridinyl]oxy}-2-(2-pyridinyl)-1H-benzimidazol-6-yl)methyl]-2-pyrrolidinone Using the alcohol compound obtained in Example 52 (step 2), the entitled compound was obtained in the same method as in Example 2 or in accordance with the method or by combining it with an ordinary method.

$^1$HNMR (CDCl$_3$) δ: 1.90-1.98 (2H, m), 2.30-2.38 (2H, m), 2.67 (3H, s), 3.29-3.35 (2H, m), 4.57 (2H×1/2, s), 4.59 (2H× 1/2, s), 7.14 (1H×1/2, s), 7.30 (1H×1/2, dd, J=9.0, 2.7 Hz), 7.33 (1H×1/2, dd, J=9.0, 2.3 Hz), 7.38 (1H×1/2, dd, J=8.2, 5.5 Hz), 7.38 (1H×1/2, dd, J=8.2, 5.1 Hz), 7.47 (1H×1/2, s), 7.57 (1H×1/2, s), 7.77 (1H×1/2, s), 7.86 (1H×1/2, t, J=8.2 Hz), 7.87 (1H×1/2, t, J=8.2 Hz), 8.02 (1H×1/2, d, J=9.0 Hz), 8.04 (1H×1/2, d, J=9.0 Hz), 8.37 (1H×1/2, d, J=8.2 Hz), 8.40 (1H×1/2, d, J=8.2 Hz), 8.47 (1H×1/2, d, J=2.3 Hz), 8.54 (1H×1/2, d, J=2.7 Hz), 8.62 (1H×1/2, d, J=5.5 Hz), 8.64 (1H×1/2, d, J=5.1 Hz), 10.84 (1H×1/2, brs), 10.94 (1H×1/2, brs).

ESI-MASS (m/e): 468(M+H).

Example 54

1-[(5-{[6-(5-Methyl-1,2,4-oxadiazol-3-yl)-3-pyridinyl]oxy}-2-(2-pyridinyl)-1H-benzimidazol-6-yl)methyl]-2-oxazolidinone Using the alcohol compound obtained in Example 52 (step 2) and 2-oxazolidone, the entitled compound was obtained in the same method as in Example 2 or in accordance with the method or by combining it with an ordinary method.

$^1$HNMR (CDCl$_3$) δ: 2.67 (3H, s), 3.46-3.53 (2H, m), 4.21-4.27 (2H, m), 4.55 (2H×1/2, s), 4.58 (2H×1/2, s), 7.17 (1H× 1/2, s), 7.32 (1H×1/2, dd, J=8.6, 2.7 Hz), 7.35 (1H×1/2, dd, J=8.6, 2.3 Hz), 7.39 (1H×1/2, dd, J=8.2, 5.5 Hz), 7.39 (1H× 1/2, dd, J=8.2, 5.0 Hz), 7.49 (1H×1/2, s), 7.64 (1H×1/2, s), 7.84-7.90 (1H, m), 7.87 (1H×1/2, s), 8.04 (1H×1/2, d, J=8.6 Hz), 8.06 (1H×1/2, d, J=8.6 Hz), 8.38 (1H×1/2, d, J=8.2 Hz), 8.40 (1H×1/2, d, J=8.2 Hz), 8.47 (1H×1/2, d, J=2.3 Hz), 8.54 (1H×1/2, d, J=2.7 Hz), 8.62 (1H×1/2, d, J=5.5 Hz), 8.65 (1H×1/2, d, J=5.0 Hz), 10.79 (1H×1/2, brs), 10.85 (1H×1/2, brs).

ESI-MASS (m/e): 470(M+H).

Example 55

1-{[5-[4-(5-Methyl-1,2,4-oxadiazol-3-yl)phenoxy]-2-(2-pyridinyl)-1H-benzimidazol-6-yl]methyl}pyrrolidine-2,5-dione (Step 1) Production of (5-[4-(5-methyl-1,2,4-oxadiazol-3-yl)phenoxy]-2-(2-pyridinyl)-1-{[2-(trimethylsilyl)ethoxy]methyl}-1H-benzimidazol-6-yl)methanol and (6-[4-(5-methyl-1,2,4-oxadiazol-3-yl) phenoxy]-2-(2-pyridinyl)-1-{[2-(trimethylsilyl) ethoxy]methyl}-1H-benzimidazol-5-yl)methanol Using 4-(5-methyl-1,2,4-oxadiazol-3-yl)phenol obtained from Reference Example 7, the entitled compound was obtained in the same method as in Example 52 (step 1, step 2) or in accordance with the method or by combining it with an ordinary method.

(Step 2) Production of 1-{[5-[4-(5-methyl-1,2,4-oxadiazol-3-yl)phenoxy]-2-(2-pyridinyl)-1H-benzimidazol-6-yl]methyl}pyrrolidine-2,5-dione Using the obtained alcohol compound, the entitled compound was obtained in the same method as in Example 19 (step 8) or in accordance with the method or by combining it with an ordinary method.

$^1$H-NMR (CDCl$_3$) δ: 2.44 (4H×1/2, s), 2.57 (4H×1/2, s), 2.63 (3H×1/2, s), 2.64 (3H×1/2, s), 4.82 (2H×1/2, s), 4.85 (2H×1/2, s), 6.99 (2H×1/2, d, J=8.6 Hz), 7.04 (2H×1/2, d, J=8.6 Hz), 7.10 (1H×1/2, s), 7.34-7.39 (1H, m), 7.45 (1H×1/ 2, s), 7.61 (1H×1/2, s), 7.73 (1H×1/2, s), 7.83-7.87 (1H, m), 7.99 (2H×1/2, d, J=8.6 Hz), 8.02 (2H×1/2, d, J=8.6 Hz), 8.35 (1H×1/2, d, J=7.0 Hz), 8.37 (1H×1/2, d, J=6.7 Hz), 8.60 (1H×1/2, d, J=5.3 Hz), 8.64 (1H×1/2, d, J=5.1 Hz), 10.46 (1H×1/2, s), 10.55 (1H×1/2, s).

ESI-MASS (m/e): 481(M+H).

Example 56

1-{[5-[4-(5-Methyl-1,2,4-oxadiazol-3-yl)phenoxy]-2-(2-pyridinyl)-1H-benzimidazol-6-yl]methyl}-2-pyrrolidinone Using the alcohol compound obtained in Example 55 (step 1), the entitled compound was obtained in the same method as in Example 2 or in accordance with the method or by combining it with an ordinary method.

$^1$HNMR (CDCl$_3$) δ: 1.87-1.95 (2H, m), 2.30-2.36 (2H, m), 3.27-3.33 (2H, m), 4.57 (2H×1/2, s), 4.59 (2H×1/2, s), 7.01 (2H×1/2, d, J=8.6 Hz), 7.03 (2H×1/2, d, J=8.6 Hz), 7.15 (1H×1/2, s), 7.35-7.39 (1H, m), 7.49 (1H×1/2, s), 7.56 (1H×

1/2, s), 7.75 (1H×1/2, s), 7.83-7.88 (1H, m), 8.00 (2H×1/2, d, J=8.6 Hz), 8.00 (2H×1/2, d, J=8.6 Hz), 8.37 (1H×1/2, d, J=8.6 Hz), 8.39 (1H×1/2, d, J=8.6 Hz), 8.61 (1H×1/2, d, J=5.5 Hz), 8.64 (1H×1/2, d, J=5.3 Hz), 10.57 (1H×1/2, brs), 10.66 (1H×1/2, brs).

ESI-MASS (m/e): 467(M+H).

Example 57

1-[5-[4-(Methylsulfonyl)phenoxy]-2-(2-pyridinyl)-1H-benzimidazol-6-yl]-1-ethanol (Step 1) Production of methyl 5-[4-(methylsulfonyl)phenoxy]-2-(2-pyridinyl)-1-{[2-(trimethylsilyl)ethoxy]methyl}-1H-benzimidazole-6-carboxylate and methyl 6-[4-(methylsulfonyl)phenoxy]-2-(2-pyridinyl)-1-{[2-(trimethyl silyl)ethoxy]methyl}-1H-benzimidazole-5-carboxylate The aldehyde compound obtained in Example 1 (step 8) was processed according to the process described in J. Org. Chem. 64(4), 1191 (1999) to obtain the entitled compound. Using 4-(methylsulfonyl)phenol obtained from Reference Example 1, the entitled compound may also be obtained in the same method as in Example 19 (step 5, step 6) or in accordance with the method or by combining it with an ordinary method.

(Step 2) Production of 1-(5-[4-(methylsulfonyl)phenoxy]-2-(2-pyridinyl)-1-{[2-(trimethylsilyl)ethoxy]methyl}-1H-benzimidazol-6-yl)-1-ethanol or 1-(6-[4-(methylsulfonyl)phenoxy]-2-(2-pyridinyl)-1-{[2-(trimethylsilyl)ethoxy]methyl}-1H-benzimidazol-5-yl)-1-ethanol 400 mg of the obtained methyl ester compound was dissolved in 4 ml of tetrahydrofuran and 4 ml of methanol, and 1.5 ml of aqueous 5 N sodium hydroxide solution was added to it and stirred at room temperature for 3 hours. This was neutralized with aqueous 10% citric acid solution, extracted with ethyl acetate and washed with saturated saline water. This was dried with anhydrous magnesium sulfate, and the solvent was evaporated away to obtain 376 mg of a yellow solid.

376 mg of the obtained yellow solid was dissolved in 5 ml of dimethylformamide, and 0.29 ml of triethylamine, 205 mg of N,O-dimethylhydroxylamine hydrochloride, 284 mg of 1-hydroxybenzotriazole monohydrate and 205 mg of 1-(3-dimethylaminopropyl)-3-ethylcarbodiimide hydrochloride were added to it and stirred overnight at room temperature. Water was added to the reaction liquid, diluted with ethyl acetate, and the organic layer was washed with saturated saline water, dried with anhydrous magnesium sulfate, then the solvent was evaporated away, and the residue was purified through silica gel column chromatography (developing solvent: hexane/ethyl acetate=9/1 to 3/1 to 1/1) to obtain 347 mg of a white amorphous substance.

110 mg of the obtained white amorphous substance was dissolved in 2 ml of tetrahydrofuran, and at −78° C., 0.76 ml of methyllithium (1.02 M diethyl ether solution) was added thereto and stirred at −78° C. for 30 minutes. Aqueous saturated ammonium chloride was added to it, diluted with ethyl acetate, and the organic layer was washed with saturated saline water. This was dried with anhydrous magnesium sulfate, the solvent was evaporated away, and the residue was purified through partitioning thin-layer chromatography (Kieselgel™ 60F$_{254}$, Art 5744 (by Merck), hexane/ethyl acetate=1/2) to obtain 66.3 mg of the entitled compound as a pale yellow oil.

(Step 3) Production of 1-(5-[4-(methylsulfonyl)phenoxy]-2-(2-pyridinyl)-1-{[2-(trimethylsilyl)ethoxy]methyl}-1H-benzimidazol-6-yl)-1-ethanol or 1-(6-[4-(methylsulfonyl)phenoxy]-2-(2-pyridinyl)-1-{[2-(trimethylsilyl)ethoxy]methyl}-1H-benzimidazol-5-yl)-1-ethanol 20 mg of the obtained acetyl compound was dissolved in 0.5 ml of methanol, and 20 mg of sodium borohydride was added to it and stirred at room temperature for 15 minutes. The reaction liquid was diluted with ethyl acetate and washed with saturated saline water. This was dried with anhydrous magnesium sulfate, the solvent was evaporated away, and the residue was purified through partitioning thin-layer chromatography (Kieselgel™ 60F$_{254}$, Art 5744 (by Merck), chloroform/methanol=20/1) to obtain 18.3 mg of the entitled compound as a colorless oil.

(Step 4) Production of 1-[5-[4-(methylsulfonyl)phenoxy]-2-(2-pyridinyl)-1H-benzimidazol-6-yl]-1-ethanol 18.3 mg of the obtained product was dissolved in 1 ml of trifluoroacetic acid, and stirred at room temperature for 2 hours. The solvent was evaporated away, and the residue was neutralized with triethylamine and purified through partitioning thin-layer chromatography (Kieselgel™ 60F$_{254}$, Art 5744 (by Merck), chloroform/methanol=10/1) to obtain 11.2 mg of the entitled compound as a white solid.

$^1$HNMR (CDCl$_3$) δ: 1.53 (3H, m), 3.06 (3H, s), 5.18 (1H, m), 7.05-7.10 (2H+1/2H, m), 7.40 (1H+1/2H, m), 7.80 (1/2H, s), 7.82-7.90 (2H, m), 8.10 (1/2H, s), 8.37-8.43 (1H, m), 8.64 (1H, m), 10.6 (1/2H, br), 10.8 (1/2H, br).

ESI-MASS (m/e): 410[M+H].

Example 58

1-[5-[4-(Methylsulfonyl)phenoxy]-2-(2-pyridinyl)-1H-benzimidazol-6-yl]-1,2-ethanediol trifluoroacetate Using the diol compound obtained in Example 1 (step 7), the entitled compound was obtained in the same method as in Example 57 (step 4) or in accordance with the method or by combining it with an ordinary method.

$^1$HNMR (CD$_3$OD) δ: 2.69 (1H, brs), 3.17 (3H, s), 3.62-3.67 (1H, m), 3.82-3.83 (1H, m), 5.12-5.13 (1H, m), 7.27-7.29 (2H, m), 7.42 (1H, s), 7.67-7.71 (1H, m), 8.00-8.02 (2H, m), 8.14-8.17 (2H, m), 8.32-8.34 (1H, m), 8.89 (1H, m).

ESI-MASS (m/e): 410[M+H].

Example 59

[5-[4-(Methylsulfonyl)phenoxy]-2-(2-pyridinyl)-1H-benzimidazol-6-yl]methanol

Using the diol compound obtained in Example 1 (step 7), the entitled compound was obtained in the same method as in Example 57 (step 4) or in accordance with the method or by combining it with an ordinary method.

$^1$HNMR (CDCl$_3$) δ: 3.18-3.19 (3H, m), 4.48-4.51 (2H, m), 5.18-5.19 (1/2H, m), 5.21-5.28 (1/2H, m), 7.05-7.13 (2H, m), 7.40 (1H, s), 7.51-7.55 (1H, m), 7.75 (1H, s), 7.86-7.90 (2H, m), 7.98-8.02 (1H, m), 8.29-8.34 (1H, m), 8.72-8.75 (1H, m), 13.12 (1/2H, brs), 13.25 (1/2H, brs).
ESI-MASS (m/e): 396(M+H).

Example 60

N-methyl-N-{1-[5-[4-(methylsulfonyl)phenoxy]-2-(2-pyridinyl)-1H-benzimidazol-6-yl]ethyl}amine (Step 1) Production of N-1-[5-[4-(methylsulfonyl) phenoxy]-2-(2-pyridinyl)-1-{[2-(trimethylsilyl) ethoxy]methyl}-1H-benzimidazol-6-yl]ethyl-N-methylamine or N-1-[6-[4-(methylsulfonyl)phenoxy]-2-(2-pyridinyl)-1-{[2-(trimethylsilyl)ethoxy]methyl}-1H-benzimidazol-5-yl]ethyl-N-methylamine 33 mg of the acetyl compound obtained in Example 57 (step 2) was dissolved in 0.2 ml of methanol, and 0.2 ml of methylamine (40% methanol solution) was added to it, and a methanol solution of 41 mg of zinc chloride and 38 mg of sodium cyanotrihydroborate was added to it, and stirred at room temperature for 6 hours. Aqueous 10% citric acid was added to it, neutralized with aqueous sodium bicarbonate, and extracted with ethyl acetate. This was dried with anhydrous magnesium sulfate, and the solvent was evaporated away to obtain 30 mg of the entitled compound as a yellow oil.

(Step 2) Production of N-methyl-N-{1-[5-[4-(methylsulfonyl)phenoxy]-2-(2-pyridinyl)-1H-benzimidazol-6-yl]ethyl}amine Using the obtained oil, the entitled compound was obtained in the same method as in Example 57 (step 4) or in accordance with the method or by combining it with an ordinary method.
$^1$HNMR (CDCl$_3$) δ: 1.36 (3H, m), 2.30 (3H, s), 3.07 (3H, s), 3.98 (1H, m), 7.08 (2H+2/5H, m), 7.39 (1H, m), 7.45 (3/5H, m), 77.75 (3/5H, m), 7.88 (3H, m), 7.98 (2/5H, m), 8.40 (1H, m), 8.65 (1H, m).
ESI-MASS (m/e): 423(M+H).

Example 61

N-methyl-N-{1-[5-[4-(methylsulfonyl)phenoxy]-2-(2-pyridinyl)-1H-benzimidazol-6-yl]ethyl}acetamide (Step 1) Production of N-methyl-N-(1-[5-[4-(methylsulfonyl)phenoxy]-2-(2-pyridinyl)-1-{[2-(trimethylsilyl)ethoxy]methyl}-1H-benzimidazol-6-yl]ethyl)acetamide or N-methyl-N-(1-[6-[4-(methylsulfonyl)phenoxy]-2-(2-pyridinyl)-1-{[2-(trimethylsilyl)ethoxy]methyl}-1H-benzimidazol-5-yl]ethyl)acetamide 30 mg of the N-methylamine compound obtained in Example 60 (step 1) was dissolved in 0.3 ml of chloroform, and 15 μl of triethylamine and 8 μl of acetyl chloride were added thereto and stirred at room temperature for 30 minutes. Water was added to it, diluted with ethyl acetate and washed with saturated saline water. This was dried with anhydrous magnesium sulfate, the solvent was evaporated away, and the residue was purified through partitioning thin-layer chromatography (Kieselgel™ 60F$_{254}$, Art 5744 (by Merck), chloroform/methanol=20/1) to obtain 19.1 mg of a colorless oil.

(Step 2) Production of N-methyl-N-{1-[5-[4-(methylsulfonyl)phenoxy]-2-(2-pyridinyl)-1H-benzimidazol-6-yl]ethyl}acetamide Using the obtained oil, the entitled compound was obtained in the same method as in Example 57 (step 4) or in accordance with the method or by combining it with an ordinary method.
$^1$HNMR (CDCl$_3$) δ: 1.55 (3H, d, J=7.0 Hz), 1.86 (3H, s), 2.68 (3H, s), 3.06 (3H, s), 6.03 (1H, m), 6.98 (2H, d, J=8.9 Hz), 7.33 (1H, s), 7.56 (1H, m), 7.85 (2H, d, J=8.9 Hz), 7.90-8.06 (2H, m), 8.53 (1H, m), 8.71 (1H, m).
ESI-MASS (m/e): 465[M+H].

Example 62

N,N-dimethyl-N-{1-[5-[4-(methylsulfonyl)phenoxy]-2-(2-pyridinyl)-1H-benzimidazol-6-yl] ethyl}amine Using N,N-dimethylamine, the entitled compound was obtained in the same method as in Example 60 (step 1) or in accordance with the method or by combining it with an ordinary method.
$^1$HNMR (CDCl$_3$) δ: 1.33 (3H, m), 2.20 (6H, m), 3.07 (3H, s), 3.57 (3/5H, m), 3.71 (2/5H, m), 7.07 (2H, m), 7.14 (2/5H, s), 7.39 (1H, m), 7.45 (3/5H, s), 7.75 (3/5H, s), 7.84-7.90 (3H, m), 8.02 (2/5H, s), 8.40 (1H, m), 8.65 (1H, m), 10.5 (1H, br).
ESI-MASS (m/e): 437[M+H].

Example 63

1-{1-[5-[4-(methylsulfonyl)phenoxy]-2-(2-pyridinyl)-1H-benzimidazol-6-yl]ethyl}pyrrolidine-2,5-dione Using the alcohol compound obtained in Example 57 (step 3), the entitled compound was obtained in the same method as in Example 1 (step 10) or in accordance with the method or by combining it with an ordinary method.
$^1$HNMR (CDCl$_3$) δ: 1.79 (3H, m), 2.10-2.28 (2H, m), 2.28-2.40 (2H, m), 3.06 (3H, s), 5.69 (1H, m), 7.00 (2H, m), 7.42 (1H+1/2H, m), 7.80-8.00 (3H+1/2H, m), 8.20-8.50 (2H, br), 8.67 (1H, m), 10.8 (1H, br).
ESI-MASS (m/e): 491[M+H].

Example 64

{5-[4-(Ethylsulfonyl)phenoxy]-2-(2-pyridinyl)-1H-benzimidazol-6-yl}(4-fluorophenyl)methanol (Step 1) Production of 5-[4-(ethylsulfonyl)phenoxy]-2-(2-pyridinyl)-1-{[2-(trimethylsilyl)ethoxy]methyl}-1H-benzimidazole-6-carbaldehyde and 6-[4-(ethylsulfonyl)phenoxy]-2-(2-pyridinyl)-1-{[2-(trimethylsilyl)ethoxy]methyl}-1H-benzimidazole-5-carbaldehyde 5 ml of triethylamine and 750 mg of pyridine-sulfur trioxide were added to a dimethyl sulfoxide (10 ml) solution of 1.0 g of the alcohol compound obtained in Example 19 (step 7), and the reaction liquid was stirred at room temperature for 15 minutes. The reaction liquid was diluted with ethyl acetate, washed with water and saturated saline water in that order, and dried with anhydrous sodium sulfate. The solvent was evaporated away under reduced pressure to obtain 1.0 g of the entitled compound as an orange solid.

(Step 2) Production of {5-[4-(ethylsulfonyl)phenoxy]-2-(2-pyridinyl)-1-{[2-(trimethylsilyl)ethoxy]methyl}-1H-benzimidazol-6-yl}(4-fluorophenyl)methanol or {6-[4-(ethylsulfonyl)phenoxy]-2-(2-pyridinyl)-1-{[2-(trimethylsilyl)ethoxy]methyl}-1H-benzimidazol-5-yl}(4-fluorophenyl)methanol At 0° C., 0.5 ml of 4-fluorophenylmagnesium bromide (1 M tetrahydrofuran solution) was added to a tetrahydrofuran (1 ml) solution of 45 mg of the obtained aldehyde compound, and the reaction liquid was stirred for 1 hour. The reaction liquid was diluted with ethyl acetate, washed with aqueous saturated ammonium chloride and saturated saline water, in that order and dried with anhydrous sodium sulfate. The solvent was evaporated away under reduced pressure, and the residue was purified through silica gel column chromatography (developing solvent: hexane/ethyl acetate=1/2) to obtain 35 mg of the entitled compound as a colorless solid.

(Step 3) Production of {5-[4-(ethylsulfonyl)phenoxy]-2-(2-pyridinyl)-1H-benzimidazol-6-yl}(4-fluorophenyl)methanol 20 mg of the obtained product was dissolved in 1 ml of trifluoroacetic acid solution, and the reaction liquid was stirred at room temperature for 3 hours. The solvent was evaporated away, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was diluted with ethyl acetate, washed with aqueous saturated sodium bicarbonate, and dried with anhydrous sodium sulfate. The solvent was evaporated away under reduced pressure to obtain 5.4 mg of the entitled compound as a colorless solid.

$^1$HNMR (CD$_3$OD) δ: 1.24 (3H, t, J=7.4 Hz), 3.18 (2H, q, J=7.4 Hz), 6.05 (1H, s), 6.88-6.95 (4H, m), 7.20-7.42 (11H, m), 7.30 (2H, dd, J=8.2, 5.5 Hz), 7.48-7.53 (1H, m), 7.76 (2H, d, J=8.6 Hz), 7.99 (1H, t, J=8.0 Hz), 8.02-8.20 (1H, m), 8.28-8.34 (1H, m), 8.73-8.78 (1H, m).

ESI-MASS (m/e): 504.

Example 65

5-[4-(Ethylsulfonyl)phenoxy]-6-(4-fluorobenzyl)-2-(2-pyridinyl)-1H-benzimidazole 0.5 ml of triethylsilane was added to a trifluoroacetic acid (0.2 ml) solution of 4.9 mg of the alcohol compound obtained in Example 64 (step 2), and the reaction liquid was stirred overnight at room temperature. The solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was diluted with ethyl acetate, washed with aqueous saturated sodium bicarbonate, and dried with anhydrous sodium sulfate. The solvent was evaporated away under reduced pressure to obtain 5.5 mg of the entitled compound as a pale yellow solid.

$^1$HNMR (CD$_3$OD) δ: 1.17 (3H, t, J=7.4 Hz), 3.12 (2H, q, J=7.4 Hz), 3.96 (2H, s), 6.83 (2H, t, J=8.8 Hz), 6.92 (2H, d, J=9.0 Hz), 7.09 (2H, dd, J=8.8, 5.0 Hz), 7.27 (11H, s), 7.43 (1H, dd, J=7.0, 5.0 Hz), 7.58 (11H, s), 7.72 (2H, d, J=9.0 Hz), 7.92 (1H, t, J=7.4 Hz), 8.22 (1H, d, J=7.4 Hz), 8.68 (1H, d, J=5.0 Hz).

ESI-MASS (m/e): 488.

Example 66

{5-[4-(Ethylsulfonyl)phenoxy]-2-(2-pyridinyl)-1H-benzimidazol-6-yl}(4-fluorophenyl)methanone 0.1 ml of triethylamine and 15 mg of pyridine-sulfur trioxide were added to a dimethylsulfoxide (0.2 ml) solution of 15 mg of the alcohol compound obtained in Example 64 (step 3), and the reaction liquid was stirred at room temperature for 20 minutes. The reaction liquid was diluted with ethyl acetate, washed with water and saturated saline in that order, and dried with anhydrous sodium sulfate. The solvent was evaporated away under reduced pressure to obtain a crude product. The obtained crude product was dissolved in 1 ml of trifluoroacetic acid, and the reaction liquid was stirred at room temperature for 1 hour. The solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was diluted with ethyl acetate, washed with aqueous saturated sodium bicarbonate, and dried with anhydrous sodium sulfate. The solvent was evaporated away under reduced pressure to obtain 7.9 mg of the entitled compound as a colorless solid.

$^1$HNMR (CD$_3$OD) δ: 1.18 (3H, t, J=7.4 Hz), 3.16 (2H, q, J=7.4 Hz), 6.93-6.99 (2H, m), 7.18 (2H, t, J=8.6 Hz), 7.40-7.60 (2H, m), 7.77 (2H, d, J=8.6 Hz), 7.82 (2H, dd, J=8.4, 5.3 Hz), 7.84-8.00 (1H, m), 8.02 (1H, t, J=7.6 Hz), 8.35 (1H, d, J=7.6 Hz), 8.77-8.80 (1H, m).

ESI-MASS (m/e): 502.

Example 67

(2-Fluorophenyl)[5-[4-(methylsulfonyl)phenoxy]-2-(2-pyridinyl)-1H-benzimidazol-6-yl]methanol (Step 1) Production of {5-[4-(ethylsulfonyl)phenoxy]-2-(2-pyridinyl)-1-{[2-(trimethylsilyl)ethoxy]methyl}-1H-benzimidazol-6-yl}(2-fluorophenyl)methanol or {6-[4-(ethylsulfonyl)phenoxy]-2-(2-pyridinyl)-1-{[2-(trimethylsilyl)ethoxy]methyl}-1H-benzimidazol-5-yl}(2-fluorophenyl)methanol Using the aldehyde compound obtained in Example 1 (step 8) and 2-fluorophenylmagnesium bromide, the entitled compound was obtained in the same method as in Example 64 (step 2) or in accordance with the method or by combining it with an ordinary method.

(Step 2) Production of (2-fluorophenyl)[5-[4-(methylsulfonyl)phenoxy]-2-(2-pyridinyl)-1H-benzimidazol-6-yl]methanol Using the obtained product, the entitled compound was obtained in the same method as in Example 64 (step 3) or in accordance with the method or by combining it with an ordinary method.

$^1$HNMR (CDCl$_3$) δ: 3.05 (3H, s), 6.39 (1H, s), 6.84 (1H, s), 6.85 (2H, d, J=8.7 Hz), 6.98-7.02 (1H, m), 7.10-7.15 (1H, m), 7.25-7.31 (3H, m), 7.49-7.53 (1H, m), 7.75 (2H, d, J=8.7 Hz), 7.97-8.01 (1H, m), 8.15 (1H, s), 8.50 (1H, d, J=8.0 Hz), 8.73 (1H, d, J=5.1 Hz).

ESI-MASS (m/e): 490(M+H).

Example 68

(2-Bromophenyl)[5-[4-(methylsulfonyl)phenoxy]-2-(2-pyridinyl)-1H-benzimidazol-6-yl]methanol Using the aldehyde compound obtained in Example 1 (step 8) and 2-bromophenylmagnesium bromide, the entitled compound was obtained in the same method as in Example 64 (step 2, step 3) or in accordance with the method or by combining it with an ordinary method.
$^1$HNMR (CDCl$_3$) δ: 3.15 (3H, s), 6.20 (1H, s), 6.95-7.60 (2H, m), 6.96 (2H, d, J=8.5 Hz), 7.08-7.13 (1H, m), 7.29-7.33 (1H, m), 7.62 (1H, d, J=8.2 Hz), 7.49-7.53 (1H, m), 7.67 (1H, s), 7.77 (2H, d, J=8.5 Hz), 7.96-8.00 (1H, m), 8.27-8.31 (1H, m), 8.70-8.72 (1H, m).
ESI-MASS (m/e): 550, 552(M+H).

Example 69

6-(2-Fluorobenzyl)-5-[4-(methylsulfonyl)phenoxy]-2-(2-pyridinyl)-1H-benzimidazole Using the aldehyde compound obtained from Example 67 (step 1), the entitled compound was obtained in the same method as in Example 65 or in accordance with the method or by combining it with an ordinary method.
$^1$HNMR (CDCl$_3$) δ: 3.06 (3H, s), 4.00-4.05 (2H, m), 6.96-7.02 (3H, m), 7.08-7.17 (2H, m), 7.25-7.28 (1H, m), 7.37-7.43 (1H, m), 7.53-7.58 (1H, m), 7.68-7.80 (1H, m), 7.80-7.94 (3H, m), 8.38-8.55 (1H, m), 8.60-8.75 (11H, m).
ESI-MASS (m/e): 474(M+H).

Example 70

1-({5-[4-(Ethylsulfonyl)phenoxy]-2-(2-pyridyl)-1H-benzimidazol-7-yl}methyl)pyrrolidine-2,5-dione (Step 1) Production of methyl 5-fluoro-2-nitrobenzoate 2 ml of concentrated sulfuric acid was added to a methanol (200 ml) solution of 10 g of 5-fluoro-2-nitrobenzoic acid, and heated under reflux for 22 hours. 200 ml of aqueous sodium hydrogencarbonate solution was added to it, and the formed solid was taken out through filtration. This was dried under reduced pressure to obtain 10.7 g of the entitled compound as a yellow solid.

(Step 2) Production of methyl 5-[4-(ethylsulfonyl)phenoxy]-2-nitrobenzoate 11 g of potassium carbonate was added to a dimethylformamide (150 ml) solution of 10.7 g of methyl 5-fluoro-2-nitrobenzoate and 11.1 g of 4-(ethylsulfonyl)phenol obtained from Reference Example 2, and stirred under heat at 80° C. for 90 minutes. The reaction liquid was restored to room temperature, then 300 ml of water was added to it, and the formed solid was taken out through filtration. This was dried under reduced pressure to obtain 19.7 g of the entitled compound as a creamy white solid.

(Step 3) Production of methyl 2-amino-5-[4-(ethylsulfonyl)phenoxy]benzoate 0.7 g of Raney nickel was added to a methanol (150 ml) solution of 6.98 g of methyl 5-[4-(ethylsulfonyl)phenoxy]-2-nitrobenzoate, and stirred overnight in a hydrogen atmosphere. The catalyst was removed through filtration, the solvent was evaporated away under reduced pressure, and the residue was purified through silica gel column chromatography (developing solvent: hexane/ethyl acetate=2/1 to 1/1) to obtain 2.65 g of the entitled compound as a colorless oil.

(Step 4) Production of methyl 5-[4-(ethylsulfonyl)phenoxy]-2-[(2-pyridinylcarbonyl)amino]benzoate With cooling with ice, 4.4 ml of triethylamine and 2.8 g of picolinic acid chloride hydrochloride were added to a chloroform (30 ml) solution of 2.65 g of methyl 2-amino-5-[4-(ethylsulfonyl)phenoxy]benzoate, and stirred at room temperature for 90 minutes. Aqueous saturated sodium hydrogencarbonate solution was added to the reaction liquid, extracted with chloroform, and the organic layer was washed with saturated saline water. After dried, the solvent was evaporated away under reduced pressure, and the residue was purified through silica gel column chromatography (developing solvent: hexane/ethyl acetate=2/1 to 1/1) to obtain 1.9 g of the entitled compound as a creamy white solid.

(Step 5) Production of methyl 5-[4-(ethylsulfonyl)phenoxy]-3-nitro-2-[(2-pyridinylcarbonyl)amino]benzoate 1.9 g of methyl 5-[4-(ethylsulfonyl)phenoxy]-2-[(2-pyridinylcarbonyl)amino]benzoate was dissolved in 20 ml of trifluoroacetic acid, and 2.2 g of potassium nitrate was added to it and stirred under heat at 80° C. for 2 hours. The reaction liquid was restored to room temperature, trifluoroacetic acid was evaporated away under reduced pressure, the residue was dissolved in chloroform, and aqueous saturated sodium hydrogencarbonate solution was added to it. This was extracted with chloroform, and the organic layer was washed with saturated saline water. After dried, the solvent was evaporated away under reduced pressure, and the residue was purified through silica gel column chromatography (developing solvent: hexane/ethyl acetate=2/1 to 1/1) to obtain 1.86 g of the entitled compound as a yellow solid.

(Step 6) Production of methyl 6-[4-(ethylsulfonyl)phenoxy]-2-(2-pyridyl)-1-{[2-(trimethylsilyl)ethoxy]methyl}-1H-benzimidazole-4-carboxylate and methyl 5-[4-(ethylsulfonyl)phenoxy]-2-(2-pyridyl)-1-{[2-(trimethylsilyl)ethoxy]methyl}-1H-benzimidazole-7-carboxylate 1.86 f of methyl 5-[4-(ethylsulfonyl)phenoxy]-3-nitro-2-[(2-pyridinylcarbonyl)amino]benzoate was suspended in 15 ml of dimethylformamide and 15 ml of methanol, and 4.3 g of tin(II) chloride dihydrate and 11 ml of concentrated hydrochloric acid were added to it, and stirred under heat at 80° C. for 81 hours. The reaction liquid was restored to room temperature, then aqueous sodium hydrogencarbonate solution was gradually added to neutralize it. Ethyl acetate was added to it, and stirred at room temperature for 30 minutes. The formed salt was removed through filtration, the filtrate was extracted with ethyl acetate, and the organic layer was washed with saturated saline water. After dried, the solvent was evaporated away to obtain 1.44 g of a crude product methyl 5-[4-(ethylsulfonyl)phenoxy]-2-(2-pyridyl)-1H-benzimidazole-7-carboxylate as yellow oil.

With cooling with ice, 0.87 ml of 2-(trimethylsilyl)ethoxymethyl chloride and 197 mg of sodium hydride (with 30% liquid paraffin added thereto) were added to a dimethylformamide (15 ml) solution of 1.44 g of methyl 5-[4-(ethylsulfonyl)phenoxy]-2-(2-pyridyl)-1H-benzimidazole-7-carboxylate, and stirred at room temperature for 30 minutes. With cooling with ice, aqueous saturated ammonium chloride solution was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate=1/1) to obtain 1.34 g of the entitled compound as a brown oil.

(Step 7) Production of (6-[4-(ethylsulfonyl)phenoxy]-2-(2-pyridyl)-1-{[2-(trimethylsilyl)ethoxy]methyl}-1H-benzimidazol-4-yl)methanol and (5-[4-(ethylsulfonyl)phenoxy]-2-(2-pyridyl)-1-{[2-(trimethylsilyl)ethoxy]methyl}-1H-benzimidazol-7-yl)methanol With cooling with ice, a tetrahydrofuran (5 ml) solution of 113 mg of lithium aluminium hydride and 681 mg of the above ester compound was gradually added to 5 ml of tetrahydrofuran. This was stirred at room temperature for 15 minutes, then sodium sulfate 10-hydrate was gradually added to it until it gave no foam, and ethyl acetate was added to it and stirred at room temperature for 1 hour. The formed salt was removed through filtration, and the solvent was evaporated away under reduced pressure. The residue was purified through silica gel column chromatography (developing solvent: chloroform/methanol=100/0 to 100/5) to obtain 519 mg of the entitled compound as a yellow oil.

(Step 8) Production of 1-({5-[4-(ethylsulfonyl)phenoxy]-2-(2-pyridyl)-1H-benzimidazol-7-yl}methyl)pyrrolidine-2,5-dione Using the obtained alcohol compound, the entitled compound was obtained in the same method as in Example 1 (step 10) or in accordance with the method or by combining it with an ordinary method.
$^1$HNMR (CDCl$_3$) δ: 1.32 (3H, t, J=7.4 Hz), 2.80 (4H, s), 3.13 (2H, q, J=7.4 Hz), 4.94 (2H, s), 7.10 (2H, d, J=9.4 Hz), 7.23 (1H, d, J=9.4 Hz), 7.40-7.42 (1H, m), 7.53-7.54 (1H, m), 7.85-7.88 (3H, m), 8.38 (1H, t, J=4.5 Hz), 8.80 (1H, dd, J=3.9, 0.8 Hz), 11.55 (1H, brs).
ESI-MASS (m/e): 491(M+H).

Example 71

Methyl 5-[4-(ethylsulfonyl)phenoxy]-2-(2-pyridyl)-1H-benzimidazole-7-carboxylate Using the product obtained in Example 70 (step 6), the entitled compound was obtained in the same method as in Example 57 (step 4) or in accordance with the method or by combining it with an ordinary method.
$^1$HNMR (CDCl$_3$) δ: 1.27 (3H, t, J=7.4 Hz), 3.11 (2H, q, J=7.4 Hz), 4.04 (3H, s), 7.09 (2H, dd, J=7.0, 2.0 Hz), 7.40-7.43 (1H, m), 7.71 (1H, d, J=2.3 Hz), 7.76 (1H, d, J=2.3 Hz), 7.82-7.90 (3H, m), 8.39 (1H, d, J=7.8 Hz), 8.70 (1H, d, J=5.1 Hz), 11.36 (1H, brs).
ESI-MASS (m/e): 438(M+H).

Example 72

[5-[4-(Ethylsulfonyl)phenoxy]-2-(2-pyridyl)-1H-benzimidazol-7-yl]methanol

Using the product obtained in Example 70 (step 7), the entitled compound was obtained in the same method as in Example 57 (step 4) or in accordance with the method or by combining it with an ordinary method.
$^1$HNMR (CDCl$_3$) δ: 1.28 (3H, t, J=11.1 Hz), 3.14 (2H, q, J=11.1 Hz), 5.12-5.16 (2H, m), 6.94 (1H, d, J=20.7 Hz), 7.07-7.12 (2H, m), 7.17 (1/2H, d, J=2.0 Hz), 7.39 (1H, dd, J=18.2, 10.7 Hz), 7.48 (1/2H, s), 7.84-7.89 (3H, m), 8.41 (1H, d, J=7.8 Hz), 8.66-8.67 (1H, m), 10.62 (1/2H, brs), 11.02 (1/2H, brs).
ESI-MASS (m/e): 410(M+H).

Example 73

5-[4-(Ethylsulfonyl)phenoxy]-7-(methoxymethyl)-2-(2-pyridyl)-1H-benzimidazole

In an ice bath, 12 μl of methyl iodide and 7.8 mg of sodium hydride (with 30% liquid paraffin added thereto) were added to a DMF (1 ml) solution of 53 mg of the product obtained in Example 70 (step 7), and stirred at room temperature for 1 hour. Aqueous saturated ammonium chloride solution was added to the reaction liquid, extracted with ethyl acetate, and the organic layer was washed with water and saturated saline water. After dried, the solvent was evaporated away under reduced pressure to obtain a crude product as brown oil. The obtained product was processed in the same method as in Example 57 (step 4) or in accordance with the method or by combining it with an ordinary method, thereby giving the entitled compound.
$^1$HNMR (CDCl$_3$) δ: 1.27 (3H, t, J=7.4 Hz), 3.10 (2H, q, J=7.4 Hz), 3.51 (9/4H, s), 3.53 (3/4H, s), 4.81 (3/2H, s), 5.02 (1/2H, s), 6.90 (1H, s), 7.09-7.12 (2H, m), 7.38-7.39 (1H, m), 7.47 (1H, s), 7.82-7.86 (3H, m), 8.39 (3/4H, d, J=7.8 Hz), 8.43 (1/4H, d, J=7.8 Hz), 8.61 (1/4H, s, J=4.7 Hz), 8.67 (3/4H, d, J=7.8 Hz), 10.67 (1/4H, brs), 10.81 (3/4H, brs).
ESI-MASS (m/e): 424(M+H).

Example 74

5-[4-(Ethylsulfonyl)phenoxy]-7-(2-phenoxymethyl)-2-(2-pyridyl)-1H-benzimidazole

Using the product obtained in Example 70 (step 7) and phenol, the entitled compound was obtained in the same method as in Example 2 or in accordance with the method or by combining it with an ordinary method.
$^1$HNMR (CDCl$_3$) δ: 1.32-1.33 (3H, m), 3.12 (2H, q, J=7.5 Hz), 5.41 (1H, s), 5.69 (1H, s), 6.82-6.76 (1/2H, m), 7.02-7.06 (5H, m), 7.30-7.42 (4H, m), 7.54-7.56 (1/2H, m), 7.83-7.89 (3H, m), 8.41-8.44 (1H, m), 8.69-8.72 (1H, m), 10.75 (1/2H, brs), 10.90 (1/2H, brs).
ESI-MASS (m/e): 486(M+H).

Example 75

N-{[5-[4-(ethylsulfonyl)phenoxy]-2-(2-pyridyl)-1H-benzimidazol-7-yl]methyl}-N,N-dimethylamine Using the product obtained in Example 70 (step 7) and dimethylamine, the entitled compound was obtained in the same method as in Example 2 or in accordance with the method or by combining it with an ordinary method.
$^1$HNMR (CDCl$_3$) δ: 1.29-1.31 (3H, m), 2.33 (6H, s), 3.07-3.15 (2H, m), 3.76 (2H, s), 6.90 (1H, s), 7.11 (2H, d, J=9.4 Hz), 7.39-7.41 (1H, m), 7.46 (1H, s), 7.82-7.90 (3H, m), 8.42 (1H, d, J=8.2 Hz), 8.71 (1H, d, J=4.3 Hz).

ESI-MASS (m/e): 437(M+H).

Example 76

7-(2,6-Difluorobenzyl)-5-[4-(ethylsulfonyl)phenoxy]-2-(2-pyridyl)-1H-benzimidazole (Step 1) Production of 6-[4-(ethylsulfonyl)phenoxy]-2-(2-pyridyl)-1-{[2-(trimethylsilyl)ethoxy]methyl}-1H-benzimidazole-4-carbaldehyde and 5-[4-(ethylsulfonyl)phenoxy]-2-(2-pyridyl)-1-{[2-(trimethylsilyl)ethoxy]methyl}-1H-benzimidazole-7-carbaldehyde Using the product obtained in Example 70 (step 7), the entitled compound was obtained in the same method as in Example 64 (step 1) or in accordance with the method or by combining it with an ordinary method.

(Step 2) Production of {6-[4-(ethylsulfonyl)phenoxy]-2-(2-pyridyl)-1-{[2-trimethylsilyl)ethoxy]methyl}-1H-benzimidazol-4-yl}(2,6-difluorophenyl)methanol or {5-[4-(ethylsulfonyl)phenoxy]-2-(2-pyridyl)-1-{[2-trimethylsilyl)ethoxy]methyl}-1H-benzimidazol-7-yl}(2,6-difluorophenyl)methanol Using the obtained aldehyde compound and 2,6-difluorophenyllithium prepared according to the method described in Journal of The American Chemical Society, 1966, Vol. 31, p. 746, the entitled compound was obtained in the same method as in Example 64 (step 2) or in accordance with the method or by combining it with an ordinary method.

(Step 3) Production of 7-(2,6-difluorobenzyl)-5-[4-(ethylsulfonyl)phenoxy]-2-(2-pyridyl)-1H-benzimidazole Using the obtained alcohol compound, the entitled compound was obtained in the same method as in Example 65 or in accordance with the method or by combining it with an ordinary method.

$^1$HNMR (CDCl$_3$) δ: 1.24-1.33 (3H, m), 3.12 (2H, q, J=25 Hz), 4.17 (1H, s), 4.59 (1H, s), 6.93 (1H, s), 7.03-7.06 (3H, m), 7.19 (1H, m), 7.39-7.48 (2H, m), 7.81-7.84 (4H, m), 8.34-8.44 (1H, m), 8.59-8.67 (1H, m).

ESI-MASS (m/e): 506(M+H).

Example 77

7-(4-Fluorobenzyl)-5-[4-(ethylsulfonyl)phenoxy]-2-(2-pyridyl)-1H-benzimidazole

Using the aldehyde compound obtained in Example 76 (step 1) and 4-fluorofluorophenylmagnesium bromide, the entitled compound was obtained in the same method as in Example 76 (step 2, step 3) or in accordance with the method or by combining it with an ordinary method.

$^1$HNMR (CDCl$_3$) δ: 1.27 (3H, t, J=13.8 Hz), 3.10 (2H, q, J=13.8 Hz), 4.23 (1H, s), 4.44 (1H, s), 6.72 (1H, s), 6.85 (1H, s), 6.97-7.01 (4H, m), 7.21 (1/2H, m), 7.34-7.38 (2H, m), 7.43 (1/2H, m), 7.81-7.85 (3H, m), 8.39-8.44 (1H, m), 8.61 (1H, s), 10.60 (1H, brs).

ESI-MASS (m/e): 488(M+H).

Example 78

1-({5-[4-(Ethylsulfonyl)phenoxy]-2-(2-pyridyl)-1H-benzimidazol-7-yl}methyl)-2-pyrrolidinone Using the product obtained in Example 70 (step 7), the entitled compound was obtained in the same method as in Example 2 or in accordance with the method or by combining it with an ordinary method.

$^1$HNMR (CDCl$_3$) δ: 1.27-1.42 (3H, m), 2.00-2.13 (2H, m), 2.51 (2H, m), 3.13 (2H, q, J=8.3 Hz), 3.43-3.50 (2H, m), 4.67 (2H, s), 6.93 (1H, d, J=2.0 Hz), 7.10 (2H, d, J=18.0 Hz), 7.38 (1H, dd, J=7.0, 4.3 Hz), 7.53 (1H, s), 7.86-7.88 (3H, m), 8.39 (1H, d, J=9.2 Hz), 8.79-8.82 (1H, m), 12.04 (1H, s).

ESI-MASS (m/e): 477(M+H).

The structures of the compounds of Examples 1 to 78 are shown in Tables 6 to 8.

TABLE 6

| | |
|---|---|
| 1 | 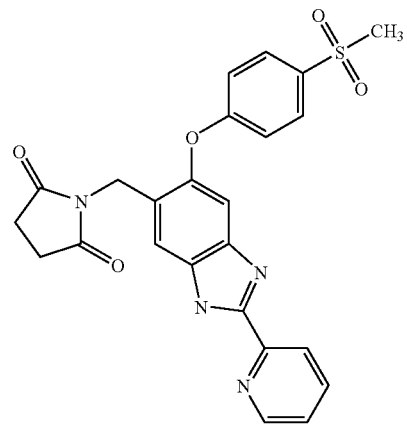 |
| 2 | 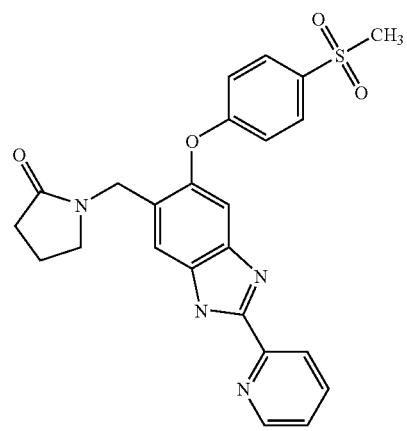 |

TABLE 6-continued
3 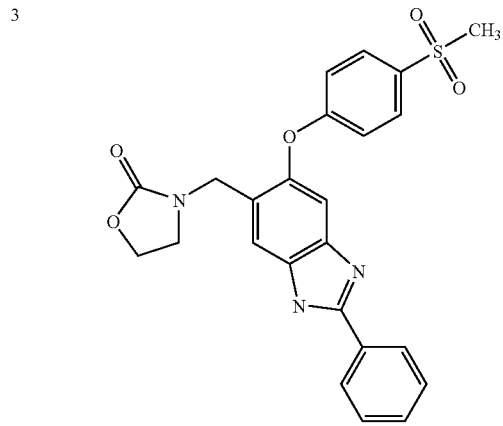
4 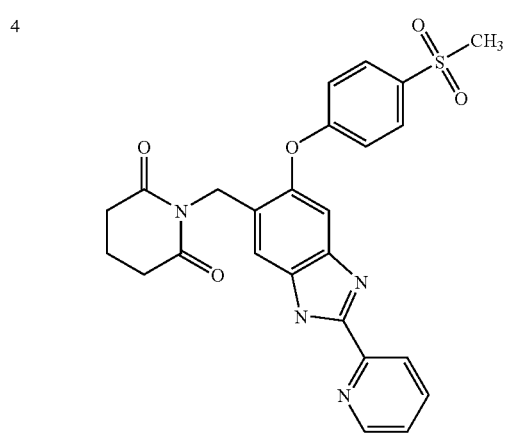
5 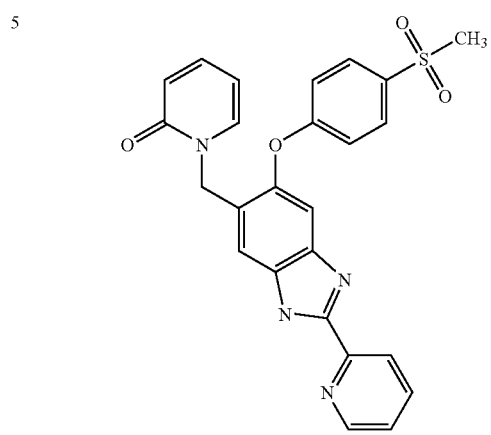
TABLE 6-continued
6 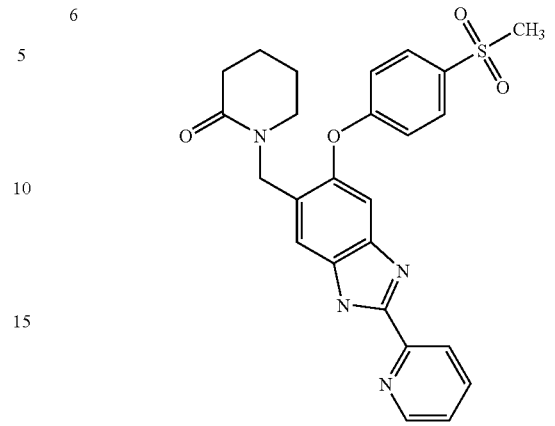
7 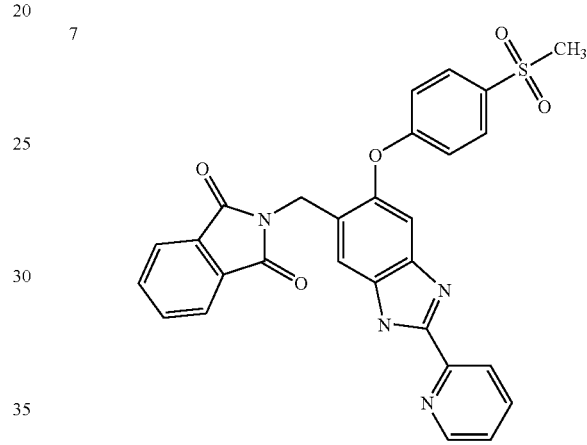
8 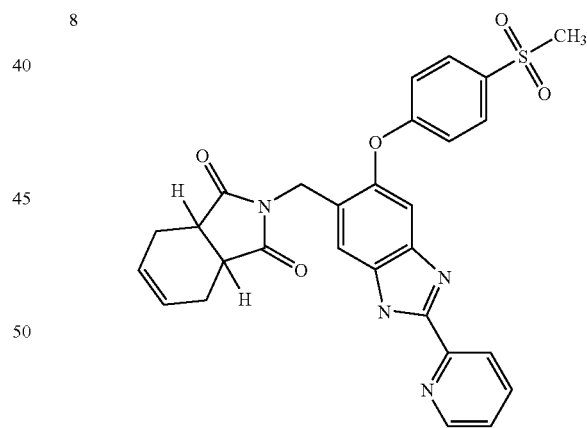

TABLE 6-continued
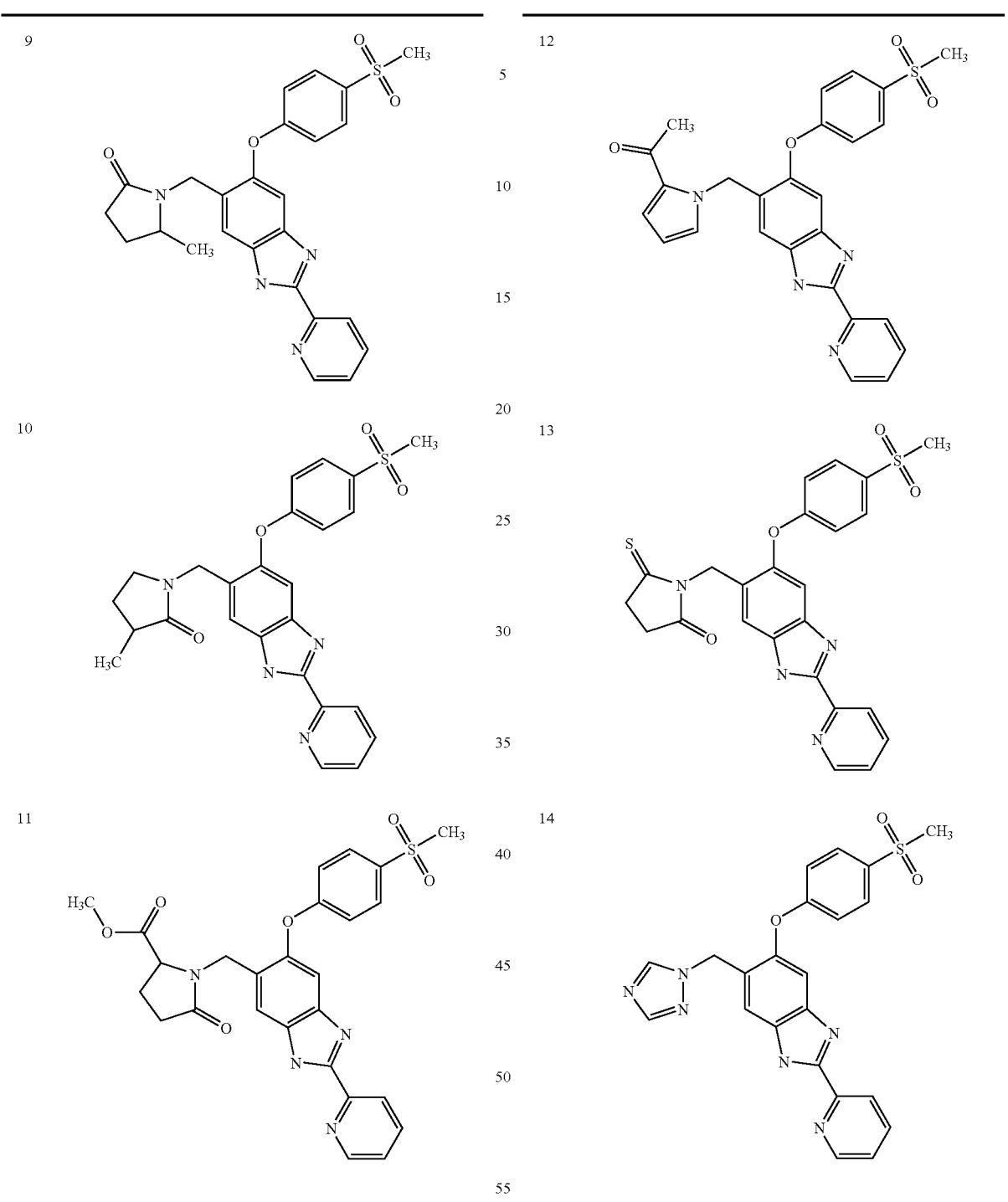

TABLE 6-continued
15
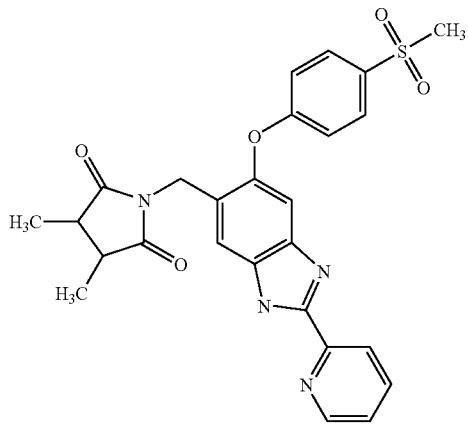
16
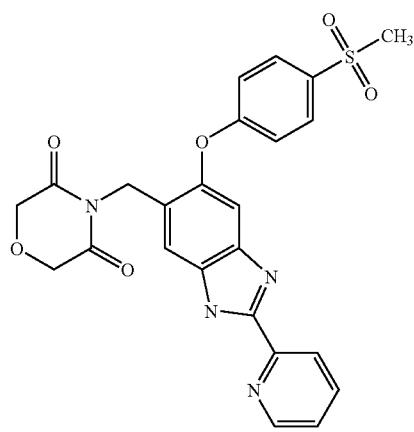
17
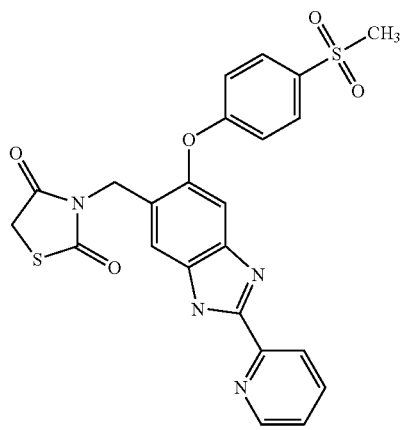
TABLE 6-continued
18
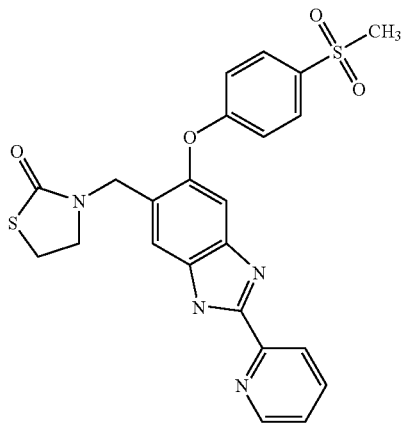
19
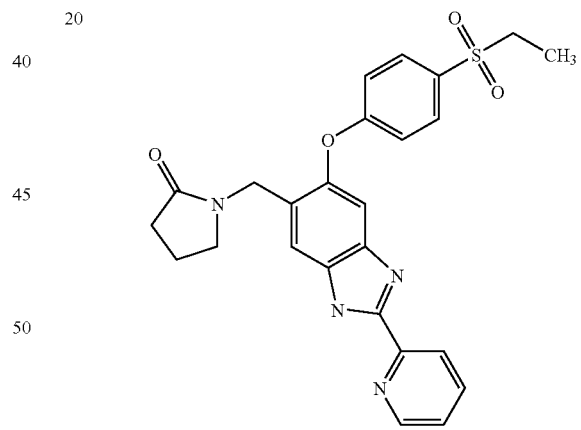
20

TABLE 6-continued
| 21 | 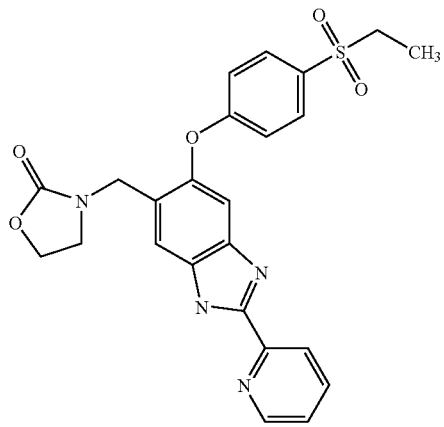 |
|---|---|
| 22 | 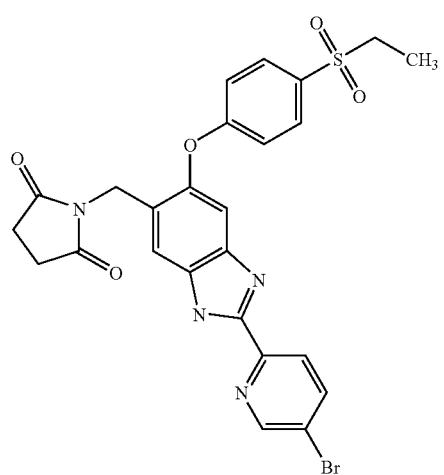 |
| 23 | 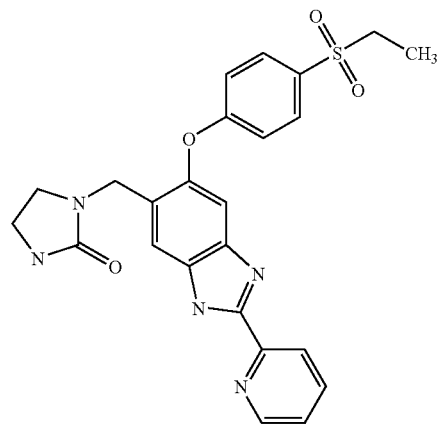 |
TABLE 6-continued
| 24 | 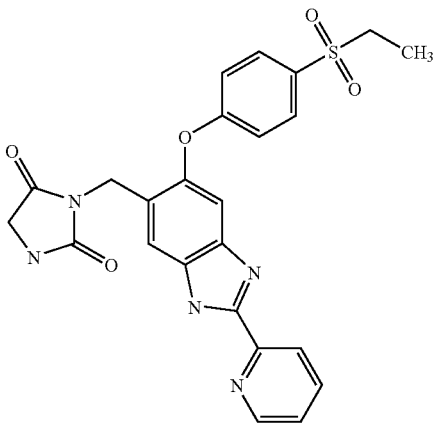 |
|---|---|
| 18 | 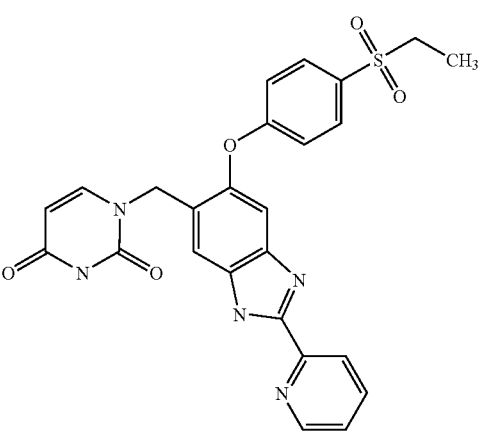 |
| 26 | 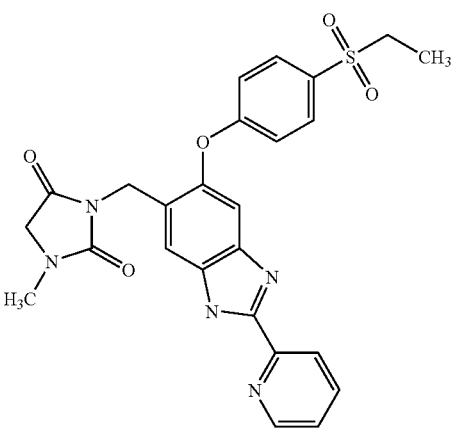 |

TABLE 6-continued
27 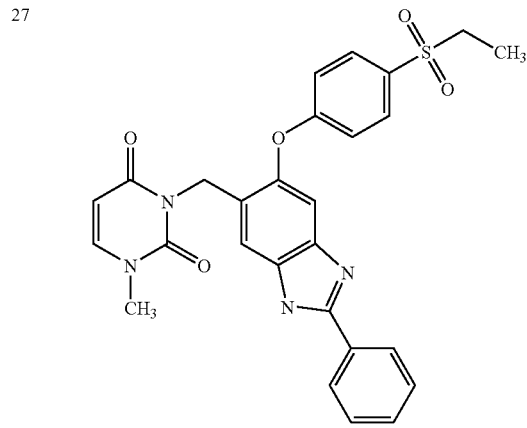
28 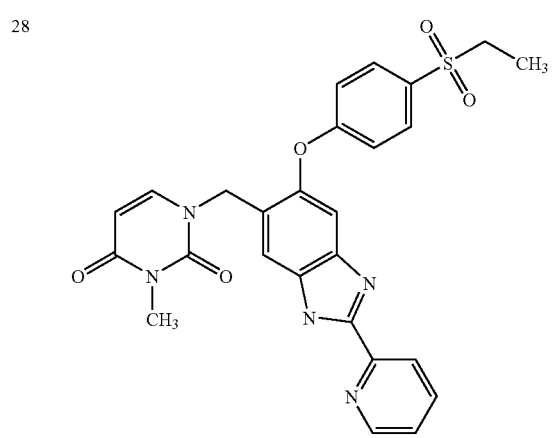
29 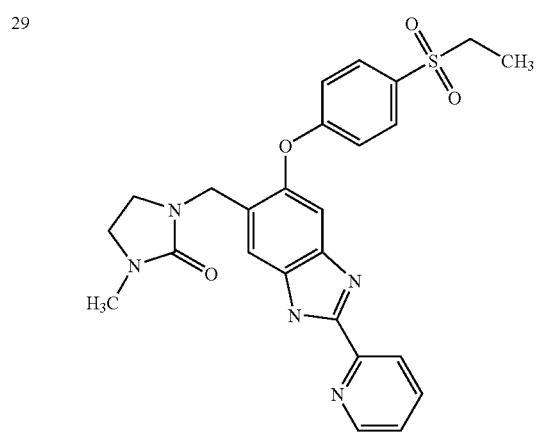
TABLE 6-continued
30 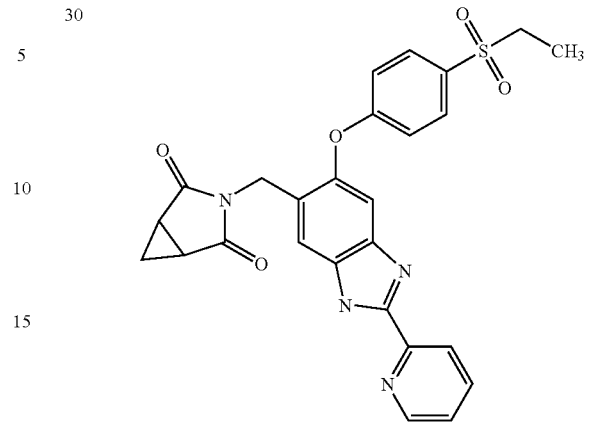
31 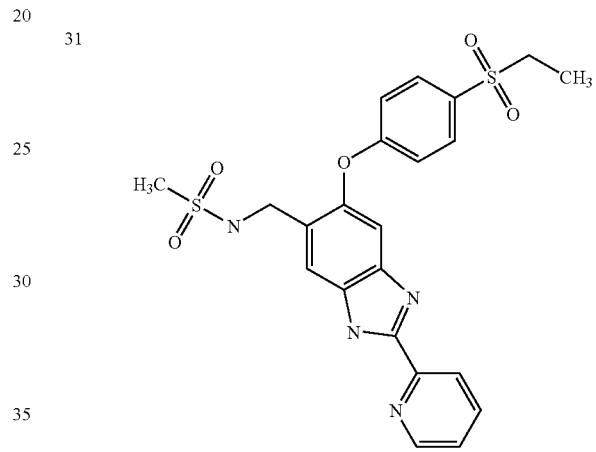
32 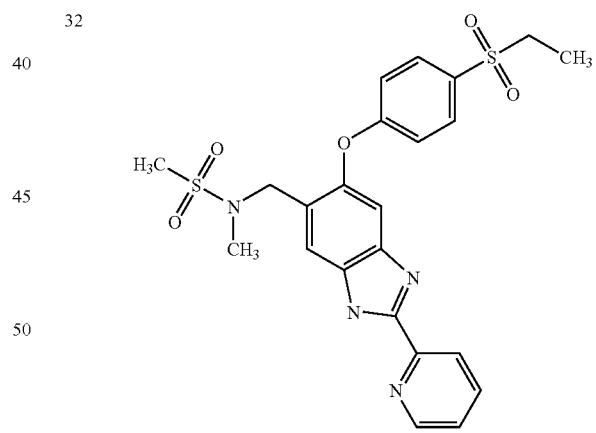

TABLE 7
33
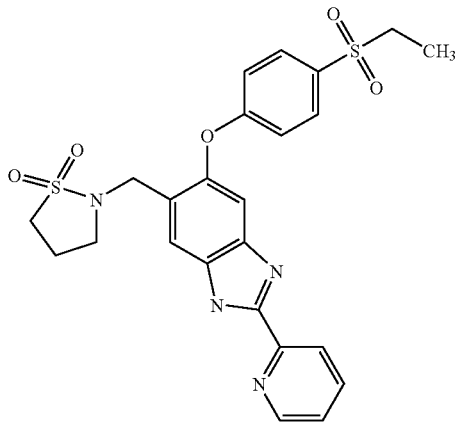
34
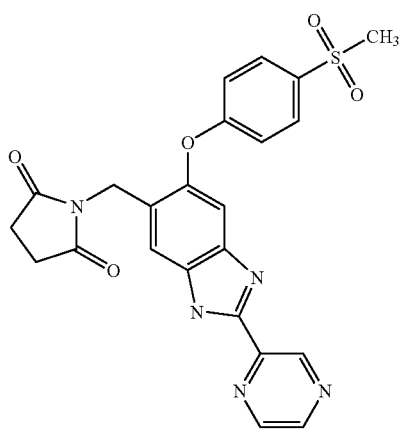
35
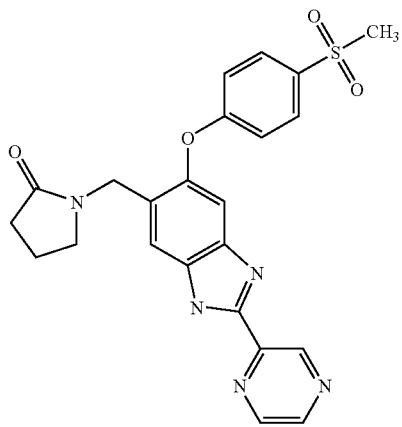
TABLE 7-continued
36
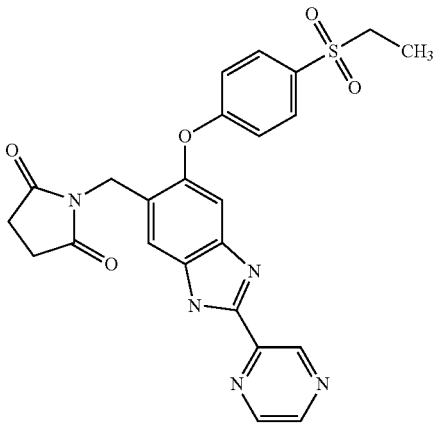
37
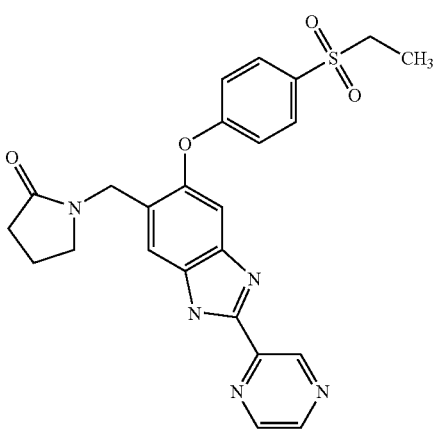
38
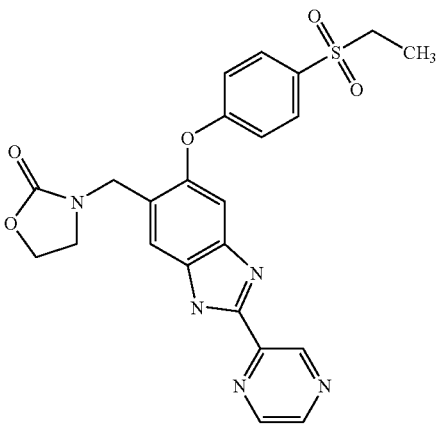

TABLE 7-continued
39
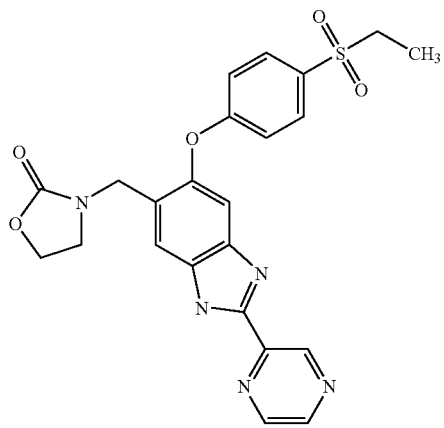
40
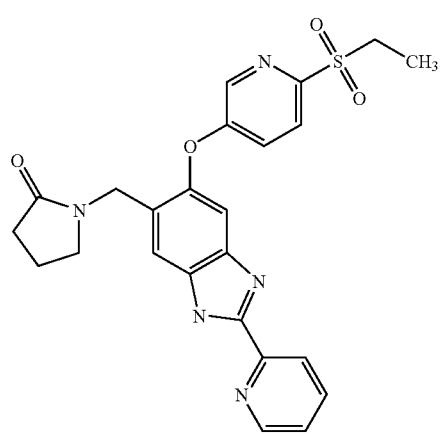
41
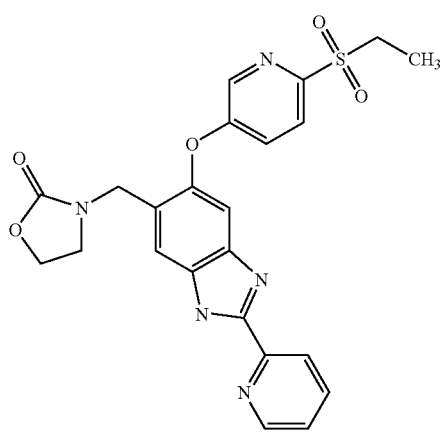
TABLE 7-continued
42
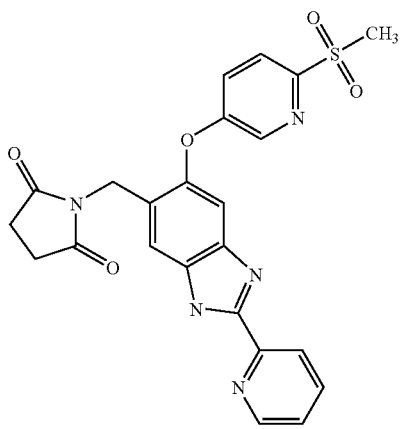
43
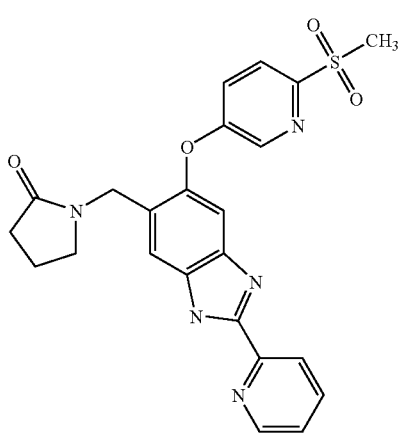
44
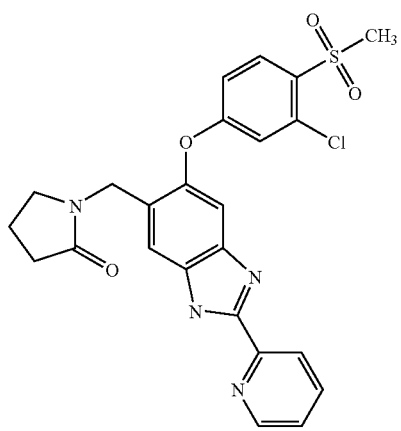

TABLE 7-continued
| 45 | 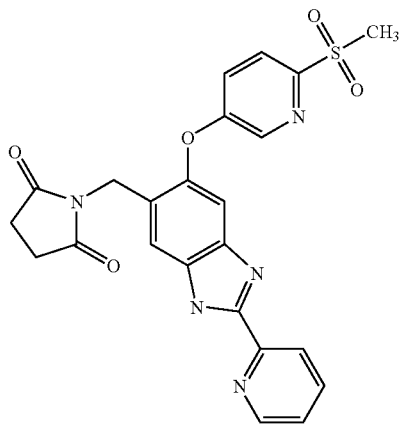 |
|---|---|
| 46 | 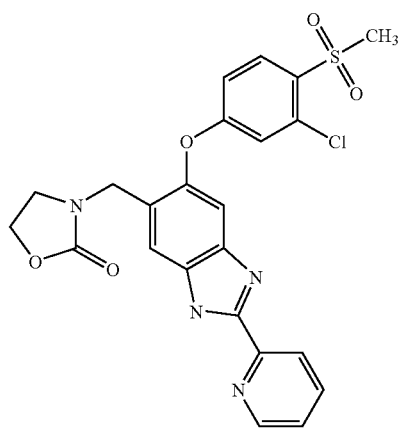 |
| 47 | 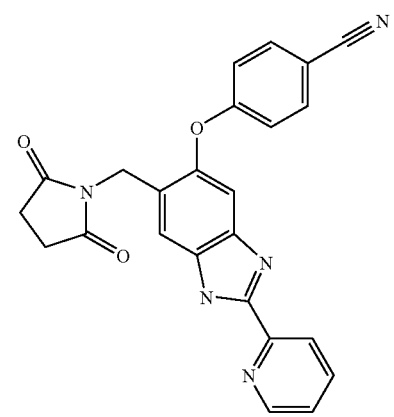 |
| 48 | 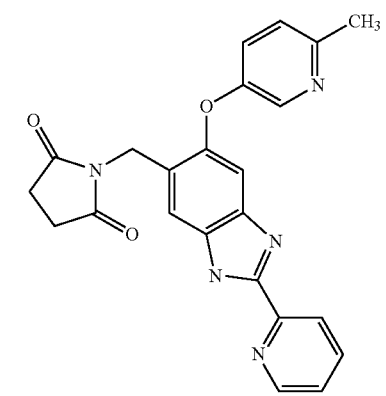 |
| 49 | 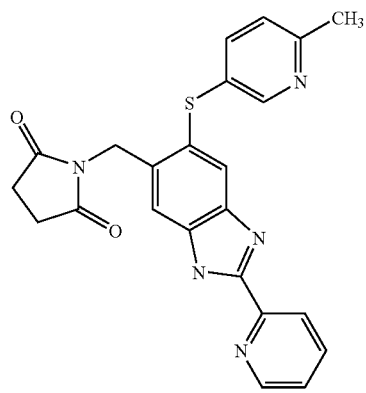 |
| 50 | 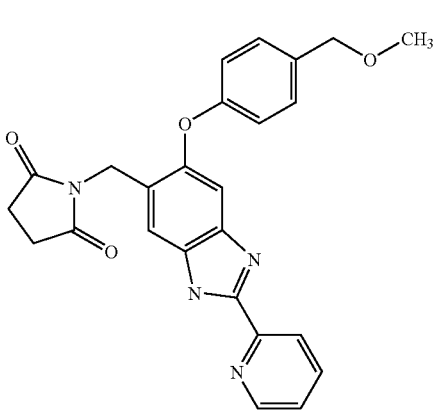 |
| 51 | 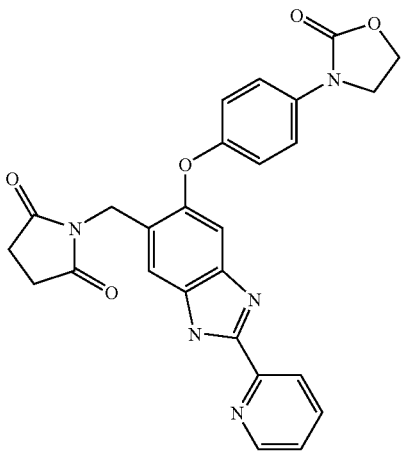 |

TABLE 7-continued
| 52 | 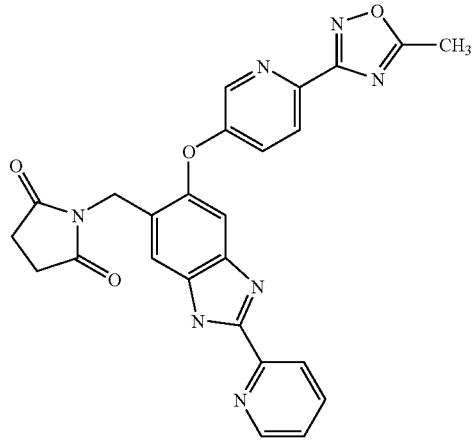 |
| --- | --- |
| 53 | 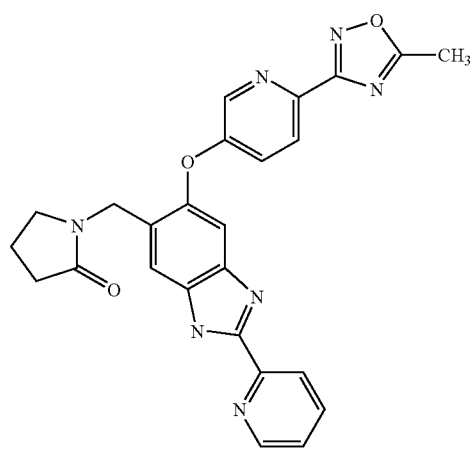 |
| 54 | 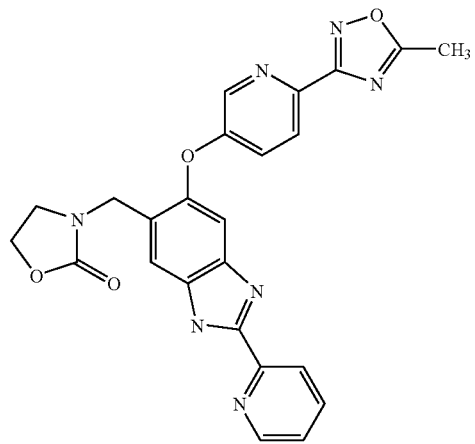 |
TABLE 7-continued
| 55 | 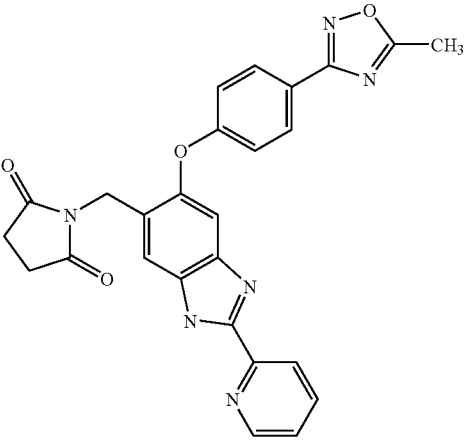 |
| --- | --- |
| 56 | 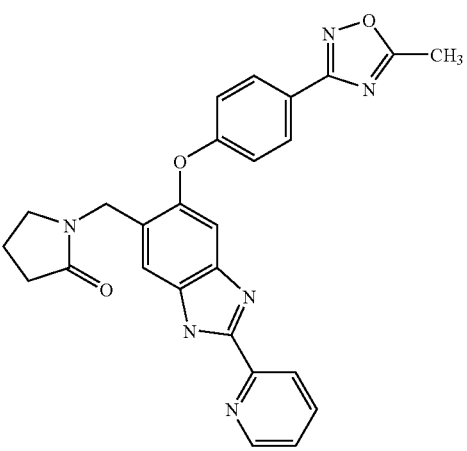 |
| 57 | 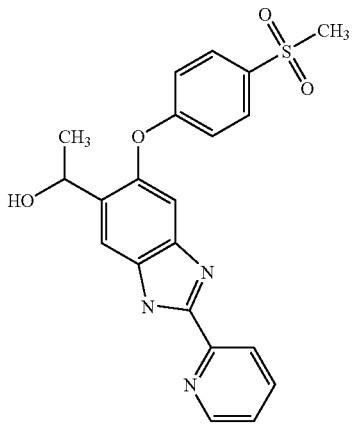 |

TABLE 7-continued
| | |
|---|---|
| 58 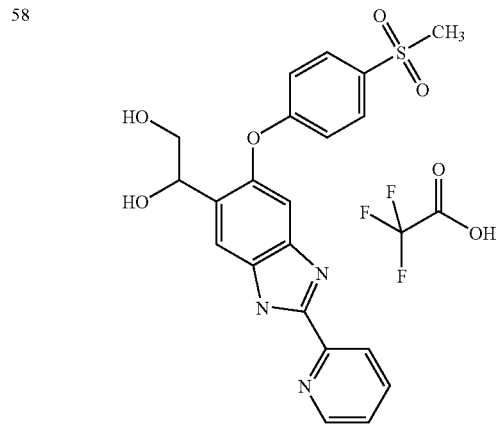 | 61 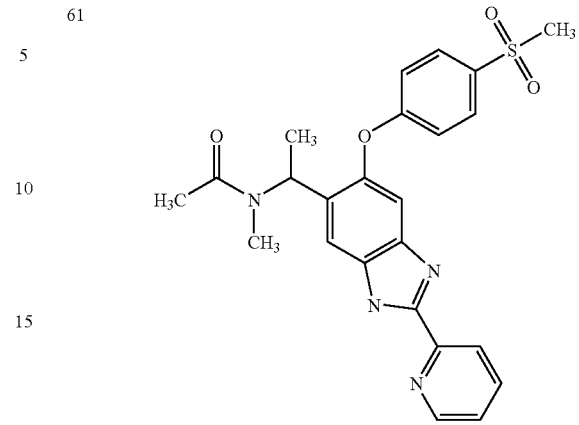 |
| 59 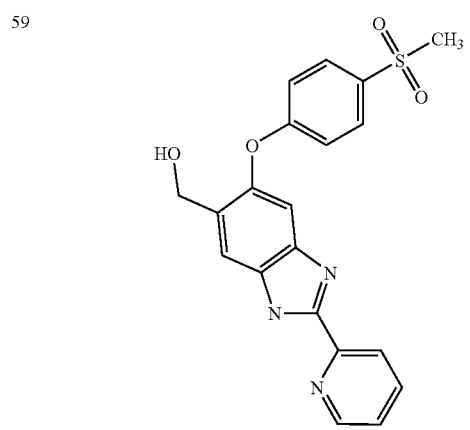 | 62 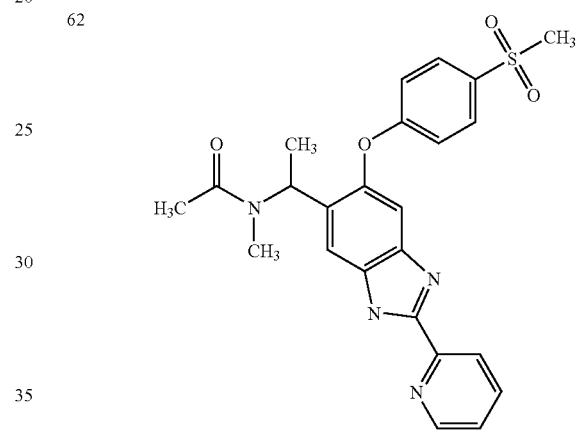 |
| 60 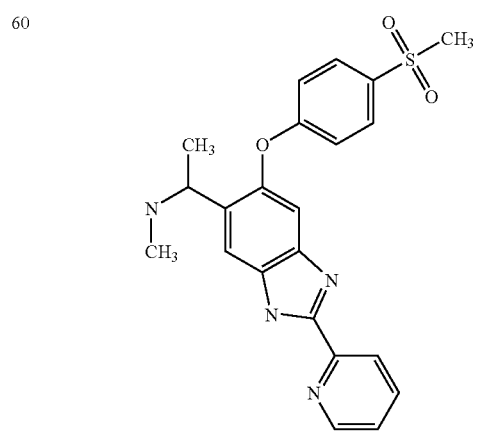 | 63 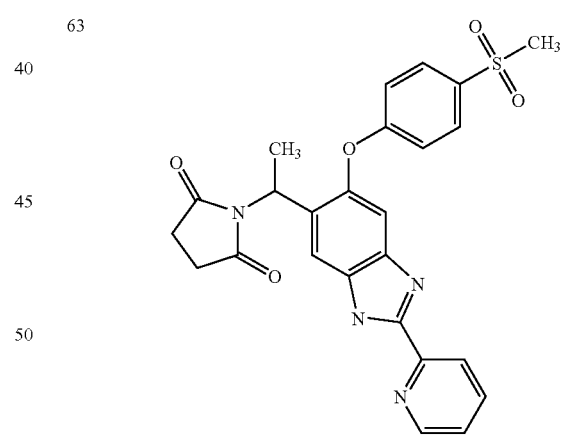 |

TABLE 8
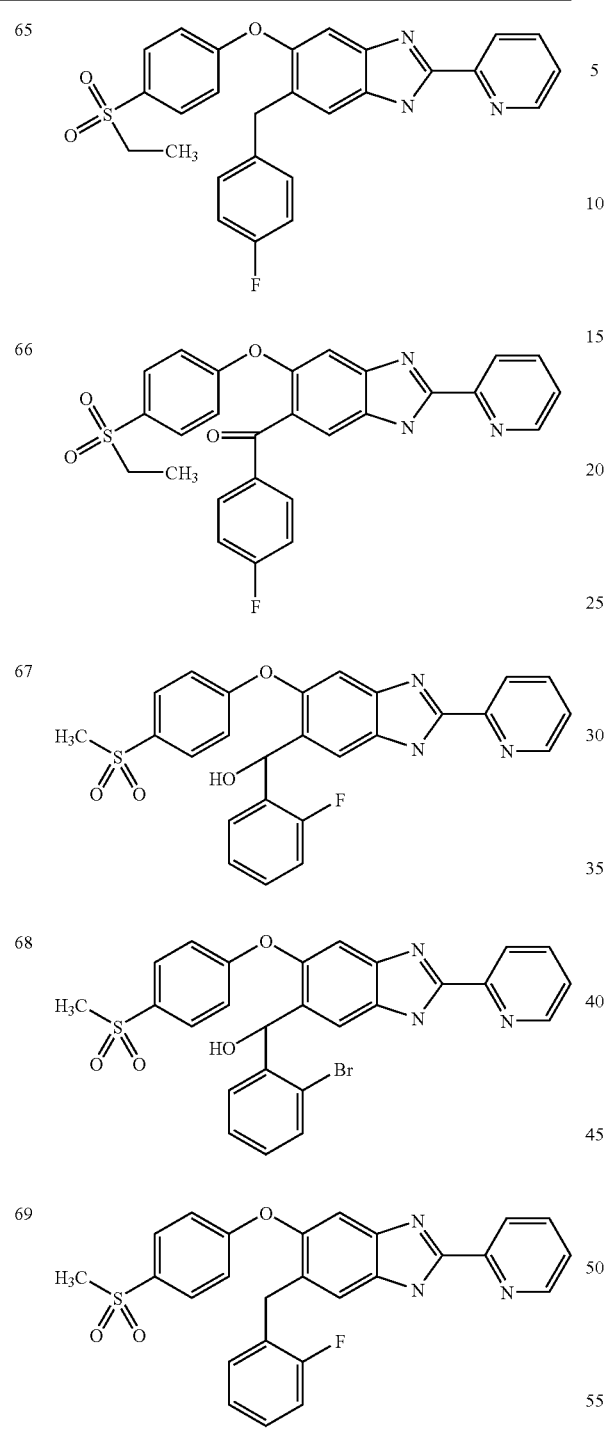
TABLE 8-continued
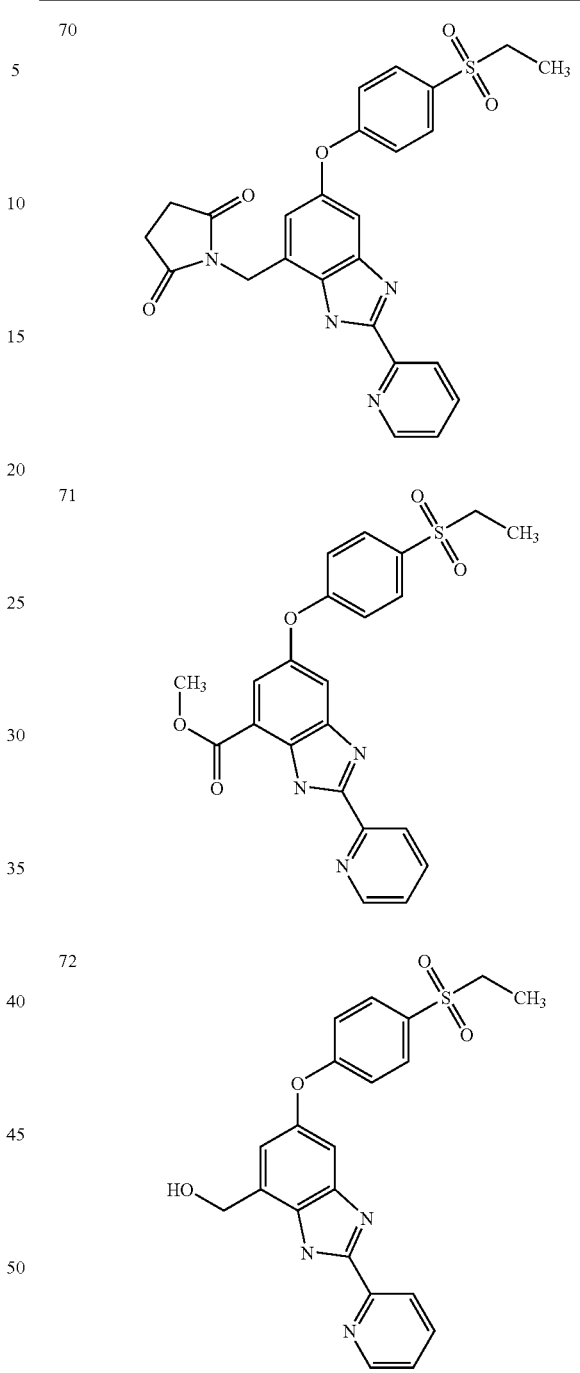

TABLE 8-continued

73 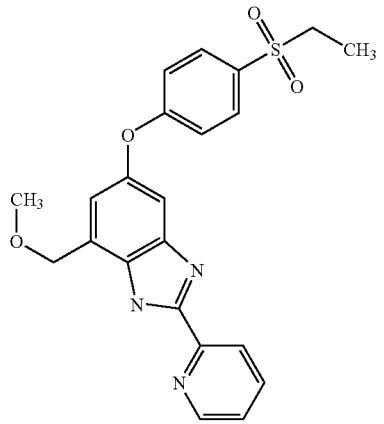

74 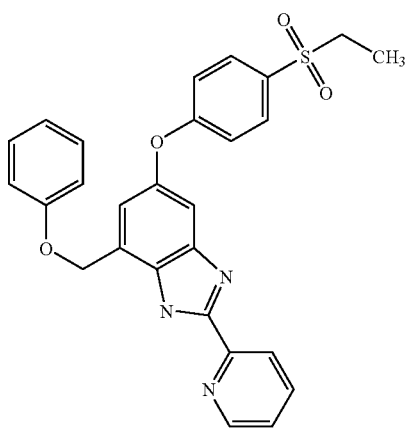

75 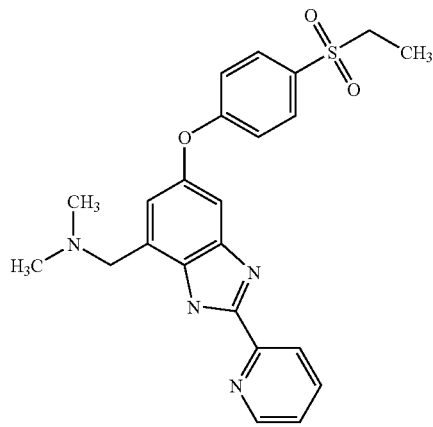

TABLE 8-continued

76 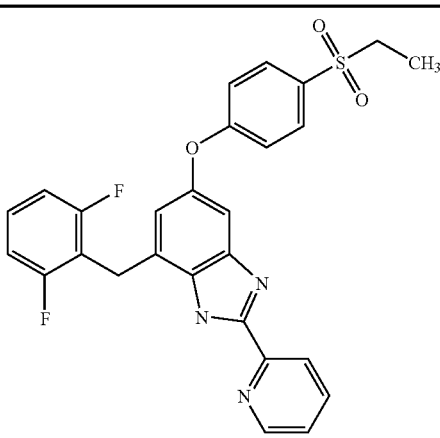

77 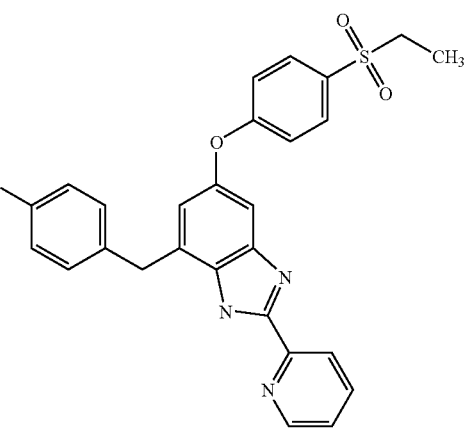

78 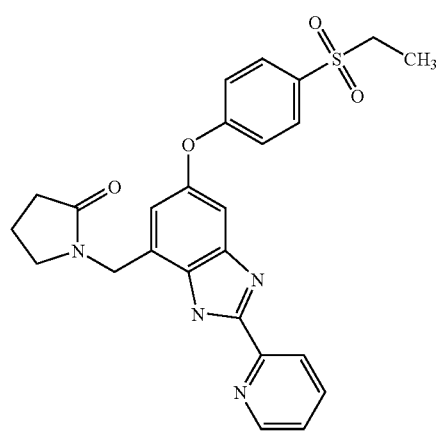

Example 79

6-[(Ethylsulfonyl)methyl]-5-[4-(ethylsulfonyl)phenoxy]-2-(2-pyridinyl)-1H-benzimidazole (Step 1) Production of 5-[4-(ethylsulfonyl)phenoxy]-6-[(ethylthio)methyl]-2-(2-pyridinyl)-1-{[2-(trimethylsilyl)ethoxy]methyl}-1H-benzimidazole and 6-[4-(ethylsulfonyl)phenoxy]-5-[(ethylthio)methyl]-2-(2-pyridinyl)-1-{[2-(trimethylsilyl)ethoxy]methyl}-1H-benzimidazole With cooling with ice, 15 μl of methanesulfonyl chloride was added to a tetrahydrofuran (0.5 ml) solution of 50 mg of the alcohol compound obtained in Example 19 (step 7) and 26 µl of triethylamine, and stirred for 30 minutes. Water was added to it, extracted with ethyl acetate, and the organic layer was washed with saturated saline water. After dried, the solvent was evaporated away under reduced pressure to obtain a pale yellow amorphous substance.

With cooling with ice, 11 mg of sodium hydride (with 30% liquid paraffin added thereto) was added to a dimethylformamide (0.5 ml) solution of the obtained amorphous substance and 15 µl of ethanethiol, and stirred at room temperature for 1 hour. With cooling with ice, aqueous saturated ammonium chloride solution was added to it, extracted with ethyl acetate, and the organic layer was washed with water and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 15.5 mg of the entitled compound.

(Step 2) Production of 6-[(ethylsulfonyl)methyl]-5-[4-(ethylsulfonyl)phenoxy]-2-(2-pyridinyl)-1H-benzimidazole 0.67 ml of a methanol solution of 0.4 M oxone was added to a methanol (0.6 ml) solution of 15.5 mg of the oil obtained in the step 1, and stirred at room temperature for 2 hours. The insoluble matter was removed through filtration, and the filtrate was diluted with chloroform and washed with water and saturated saline water. After dried, the solvent was evaporated away under reduced pressure to obtain a yellow amorphous substance.

The obtained yellow amorphous substance was dissolved in 1 ml of trifluoroacetic acid, and stirred at room temperature for 1 hour. The solvent was evaporated away, and the residue was neutralized with triethylamine and purified through partitioning thin-layer chromatography (Kieselgel™ 60F$_{254}$, Art 5744 (by Merck), chloroform/methanol=10/1) to obtain 9.8 mf of the entitled compound as a pale yellow solid.

$^1$HNMR (CDCl$_3$) δ: 1.31 (3H, t, J=7.5 Hz), 1.39 (3H, t, J=7.0 Hz), 2.98 (2H, q, J=7.5 Hz), 3.13 (2H, q, J=7.0 Hz), 4.39 (2H×1/2, s), 4.41 (2H×1/2, s), 7.10-7.20 (3H+1/2H, m), 7.42 (1H, m), 7.47 (1/2H, s), 7.81 (1/2H, s), 7.88 (3H, m), 8.02 (1/2H, s), 8.38 (1H, m), 8.67 (1H, m), 10.7 (1/2H, br), 10.8 (1/2H, br).

ESI-MASS (m/e): 486(M+H).

Example 80

1-{[5-[4-(Isopropylsulfonyl)phenoxy]-2-(2-pyridinyl) -1H-benzimidazol-6-yl]methyl}-2-pyrrolidinone (Step 1) Production of 6-({[t-butyl(dimethyl)silyl]oxy}methyl}-5-[4-(ethylsulfonyl)phenoxy]-2-(2-pyridinyl)-1-{[2-(trimethylsilyl)ethoxy]methyl}-1H-benzimidazole and 5-({[t-butyl(dimethyl)silyl]oxy}methyl}-6-[4-(ethylsulfonyl)phenoxy]-2-(2-pyridinyl)-1-{[2-(trimethylsilyl)ethoxy]methyl}-1H-benzimidazole 34 mg of imidazole and 30 mg of t-butyl(dimethyl)silyl chloride were added to an N,N-dimethylformamide (2 ml) solution of 100 mg of the alcohol compound obtained in Example 19 (step 7), and stirred overnight at room temperature. With cooling with ice, aqueous saturated ammonium chloride solution was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate) to obtain 69 mg of the entitled compound as yellow oil.

(Step 2) Production of 6-({[t-butyl(dimethyl)silyl]oxy}methyl}-5-[4-(isopropylsulfonyl)phenoxy]-2-(2-pyridinyl)-1-{[2-(trimethylsilyl)ethoxy]methyl}-1H-benzimidazole and 5-({[t-butyl(dimethyl)silyl]oxy}methyl}-6-[4-(isopropylsulfonyl)phenoxy]-2-(2-pyridinyl)-1-{[2-(trimethylsilyl)ethoxy]methyl}-1H-benzimidazole In a nitrogen atmosphere at −78° C., 1 ml of a tetrahydrofuran solution of 0.126 M lithium diisopropylamide that had been previously prepared was added to a tetrahydrofuran (1 ml) solution of 69 mg of the silyl ether compound obtained in the step 1, and stirred at that temperature for 30 minutes. At −78° C., a tetrahydrofuran (1 ml) solution of 45 mg of iodomethane was dropwise added to it, and further stirred for 1 hours. Then, this was gradually heated up to 0° C., and aqueous saturated ammonium chloride solution was added to it, extracted with ethyl acetate, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), developing solvent: hexane/ethyl acetate=1/1) to obtain 30 mg of the entitled compound as a yellow oil.

(Step 3) Production of (5-[4-(isopropylsulfonyl)phenoxy]-2-(2-pyridinyl)-1-{[2-(trimethylsilyl)ethoxy]methyl}-1H-benzimidazol-6-yl)methanol and (6-[4-(isopropylsulfonyl)phenoxy]-2-(2-pyridinyl)-1-{[2-(trimethylsilyl)ethoxy]methyl}-1H-benzimidazol-5-yl)methanol With cooling with ice, 49 µl of a tetrahydrofuran solution of 1.0 M tetrabutylammonium fluoride was dropwise added to a tetrahydrofuran (1 ml) solution of 30 mg of the silyl ether compound obtained in the step 2, and stirred for 10 minutes. Aqueous saturated ammonium chloride solution was added to it, extracted with ethyl acetate, and the organic layer was washed with a phosphate buffer (pH 7.0). After dried, the solvent was evaporated away under reduced pressure, and the residue was purified through partitioning thin-layer chromatography (Kieselgel™ 60F$_{254}$, Art 5744 (by Merck), developing solvent: hexane/ethyl acetate=1/2) to obtain 24 mg of the entitled compound as a yellow oil.

(Step 4) Production of 1-{[5-[4-(isopropylsulfonyl)phenoxy]-2-(2-pyridinyl)-1H-benzimidazol-6-yl]methyl}-2-pyrrolidinone Using the alcohol product obtained in the step 3, the entitled compound was obtained in the same method as in Example 2 or in accordance with the method or by combining it with an ordinary method.

$^1$HNMR (CDCl$_3$) δ: 1.30 (6H, d, J=7.0 Hz), 1.88-1.96 (2H, m), 2.29-2.36 (2H, m), 3.17 (1H, septet, J=7.0 Hz), 3.26-3.31 (2H, m), 4.53 (2H×1/2, s), 4.54 (2H×1/2, s), 7.04 (2H×1/2, d, J=9.0 Hz), 7.06 (2H×1/2, d, J=9.0 Hz), 7.17 (1H×1/2, s), 7.37-7.41 (1H, m), 7.48 (1H×1/2, s), 7.56 (1H×1/2, s), 7.76 (1H×1/2, s), 7.80 (2H×1/2, d, J=9.0 Hz), 7.80 (2H×1/2, d, J=9.0 Hz), 7.84-7.90 (1H, m), 8.36-8.41 (1H, m), 8.62-8.66 (1H, m), 10.66 (1H×1/2, brs), 10.73 (1H×1/2, brs).

ESI-MASS (m/e): 491(M+H).

Example 81

4-({5-[4-(Ethylsulfonyl)phenoxy]-2-(2-pyridinyl)-1H-benzimidazol-6-yl}methyl)morpholin-3-one Using the alcohol compound obtained in Example 19 (step 7) and morpholin-3-one (produced according to the method described in U.S. Pat. No. 5,349,045), the entitled compound was obtained in the same method as in Example 2 or in accordance with the method or by combining it with an ordinary method.

$^1$HNMR (CDCl$_3$) δ: 1.30 (3H, t, J=7.4 Hz), 3.11 (2H, q, J=7.4 Hz), 3.34 (2H, m), 3.81 (2H, m), 4.15 (2H, m), 4.72 (2H, m), 7.07 (2H, m), 7.18 (1/2H, s), 7.40 (1H, m), 7.49 (1/2H, s), 7.68 (1/2H, s), 7.80-7.90 (1H+1/2H, m), 7.84 (2H, d, J=8.8 Hz), 8.39 (1H, m), 8.66 (1H, m), 10.7 (1/2H, br), 10.8 (1/2H, br).

ESI-MASS (m/e): 493(M+H).

Example 82

1-({5-[4-(Ethylsulfonyl)phenoxy]-2-(2-pyridinyl)-1H-benzimidazol-6-yl}methyl)-1H-imidazole-2-carbonitrile (Step 1) Production of 2-cyanoimidazole This was produced according to the method described in WO2003/011836.

(Step 2) Production of 1-({5-[4-(ethylsulfonyl)phenoxy]-2-(2-pyridinyl)-1H-benzimidazol-6-yl}methyl)-1H-imidazole-2-carbonitrile Using the alcohol compound obtained in Example 19 (step 7) and 2-cyanoimidazole, the entitled compound was obtained in the same method as in Example 2 or in accordance with the method or by combining it with an ordinary method.

$^1$HNMR (CDCl$_3$) δ: 1.31 (3H, m), 3.13 (2H, m), 5.41 (2H, s), 7.00-7.15 (4H+1/2H, m), 7.42 (1H, m), 7.47 (1/2H, m), 7.55 (1/2H, s), 7.80-7.95 (3H+1/2H, m), 8.39 (1H, m), 8.65 (1H, m), 10.75 (1/2H, br), 10.83 (1/2H, br).

ESI-MASS (m/e): 485(M+H).

Example 83

N-({5-[4-(ethylsulfonyl)phenoxy]-2-(2-pyridinyl)-1H-benzimidazol-6-yl}methyl)acetamide (Step 1) Production of N-({5-[4-(ethylsulfonyl)phenoxy]-2-(2-pyridinyl)-1-{[2-(trimethylsilyl)ethoxy]methyl}-1H-benzimidazol-6-yl}methyl)acetamide or N-({6-[4-(ethylsulfonyl)phenoxy]-2-(2-pyridinyl)-1-{[2-(trimethylsilyl)ethoxy]methyl}-1H-benzimidazol-5-yl}methyl)acetamide 21 μl of acetyl chloride was added to a chloroform (0.8 ml) solution of 81.5 mg of the amine compound obtained in Example 31 (step 1) and 42 μl of triethylamine. This was stirred for 30 minutes, aqueous saturated sodium bicarbonate solution was added to it, extracted with ethyl acetate, and the organic layer was washed with saturated saline water. After dried, the solvent was evaporated away under reduced pressure, and the residue was purified through silica gel column chromatography (developing solvent: chloroform to chloroform/methanol=20/1) to obtain 82 mg of the entitled compound as a yellow oil.

(Step 2) Production of N-({5-[4-(ethylsulfonyl)phenoxy]-2-(2-pyridinyl)-1H-benzimidazol-6-yl}methyl)acetamide 12 mg of the obtained yellow oil was dissolved in 0.5 ml of trifluoroacetic acid, and stirred at room temperature for 2 hours. The solvent was evaporated away, the residue was neutralized with triethylamine, and purified through partitioning thin-layer chromatography (Kieselgel™ 60F$_{254}$, Art 5744 (by Merck), chloroform/methanol=10/1) to obtain 9.8 mg of the entitled compound as a pale yellow solid.

$^1$HNMR (CDCl$_3$) δ: 1.30 (3H, t, J=7.4 Hz), 1.95 (3H, s), 3.11 (2H, q, J=7.4 Hz), 4.49 (2H, m), 5.83 (1/2H, br), 5.97 (1/2H, br), 7.15 (1/2H, s), 7.40 (1H, m), 7.46 (1/2H, s), 7.65 (1/2H, s), 7.85 (3H+1/2H, m), 8.39 (1H, m), 8.65 (1H, m), 10.7 (1/2H, br), 10.8 (1/2H, br).

ESI-MASS (m/e): 451(M+H).

Example 84

N-({5-[4-(ethylsulfonyl)phenoxy]-2-(2-pyridinyl)-1H-benzimidazol-6-yl}methyl)-N-methylacetamide With cooling with ice, 18 μl of methyl iodide and 5.2 mg of sodium hydride (with 30% liquid paraffin added thereto) were added to a dimethylformamide (0.3 ml) solution of 38 mg of the acetamide compound obtained in Example 83 (step 1). This was stirred at room temperature for 2 hours, then aqueous saturated ammonium chloride solution was added to it, extracted with ethyl acetate, and the organic layer was washed with water and saturated saline water. After dried, the solvent was evaporated away under reduced pressure to obtain 18.1 mg an yellow oil.

0.5 ml of trifluoroacetic acid was added to 18.1 mg of the obtained yellow oil, and stirred at room temperature for 2 hours. The solvent was evaporated away, and the residue was neutralized with triethylamine and purified through partitioning thin-layer chromatography (Kieselgel™ 60F$_{254}$, Art 5744 (by Merck), chloroform/methanol=10/1) to obtain 13.2 mg of the entitled compound as a white amorphous substance.

$^1$HNMR (CDCl$_3$) δ: 1.28 (3H, m), 2.05 and 2.08 (total 3H, s), 2.96 and 2.99 (total 3H, s), 3.12 (2H, m), 4.58 and 4.66 (total 2H, m), 7.08 (2H, m), 7.17-7.73 (total 3H, m), 7.82-7.90 (3H, m), 8.40 (1H, m), 8.65 (1H, m), 10.8 (1H, br).

ESI-MASS (m/e): 465(M+H).

Example 85

3-{[5-[4-(ethylsulfonyl)phenoxy]-2-(2-pyridinyl)-1H-benzimidazol-6-yl]methyl}-1,3-oxazolidine-2,4-dione Using 1,3-oxazolidine-2,4-dione produced according to the method described in JOURNAL OF MEDICINAL CHEMISTRY, 1991, Vol. 34, No. 5, pp. 1538-1544, the entitled compound was obtained in the same method as in Example 19 (step 8) or in accordance with the method or by combining it with an ordinary method.

$^1$HNMR (CDCl$_3$) δ: 1.30 (3H, t, J=7.4 Hz), 3.12 (2H, q, J=7.4 Hz), 4.52 (2H×1/2, s), 4.59 (2H×1/2, s), 4.81 (2H×1/2, s), 4.83 (2H×1/2, s), 7.10 (2H, d, J=8.2 Hz), 7.11 (1H×1/2, s), 7.38-7.44 (1H, m), 7.47 (1H×1/2, s), 7.70 (1H×1/2, s), 7.83-

7.92 (3H, m), 7.83-7.92 (1H×1/2, m), 8.37-8.42 (1H, m), 8.62-8.67 (1H, m), 10.85 (1H×1/2, brs), 10.90 (1H×1/2, brs).
ESI-MASS (m/e): 493(M+H).

Example 86

N-acetyl-N-({5-[4-(ethylsulfonyl)phenoxy]-2-(2-pyridinyl)-1H-benzimidazol-6-yl}methyl)acetamide Using the alcohol compound obtained in Example 19 (step 7) and diacetamide, the entitled compound was obtained in the same method as in Example 2 or in accordance with the method or by combining it with an ordinary method.
$^1$HNMR (CDCl$_3$) δ: 1.30 (3H, t, J=7.4 Hz), 3.11 (2H, q, J=7.4 Hz), 2.42 (6H×1/2, s), 2.43 (6H×1/2, s), 5.00 (2H, s), 7.11 (2H, d, J=8.6 Hz), 7.15 (1/2H, s), 7.25 (1/2H, s), 7.41 (1H, m), 7.48 (1/2H, s), 7.57 (1/2H, s), 7.88 (3H, m), 8.38 (1H, m), 8.64 (1H, m), 10.75 (1H, br).
ESI-MASS (m/e): 493(M+H).

Example 87

5-[4-(Ethylsulfonyl)phenoxy]-6-(1H-pyrazol-1-ylmethyl)-2-(2-pyridinyl)-1H-benzimidazole Using the alcohol compound obtained in Example 19 (step 7) and pyrazole, the entitled compound was obtained in the same method as in Example 2 or in accordance with the method or by combining it with an ordinary method.
$^1$HNMR (CDCl$_3$) δ: 1.29 (3H, t, J=7.4 Hz), 3.11 (2H, q, J=7.4 Hz), 5.41 (2H, s), 6.19 (1H, s), 7.01 (2H, m), 7.11 (1/2H, s), 7.35-7.50 (4H, m), 7.65 (1/2H, s), 7.80 (2H, m), 7.86 (1H, m), 8.38 (1H, m), 8.62 (1H, m), 10.8 (1/2H, br), 10.9 (1/2H, br).
ESI-MASS (m/e): 460(M+H).

Example 88

5-[4-(Ethylsulfonyl)phenoxy]-6-(1H-imidazol-1-ylmethyl)-2-(2-pyridinyl)-1H-benzimidazole Using the alcohol compound obtained in Example 19 (step 7) and imidazole, the entitled compound was obtained in the same method as in Example 2 or in accordance with the method or by combining it with an ordinary method.
$^1$HNMR (CDCl$_3$) δ: 1.34 (3H, m), 3.13 (2H, m), 5.20 (2H, s), 6.88-7.20 (4H, m), 7.40 (1H, m), 7.45-7.60 (2H, m), 7.70-7.80 (1H, m), 7.80-7.94 (3H, m), 8.39 (1H, m), 8.64 (1H, m), 10.7 (1/2H, br), 10.8 (1/2H, br).
ESI-MASS (m/e): 460(M+H).

Example 89

4-[({5-[4-(Ethylsulfonyl)phenoxy]-2-(2-pyridinyl)-1H-benzimidazol-6-yl}methyl)amino]-4-oxobutyric acid (trifluoroacetate)

50 mg of the final product obtained in Example 19 was dissolved in 1 ml of tetrahydrofuran and 0.2 ml of water, and 60 μl of 5 N sodium hydroxide was added to it and stirred at room temperature for 1 hour. This was neutralized with 2 N hydrochloric acid, diluted with chloroform, and dried with anhydrous magnesium sulfate. After filtered, the solvent was evaporated away under reduced pressure, and the residue was purified through reversed-phase middle-pressure chromatography [ODS-AS-360-CC (by YMC), mobile phase: water/acetonitrile/0.1% trifluoroacetic acid]. The solvent of the obtained fraction was evaporated away under reduced pressure to obtain 21.1 mg of the entitled compound as a colorless solid.
$^1$HNMR (DMSO-d$_6$) δ: 1.12 (3H, t, J=7.5 Hz), 2.34 (2H, m), 2.41 (2H, m), 3.28 (2H, q, J=7.5 Hz), 4.29 (2H, d, J=5.5 Hz), 7.14 (2H, J=8.8 Hz), 7.37 (1H, s), 7.60 (1H, m), 7.69 (1H, s), 7.87 (2H, d, J=8.8 Hz), 8.07 (1H, m), 8.34 (2H, m), 8.79 (1H, d, J=4.5 Hz).
ESI-MASS (m/e): 508(M+H).

Example 90

N-(cyanomethyl)-N-({5-[4-(ethylsulfonyl)phenoxy]-2-(2-pyridinyl)-1H-benzimidazol-6-yl}methyl)acetamide (Step 1) Production of [5-[4-(ethylsulfonyl)phenoxy]-2-(2-pyridinyl)-1H-benzimidazol-6-yl]methanol Using the alcohol compound obtained in Example 19 (step 7), the entitled compound was obtained in the same method as in Example 57 (step 4) or in accordance with the method or by combining it with an ordinary method.

(Step 2) Production of 6-(chloromethyl)-5-[4-(ethylsulfonyl)phenoxy]-2-(2-pyridinyl)-1H-benzimidazole 11 μl of thionyl chloride was added to a chloroform (3 ml) solution of 30 mg of the obtained alcohol compound, and stirred at room temperature for 1 hour. This was neutralized with aqueous saturated sodium bicarbonate, extracted with chloroform, and the organic layer was washed with saturated saline water. After dried, the solvent was evaporated away under reduced pressure to obtain 30 mg of the entitled compound as a pale yellow amorphous substance.

(Step 3) N-(cyanomethyl)-N-({5-[4-(ethylsulfonyl)phenoxy]-2-(2-pyridinyl)-1H-benzimidazol-6-yl}methyl)acetamide 2.1 g of acetonitrile was dissolved in 50 ml of chloroform, and with cooling with ice, 5.6 ml of triethylamine and 2 ml of acetyl chloride were added to it, and stirred at room temperature for 3 hours. Aqueous saturated sodium bicarbonate was added to it, extracted with chloroform, and the organic layer was washed with saturated saline water. After dried, the solvent was evaporated away under reduced pressure, and the residue was purified through silica gel column chromatography (developing solvent: hexane/ethyl acetate=4/1 to 1/1 to 1/9, to chloroform/methanol) to obtain 0.85 g of N-(cyanomethyl)acetamide as a white crystal.
With cooling with ice, 5.2 mg of sodium hydride (with 30% liquid paraffin added thereto) was added to a dimethylformamide (0.25 ml) solution of 21.6 mg of the obtained N-(cyanomethyl)acetamide. This was stirred at room temperature for 30 minutes, the a dimethylformamide (0.75 ml) solution of 30 mg of the chloride compound obtained in the step 2 was added to it, and stirred for 1 hour. Aqueous saturated ammonium chloride solution was added to it, extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 3.3 mg of the entitled compound as a white amorphous substance.

$^1$HNMR (CDCl$_3$) δ: 1.31 (3H, m), 2.22 (3H, m), 3.15 (2H, m), 4.10-4.30 (2H, m), 4.75 (2H, m), 7.12-7.20 (2H+1/2H, m), 7.42 (1H, m), 7.50 (1H, s), 7.77 (1/2H, s), 7.90 (3H, m), 8.39 (1H, m), 8.65 (1H, m), 10.6 (1/2H, br), 10.7 (1/2H, br).

ESI-MASS (m/e): 490(M+H).

Example 91

1-({5-[4-(Ethylsulfonyl)phenoxy]-2-(2-pyridinyl)-1H-benzimidazol-6-yl]}methyl)-1H-pyrrole-2,5-dione At −78° C., 0.21 ml of diethylazodicarboxylate (40% toluene solution) was added to a tetrahydrofuran (0.5 ml) solution of 50 mg of triphenyl phosphine, and stirred for 5 minutes. At −78° C., a tetrahydrofuran (0.5 ml) solution of 100 mg of the alcohol compound obtained in Example 19 (step 7) was gradually added to the reaction liquid, and 18 mg of maleimide was added thereto. After maleimide dissolved therein, the reaction liquid was restored to room temperature and stirred for 2 hours. The solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure to obtain 11 mg of a yellow oil.

11 mg of the obtained yellow oil was dissolved in 0.3 ml of trifluoroacetic acid, and stirred at room temperature for 2 hours. The solvent was evaporated away, and the residue was neutralized with triethylamine and purified through partitioning thin-layer chromatography (Kieselgel™ 60F$_{254}$, Art 5744 (by Merck), chloroform/methanol=10/1) to obtain 4.1 mg of the entitled compound as a pale yellow amorphous substance.

$^1$HNMR (CDCl$_3$) δ: 1.30 (3H, m), 3.12 (2H, m), 4.80 (2H, s), 6.62 (2H×1/2, s), 6.67 (2H×1/2, s), 7.08 (2H, m), 7.13 (1/2H, s), 7.40 (1H, m), 7.46 (1/2H, s), 7.59 (1/2H, s), 7.78 (1/2H, s), 7.80 (3H, m), 8.37 (1H, m), 8.67 (1H, m), 10.6 (1H, m).

ESI-MASS (m/e): 489(M+H).

Example 92

1-[1-({5-[4-(Ethylsulfonyl)phenoxy]-2-(2-pyridinyl)-1H-benzimidazol-6-yl]}methyl)-1H-imidazol-2-yl]ethanone (Step 1) Production of 2-acetylimidazole At −78° C., 1.6 ml of methylmagnesium bromide (3 M, diethyl ether solution) was added to a tetrahydrofuran (3 ml) solution of 151 mg of 1H-imidazole-2-carbonitrile obtained in Example 82 (step 1), and stirred at that temperature for 1 hour. Aqueous saturated ammonium chloride solution was added to it, extracted with ethyl acetate and chloroform, and the organic layer was dried, and the solvent was evaporated away under reduced pressure to obtain 187 mg of the entitled compound as a yellow solid.

(Step 2) Production of 1-[1-({5-[4-(ethylsulfonyl)phenoxy]-2-(2-pyridinyl)-1H-benzimidazol-6-yl]}methyl)-1H-imidazol-2-yl]ethanone Using the obtained 2-acetylimidazole and the alcohol compound obtained in Example 19 (step 7), the entitled compound was obtained in the same method as in Example 2 or in accordance with the method or by combining it with an ordinary method.

$^1$HNMR (CDCl$_3$) δ: 1.31 (3H, t, J=7.2 Hz), 2.61 (3H×1/2, s), 2.64 (3H×1/2, s), 3.13 (2H, d, J=7.2 Hz), 5.71 (2H×1/2, s), 5.74 (2H×1/2, s), 7.05-7.15 (4H+1/2H, m), 7.32 (1/2H, s), 7.38 (1H, m), 7.41 (1/2H, s), 7.53 (1/2H, s), 7.85 (3H, m), 8.37 (1H, m), 8.67 (1H, m), 10.80 (1/2H, br), 10.82 (1/2H, br).

ESI-MASS (m/e): 502(M+H).

Example 93

N-({5-[4-(ethylsulfonyl)phenoxy]-2-(2-pyridinyl)-1H-benzimidazol-6-yl]}methyl)-2,2,2-trifluoro-N-methylacetamide With cooling with ice, 40 μl of trifluoroacetic anhydride was added to a pyridine (0.5 ml) solution of 50 mg of the amine compound obtained in Example 31 (step 1), and stirred for 30 minutes. Water was added to it, extracted with ethyl acetate, and the organic layer was washed with saturated saline water. After dried, the solvent was evaporated away under reduced pressure, and the residue was purified through silica gel column chromatography (developing solvent: chloroform to chloroform/methanol=20/1) to obtain 37.8 mg of the entitled compound as a white solid.

Using 25 mg of the obtained white solid, the entitled compound was obtained in the same method as in Example 84 or in accordance with the method or by combining it with an ordinary method.

$^1$HNMR (CDCl$_3$) δ: 1.28 (3H, m), 3.00-3.20 (5H, m), 4.73 (2H×1/2, s), 4.76 (2H×1/2, s), 7.00-7.10 (2H, m), 7.19 (1/2H, s), 7.41 (1H, m), 7.50 (1/2H, s), 7.55 (1/2H, s), 7.70-7.90 (3H+1/2H, m), 8.41 (1H, m), 8.64 (1H, m), 10.8 (1H, br).

ESI-MASS (m/e): 519(M+H).

Example 94

N-ethyl-N-({5-[4-(ethylsulfonyl)phenoxy]-2-(2-pyridinyl)-1H-benzimidazol-6-yl]}methyl)acetamide Using ethyl iodide, the entitled compound was obtained in the same method as in Example 84 or in accordance with the method or by combining it with an ordinary method.

$^1$HNMR (CDCl$_3$) δ: 1.13 (3H, m), 1.29 (3H, m), 2.07 (3H×1/2, s), 2.11 (3H×1/2, s), 3.11 (2H, m), 3.29 (2H×2, m), 3.45 (2H×1/2, m), 4.56 (2H×1/2, s), 4.66 (2H×1/2, m), 7.00-7.11 (2H+1/2H, m), 7.41 (1H+1/2H, m), 7.64 (1/2H, m), 7.86 (3H+1/2H, m), 8.39 (1H, m), 8.64 (1H, m), 10.8 (1H, br).

ESI-MASS (m/e): 479(M+H).

Example 94

1-({5-[4-(Ethylsulfonyl)phenoxy]-2-(2-pyridinyl)-1H-benzimidazol-6-yl]}methyl)-3-hydroxypyrrolidine-2,5-dione (Step 1) Production of 1-[(5-[4-(ethylsulfonyl)phenoxy]-2-(2-pyridinyl)-1-{[2-(trimethylsilyl)ethoxy]methyl}-1H-benzimidazol-6-yl)methyl]-3-hydroxypyrrolidine-2,5-dione or 1-[(6-[4-(ethylsulfonyl)phenoxy]-2-(2-pyridinyl)-1-{[2-(trimethylsilyl)ethoxy]methyl}-1H-benzimidazol-5-yl)methyl]-3-hydroxypyrrolidine-2,5-dione 31 mg of [5-oxo-2-(trichloromethyl)-1,3-dioxolan-4-yl]acetyl chloride produced according to the method described in Synthesis, 2002, Vol. 15, pp. 2165-2166, and 40 μl of pyridine were added to a chloroform (0.5 ml) solution of 54 mg of the amine compound obtained in Example 31 (step 1), and stirred at 80° C. for 3 hours. The reaction liquid was restored to room temperature, diluted with ethyl acetate, and washed with saturated saline water. After dried, the solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure, the residue was diluted with ethyl acetate, washed with aqueous saturated sodium bicarbonate, and dried with anhydrous sodium sulfate. The solvent was evaporated away under reduced pressure to obtain 20.8 mg of the entitled compound as a colorless crystal.

(Step 2) Production of 1-({5-[4-(ethylsulfonyl)phenoxy]-2-(2-pyridinyl)-1H-benzimidazol-6-yl}methyl)-3-hydroxypyrrolidine-2,5-dione 20.8 mg of the obtained crystal was dissolved in 0.5 ml of trifluoroacetic acid, and stirred at room temperature for 2 hours. The solvent was evaporated away, aqueous saturated sodium bicarbonate was added to it, extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 9.1 mg of the entitled compound as a colorless crystal.

$^1$HNMR (CDCl$_3$) δ: 1.27 (3H, t, J=7.2 Hz), 2.47 (1H, m), 2.97 (1H, m), 3.23 (2H, q, J=7.2 Hz), 4.79 (1H, m), 4.88 (2H, m), 7.16 (2H, d, J=8.8 Hz), 7.35 (1H, m), 7.52 (1H, m), 7.78 (1H, m), 7.91 (2H, d, J=8.8 Hz), 8.00 (1H, t, J=8.2 Hz), 8.30 (1H, d, J=8.2 Hz), 8.76 (1H, m).

ESI-MASS (m/e): 507(M+H).

Example 96

4-[({5-[4-(Ethylsulfonyl)phenoxy]-2-(2-pyridinyl)-1H-benzimidazol-6-yl}methyl)amino]-2-hydroxy-4-oxobutyric acid (trifluoroacetate)

Aqueous 1 N sodium hydroxide solution was added to a tetrahydrofuran (0.5 ml) solution of 50 mg of the compound obtained in Example 95 (step 1), and stirred at room temperature for 15 minutes. This was neutralized with 2 N hydrochloric acid, then diluted with chloroform, and dried with anhydrous magnesium sulfate. After filtered, the solvent was evaporated away under reduced pressure, and the residue was purified through reversed-phase middle-pressure chromatography [ODS-AS-360-CC (by YMC), mobile phase: water/acetonitrile/0.1% trifluoroacetic acid]. The solvent of the obtained fraction was evaporated away under reduced pressure to obtain 43.5 mg of a yellow amorphous substance.

The obtained crystal was dissolved in 1 ml of trifluoroacetic acid, and stirred at room temperature for 2 hours. The solvent was evaporated away, and the residue was purified through reversed-phase middle-pressure chromatography [ODS-AS-360-CC (by YMC), mobile phase: water/acetonitrile/0.1% trifluoroacetic acid]. The solvent of the obtained fraction was evaporated away under reduced pressure to obtain 19.9 mg of the entitled compound as a pale yellow amorphous substance.

$^1$HNMR (CD$_3$OD) δ: 1.27 (3H, t, J=7.4 Hz), 2.59 (1H, dd, J=8.2 Hz, 14.5 Hz), 2.71 (1H, d, J=4.1, 14.5 Hz), 3.25 (2H, q, J=7.4 Hz), 4.55 (1H, m), 4.56 (2H, m), 7.27 (2H, d, J=8.8 Hz), 7.45 (1H, s), 7.70 (1H, m), 7.94 (1H, s), 7.97 (2H, d, J=8.8 Hz), 8.15 (1H, t, J=7.6 Hz), 8.32 (1H, d, J=7.6 Hz), 8.90 (1H, d, J=4.7 Hz).

ESI-MASS (m/e): 507(M+H).

Example 97

(2Z)-4-[({5-[4-(ethylsulfonyl)phenoxy]-2-(2-pyridinyl)-1H-benzimidazol-6-yl}methyl)amino]-4-oxo-2-butenoic acid (trifluoroacetate)

27 mg of maleic anhydride was added to a chloroform (1 ml) solution of 100 mg of the amine compound obtained in Example 31 (step 1), and stirred at room temperature for 1 hour. The solvent was evaporated away, and the residue was purified through reversed-phase middle-pressure chromatography [ODS-AS-360-CC (by YMC), mobile phase: water/acetonitrile/0.1% trifluoroacetic acid]. The solvent of the obtained fraction was evaporated away under reduced pressure to obtain 121.8 g of a yellow oil.

40 mg of the obtained yellow oil was dissolved in 0.5 ml of trifluoroacetic acid, and stirred at room temperature for 2 hours. The solvent was evaporated away, and the residue was purified through reversed-phase middle-pressure chromatography [ODS-AS-360-CC (by YMC), mobile phase: water/acetonitrile/0.1% trifluoroacetic acid]. The solvent of the obtained fraction was evaporated away under reduced pressure to obtain 19.3 mg of the entitled compound as a colorless crystal.

$^1$HNMR (DMSO-d$_6$) δ: 1.12 (3H, t, J=7.2 Hz), 3.27 (2H, q, J=7.2 Hz), 4.45 (2H, d, J=5.3 Hz), 6.23 (1H, d, J=12.3 Hz), 6.35 (1H, d, J=12.3 Hz), 7.15 (2H, d, J=8.8 Hz), 7.39 (1H, s), 7.60 (1H, m), 7.79 (1H, s), 7.86 (2H, d, J=8.8 Hz), 8.06 (1H, t, J=7.6 Hz), 8.35 (1H, d, J=7.6 Hz), 8.79 (1H, d, J=7.6 Hz), 9.39 (1H, m).

ESI-MASS (m/e): 507(M+H).

Example 98

(4S)-1-({5-[4-(ethylsulfonyl)phenoxy]-2-(2-pyridinyl)-1H-benzimidazol-6-yl]}methyl)-4-hydroxypyrrolidin-2-one (Step 1) Production of (S)-4-{[t-butyl(dimethyl)silyl]oxy}pyrrolidin-2-one 1.02 g of imidazole and 1.58 g of t-butyldimethylchlorosilane were added to a dimethylformamide (5 ml) solution of 1.01 g of (S)-4-hydroxy-2-pyrrolidone, and stirred overnight at room temperature. Water was added to the reaction liquid, and stirred with cooling with ice.

The precipitated crystal was taken out through filtration and dried to obtain 2.07 g of the entitled compound as a colorless crystal.

(Step 2) Production of (4S)-4-{[t-butyl(dimethyl)silyl]oxy}-1-({5-[4-ethylsulfonyl)phenoxy]-2-(2-pyridinyl)-1-{[2-(trimethylsilyl)ethoxy]methyl}-1H-benzimidazol-6-yl]}methyl)pyrrolidin-2-one or (4S)-4-{[t-butyl(dimethyl)silyl]oxy}-1-({6-[4-ethylsulfonyl)phenoxy]-2-(2-pyridinyl)-1-{[2-(trimethylsilyl)ethoxy]methyl}-1H-benzimidazol-5-yl]}methyl)pyrrolidin-2-one With cooling with ice, 15 μl of methanesulfonyl chloride was added to a tetrahydrofuran (0.5 ml) solution of 50 mg of the alcohol compound obtained in Example 19 (step 7) and 26 µl of triethylamine, and stirred for 30 minutes. Water was added to it, extracted with ethyl acetate, and the organic layer was washed with saturated saline water. After dried, the solvent was evaporated away under reduced pressure to obtain a pale yellow amorphous substance.

With cooling with ice, 22 mg of sodium hydride (with 30% liquid paraffin added thereto) was added to a dimethylformamide (1 ml) solution of 120 mg of the colorless crystal obtained in the step 1, and stirred at room temperature for 1 hour. A tetrahydrofuran (1.5 ml) solution of the pale yellow amorphous substance obtained in the above operation was added to the reaction liquid, and further stirred at room temperature for 1 hour. With cooling with ice, aqueous saturated ammonium chloride solution was added to it, extracted with ethyl acetate, and the organic layer was washed with water and saturated saline water. After dried, the solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure, the residue was diluted with ethyl acetate, washed with aqueous saturated sodium bicarbonate, and dried with anhydrous sodium sulfate. The solvent was evaporated away under reduced pressure to obtain 55.5 mg of the entitled compound as a yellow oil.

(Step 3) Production of (4S)-1-({5-[4-(ethylsulfonyl)phenoxy]-2-(2-pyridinyl)-1H-benzimidazol-6-yl]}methyl)-4-hydroxypyrrolidin-2-one 55.5 mg of the obtained yellow oil was dissolved in 1 ml of trifluoroacetic acid and 0.2 ml of water, and stirred at room temperature for 2 hours. The solvent was evaporated away, aqueous saturated sodium bicarbonate was added to the residue, extracted with chloroform, and the organic layer was washed with saturated saline water. After dried, the solvent was evaporated away under reduced pressure and the residue was purified through partitioning thin-layer chromatography (Kieselgel™ 60F$_{254}$, Art 5744 (by Merck), chloroform/methanol=10/1) to obtain 24.2 mg of the entitled compound as a white amorphous substance.

$^1$HNMR (CDCl$_3$) δ: 1.28 (3H, t, J=7.4 Hz), 2.43 (1H, m), 2.65 (1H, m), 3.10 (2H, q, J=7.4 Hz), 3.30 (1H, m), 3.55 (1H, m), 4.30-4.70 (3H, m), 7.00 (2H, d, J=8.4 Hz), 7.09 (1/3H, s), 7.30-7.45 (1H+2/3H), 5.51 (2/3H, m), 7.62-7.90 (3H+1/3H, m), 8.36 (1H, d, J=7.6 Hz), 8.62 (1H, d, J=4.5 Hz), 11.0 (1/3H, br), 11.4 (2/3H, br).

ESI-MASS (m/e): 493(M+H).

Example 99

(4R)-1-({5-[4-(ethylsulfonyl)phenoxy]-2-(2-pyridinyl)-1H-benzimidazol-6-yl]}methyl)-4-hydroxypyrrolidin-2-one Using (R-4-hydroxy-2-pyrrolidone, the entitled compound was obtained in the same method as in Example 98 or in accordance with the method or by combining it with an ordinary method.

$^1$HNMR (CDCl$_3$) δ: 1.28 (3H, t, J=7.4 Hz), 2.43 (1H, m), 2.65 (1H, m), 3.10 (2H, q, J=7.4 Hz), 3.30 (1H, m), 3.55 (1H, m), 4.30-4.70 (3H, m), 7.00 (2H, d, J=8.4 Hz), 7.09 (1/3H, s), 7.30-7.45 (1H+2/3H), 5.51 (2/3H, m), 7.62-7.90 (3H+1/3H, m), 8.36 (1H, d, J=7.6 Hz), 8.62 (1H, d, J=4.5 Hz), 11.0 (1/3H, br), 11.4 (2/3H, br).

ESI-MASS (m/e): 493(M+H).

Example 100

(4R)-1-({5-[4-(ethylsulfonyl)phenoxy]-2-(2-pyridinyl)-1H-benzimidazol-6-yl]}methyl)-4-fluoropyridin-2-one (Step 1) Production of (4S)-1-({5-[4-(ethylsulfonyl)phenoxy]-2-(2-pyridinyl)-1-{[2-(trimethylsilyl)ethoxy]methyl}-1H-benzimidazol-6-yl]}methyl)-4-hydroxypyridin-2-one or (4S)-1-({6-[4-(ethylsulfonyl)phenoxy]-2-(2-pyridinyl)-1-{[2-(trimethylsilyl)ethoxy]methyl}-1H-benzimidazol-5-yl]}methyl)-4-hydroxypyridin-2-one 0.72 ml of a tetrahydrofuran solution of 1 M tetrabutylammonium fluoride was added to a tetrahydrofuran (2.5 ml) solution of 267 mg of the compound obtained in Example 98 (step 2), and stirred at room temperature for 30 minutes. 0.1 M phosphate buffer (pH 6) was added to the reaction liquid, extracted with ethyl acetate, and the organic layer was washed with saturated saline water. After dried, the solvent was evaporated away under reduced pressure, and the residue was purified through silica gel column chromatography (developing solvent: chloroform to chloroform/methanol=20/1) to obtain 77.5 mg of the entitled compound as a colorless oil.

(Step 2) (4R)-1-({5-[4-(ethylsulfonyl)phenoxy]-2-(2-pyridinyl)-1H-benzimidazol-6-yl]}methyl)-4-fluoropyridin-2-one 46 µl of bis(2-methoxymethyl)aminosulfur trifluoride was added to a chloroform (0.8 ml) solution of 77.5 mg of the obtained oil, and stirred at room temperature for 15 minutes. This was purified through silica gel column chromatography (developing solvent: chloroform to chloroform/methanol=20/1) to obtain 42.1 mg of the entitled compound as a colorless oil.

42.1 mg of the obtained yellow oil was dissolved in 1 ml of trifluoroacetic acid, and stirred at room temperature for 2 hours. The solvent was evaporated away, aqueous saturated sodium bicarbonate was added to the residue, extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 11.1 mg of the entitled compound as a white amorphous substance.

$^1$HNMR (CDCl$_3$) δ: 1.30 (3H, t, J=7.4 Hz), 2.55-2.75 (2H, m), 3.11 (2H, q, J=7.4 Hz), 3.45-3.70 (2H, m), 4.47-4.75 (2H, m), 5.10-5.30 (1H, m), 7.03-7.10 (2H, m), 7.16 (1/2H, s), 7.40 (1H, m), 7.49 (1/2H, s), 7.56 (1/2H, s), 7.75-7.92 (3H+1/2H, m), 8.40 (1H, m), 8.64 (1H, m), 10.9 (1/2H, br), 11.0 (1/2H, br).

ESI-MASS (m/e): 495(M+H).

Example 101

6-[(1,1-Dioxidoisothiazolidin-2-yl)methyl]-5-[(6-methylpyridin-3-yl)oxy]-2-(2-pyridinyl)-1H-benzimidazole (Step 1) Production of (5-[(6-methylpyridin-3-yl)oxy]-2-(2-pyridinyl)-1-{[2-(trimethylsilyl)ethoxy]methyl}-1H-benzimidazol-6-yl)methanol and (6-[(6-methylpyridin-3-yl)oxy]-2-(2-pyridinyl)-1-{[2-(trimethylsilyl)ethoxy]methyl}-1H-benzimidazol-5-yl)methanol Using 4-hydroxy-6-methylpyridine, the entitled compound was obtained in the same method as in Example 19 (step 5 to step 7) or in accordance with the method or by combining it with an ordinary method.

(Step 2) Production of 6-[(1,1-dioxidoisothiazolidin-2-yl)methyl]-5-[(6-methylpyridin-3-yl)oxy]-2-(2-pyridinyl)-1H-benzimidazole Using the obtained alcohol compound, the entitled compound was obtained in the same method as in Example 33 or in accordance with the method or by combining it with an ordinary method.

$^1$HNMR (CDCl$_3$) δ: 2.29 (2H, m), 2.54 (3H, s), 3.14 (2H, m), 3.24 (2H, m), 4.37 (2H×1/2, s), 4.38 (2H×1/2, s), 7.00 (1/2H, s), 7.05-7.24 (2H, m), 7.35 (1/2H, s), 7.38 (1H, m), 7.67 (1/2H, s), 7.86 (1H, m), 7.92 (1/2H, s), 8.27 (1H, m), 8.38 (1H, m), 8.64 (1H, m), 10.6 (1/2H, br), 10.7 (1/2H, br).

ESI-MASS (m/e): 495(M+H).

Example 102

1-[4-[(6-((2-Oxopyrrolidin-1-yl)methyl)-2-(2-pyridinyl)-1H-benzimidazol-5-yl)oxy]phenyl]-2-pyrrolidinone (Step 1) Production of 2-fluoro-4-nitrobenzaldehyde 43.3 g of 2-fluoro-4-nitrobenzoic acid was dissolved in 600 ml of dimethylformamide, and 1,1'-carbodiimide was added to it, and stirred at room temperature for 2 hours. 11.1 g of sodium borohydride was added thereto, and further stirred for 30 minutes. Aqueous saturated ammonium chloride solution was added to it, 800 ml of water was added thereto, extracted with 1.2 liters of ethyl acetate, and the organic layer was washed with saturated saline water. The solvent was evaporated away under reduced pressure, the residue was again diluted with ethyl acetate, and the organic layer was washed with water and saturated saline water. This was dried with anhydrous sodium sulfate, and the solvent was evaporated away to obtain 32.7 g of a brown oil.

The obtained oil was dissolved in 200 ml of dimethyl sulfoxide and 60 ml of triethylamine, and 88.7 g of sulfur trioxide/pyridine complex was gradually added to it, and stirred at room temperature for 2 hours. This was diluted with ethyl acetate, and the organic layer was washed with water, aqueous 0.1 N hydrochloric acid solution and saturated saline water. The solvent was evaporated away under reduced pressure, and the residue was purified through silica gel column chromatography (developing solvent: hexane/ethyl acetate) and through crystallization (methanol/diethyl ether) to obtain 14.0 g of the entitled compound as an orange solid.

(Step 2) Production of 1-(2-fluoro-4-nitrobenzyl)pyrrolidin-2-one 100 ml of methanol was added to 1 g of the obtained 2-fluoro-4-nitrobenzaldehyde and 3.0 g of methyl 4-aminobutyrate hydrochloride, then 87 ml of 0.3 M zinc cyanotrihydroborate/methanol solution (1/2 methanol solution of zinc chloride and sodium cyanotrihydroborate) was added thereto, and stirred for 1 hour. Aqueous saturated sodium bicarbonate was added to it, diluted with ethyl acetate, and washed with water and saturated saline water. After dried, the solvent was evaporated away under reduced pressure to obtain 5.2 g of a red amorphous substance.

The obtained amorphous substance was dissolved in methanol, and 1.5 ml of 4.7 M sodium methoxide/methanol solution was added to it, and stirred at room temperature for 1.5 hours and then at 45° C. for 30 minutes. The solvent was evaporated away, and the residue was purified through silica gel column chromatography (developing solvent: hexane/ethyl acetate=5/1 to 1/1 to 0/1) to obtain 1.9 g of the entitled compound as an orange oil.

(Step 3) Production of 1-(4-amino-2-fluorobenzyl)pyrrolidin-2-one

Raney nickel was added to a methanol (20 ml) solution of 1.5 g of the compound obtained in the step 2, and stirred overnight at room temperature. After filtered, the filtrate was evaporated under reduced pressure to obtain 1.4 g of the entitled compound as an orange oil.

(Step 4) Production or N-{5-fluoro-2-nitro-4-[(2-oxopyrrolidin-1-yl)methyl]phenyl}pyridine-2-carboxamide 1-Ethyl-3-(3-dimethylaminopropyl)carbodiimide hydrochloride was added to a pyridine (25 ml) solution of 1.13 g of the compound obtained in the step 3 and 801 mg of 2-picolinic acid, and stirred overnight at room temperature. The solvent was evaporated away under reduced pressure, and the residue was dissolved in 200 ml of chloroform, and washed with 80 ml of 0.2 N hydrochloric acid (×4), 50 ml of 0.5 N sodium hydroxide solution (×3), and saturated saline water. After dried, the solvent was evaporated away under reduced pressure to obtain 1.51 g of a pale yellow solid.

A fuming nitric acid (7 ml) solution of 1.51 g of the pale yellow solid was stirred at room temperature for 1 hour, then poured into aqueous saturated sodium hydrogencarbonate solution with cooling with ice, and stirred at room temperature for 1 hour. The insoluble matter was taken out through filtration, washed with water, then dried overnight under reduced pressure to obtain 1.56 g of the entitled compound as a pale yellow solid.

(Step 5) Production of 1-[4-[(6-((2-oxopyrrolidin-1-yl)methyl)-2-(2-pyridinyl)-1H-benzimidazol-5-yl)oxy]phenyl]-2-pyrrolidinone 20 mg of calcium carbonate was added to a dimethylformamide (0.5 ml) solution of 20 mg of the compound obtained in the step 4 and 12 mg of 1-(4-hydroxyphenyl)pyrrolidin-2-one, and stirred at 80° C. for 30 minutes. Then, 126 mg of tin chloride dihydrate was added to it, and stirred at 80° C. for 30 minutes. Water and chloroform were added to the reaction liquid, and the insoluble matter was taken out through filtration. The filtrate was extracted with chloroform, and the organic layer was washed with saturated saline water. After dried, the solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure, the residue was diluted with chloroform, washed with aqueous saturated sodium bicarbonate, and dried with anhydrous sodium sulfate. The solvent was evaporated away under reduced pressure.

Further, the residue was purified through partitioning thin-layer chromatography (Kieselgel™ 60F$_{254}$, Art 5744 (by Merck), chloroform/methanol=10/1) to obtain 13.7 mg of the entitled compound as a white amorphous substance.

$^1$HNMR (CDCl$_3$) δ: 1.91-2.02 (2H, m), 2.14-2.22 (2H, m), 2.36-2.41 (2H, m), 2.60-2.65 (2H, m), 3.33-3.39 (2H, m), 3.84-3.88 (2H, m), 4.60 (2H×1/2, s), 4.63 (2H×1/2, s), 6.96 (1H×1/2, s), 6.98 (2H×1/2, d, J=9.0 Hz), 6.99 (2H×1/2, d, J=9.0 Hz), 7.34-7.39 (1H, m), 7.38 (1H×1/2, s), 7.53 (1H×1/2, s), 7.54 (2H×1/2, d, J=9.0 Hz), 7.55 (2H×1/2, d, J=9.0 Hz), 7.71 (1H×1/2, s), 7.82-7.88 (1H, m), 8.34-8.40 (1H, m), 8.60-8.65 (1H, m), 10.55 (1H×1/2, brs), 10.63 (1H×1/2, brs).

ESI-MASS (m/e): 468(M+H).

Example 103

1-[4-[(6-((2-Oxopyrrolidin-1-yl)methyl)-2-(2-pyridinyl)-1H-benzimidazol-5-yl)oxy]phenyl]pyridin-2(1H)-one Using 1-(4-hydroxyphenyl)pyridin-2(1H)-one obtained in Reference Example 12, the entitled compound was obtained in the same method as in Example 102 (step 5) or in accordance with the method or by combining it with an ordinary method.

$^1$HNMR (CDCl$_3$) δ: 1.93-2.00 (2H, m), 2.35-2.41 (2H, m), 3.31-3.38 (2H, m), 4.60 (2H×1/2, s), 4.61 (2H×1/2, s), 6.22-6.28 (1H, m), 6.64-6.69 (1H, m), 7.01 (2H×1/2, d, J=8.6 Hz), 7.05 (2H×1/2, d, J=8.6 Hz), 7.10 (1H×1/2, s), 7.31-7.43 (3H, m), 7.32 (2H, d, J=8.6 Hz), 7.48 (1H×1/2, s), 7.56 (1H×1/2, s), 7.74 (1H×1/2, s), 7.84-7.89 (1H, m), 8.36-8.40 (1H, m), 8.63-8.66 (1H, m), 10.73 (1H×1/2, brs), 10.82 (1H×1/2, brs).

ESI-MASS (m/e): 478(M+H).

Example 104

5-((6-((2-Oxopyrrolidin-1-yl)methyl)-2-(2-pyridinyl)-1H-benzimidazol-5-yl)oxy)pyridine-2-carbonitrile Using 5-hydroxypyridine-2-carbonitrile obtained in Reference Example 10, the entitled compound was obtained in the same method as in Example 102 (step 5) or in accordance with the method or by combining it with an ordinary method.

$^1$HNMR (CDCl$_3$) δ: 1.91-1.99 (2H, m), 2.27-2.37 (2H, m), 3.27-3.33 (2H, m), 4.53 (2H, s), 7.20 (1H×1/2, s), 7.23-7.28 (1H, m), 7.40-7.43 (1H, m), 7.49 (1H×1/2, s), 7.57 (1H×1/2, s), 7.62 (1H×1/2, d, J=8.6 Hz), 7.64 (1H×1/2, d, J=8.2 Hz), 7.79 (1H×1/2, s), 7.87-7.92 (1H, m), 8.37-8.45 (2H, m), 8.64-8.67 (1H, m), 10.75 (1H×1/2, brs), 10.84 (1H×1/2, brs).

ESI-MASS (m/e): 411(M+H).

Example 105

1-{[5-[(6-(Methoxymethyl)pyridin-3-yl)oxy]-2-(2-pyridinyl)-1H-benzimidazol-6-yl]methyl}-2-pyrrolidinone Using 6-(methoxymethyl)pyridin-3-ol obtained in Reference Example 11, the entitled compound was obtained in the same method as in Example 102 (step 5) or in accordance with the method or by combining it with an ordinary method.

$^1$HNMR (CDCl$_3$) δ: 1.93-2.00 (2H, m), 2.35-2.41 (2H, m), 3.32-3.39 (2H, m), 3.48 (3H×1/2, s), 3.48 (3H×1/2, s), 4.57 (2H, s), 4.61 (2H×1/2, s), 4.63 (2H×1/2, s), 7.03 (1H×1/2, s), 7.25-7.29 (1H, m), 7.35 (1H×1/2, s), 7.36-7.40 (2H, m), 7.55 (1H×1/2, s), 7.74 (1H×1/2, s), 7.84-7.90 (1H, m), 8.30-8.41 (2H, m), 8.61-8.65 (1H, m), 10.73 (1H×1/2, brs), 10.84 (1H×1/2, brs).

ESI-MASS (m/e): 430(M+H).

Example 106

1-({5-[4-(5-Methyl-1,3,4-oxadiazol-2-yl)phenoxy]-2-(2-pyridinyl)-1H-benzimidazol-6-yl}methyl)pyrrolidin-2-one Using 6-(5-methyl-1,3,4-oxadiazol-2-yl)pyridin-3-ol obtained in Reference Example 12, the entitled compound was obtained in the same method as in Example 102 (step 5) or in accordance with the method or by combining it with an ordinary method.

$^1$HNMR (CDCl$_3$) δ: 1.95 (2H, m), 2.33 (2H, m), 2.61 (3H, s), 3.31 (2H, m), 4.58 (2H, s), 7.04 (2H, d, J=8.8 Hz), 7.10-7.80 (2H, br), 7.39 (1H, m), 7.88 (1H, dt, J=1.7, 8.0 Hz), 7.97 (2H, d, J=8.8 Hz), 8.39 (1H, d, J=8.0 Hz), 8.65 (1H, d, J=5.0 Hz), 10.0-11.0 (1H, br).

ESI-MASS (m/e): 467(M+H).

Example 107

1-({5-[4-(3-Methyl-1,2,4-oxadiazol-5-yl)phenoxy]-2-(2-pyridinyl)-1H-benzimidazol-6-yl}methyl)pyrrolidin-2-one Using 6-(3-methyl-1,2,4-oxadiazol-5-yl)pyridin-3-ol obtained in Reference Example 13, the entitled compound was obtained in the same method as in Example 102 (step 5) or in accordance with the method or by combining it with an ordinary method.

$^1$HNMR (CDCl$_3$) δ: 1.93 (2H, m), 2.33 (2H, m), 2.46 (3H, m), 3.30 (2H, m), 4.57 (2H, m), 7.05 (2H, m), 7.19 (1/2H, s), 7.40 (1H, m), 7.52 (1/2H, s), 7.57 (1/2H, s), 7.78 (1/2H, s), 7.86 (1H, m), 8.06 (2H, d, J=8.8 Hz), 8.40 (1H, m), 8.66 (1H, m), 10.7 (1H, br), 10.8 (1/2H, br).

ESI-MASS (m/e): 467(M+H).

Example 108

1-({5-[4-(1-Methyl-1H-tetrazol-5-yl)phenoxy]-2-(2-pyridinyl)-1H-benzimidazol-6-yl}methyl)pyrrolidin-2-one Using 6-(1-methyl-1H-tetrazol-5-yl)pyridin-3-ol obtained in Reference Example 14, the entitled compound was obtained in the same method as in Example 102 (step 5) or in accordance with the method or by combining it with an ordinary method.

$^1$HNMR (CDCl$_3$) δ: 1.94 (2H, m), 2.35 (2H, m), 3.33 (2H, m), 4.18 (3H, s), 4.59 (2H, s), 7.13 (2H, s), 7.20 (1/2H, s), 7.40 (1H, m), 7.51 (1/2H, s), 7.56 (1/2H, s), 7.70 (2H, d, J=8.8 Hz), 7.77 (1/2H, s), 7.88 (1H, m), 8.39 (1H, m), 8.64 (1H, m), 10.9 (1/2H, br), 11.0 (1/2H, br).

ESI-MASS (m/e): 467(M+H).

Example 109

1-({5-[4-(1,3-Oxazol-4-yl)phenoxy]-2-(2-pyridinyl)-1H-benzimidazol-6-yl}methyl)pyrrolidin-2-one Using 6-(1,3-oxazol-4-yl)pyridin-3-ol obtained in Reference Example 15, the entitled compound was obtained in the same method as in Example 102 (step 5) or in accordance with the method or by combining it with an ordinary method.
$^1$HNMR (CDCl$_3$) δ: 1.94 (2H, m), 2.36 (2H, m), 3.34 (2H, m), 4.62 (2H, m), 7.00 (2H, m), 7.07 (1/2H, m), 7.37 (1H, m), 7.46 (1/2H, s), 7.54 (1/2H, s), 7.69 (2H, d, J=8.8 Hz), 7.74 (1/2H, s), 7.86 (1H, m), 7.90 (1H, s), 7.94 (1H, s), 8.39 (1H, m), 8.63 (1H, m), 10.8 (1/2H, br), 10.9 (1/2H, br).
ESI-MASS (m/e): 452(M+H).

Example 110

1-[(5-((2'-Fluorobiphenyl-4-yl)oxy)-2-(2-pyridinyl)-1H-benzimidazol-6-yl}methyl)-2-pyrrolidinone (Step 1) Production of N-{5-fluoro-2-nitro-4-([(2-oxopyrrolidin-1-yl)methyl]phenyl}pyrazine-2-carboxamide Using pyrazine-2-carboxylic acid, the entitled compound was obtained in the same method as in Example 102 (step 4) or in accordance with the method or by combining it with an ordinary method.

(Step 2) Production of 1-[(5-((2'-fluorobiphenyl-4-yl)oxy) -2-(2-pyridinyl)-1H-benzimidazol-6-yl}methyl)-2-pyrrolidinone Using the compound obtained in the step 1 and 6-(2-fluorophenyl)pyridin-3-ol obtained in Reference Example 16, the entitled compound was obtained in the same method as in Example 102 (step 5) or in accordance with the method or by combining it with an ordinary method.
$^1$HNMR (CDCl$_3$) δ: 1.94-2.02 (2H, m), 2.37-2.44 (2H, m), 3.36-3.46 (2H, m), 4.67 (2H, s), 7.05 (2H, d, J=8.6 Hz), 7.13-7.34 (3H, 1H×1/2, m), 7.40-7.45 (1H, m), 7.48 (1H×1/2, s), 7.51 (2H, d, J=8.6 Hz), 7.66 (1H×1/2, s), 7.77 (1H×1/2, s), 8.59 (1H, s), 8.64 (2H, d, J=2.7 Hz), 9.62 (1H, s), 10.47 (1H×1/2, brs), 10.95 (1H×1/2, brs).
ESI-MASS (m/e): 480(M+H).

Example 111

1-{[2-(5-Bromo-2-pyridinyl)-5-[(6-(5-methyl-1,2,4-oxadiazol-3-yl)-3-pyridinyl)oxy]-1H-benzimidazol-6-yl]methyl}-2-pyrrolidinone (Step 1) Production of methyl 4-{[(5-bromopyrazin-2-yl)carbonylamino]-2-fluorobenzoate Using methyl 4-amino-2-fluorobenzoate obtained in Example 19 (step 2) and 5-bromopyrazine-2-carboxylic acid, the entitled compound was obtained in the same method as in Example 19 (step 3) or in accordance with the method or by combining it with an ordinary method.

(Step 2) Production of (2-(5-bromopyrazin-2-yl)-5-{[6-(5-methyl-1,2,4-oxadiazol-3-yl)pyridin-3-yl]oxy}-1-{[2-(trimethylsilyl)ethoxy]methyl}-1H-benzimidazol-6-yl)methanol and (2-(5-bromopyrazin-2-yl)-6-{[6-(5-methyl-1,2,4-oxadiazol-3-yl)pyridin-3-yl]oxy}-1-{[2-(trimethylsilyl)ethoxy]methyl}-1H-benzimidazol-5-yl)methanol Using the compound obtained in the step 1, the entitled compound was obtained in the same method as in Example 52 (steps 1, 2) or in accordance with the method or by combining it with an ordinary method.

(Step 3) Production of 1-{[2-(5-bromo-2-pyridinyl)-5-[(6-(5-methyl-1,2,4-oxadiazol-3-yl)-3-pyridinyl)oxy]-1H-benzimidazol-6-yl]methyl}-2-pyrrolidinone Using the alcohol obtained in the step 2, the entitled compound was obtained in the same method as in Example 2 or in accordance with the method or by combining it with an ordinary method.
$^1$HNMR (CDCl$_3$) δ: 1.92-1.99 (2H, m), 2.31-2.39 (2H, m), 3.30-3.36 (2H, m), 4.59 (2H×1/2, s), 4.61 (2H×1/2, s), 7.17 (1H×1/2, s), 7.30-7.37 (1H, m), 7.47 (1H×1/2, s), 7.60 (1H×1/2, s), 7.78 (1H×1/2, s), 7.98-8.02 (1H, m), 8.04 (1H×1/2, d, J=8.6 Hz), 8.07 (1H×1/2, d, J=9.0 Hz), 8.26 (1H×1/2, d, J=8.6 Hz), 8.29 (1H×1/2, d, J=8.6 Hz), 8.49 (1H×1/2, d, J=2.3 Hz), 8.55 (1H×1/2, d, J=2.3 Hz), 8.69 (1H×1/2, d, J=1.6 Hz), 8.71 (1H×1/2, d, J=2.0 Hz), 10.40 (1H×1/2, brs), 10.52 (1H×1/2, brs).
ESI-MASS (m/e): 546, 548(M+H).

Example 112

1-Methyl-3-{[5-[(6-(5-methyl-1,2,4-oxadiazol-3-yl)-3-pyridinyl)oxy]-2-(2-pyridinyl)-1H-benzimidazol-6-yl]methyl}imidazolidine-2,4-dione Using the alcohol compound obtained in Example 52 (step 2) and 1-methylhydantoin, the entitled compound was obtained in the same method as in Example 19 (step 8) or in accordance with the method or by combining it with an ordinary method.
$^1$HNMR (CDCl$_3$) δ: 2.68 (3H, s), 2.89 (3H×1/2, s), 2.95 (3H×1/2, s), 3.70 (2H×1/2, s), 3.82 (2H×1/2, s), 4.83 (2H×1/2, s), 4.85 (2H×1/2, s), 7.07 (1H×1/2, s), 7.30-7.41 (2H, m), 7.45 (1H×1/2, s), 7.66 (1H×1/2, s), 7.81 (1H×1/2, s), 7.84-7.89 (1H, m), 8.02 (1H×1/2, d, J=8.6 Hz), 8.05 (1H×1/2, d, J=9.0 Hz), 8.36 (1H×1/2, d, J=7.8 Hz), 8.38 (1H×1/2, d, J=7.8 Hz), 8.55-8.59 (1H, m), 8.61-8.65 (1H, m), 10.63 (1H, brs).
ESI-MASS (m/e): 497(M+H).

Example 113

6-((1,1-Dioxidoisothiazolin-2-yl)methyl)-5-((6-(5-methyl-1,2,4-oxadiazol-3-yl)-3-pyridinyl)oxy)-2-(2-pyridinyl)-1H-benzimidazole Using the alcohol compound obtained in Example 52 (step 2), the entitled compound was obtained in the same method as in Example 33 or in accordance with the method or by combining it with an ordinary method.
$^1$HNMR (CDCl$_3$) δ: 2.19-2.27 (2H, m), 2.69 (3H, s), 3.04-3.12 (2H, m), 3.16-3.23 (2H, m), 4.33 (2H×1/2, s), 4.35

(2H×1/2, s), 7.18 (1H×1/2, s), 7.31-7.43 (2H, m), 7.50 (1H×1/2, s), 7.72 (1H×1/2, s), 7.85-7.92 (1H, m), 7.96 (1H×1/2, s), 8.04 (1H×1/2, d, J=8.6 Hz), 8.07 (1H×1/2, d, J=8.6 Hz), 8.38 (1H×1/2, d, J=7.8 Hz), 8.41 (1H×1/2, d, J=8.2 Hz), 8.48 (1H×1/2, d, J=2.7 Hz), 8.55 (1H×1/2, d, J=2.3 Hz), 8.64 (1H×1/2, d, J=4.3 Hz), 8.66 (1H×1/2, d, J=4.7 Hz), 10.57 (1H×1/2, brs), 10.60 (1H×1/2, brs).
ESI-MASS (m/e): 504(M+H).

Example 114

4-{[5-[(6-(5-Methyl-1,2,4-oxadiazol-3-yl)-3-pyridinyl)oxy]-2-(2-pyridinyl)-1H-benzimidazol-6-yl]methyl}morpholin-3-one Using the alcohol compound obtained in Example 52 (step 2), the entitled compound was obtained in the same method as in Example 81 or in accordance with the method or by combining it with an ordinary method.
$^1$HNMR (CDCl$_3$) δ: 2.69 (3H, s), 3.35 (2H×1/2, t, J=5.1 Hz), 3.39 (2H×1/2, t, J=5.1 Hz), 3.83 (2H×1/2, t, J=5.1 Hz), 3.84 (2H×1/2, t, J=5.1 Hz), 4.15 (2H×1/2, s), 4.19 (2H×1/2, s), 4.76 (2H×1/2, s), 4.78 (2H×1/2, s), 7.17 (1H×1/2, s), 7.29-7.35 (1H, m), 7.38-7.42 (1H, m), 7.49 (1H×1/2, s), 7.65 (1H×1/2, s), 7.83 (1H×1/2, s), 7.85-7.91 (1H, m), 8.04 (1H×1/2, d, J=8.6 Hz), 8.07 (1H×1/2, d, J=8.6 Hz), 8.37 (1H×1/2, d, J=7.8 Hz), 8.40 (1H×1/2, d, J=8.2 Hz), 8.52 (1H×1/2, d, J=2.7 Hz), 8.57 (1H×1/2, d, J=2.7 Hz), 8.64 (1H×1/2, d, J=5.1 Hz), 8.66 (1H×1/2, d, J=5.5 Hz), 10.59 (1H×1/2, brs), 10.68 (1H×1/2, brs).
ESI-MASS (m/e): 484(M+H).

Example 115

3-{[5-[(6-(5-Methyl-1,2,4-oxadiazol-3-yl)-3-pyridinyl)oxy]-2-(2-pyridinyl)-1H-benzimidazol-6-yl]methyl}1,3-oxazolidine-2,4-dione Using the alcohol compound obtained in Example 52 (step 2), the entitled compound was obtained in the same method as in Example 85 or in accordance with the method or by combining it with an ordinary method.
$^1$HNMR (CDCl$_3$) δ: 2.68 (3H, s), 4.58 (2H×1/2, s), 4.64 (2H×1/2, s), 4.86 (2H×1/2, s), 4.89 (2H×1/2, s), 7.06 (1H×1/2, s), 7.32-7.42 (2H, m), 7.46 (1H×1/2, s), 7.68 (1H×1/2, s), 7.86 (1H×1/2, s), 7.89 (1H, d, J=6.3 Hz), 8.02-8.08 (1H, m), 8.37-8.42 (1H, m), 8.53-8.58 (1H, m), 8.61-8.66 (1H, m), 10.97 (1H, brs).
ESI-MASS (m/e): 484(M+H).

Example 116

1-{[5-[(6-(5-Methyl-1,2,4-oxadiazol-3-yl)-3-pyridinyl)oxy]-2-(2-pyridinyl)-1H-benzimidazol-6-yl]methyl}-1H-imidazole-2-carbonitrile Using the alcohol compound obtained in Example 52 (step 2), the entitled compound was obtained in the same method as in Example 82 or in accordance with the method or by combining it with an ordinary method.
$^1$HNMR (DMSO-d$_6$) δ: 2.66 (3H, s), 5.52 (2H, s), 7.09 (1H, d, J=6.7 Hz), 7.15 (1H×1/2, s), 7.26-7.35 (1H, m), 7.50-7.62 (2H, m), 7.50-7.62 (1H×1/2, s, overlap), 7.71 (1H×1/2, s), 7.93-8.04 (2H, m), 7.93-8.04 (1H×1/2, s, invisible), 8.29-8.34 (1H, m), 8.42-8.45 (1H, m), 8.72-8.77 (1H, m), 13.26 (1H×1/2, brs), 13.45 (1H×1/2, brs).
ESI-MASS (m/e): 476(M+H).

Example 117

4-{[5-[(6-(5-Methyl-1,2,4-oxadiazol-3-yl)-3-pyridinyl)oxy]-2-(2-pyridinyl)-1H-benzimidazol-6-yl]methyl}morpholine-3,5-dione Using the alcohol compound obtained in Example 52 (step 2), the entitled compound was obtained in the same method as in Example 16 or in accordance with the method or by combining it with an ordinary method.
$^1$HNMR (CDCl$_3$) δ: 2.69 (3H, s), 4.29 (4H×1/2, s), 4.36 (4H×1/2, s), 5.13 (2H×1/2, s), 5.13 (2H×1/2, s), 7.08 (1H×1/2, s), 7.30-7.39 (2H, m), 7.45 (1H×1/2, s), 7.53 (1H×1/2, s), 7.73 (1H×1/2, s), 7.85-7.89 (1H, m), 8.03 (1H×1/2, d, J=9.0 Hz), 8.07 (1H×1/2, d, J=9.4 Hz), 8.37 (1H×1/2, d, J=7.0 Hz), 8.39 (1H×1/2, d, J=7.0 Hz), 8.58-8.65 (2H, m), 10.74 (1H, brs).
ESI-MASS (m/e): 498(M+H).

Example 118

3-{[5-[(6-(5-Methyl-1,2,4-oxadiazol-3-yl)-3-pyridinyl)oxy]-2-(2-pyridinyl)-1H-benzimidazol-6-yl]methyl}-1,3-thiazolidine-2,4-dione Using the alcohol compound obtained in Example 52 (step 2), the entitled compound was obtained in the same method as in Example 17 or in accordance with the method or by combining it with an ordinary method.
$^1$HNMR (CDCl$_3$) δ: 2.69 (3H, s), 3.82 (2H×1/2, s), 3.90 (2H×1/2, s), 4.94 (2H×1/2, s), 4.97 (2H×1/2, s), 7.08 (1H×1/2, s), 7.30-7.41 (2H, m), 7.45 (1H×1/2, s), 7.60 (1H×1/2, s), 7.80 (1H×1/2, s), 7.86-7.90 (1H, m), 8.03-8.08 (1H, m), 8.36-8.40 (1H, m), 8.55-8.65 (2H, m), 10.74 (1H×1/2, brs), 10.79 (1H×1/2, brs).
ESI-MASS (m/e): 500(M+H).

Example 119

1-{[5-[4-(5-Methyl-1,2,4-oxadiazol-3-yl)phenoxy]-2-(2-pyrazinyl)-1H-benzimidazol-6-yl]methyl}-2-pyrrolidinone Using N-{5-fluoro-2-nitro-4-[(2-oxopyrrolidin-1-yl)methyl]phenyl}pyrazine-2-carboxamide obtained in Example 110 (step 1) and 4-(5-methyl-1,2,4-oxadiazol-3-yl)phenol obtained in Reference Example 7, the entitled compound was obtained in the same method as in Example 102 (step 5) or in accordance with the method or by combining it with an ordinary method.
$^1$HNMR (CDCl$_3$) δ: 1.92-2.00 (2H, m), 2.34-2.41 (2H, m), 3.32-3.39 (2H, m), 4.61 (2H×1/2, s), 4.62 (2H×1/2, s), 7.04 (2H×1/2, d, J=8.6 Hz), 7.05 (2H×1/2, d, J=8.6 Hz), 7.17 (1H×1/2, s), 7.51 (1H×1/2, s), 7.65 (1H×1/2, s), 7.79 (1H×1/2, s), 8.02 (2H, d, J=8.6 Hz), 8.57-8.61 (1H, m), 8.66 (1H, d, J=2.0 Hz), 9.61-9.64 (1H, m), 10.45 (1H×1/2, brs), 10.83 (1H×1/2, brs).
ESI-MASS (m/e): 468(M+H).

Example 120

3-{[5-[4-(5-Methyl-1,2,4-oxadiazol-3-yl)phenoxy]-2-(2-pyridinyl)-1H-benzimidazol-6-yl]methyl}-1,3-oxazolidine-2,4-dione Using the alcohol compound obtained in Example 55 (step 1), the entitled compound was obtained in the same method as in Example 85 or in accordance with the method or by combining it with an ordinary method.

$^1$HNMR (CDCl$_3$, 2 drops of CD$_3$OD) δ: 2.66 (3H, s), 4.44 (2H×1/2, s), 4.52 (2H×1/2, s), 4.87 (2H×1/2, s), 4.90 (2H×1/2, s), 7.03 (2H×1/2, d, J=8.6 Hz), 7.06 (2H×1/2, d, J=8.6 Hz), 7.17 (1H×1/2, s), 7.38-7.43 (1H, m), 7.47 (1H×1/2, s), 7.71 (1H×1/2, s), 7.88-7.91 (1H, m), 7.92 (1H×1/2, s), 8.01 (2H×1/2, d, J=8.6 Hz), 8.03 (2H×1/2, d, J=8.6 Hz), 8.38-8.42 (1H, m), 8.61-8.67 (1H, m), peak of NH is invisible.

ESI-MASS (m/e): 483(M+H).

Example 121

3-{[5-[(6-(5-Methyl-1,2,4-oxadiazol-3-yl)-3-pyridinyl)oxy]-2-(2-pyridinyl)-1H-benzimidazol-6-yl]methyl}-2-pyrrolidinone Using N-{5-fluoro-2-nitro-4-[(2-oxopyrrolidin-1-yl)methyl]phenyl}pyrazine-2-carboxamide obtained in Example 110 (step. 1) and 6-(5-methyl-1,2,4-oxadiazol-3-yl)-3-pyridinol obtained in Reference Example 6, the entitled compound was obtained in the same method as in Example 102 (step 5) or in accordance with the method or by combining it with an ordinary method.

$^1$HNMR (CDCl$_3$) δ: 1.95-2.02 (2H, m), 2.36-2.42 (2H, m), 2.69 (3H, s), 3.34-3.41 (2H, m), 4.62 (2H, s), 7.18 (1H×1/2, s), 7.34 (1H, d, J=7.8 Hz), 7.50 (1H×1/2, s), 7.69 (1H×1/2, s), 7.79 (1H×1/2, s), 8.06 (1H, d, J=8.6 Hz), 8.49-8.57 (1H, m), 8.60 (1H, s), 8.67 (1H, d, J=2.7 Hz), 9.63 (1H, s), 10.58 (1H×1/2, brs), 10.98 (1H×1/2, brs).

ESI-MASS (m/e): 469(M+H).

Example 122

5-Hydroxy-1-[(6-{[6-(5-methyl-1,2,4-oxadiazol-3-yl)pyridin-3-yl]oxy}-2-pyridin-2-yl-1H-benzimidazol-5-yl)methyl]pyrrolidin-2-one 7 mg of sodium borohydride and 8 mg of lithium chloride were added to a solution of 30 mg of the compound obtained in Example 51 in 2 ml of tetrahydrofuran and 0.2 ml methanol, and stirred at room temperature for 1 hour. Aqueous 10% citric acid solution was added to it, extracted with chloroform, and the organic layer was dried and the solvent was evaporated away under reduced pressure. The residue was purified through thin-layer chromatography (developing solvent: chloroform/methanol=9/2) to obtain 7 mg of the entitled compound as a white solid.

$^1$HNMR (CDCl$_3$) δ: 1.91-1.88 (1H, m), 2.22-2.20 (2H, m), 2.57-2.55 (1H, m), 2.64 (3H, s), 4.37 (2H, d, J=15.5 Hz), 5.24 (1H, m), 7.36-7.35 (2H, m), 7.83 (2H, d, J=7.8 Hz), 7.96 (1H, d, J=8.8 Hz), 8.34-8.33 (3H, m), 8.63-8.60 (1H, m).

ESI-MASS (m/e): 484(M+H).

Example 123

1-{[5-[(6-(5-methyl-1,2,4-oxadiazol-3-yl) pyridin-3-yl)oxy]-2-(1-oxidopyridin-2-yl)-1H-benzimidazol-6-yl]methyl}-2-pyrrolidinone 2 mg of methyl trioxolenium(VII) was added to a chloroform (2 ml) solution of 20 mg of the compound obtained in Example 53, and 100 μl of aqueous 30% hydrogen peroxide was added to it and stirred at room temperature for 4 hours. Aqueous sodium thiosulfate solution was added to it, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=5/1) to obtain 1.0 mg of the entitled compound as a white crystal.

$^1$HNMR (CDCl$_3$) δ: 1.99 (2H, m), 2.40 (2H, m), 2.71 (3H, s), 3.36 (2H, m), 4.46 (2H×1/2, m), 4.65 (2H×1/2, s), 7.27 (1/2H, s), 7.40 (2H, m), 7.45-7.60 (1H+1/2H, m), 7.66 (1/2H, m), 7.82 (1/2H, s), 8.09 (1H, m), 8.41 (1H, m), 8.57 (1H, m), 8.72 (1H, m), 13.2 (1/2H, s), 13.3 (1/2H, s).

ESI-MASS (m/e): 484(M+H).

Example 124

4-Hydroxy-1-{[5-[(6-(5-methyl-1,2,4-oxadiazol-3-yl)pyridin-3-yl)oxy]-2-(2-pyridinyl)-1H-benzimidazol-6-yl]methyl}pyrrolidin-2-one Using the alcohol compound obtained in Example 52 (step 2), the entitled compound was obtained in the same method as in Example L-001471821 or in accordance with the method or by combining it with an ordinary method.

$^1$HNMR (CDCl$_3$) δ: 2.30-2.50 (1H, m), 2.60-2.75 (1H, m), 2.68 (3H, s), 3.30-3.55 (1H, m), 3.55-3.70 (1H, m), 4.40-4.80 (3H, m), 7.10-7.80 (4H, m), 7.86 (1H, m), 8.02 (1H, d, J=8.8 Hz), 8.38 (1H, d, J=7.8 Hz), 8.46 (1H, d, J=2.7 Hz), 8.65 (1H, d, J=4.9 Hz).

ESI-MASS (m/e): 484(M+H).

Example 125

1-[Hydroxy-(5-{[6-[5-methyl-1,2,4-oxadiazol-3-yl]-3-pyridinyl]oxy}-2-(2-pyridinyl)-1H-benzimidazol-6-yl)methyl]-2-pyrrolidinone (Step 1) Production of (5-[{6-(5-methyl-1,2,4-oxadiazol-3-yl)pyridin-3-yl]oxy]-2-(2-pyridinyl)-1H-benzimidazol-6-yl}methanol Using the alcohol compound obtained in Example 52 (step 2), the entitled compound was obtained in the same method as in Example 59 or in accordance with the method or by combining it with an ordinary method.

(Step 2) Production of 5-{[6-(5-methyl-1,2,4-oxadiazol-3-yl)pyridin-3-yl]oxy}-2-(2-pyridinyl)-1H-benzimidazole-6-carbaldehyde 1.5 ml of triethylamine and 796 mg of sulfur trioxide/pyridine complex were added to a dimethylsulfoxide (5 ml) solution of 400 mg of the obtained alcohol compound, and stirred at room temperature for 30 minutes. Water was added to it, extracted with chloroform, and the organic layer was washed with saturated saline water. After dried, the solvent was evaporated away under reduced pressure, and the residue was crystallized in diethyl ether/methanol to obtain 183 mg of the entitled compound as a pale yellow amorphous substance.

(Step 3) Production of 1-[hydroxy-(5-{[6-[5-methyl-1,2,4-oxadiazol-3-yl]-3-pyridinyl]oxy}-2-(2-pyridinyl)-1H-benzimidazol-6-yl)methyl]-2-pyrrolidinone 7 mg of sodium carbonate was added to an N,N-dimethylformamide (500 μl) solution of 8.7 μl of 1-pyrrolidone. With stirring at 80° C., 10 mg of the aldehyde compound produced previously was added to it, and stirred overnight at 80° C. The solvent was evaporated away under reduced pressure, and the residue was purified through partitioning thin-layer chromatography (Kieselgel™ 60F$_{254}$, Art 5744 (by Merck), chloroform/methanol=5/1) to obtain 1.0 mg of the entitled compound as a pale yellow amorphous substance.

$^1$HNMR (CDCl$_3$) δ: 0.79-0.94 (1H, m), 1.77-1.91 (1H, m), 1.97-2.09 (1H, m), 2.14-2.34 (1H, m), 2.68 (3H, s), 2.83-2.94 (1H, m), 3.37-3.52 (1H, m), 6.87-6.95 (1H, m), 7.18 (1H×1/2, s), 7.33-7.46 (2H, m), 7.50 (1H×1/2, s), 7.86-7.94 (1H, m), 7.99-8.08 (1H, m, 1H×1/2, s), 8.31 (1H×1/2, s), 8.36-8.46 (2H, m), 8.60-8.72 (1H, m), 10.58 (1H×1/2, brs), 10.86 (1H×1/2, brs).

ESI-MASS (m/e): 484(M+H).

Example 126

5-[4-(Ethylsulfonyl)phenoxy]-6-[(2-fluoropyridin-3-yl]-methyl]-2-(2-pyridinyl)-1H-benzimidazole (Step 1) Production of (5-[4-(ethylsulfonyl)phenoxy]-2-(2-pyridinyl)-1-{[2-(trimethylsilyl)ethoxy]methyl}-1H-benzimidazol-6-yl)(2-fluorophenyl)methanol or (6-[4-(ethylsulfonyl)phenoxy]-2-(2-pyridinyl)-1-{[2-(trimethylsilyl)ethoxy]methyl}-1H-benzimidazol-5-yl)(2-fluorophenyl)methanol At −78° C., 6.2 ml of 1.5 M butyllithium/hexane solution was added to a tetrahydrofuran (10 ml) solution of 1.31 ml of diisopropylethylamine, and stirred at 0° C. for 30 minutes. At −78° C., 0.8 ml of 2-fluoropyridine was added to the reaction liquid, and stirred at −78° C. for 2 hours. Then, a tetrahydrofuran (5 ml) solution of 1 g of the aldehyde obtained in Example 64 (step 1) was added to it, and stirred at −78° C. for 1 hour. Aqueous saturated ammonium chloride solution was added to it, extracted with ethyl acetate, and the organic layer was washed with saturated saline water. After dried, this was purified through silica gel column chromatography (developing solvent: chloroform to chloroform/methanol=50/1) to obtain 0.72 g of the entitled compound as a brown oil.

(Step 2) Production of 5-[4-(ethylsulfonyl)phenoxy]-6-[(2-fluoropyridin-3-yl)methyl]-2-(2-pyridinyl)-1H-benzimidazole 26 μl of thionyl chloride was added to a chloroform (0.75 ml) solution of 75 mg of the obtained oil, and stirred at room temperature for 20 minutes. The solvent was evaporated away under reduced pressure, and 0.7 ml of trifluoroacetic acid and 39 mg of zinc were added to it, and heated under reflux for 30 minutes. The solvent was evaporated away under reduced pressure, the residue was diluted with chloroform, and aqueous saturated sodium bicarbonate and aqueous ammonia were added to it, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 15.2 mg of the entitled compound as a colorless crystal.

$^1$HNMR (CDCl$_3$) δ: 1.30 (3H, m), 3.11 (2H, m), 4.03 (2H, s), 7.00 (3H, m), 7.15 (1/2H, s), 7.37-7.57 (3H, m), 7.75 (1/2H, s), 7.79 (2H, m), 7.87 (2H, m), 8.02 (1H, m), 8.39 (1H, m), 8.64 (1H, m), 10.6 (1/2H, br), 10.7 (1/2H, br).

ESI-MASS (m/e): 489(M+H).

Example 127

(5-(4-Ethylsulfonyl)phenoxy)-2-(2-pyridinyl)-1H-benzimidazol-6-yl)acetonitrile (Step 1) Production of (5-[4-(ethylsulfonyl)phenoxy]-2-(2-pyridinyl)-1-[{2-(trimethylsilyl)ethoxy]methyl}-1H-benzimidazol-6-yl)acetonitrile or (6-[4-(ethylsulfonyl)phenoxy]-2-(2-pyridinyl)-1-[{2-(trimethylsilyl)ethoxy]methyl}-1H-benzimidazol-6-yl)acetonitrile With cooling with ice, 268 μl of methanesulfonyl chloride was added to a tetrahydrofuran (20 ml) solution of 930 mg of the alcohol compound obtained in Example 19 (step 7) and 494 μl of triethylamine, and stirred for 20 minutes. This was diluted with 60 ml of ethyl acetate, and water was added thereto. The organic layer was separated, and washed with saturated saline water. After dried, the solvent was evaporated away under reduced pressure to obtain a colorless amorphous substance.

With cooling with ice, 269 mg of sodium cyanide was added to an N,N-dimethylformamide (20 ml) solution of the obtained amorphous substance, and stirred at room temperature for 3 hours. With cooling with ice, aqueous saturated sodium hydrogencarbonate solution was added to it, extracted with ethyl acetate, and the organic layer was washed with saturated saline water. After dried, the solvent was evaporated away under reduced pressure, the residue was purified through silica gel column chromatography (developing solvent: hexane/ethyl acetate) to obtain 623 mg of a yellow oil.

(Step 2) Production of (5-(4-ethylsulfonyl)phenoxy)-2-(2-pyridinyl)-1H-benzimidazol-6-yl)acetonitrile 28 mg of the obtained oil was dissolved in 1 ml of trifluoroacetic acid, and stirred at room temperature for 1 hour. The solvent was evaporated away under reduced pressure, the residue was diluted with chloroform, and then neutralized with aqueous saturated sodium hydrogencarbonate solution. This was extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 14 mg of the entitled compound as a colorless amorphous substance.

$^1$HNMR (CDCl$_3$) δ: 1.30 (3H, t, J=7.4 Hz), 3.13 (2H, q, J=7.4 Hz), 3.82 (2H, s), 7.10-7.16 (1H×1/2, s, overlap), 7.13 (2H, d, J=8.2 Hz), 7.39-7.44 (1H, m), 7.48 (1H×1/2, s), 7.71 (1H×1/2, s), 7.85-7.91 (1H, m), 7.88 (2H, d, J=8.2 Hz), 7.91 (1H×1/2, s), 8.37-8.42 (1H, m), 8.63-8.69 (1H, m), 10.72 (1H×1/2, brs), 10.79 (1H×1/2, brs).

ESI-MASS (m/e): 419(M+H).

Example 128

2-(5-(4-(Ethylsulfonyl)phenoxy)-2-(2-pyridinyl)-1H-benzimidazol-6-yl)acetamide

A 80% sulfuric acid (1 ml) solution of 30 mg of the cyano compound obtained in Example 127 was stirred overnight at 70° C. With cooling with ice, the reaction solution was dripped into an aqueous saturated sodium hydrogencarbonate solution to be neutralized with it, and then extracted with chloroform. The organic layer was dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 5.7 mg of the entitled compound as a colorless amorphous substance.

$^1$HNMR (CDCl$_3$, 2 drops of CD$_3$OD) δ: 1.30 (3H, t, J=7.4 Hz), 3.13 (2H, q, J=7.4 Hz), 3.61 (2H×1/2, s), 3.63 (2H×1/2, s), 7.10 (2H, d, J=9.0 Hz), 7.18 (1H×1/2, s), 7.40-7.43 (1H, m), 7.47 (1H×1/2, s), 7.62 (1H×1/2, s), 7.83 (1H×1/2, s), 7.84 (2H, d, J=9.0 Hz), 7.88-7.93 (1H, m), 8.37-8.42 (1H, m), 8.62-8.66 (1H, m), peaks of NH and NH2 are invisible.

ESI-MASS (m/e): 437(M+H).

Example 129

2-[5-(4-(Ethylsulfonyl)phenoxy)-2-(2-pyridinyl)-1H-benzimidazol-6-yl]-N,N-dimethylacetamide (Step 1) Production of (5-[4-(ethylsulfonyl)phenoxy]-2-(2-pyridinyl)-1-{[2-(trimethylsilyl)ethoxy]methyl}-1H-benzimidazol-6-yl)acetic acid or (6-[4-(ethylsulfonyl)phenoxy]-2-(2-pyridinyl)-1-{[2-(trimethylsilyl)ethoxy]methyl}-1H-benzimidazol-5-yl)acetic acid 10 ml of aqueous 5 N sodium hydroxide solution was added to an ethanol (15 ml) solution of 1.04 g of the cyano compound obtained in Example 127 (step 1), and stirred overnight at 70° C. Ethanol was evaporated away under reduced pressure, the residue was diluted with chloroform, and with cooling with ice, aqueous 10% citric acid solution was added to the reaction solution to thereby make it weakly acidic. This was extracted with chloroform, and the organic layer was washed with saturated saline water. After dried, the solvent was evaporated away under reduced pressure, and the residue was purified through silica gel column chromatography (developing solvent: hexane/ethyl acetate) to obtain 631 mg of a yellow amorphous substance.

(Step 2) Production of the Entitled Compound 8.7 mg of 1-hydroxybenzotriazole and 1-ethyl-3-(3-dimethylaminopropyl)carbodiimide hydrochloride were added to a chloroform (1 ml) solution of 17.7 mg of the obtained carboxylic acid, and then 48 µl of a tetrahydrofuran solution of 2.0 M dimethylamine was added to it and stirred at room temperature for 1.5 hours. With cooling with ice, water was added to it, and the organic layer was washed with aqueous saturated sodium hydrogencarbonate solution and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=20/1) to obtain 10.8 g of a yellow amorphous substance.

Using 10.8 mg of the obtained amorphous substance, 8.6 mg of the entitled compound was obtained as a colorless amorphous substance in the same method as in Example 127 (step 2) or in accordance with the method or by combining it with an ordinary method.

$^1$HNMR (CDCl$_3$) δ: 1.29 (3H, t, J=7.4 Hz), 2.90 (3H×1/2, s), 2.91 (3H×1/2, s), 2.98 (3H, s), 3.11 (2H, q, J=7.4 Hz), 3.73 (2H×1/2, s), 3.74 (2H×1/2, s), 7.08 (2H, d, J=9.0 Hz), 7.12 (1H×1/2, s), 7.37-7.40 (1H, m), 7.44 (1H×1/2, s), 7.55 (1H×1/2, s), 7.77 (1H×1/2, s), 7.80-7.89 (1H, m), 7.82 (2H, d, J=9.0 Hz), 8.36-8.42 (1H, m), 8.61-8.65 (1H, m), 10.88 (1H×1/2, brs), 10.94 (1H×1/2, brs).

ESI-MASS (m/e): 465(M+H).

Example 130

Methyl [5-[4-(ethylsulfonyl)phenoxy]-2-(2-pyridinyl)-1H-benzimidazol-6-yl]acetate 80 µl of (trimethylsilyl)diazomethane was added to a solution of 27.8 mg of the carboxylic acid obtained in Example 129 (step 1) in a mixture of 500 µl of tetrahydrofuran and 500 µl of methanol, and stirred for 1 hour. Then, 80 µl of (trimethylsilyl)diazomethane was added to it, and stirred for 30 minutes. The solvent was evaporated away under reduced pressure, the residue was diluted with ethyl acetate, and aqueous saturated sodium hydrogencarbonate solution was added to it. This was extracted with ethyl acetate, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=20/1) to obtain 11.9 mg of an SEM compound.

Using 10.8 mg of the obtained SEM compound, 7.4 mg of the entitled compound was obtained in the same method as in Example 127 (step 2) or in accordance with the method or by combining it with an ordinary method.

$^1$HNMR (CDCl$_3$) δ: 1.29 (3H, t, J=7.4 Hz), 3.12 (2H, q, J=7.4 Hz), 3.57 (3H×1/2, s), 3.58 (3H×1/2, s), 3.72 (2H, s), 7.09 (2H, d, J=9.0 Hz), 7.10 (1H×1/2, s), 7.38-7.42 (1H, m), 7.47 (1H×1/2, s), 7.50 (1H×1/2, s), 7.83 (1H×1/2, s), 7.83 (2H, d, J=9.0 Hz), 7.86-7.91 (1H, m), 8.38-8.43 (1H, m), 8.62-8.67 (1H, m), 10.82 (1H, brs).

ESI-MASS (m/e): 452(M+H).

Example 131

5-[4-(Ethylsulfonyl)phenoxy]-6-(2-oxo-2-(1-pyrrolidinyl)ethyl)-2-(2-pyridinyl)-1H-benzimidazole Using pyrrolidine, the entitled compound was obtained in the same method as in Example 129 (step 2) or in accordance with the method or by combining it with an ordinary method.

$^1$HNMR (CDCl$_3$) δ: 1.29 (3H, t, J=7.4 Hz), 1.72-1.89 (4H, m), 3.11 (2H, q, J=7.4 Hz), 3.38 (4H, t, J=6.7 Hz), 3.68 (2H×1/2, s), 3.69 (2H×1/2, s), 7.06 (2H×1/2, d, J=9.0 Hz), 7.06 (2H×1/2, d, J=9.0 Hz), 7.09 (1H×1/2, s), 7.36-7.40 (1H, m), 7.43 (1H×1/2, s), 7.60 (1H×1/2, s), 7.79-7.89 (3H, m), 7.81 (1H×1/2, s), 8.36 (1H×1/2, d, J=8.2 Hz), 8.40 (1H×1/2, d, J=8.2 Hz), 8.61-8.65 (1H, m), 10.78 (1H×1/2, brs), 10.90 (1H×1/2, brs).

ESI-MASS (m/e): 491(M+H).

Example 132

N,N-diethyl-2-[5-[4-(ethylsulfonyl)phenoxy]-2-(2-pyridinyl)-1H-benzimidazol-6-yl]acetamide Using N,N-diethylamine, the entitled compound was obtained in the same method as in Example 129 (step 2) or in accordance with the method or by combining it with an ordinary method.

$^1$HNMR (CDCl$_3$) δ: 0.98 (3H×1/2, t, J=5.9 Hz), 1.00 (3H×1/2, t, J=5.9 Hz), 1.05 (3H, t, J=7.0 Hz), 1.24 (3H, t, J=7.4 Hz), 3.07 (2H, q, J=7.4 Hz), 3.22-3.32 (4H, m), 3.67 (2H×1/2, s), 3.69 (2H×1/2, s), 7.04 (2H, d, J=9.0 Hz), 7.05 (1H×1/2, s), 7.32-7.37 (1H, m), 7.40 (1H×1/2, s), 7.51 (1H×1/2, s), 7.77 (2H, d, J=9.0 Hz), 7.79 (1H×1/2, s), 7.83 (1H, t, J=8.0 Hz), 8.33 (1H×1/2, d, J=8.0 Hz), 8.36 (1H×1/2, d, J=8.0 Hz), 8.57-8.61 (1H, m), 10.76 (1H×1/2, brs), 10.86 (1H×1/2, brs).
ESI-MASS (m/e): 493(M+H).

Example 133

6-(2-(1-Azetidinyl)-2-oxoethyl)-5-[4-(ethylsulfonyl)phenoxy]-2-(2-pyridinyl)-1H-benzimidazole Using azetidine hydrochloride and diisopropylethylamine, the entitled compound was obtained in the same method as in Example 129 (step 2) or in accordance with the method or by combining it with an ordinary method.
$^1$HNMR (CDCl$_3$) δ: 1.29 (3H, t, J=7.4 Hz), 2.11-2.21 (2H, m), 3.12 (2H, q, J=7.4 Hz), 3.47 (2H×1/2, s), 3.49 (2H×1/2, s), 3.88-3.94 (2H, m), 4.03-4.08 (2H, m), 7.07-7.11 (2H, 1H×1/2, m), 7.37-7.41 (1H, m), 7.43 (1H×1/2, s), 7.63 (1H×1/2, s), 7.82-7.90 (2H, 1H, 1H×1/2, m), 8.36 (1H×1/2, d, J=7.8 Hz), 8.40 (1H×1/2, d, J=7.8 Hz), 8.62-8.66 (1H, m), 10.78 (1H, brs), 10.90 (1H, brs).
ESI-MASS (m/e): 477(M+H).

Example 134

2-[5-[4-(Ethylsulfonyl)phenoxy]-2-(2-pyridinyl)-1H-benzimidazol-6-yl]-N-methylacetamide Using methylamine hydrochloride and diisopropylethylamine, the entitled compound was obtained in the same method as in Example 129 (step 2) or in accordance with the method or by combining it with an ordinary method.
$^1$HNMR (CDCl$_3$) δ: 1.29 (3H, t, J=7.4 Hz), 2.70 (3H×1/2, s), 2.72 (3H×1/2, s), 3.11 (2H, q, J=7.4 Hz), 3.59 (2H×1/2, s), 3.62 (2H×1/2, s), 5.52 (1H×1/2, brs), 5.59 (1H×1/2, brs), 7.05 (2H×1/2, d, J=8.6 Hz), 7.07 (2H×1/2, d, J=8.6 Hz), 7.15 (1H×1/2, s), 7.39-7.43 (1H, m), 7.48 (1H×1/2, s), 7.56 (1H×1/2, s), 7.83 (2H, d, J=8.6 Hz), 7.87-7.91 (1H, m), 7.88 (1H×1/2, s), 8.37-8.42 (1H, m), 8.63-8.67 (1H, m), 10.81 (1H×1/2, brs), 10.85 (1H×1/2, brs).
ESI-MASS (m/e): 451(M+H).

Example 135

2-[5-[4-(Ethylsulfonyl)phenoxy]-2-(2-pyridinyl)-1H-benzimidazol-6-yl]ethanol (Step 1) Production of 2-(5-[4-(ethylsulfonyl)phenoxy]-2-(2-pyridinyl)-1-{[2-(trimethylsilyl)ethoxy]methyl}-1H-benzimidazol-6-yl)ethanol or 2-(6-[4-(ethylsulfonyl)phenoxy]-2-(2-pyridinyl)-1-{[2-(trimethylsilyl)ethoxy]methyl}-1H-benzimidazol-5-yl)ethanol With cooling with ice, 43 mg of 1,1'-biscarbonyl-1H-imidazole was added to a tetrahydrofuran (2 ml) solution of 100 mg of the carboxylic acid obtained in Example 129 (step 1), and stirred at room temperature for 2.5 hours. With cooling with ice, the obtained reaction mixture was dropwise added to 1.5 ml of an aqueous solution of 34 mg of sodium borohydride, and stirred for 5 minutes. This was neutralized with 10% citric acid added thereto, extracted with ethyl acetate, and the organic layer was washed with saturated saline water. After dried, the solvent was evaporated away under reduced pressure, and the residue was purified through silica gel column chromatography (developing solvent: chloroform/methanol) to obtain 95.3 mg of an alcohol compound.

(Step 2) Production of 2-[5-[4-(ethylsulfonyl)phenoxy]-2-(2-pyridinyl)-1H-benzimidazol-6-yl]ethanol 9.0 mg of the obtained alcohol compound was dissolved in 1 ml of trifluoroacetic acid, and stirred at room temperature for 1.5 hours. The solvent was evaporated away, and the residue was diluted with chloroform and neutralized with aqueous saturated sodium hydrogencarbonate solution. This was extracted with chloroform, and the organic layer was washed with saturated saline water. After dried, the solvent was evaporated away under reduced pressure, to obtain 9.0 mg of a trifluoroacetate. Potassium carbonate was added to a methanol (1 ml) solution of 9.0 mg of the trifluoroacetate, and stirred at room temperature for 30 minutes. This was diluted with chloroform, and aqueous saturated ammonium chloride solution was added to it, extracted with chloroform, and the organic layer was washed with aqueous saturated sodium hydrogencarbonate solution and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 6.6 mg of the entitled compound as a colorless amorphous substance.
$^1$HNMR (CDCl$_3$, 2 drops of CD$_3$OD) δ: 1.30 (3H, t, J=7.4 Hz), 2.89-2.93 (2H, m), 3.12 (2H, q, J=7.4 Hz), 3.85-3.89 (2H, m), 7.05 (2H, d, J=8.6 Hz), 7.16 (1H×1/2, s), 7.39-7.44 (1H, m), 7.41 (1H×1/2, s), 7.53 (1H×1/2, s), 7.79 (1H×1/2, s), 7.82 (2H, d, J=8.6 Hz), 7.88-7.93 (1H, m), 8.37-8.41 (1H, m), 8.62-8.67 (1H, m), peaks of NH and OH are invisible.
ESI-MASS (m/e): 424(M+H).

Example 136

1-(2-[5-[4-(Ethylsulfonyl)phenoxy]-2-(2-pyridinyl)-1H-benzimidazol-6-yl]ethyl)pyrrolidine-2,5-dione 10.7 mg of succinimide and 28.3 mg of triphenyl phosphine were added to a tetrahydrofuran (1 ml) solution of 20 mg of the alcohol compound obtained in Example 135 (step 1), and with cooling with ice, 42 µl of diethylazodicarboxylate (40% toluene solution) was added to it, and stirred at room temperature for 30 minutes. Water was added to it, extracted with ethyl acetate, and the organic layer was washed with saturated saline water. After dried, the solvent was evaporated away under reduced pressure, and the residue was purified through silica gel column chromatography (developing solvent: chloroform/methanol) and reversed-phase partitioning LC to obtain 14.8 mg of a yellow oil.
14.8 mg of the obtained oil was dissolved in 1 ml of trifluoroacetic acid, and stirred at room temperature for 1 hour. The solvent was evaporated away, the residue was diluted with chloroform, and neutralized with aqueous saturated sodium hydrogencarbonate solution. This was extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 11 mg of the entitled compound as a colorless amorphous substance.
$^1$HNMR (CDCl$_3$) δ: 1.29 (3H×1/2, t, J=7.2 Hz), 1.30 (3H×1/2, t, J=7.2 Hz), 2.63 (4H×1/2, s), 2.65 (4H×1/2, s), 2.90-2.96 (2H, m), 3.11 (2H×1/2, q, J=7.2 Hz), 3.12 (2H×1/2, q, J=7.2 Hz), 3.79-3.83 (2H, m), 7.12 (2H×1/2, d, J=8.6 Hz), 7.17 (2H×1/2, d, J=9.0 Hz), 7.37-7.42 (1H, m), 7.46 (1H×1/2, s), 7.48 (1H×1/2, s), 7.65 (1H×1/2, s), 7.82-7.89 (1H, m), 7.83 (2H×1/2, d, J=8.6 Hz), 7.86 (2H×1/2, d, J=9.0 Hz), 7.89 (1H×1/2, s), 8.36-8.40 (1H, m), 8.62-8.67 (1H, m), 10.54 (1H, brs).
ESI-MASS (m/e): 505(M+H).

Example 137

1-(2-[5-[4-(Ethylsulfonyl)phenoxy]-2-(2-pyridinyl)-1H-benzimidazol-6-yl]ethyl)-2-pyrrolidinone (Step 1) Production of (5-[4-(ethylsulfonyl)phenoxy]-2-(2-pyridinyl)-1-{[2-(trimethylsilyl)ethoxy]methyl}-1H-benzimidazol-6-yl)acetaldehyde or (6-[4-(ethylsulfonyl)phenoxy]-2-(2-pyridinyl)-1-{[2-(trimethylsilyl)ethoxy]methyl}-1H-benzimidazol-5-yl)acetaldehyde 300 μl of triethylamine and 120 mg of sulfur trioxide/pyridine complex were added to a dimethylsulfoxide (1 ml) solution of 28.9 mg of the alcohol compound previously produced in Example 135 (step 1), and stirred at room temperature for 5 minutes. Water was added to it, extracted with ethyl acetate, and the organic layer was washed with water and saturated saline water. After dried, the solvent was evaporated away under reduced pressure, and the residue was purified through reversed-phase partitioning liquid chromatography to obtain 11.7 mg of the entitled compound as a colorless amorphous substance.

(Step 2) Production of 1-(2-[5-[4-(ethylsulfonyl)phenoxy]-2-(2-pyridinyl)-1H-benzimidazol-6-yl]ethyl)-2-pyrrolidinone 6.6 mg of methyl 4-aminobutanoate hydrochloride was added a tetrahydrofuran (1 ml) solution of 11.7 mg of the obtained aldehyde compound, and stirred at room temperature for 10 minutes. Then, 106 μl of a methanol solution of 0.25 M sodium cyanoborate-1/2 zinc chloride complex was added to it, and stirred at room temperature for 1 hour. With cooling with ice, aqueous saturated sodium hydrogencarbonate solution was added to it, extracted with chloroform, and the organic layer was washed with saturated saline water. After dried, the solvent was evaporated away, and the residue was purified through partitioning thin-layer chromatography (Kieselgel™ 60F$_{254}$, Art 5744 (by Merck), chloroform/methanol=10/1) to obtain 4.4 mg of a colorless amorphous substance.
100 μl of aqueous 5 N sodium hydroxide solution was added to a solution of 4.4 mg of the amorphous substance in a mixture of 250 μl of tetrahydrofuran and 250 μl of methanol, and stirred at room temperature for 45 minutes. With cooling with ice, this was neutralized with 10% citric acid, extracted with chloroform, and the organic layer was washed with saturated saline water. After dried, the solvent was evaporated away under reduced pressure, and the residue was dissolved in 500 μl of trifluoroacetic acid, and stirred at room temperature for 2.5 hours. The solvent was evaporated away, and the residue was diluted with chloroform, and neutralized with aqueous saturated sodium hydrogencarbonate solution. This was extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 3.3 mg of the entitled compound as a colorless amorphous substance.
$^1$HNMR (CDCl$_3$) δ: 1.30 (3H, t, J=7.6 Hz), 1.90-1.98 (2H, m), 2.30-2.38 (2H, m), 2.87 (2H, t, J=7.0 Hz), 3.12 (2H, q, J=7.6 Hz), 3.20-3.29 (2H, m), 3.57 (2H, t, J=7.0 Hz), 7.09 (2H, d, J=8.6 Hz), 7.11 (1H×1/2, s), 7.12 (2H, d, J=8.6 Hz), 7.37-7.42 (1H, m), 7.48 (1H×1/2, s), 7.52 (1H×1/2, s), 7.73 (1H×1/2, s), 7.82-7.90 (3H, m), 8.37-8.41 (1H, m), 8.62-8.68 (1H, m), 10.64 (1H×1/2, brs), 10.71 (1H×1/2, brs).
ESI-MASS (m/e): 491(M+H).

Example 138

2-[5-[4-(Ethylsulfonyl)phenoxy]-2-(2-pyridinyl)-1H-benzimidazol-6-yl]-N-methoxy-N-methylacetamide Using N,O-dimethylhydroxyamine hydrochloride and diisopropylethylamine, the entitled compound was obtained in the same method as in Example 129 (step 2) or in accordance with the method or by combining it with an ordinary method.
$^1$HNMR (CDCl$_3$) δ: 1.29 (3H, t, J=7.4 Hz), 3.11 (2H, q, J=7.6 Hz), 3.12 (3H×1/2, s), 3.13 (3H×1/2, s), 3.58 (3H×1/2, s), 3.60 (3H×1/2, s), 3.84 (2H, s), 7.09 (1H×1/2, s), 7.10 (2H, d, J=8.6 Hz), 7.36-7.40 (1H, m), 7.45 (1H×1/2, s), 7.53 (1H×1/2, s), 7.80-7.85 (1H×1/2, m(s)), 7.82 (2H×1/2, d, J=8.6 Hz), 7.83 (2H×1/2, d, J=8.6 Hz), 7.85-7.90 (1H, m), 8.36-8.42 (1H, m), 8.62-8.66 (1H, m), 10.76 (1H, brs).
ESI-MASS (m/e): 481(M+H).

Example 139

1-[5-[4-(Ethylsulfonyl)phenoxy]-2-(2-pyridinyl)-1H-benzimidazol-6-yl]acetone

With cooling with ice, 14 μl of a tetrahydrofuran solution of 3.0 M methylmagnesium bromide was added to a tetrahydrofuran (500 μl) solution of 8.7 mg of the compound obtained from Example 138, and stirred at room temperature for 30 minutes. then, 14 μl of a tetrahydrofuran solution of 3.0 M methylmagnesium bromide was added to it, and stirred at room temperature for 5 minutes. With cooling with ice, aqueous saturated ammonium chloride solution was added to it, extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=20/1) to obtain 4.0 mg of the entitled compound.
$^1$HNMR (CDCl$_3$) δ: 1.30 (3H, t, J=7.4 Hz), 2.16 (3H, s), 3.12 (2H, q, J=7.4 Hz), 3.78 (2H, s), 7.09 (2H, d, J=8.6 Hz), 7.12 (1H×1/2, s), 7.37-7.44 (1H, m), 7.43 (1H×1/2, s), 7.47 (1H×1/2, s), 7.74 (1H×1/2, s), 7.84 (2H×1/2, d, J=8.6 Hz), 7.85 (2H×1/2, d, J=8.6 Hz), 7.85-7.91 (1H, m), 8.36-8.42 (1H, m), 8.63-8.67 (1H, m), 10.68 (1H, brs).
ESI-MASS (m/e): 436(M+H).

Example 140

5-[4-(Ethylsulfonyl)phenoxy]-6-((5-methyl-1,2,4-oxadiazol-3-yl)methyl)-2-(2-pyridinyl)-1H-benzimidazole 8 μl of aqueous 50% hydroxylamine solution was added to an ethanol (1 ml) solution of 33 mg of the cyano compound obtained in Example 127 (step 1), and stirred overnight. After this was concentrated, 6 μl of acetic anhydride was added to an acetic acid (500 μl) solution of the resulting residue, and stirred at room temperature for 1 hour and then at 70° C. for 5 hours. After concentrated, this was dissolved in 1 ml of trifluoroacetic acid, and stirred at room temperature for 1 hour. The solvent was evaporated away, the residue was diluted with chloroform, and neutralized with aqueous saturated sodium hydrogencarbonate solution. This was extracted with chloroform, and the organic layer was washed with saturated saline water. After dried, the solvent was evaporated away under reduced pressure, and the residue was purified through partitioning reversed-phase liquid chromatography and partitioning thin-layer chromatography (Kieselgel™ 60F$_{254}$, Art 5744 (by Merck), chloroform/methanol=15/1) to obtain 9.1 mg of the entitled compound as a colorless amorphous substance.

$^1$HNMR (CDCl$_3$) δ: 1.29 (3H, t, J=7.2 Hz), 2.48 (3H×1/2, s), 2.49 (3H×1/2, s), 3.11 (2H, q, J=7.2 Hz), 4.12 (2H, s), 7.06 (2H, d, J=8.2 Hz), 7.14 (1H×1/2, s), 7.37-7.43 (1H, m), 7.49 (1H×1/2, s), 7.55 (1H×1/2, s), 7.78 (1H×1/2, s), 7.82 (2H, d, J=8.2 Hz), 7.86-7.90 (1H, m), 8.37-8.41 (1H, m), 8.62-8.66 (1H, m), 10.70 (1H, brs).

ESI-MASS (m/e): 476(M+H).

Example 141

5-[4-(Ethylsulfonyl)phenoxy]-2-(2-pyridinyl)-6-(2H-tetrazol-5-ylmethyl)-1H-benzimidazole (trifluoroacetate)

(Step 1) Production of 5-[4-(ethylsulfonyl)phenoxy]-2-(2-pyridinyl)-6-(2H-tetrazol-5-ylmethyl)-1-[{2-(trimethylsilyl)ethoxy]methyl}-1H-benzimidazole or 6-[4-(ethylsulfonyl)phenoxy]-2-(2-pyridinyl)-6-(2H-tetrazol-5-ylmethyl)-1-[{2-(trimethylsilyl)ethoxy]methyl}-1H-benzimidazole 162 μl of trimethylsilylazide and 30.4 mg of dibutyltin oxide were added to a toluene (3 ml) solution of 35 mg of the cyano compound obtained in Example 127 (step 1), and overnight heated under reflux. The solvent was evaporated away under reduced pressure, and the residue was purified through silica gel column chromatography (developing solvent: chloroform/methanol) to obtain 160 mg of a yellow amorphous K substance.

(Step 2) Production of 5-[4-(ethylsulfonyl)phenoxy]-2-(2-pyridinyl)-6-(2H-tetrazol-5-ylmethyl)-1H-benzimidazole (trifluoroacetate)

13.3 g of the obtained yellow amorphous substance was dissolved in 1 ml of trifluoroacetic acid, and stirred at room temperature for 1.5 hours. The solvent was evaporated away under reduced pressure, and the residue was purified through partitioning reversed-phase liquid chromatography to obtain 11.1 mg of the entitled compound as a colorless amorphous substance.

$^1$HNMR (CD$_3$OD) δ: 1.23 (3H, t, J=7.4 Hz), 3.19 (2H, q, J=7.4 Hz), 4.48 (2H, s), 7.07 (2H, d, J=9.0 Hz), 7.41 (1H, s), 7.63 (1H, dd, J=8.2, 4.7 Hz), 7.84 (2H, d, J=9.0 Hz), 7.95 (1H, s), 8.09 (1H, td, J=8.2, 1.6 Hz), 8.30 (1H, d, J=8.2 Hz), 8.84 (1H, d, J=4.7 Hz).

ESI-MASS (m/e): 462(M+H).

Example 142

5-[4-(Ethylsulfonyl)phenoxy]-6-((2-methyl-2H-tetrazol-5-yl)methyl)-2-(2-pyridinyl)-1H-benzimidazole (Step 1) Production of 5-[4-(ethylsulfonyl)phenoxy]-2-(2-pyridinyl)-6-(2-methyl-2H-tetrazol-5-ylmethyl)-1-{[2-(trimethylsilyl)ethoxy]methyl}-1H-benzimidazole or (6-[4-(ethylsulfonyl)phenoxy]-2-(2-pyridinyl)-6-(2-methyl-2H-tetrazol-5-ylmethyl)-1-{[2-(trimethylsilyl)ethoxy]methyl}-1H-benzimidazole 12.5 mg of potassium tert-butoxide and 13.3 mg of iodomethane were added to an N,N-dimethylformamide, (1 ml) solution of 50 mg of the tetrazole compound obtained from Example 141 (step 1), and stirred at room temperature for 1 hour. 12.5 mg of potassium tert-butoxide was added to it, and stirred at room temperature for 30 minutes. With cooling with ice, aqueous saturated ammonium chloride solution was added to it, extracted with ethyl acetate, and the organic layer was washed with water and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=15/1) to obtain 15.0 mg of a low-polarity compound (the entitled compound) and 17.5 mg of a high-polarity compound as a colorless amorphous substance.

(Step 2) Production of 5-[4-(ethylsulfonyl)phenoxy]-6-((2-methyl-2H-tetrazol-5-yl)methyl)-2-(2-pyridinyl)-1H-benzimidazole Using 15 mg of the obtained low-polarity compound, the entitled compound was obtained in the same method as in Example 127 (step 2) or in accordance with the method or by combining it with an ordinary method.

$^1$HNMR (CDCl$_3$) δ: 1.29 (3H×1/2, t, J=7.4 Hz), 1.30 (3H×1/2, t, J=7.4 Hz), 3.11 (2H×1/2, q, J=7.4 Hz), 3.11 (2H×1/2, q, J=7.4 Hz), 4.18 (3H×1/2, s), 4.21 (3H×1/2, s), 4.31 (2H, s), 7.00 (2H×1/2, d, J=8.6 Hz), 7.02 (2H×1/2, d, J=8.6 Hz), 7.17 (1H×1/2, s), 7.37-7.42 (1H, m), 7.49 (1H×1/2, s), 7.59 (1H×1/2, s), 7.77 (2H×1/2, d, J=8.6 Hz), 7.80 (2H×1/2, d, J=8.6 Hz), 7.81 (1H×1/2, s), 7.85-7.91 (1H, m), 8.36-8.41 (1H, m), 8.62-8.67 (1H, m), 10.58 (1H, brs).

ESI-MASS (m/e): 476(M+H).

Example 143

5-[4-(Ethylsulfonyl)phenoxy]-6-((1-methyl-1H-tetrazol-5-yl)methyl)-2-(2-pyridinyl)-1H-benzimidazole Using 17.5 mg of the high-polarity compound obtained in Example 142 (step 1), the entitled compound was obtained in the same method as in Example 127 (step 2) or in accordance with the method or by combining it with an ordinary method.

$^1$HNMR (CDCl$_3$) δ: 1.31 (3H, t, J=7.4 Hz), 3.13 (2H, q, J=7.4 Hz), 3.90 (3H×1/2, s), 3.91 (3H×1/2, s), 4.34 (2H, s), 7.02 (2H×1/2, d, J=8.6 Hz), 7.05 (2H×1/2, d, J=8.6 Hz), 7.17 (1H×1/2, s), 7.39-7.43 (1H, m), 7.46 (1H×1/2, s), 7.48 (1H×1/2, s), 7.70 (1H×1/2, s), 7.84 (2H, d, J=8.6 Hz), 7.85-7.91 (1H, m), 8.35-8.40 (1H, m), 8.63-8.67 (1H, m), 10.65 (1H, brs).

ESI-MASS (m/e): 476(M+H).

Example 114

5-[4-(Ethylsulfonyl)phenoxy]-6-(1-(1-methyl-1H-tetrazol-5-yl)methyl)-2-(2-pyridinyl)-1H-benzimidazole With cooling with ice, 7.1 mg of sodium hydride and 20 mg of iodomethane were added to an N,N-dimethylformamide (2 ml) solution of 64 mg of the tetrazole compound obtained from Example 141 (step 1), and stirred at room temperature for 2 hours. With cooling with ice, aqueous saturated ammonium chloride solution was added to it, extracted with ethyl acetate, and the organic layer was washed with water and saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=15/1) to obtain 10.0 mg of a pale yellow amorphous substance. 10.0 mg of the pale yellow amorphous substance was dissolved in 1 ml of trifluoroacetic acid, and stirred at room temperature for 1 hour. The solvent was evaporated away, the residue was diluted with chloroform, and neutralized with aqueous saturated sodium hydrogencarbonate solution. This was extracted with chloroform, and the organic layer was washed with saturated saline water. After dried, the solvent was evaporated away under reduced pressure, and the residue was purified through partitioning thin-layer chromatography (Kieselgel™ 60F$_{254}$, Art 5744 (by Merck), chloroform/methanol=10/1) to obtain 7.1 mg of the entitled compound as a colorless amorphous substance.

$^1$HNMR (CDCl$_3$) δ: 1.31 (3H, t, J=7.4 Hz), 1.81 (3H×1/2, d, J=7.2 Hz), 1.84 (3H×1/2, d, J=6.8 Hz), 3.14 (2H, q, J=7.4 Hz), 3.74 (3H×1/2, s), 3.79 (3H×1/2, s), 4.60-4.75 (1H, m), 7.03-7.13 (2H, m), 7.16 (1H×1/2, s), 7.37-7.44 (1H, m), 7.39 (1H×1/2, s), 7.48 (1H×1/2, s), 7.71 (1H×1/2, s), 7.75-7.91 (3H, m), 8.32-8.42 (1H, m), 8.58-8.70 (1H, m), 10.63 (1H×1/2, brs), 10.66 (1H×1/2, brs).
ESI-MASS (m/e): 490(M+H).

Example 145

N-[{6-[(4-ethylsulfonyl)phenoxy]-2-pyridin-2-yl-1H-benzimidazol-4-yl}methyl]methanesulfonamide Using the product obtained in Example 70 (step 7), the entitled compound was obtained in the same method as in Example 31 or in accordance with the method or by combining it with an ordinary method.

$^1$HNMR (CDCl$_3$) δ: 1.28 (3H, q, J=10.6 Hz), 2.83 (3H, s), 3.10 (2H, t, J=10.6 Hz), 4.74 (2H, d, J=6.3 Hz), 6.34 (1H, s), 6.98 (1H, s), 7.08 (2H, d, J=6.3 Hz), 7.18 (1H, s), 7.48-7.42 (1H, m), 7.90-7.85 (3H, m), 8.37 (1H, d, J=7.4 Hz), 8.64 (1H, d, J=5.1 Hz), 10.64 (1H, brs).
ESI-MASS (m/e): 487(M+H).

Example 146

3-[{6-[4-Ethylsulfonyl)phenoxy]-2-pyridin-2-yl-1H-benzimidazol-4-yl}methyl]-1,3-oxazolidin-2-one Using the product obtained in Example 70 (step 7), the entitled compound was obtained in the same method as in Example 3 or in accordance with the method or by combining it with an ordinary method.

$^1$HNMR (CDCl$_3$) δ: 1.29 (3H, t, J=7.4 Hz), 3.11 (2H, q, J=7.4 Hz), 3.62-3.57 (2H, m), 4.35-4.33 (2H, m), 4.67 (2H, s), 6.91 (1H, s), 7.09 (2H, d, J=8.6 Hz), 7.37-7.35 (1H, m), 7.52 (1H, s), 7.84-7.82 (3H, m), 8.34 (1H, d, J=8.2 Hz), 8.74 (1H, d, J=3.9 Hz), 11.72 (1H, brs).
ESI-MASS (m/e): 479(M+H).

Example 147

1-[{6-[4-Ethylsulfonyl)phenoxy]-2-pyridin-2-yl-1H-benzimidazol-4-yl}methyl]piperidin-2-one Using the product obtained in Example 70 (step 7), the entitled compound was obtained in the same method as in Example 6 or in accordance with the method or by combining it with an ordinary method.

$^1$HNMR (CDCl$_3$) δ: 1.29 (3H, t, J=7.4 Hz), 1.77-1.70 (4H, m), 2.51 (2H, m), 3.11 (2H, q, J=7.4 Hz), 3.34-3.32 (2H, m), 4.76 (2H, s), 6.90-6.98 (1H, m), 7.08 (2H, d, J=8.8 Hz), 7.36-7.34 (1H, m), 7.51-7.50 (1H, m), 7.83-7.82 (3H, m), 8.34 (1H, d, J=7.8 Hz), 8.78 (1H, d, J=5.1 Hz), 12.13 (1H, brs).
ESI-MASS (m/e): 491(M+H).

Example 148

6-[4-(Ethylsulfonyl)phenoxy]-4-(3-fluorobenzyl)-2-pyridin-2-yl-1H-benzimidazole

Using the aldehyde compound obtained in Example 76 (step 1) and 3-fluorophenylmagnesium bromide, the entitled compound was obtained in the same method as in Example 76 (steps 2, 3) or in accordance with the method or by combining it with an ordinary method.

$^1$HNMR (CDCl$_3$) δ: 1.26-1.23 (3H, m), 3.11-2.92 (2H, m), 4.23 (1H, s), 4.44 (1H, s), 6.72 (1/2H, s), 6.89-6.86 (2H, m), 7.12-7.02 (5H, m), 7.35-7.33 (1H, m), 7.84-7.75 (4H, m), 8.43 (1/2H, d, J=8.6 Hz), 8.58-8.54 (1H, m), 10.66 (1H, brs).
ESI-MASS (m/e): 488(M+H).

Example 149

4-(3,4-Difluorobenzyl)-6-[4-(ethylsulfonyl)phenoxy]-2-pyridin-2-yl-1H-benzimidazole Using the aldehyde compound obtained in Example 76 (step 1) and 3,4-difluorophenylmagnesium bromide, the entitled compound was obtained in the same method as in Example 76 (steps 2, 3) or in accordance with the method or by combining it with an ordinary method.

$^1$HNMR (CDCl$_3$) δ: 1.28-1.22 (3H, m), 3.11-3.05 (2H, m), 4.11 (1H, s), 4.39 (1H, s), 6.72 (1H, s), 7.06-7.03 (5H, m), 7.40-7.35 (2H, m), 7.85-7.78 (3H, m), 8.41 (1H, s), 8.60-8.54 (1H, m), 10.59 (1H, brs).
ESI-MASS (m/e): 506(M+H).

Example 150

1-[(6-{[6-(Ethylsulfonyl)pyridin-3-yl]oxy}-2-pyridin-2-yl-1H-benzimidazol-4-yl)methyl]pyrrolidin-2-one (Step 1) Production of (6-{[6-(ethylsulfonyl)pyridin-3-yl]oxy}-2-(2-pyridyl)-1-{[2-(trimethylsilyl)ethoxy]methyl}-1H-benzimidazol-4-yl)methanol and (5-{[6-(ethylsulfonyl)pyridin-3-yl]oxy}-2-(2-pyridyl)-1-{[2-(trimethylsilyl)ethoxy]methyl}-1H-benzimidazol-7-yl)methanol Using 6-(ethylsulfonyl)-3-pyridinol obtained in Reference Example 4, the entitled compound was obtained in the same method as in Example 70 (steps 2 to 7) or in accordance with the method or by combining it with an ordinary method.

(Step 2) Production of 1-[(6-{[6-(ethylsulfonyl)pyridin-3-yl]oxy}-2-pyridin-2-yl-1H-benzimidazol-4-yl)methyl]pyrrolidin-2-one Using the obtained alcohol compound, the entitled compound was obtained in the same method as in Example 2 or in accordance with the method or by combining it with an ordinary method.

$^1$HNMR (CDCl$_3$) δ: 1.28 (3H, t, J=7.6 Hz), 2.05-1.97 (2H, m), 2.48-2.46 (2H, m), 3.39-3.36 (4H, m), 4.64 (2H, s), 6.89 (1H, d, J=1.6 Hz), 7.36-7.34 (2H, m), 7.49 (1H, s), 7.82 (1H, t, J=7.0 Hz), 7.98 (1H, d, J=8.6 Hz), 8.33 (1H, d, J=7.8 Hz), 8.46 (1H, d, J=2.7 Hz), 8.75-8.73 (1H, m).

ESI-MASS (m/e): 478(M+H).

Example 151

4-({6-[4-(Ethylsulfonyl)phenoxy]-2-pyridin-2-yl-1H-benzimidazol-4-yl}methyl)morpholin-3-one Using the alcohol compound obtained in Example 150 (step 1), the entitled compound was obtained in the same method as in Example 81 or in accordance with the method or by combining it with an ordinary method.

$^1$HNMR (CDCl$_3$) δ: 1.26 (3H, t, J=7.4 Hz), 3.08 (2H, q, J=7.4 Hz), 3.40 (2H, s), 3.82-3.80 (2H, m), 4.26 (2H, s), 4.77 (2H, s), 6.89 (1H, s), 7.07-7.05 (2H, m), 7.35-7.33 (1H, m), 7.51 (1H, s), 7.81 (3H, d, J=9.0 Hz), 8.33 (1H, d, J=7.4 Hz), 8.76-8.73 (1H, m), 11.93 (1H, brs).

ESI-MASS (m/e): 493(M+H).

Example 152

1-[(6-{[6-(Ethylsulfonyl)pyridin-3-yl]oxy}-2-pyridin-2-yl-1H-benzimidazol-4-yl)methyl]pyridin-2(1H)-one Using the alcohol compound obtained in Example 150 (step 1), the entitled compound was obtained in the same method as in Example 5 or in accordance with the method or by combining it with an ordinary method.

$^1$HNMR (CDCl$_3$) δ: 1.26 (3H, t, J=8.6 Hz), 3.39-3.32 (2H, m), 5.36 (2H, s), 6.26 (1H, t, J=6.8 Hz), 6.75 (1H, d, J=9.0 Hz), 7.03 (1H, d, J=2.0 Hz), 7.36-7.34 (3H, m), 7.43 (1H, d, J=6.7 Hz), 7.51 (1H, d, J=2.0 Hz), 7.86-7.78 (1H, m), 7.99-7.95 (1H, m), 8.31 (1H, d, J=7.8 Hz), 8.47 (1H, d, J=2.7 Hz), 8.77 (1H, d, J=4.7 Hz), 12.49 (1H, s).

ESI-MASS (m/e): 488(M+H).

Example 153

6-{[6-(Ethylsulfonyl)pyridin-3-yl]oxy}-2-pyridin-2-yl-4-[(pyridin-2-yloxy)methyl]-1H-benzimidazole Using the alcohol compound obtained in Example 150 (step 1), the entitled compound was obtained in the same method as in Example 5 or in accordance with the method or by combining it with an ordinary method.

$^1$HNMR (CDCl$_3$) δ: 1.30-1.22 (3H, m), 3.36 (2H, q, J=7.6 Hz), 5.68 (2H, s), 6.82 (1H, d, J=8.2 Hz), 6.97-6.95 (1H, m), 7.12 (1H, s), 7.37-7.34 (2H, m), 7.51 (1H, s), 7.62-7.60 (1H, m), 7.85-7.83 (1H, m), 7.97 (1H, d, J=8.6 Hz), 8.35 (1H, d, J=7.8 Hz), 8.43-8.42 (1H, m), 8.49-8.48 (1H, m), 8.70 (1H, d, J=5.1 Hz), 12.27 (1H, s).

ESI-MASS (m/e): 488(M+H).

Example 154

1-[(6-{[6-(Ethylsulfonyl)pyridin-3-yl]oxy}-2-pyridin-2-yl-1H-benzimidazol-4-yl)methyl]-3-methylpyrrolidin-2-one Using the alcohol compound obtained in Example 150 (step 1), the entitled compound was obtained in the same method as in Example 10 or in accordance with the method or by combining it with an ordinary method.

$^1$HNMR (CDCl$_3$) δ: 1.28-1.23 (6H, m), 1.64-1.55 (1H, m), 2.18-2.14 (1H, m), 2.43-2.34 (1H, m), 2.58-2.50 (1H, m), 3.36 (2H, q, J=7.4 Hz), 3.61 (1H, m), 4.40 (1H, d, J=14.9 Hz), 4.89 (1H, d, J=14.9 Hz), 6.88 (1H, s), 7.34-7.32 (2H, m), 7.48 (1H, s), 7.82-7.80 (1H, m), 7.98 (1H, d, J=8.6 Hz), 8.34 (1H, d, J=10.4 Hz), 8.45-8.44 (1H, m), 8.77-8.74 (1H, m), 12.12 (1H, brs).

ESI-MASS (m/e): 492(M+H).

Example 155

1-[(6-{[6-(Ethylsulfonyl)pyridin-3-yl]oxy}-2-pyridin-2-yl-1H-benzimidazol-4-yl)methyl]-1H-imidazole-4,5-dicarbonitrile Using the alcohol compound obtained in Example 150 (step 1) and 4,5-dicyanoimidazole, the entitled compound was obtained in the same method as in Example 2 or in accordance with the method or by combining it with an ordinary method.

$^1$HNMR (CDCl$_3$) δ: 1.29 (3H, t, J=7.4 Hz), 3.37 (2H, q, J=7.4 Hz), 5.66 (2H, s), 7.12 (1H, d, J=2.0 Hz), 7.32 (1H, d, J=2.0 Hz), 7.40 (11H, dd, J=8.6, 2.7 Hz), 7.49-7.47 (11H, m), 7.99-7.97 (11H, m), 8.03 (1H, d, J=8.6 Hz), 8.22 (11H, s), 8.42 (1H, s, J=8.2 Hz), 8.47 (11H, m), 8.64-8.63 (1H, m).

ESI-MASS (m/e): 511(M+H).

Example 156

1-{1-[(6-{[6-(Ethylsulfonyl)pyridin-3-yl]oxy}-2-pyridin-2-yl-1H-benzimidazol-4-yl)methyl]-1H-pyrrol-3-yl}ethanone Using the alcohol compound obtained in Example 150 (step 1) and 3-acetylpyrrole, the entitled compound was obtained in the same method as in Example 2 or in accordance with the method or by combining it with an ordinary method.

$^1$HNMR (CDCl$_3$) δ: 1.27 (3H, t, J=7.4 Hz), 2.36 (3H, s), 3.35 (2H, q, J=7.4 Hz), 5.55 (2H, s), 6.57 (1H, s), 6.67 (1H, s), 6.80 (1H, s), 7.12 (1H, s), 7.36-7.32 (2H, m), 7.48 (1H, s), 7.88-7.86 (1H, m), 7.97 (1H, d, J=8.6 Hz), 8.42-8.39 (2H, m), 8.60 (1H, s), 10.95 (1H, s).

ESI-MASS (m/e): 502(M+H).

Example 157

1-{1-[(6-{[6-(Ethylsulfonyl)pyridin-3-yl]oxy}-2-pyridin-2-yl-1H-benzimidazol-4-yl)methyl]-1H-pyrrol-2-yl}ethanone Using the alcohol compound obtained in Example 150 (step 1) and 2-acetylpyrrole, the entitled compound was obtained in the same method as in Example 2 or in accordance with the method or by combining it with an ordinary method.

$^1$HNMR (CDCl$_3$) δ: 1.30-1.22 (3H, m), 2.39 (1H, s), 2.54 (2H, s), 3.39-3.32 (2H, m), 5.81 (1H, s), 6.08 (1H, s), 6.15-6.14 (1/2H, s), 6.21-6.20 (1/2H, s), 6.61 (1/2H, s), 6.97-6.95 (1H, m), 7.07-7.02 (2H, m), 7.38-7.30 (2H, m), 7.47 (1/2H, s), 7.88-7.80 (1H, m), 7.96-7.94 (1H, m), 8.31 (1H, d, J=7.4 Hz), 8.38-8.37 (1/2H, s), 8.46-8.43 (1H, m), 8.60-8.59 (1/2H, m), 8.70-8.69 (1/2H, s), 10.62 (1/2H, brs), 11.61 (1/2H, brs).
ESI-MASS (m/e): 502(M+H).

Example 158

1-[(6-{[6-(Ethylsulfonyl)pyridin-3-yl]oxy}-2-pyridin-2-yl-1H-benzimidazol-4-yl)methyl]-5-methylpyrrolidin-2-one Using the alcohol compound obtained in Example 150 (step 1), the entitled compound was obtained in the same method as in Example 9 or in accordance with the method or by combining it with an ordinary method.
$^1$HNMR (CDCl$_3$) δ: 1.21-1.20 (3H, m), 1.28 (3H, t, J=7.4 Hz), 1.63-1.56 (1H, m), 2.24-2.23 (1H, m), 2.56-2.54 (1H, m), 3.36-3.31 (4H, m), 4.36 (2H, s), 6.89 (1H, m), 7.36-7.34 (2H, m), 7.49 (1H, s), 7.83-7.80 (1H, m), 7.99 (1H, d, J=8.6 Hz), 8.33 (1H, d, J=7.8 Hz), 8.46-8.45 (1H, m), 8.84-8.75 (1H, m).
ESI-MASS (m/e): 492(M+H).

Example 159

1-[(6-{[6-(Ethylsulfonyl)pyridin-3-yl]oxy}-2-pyridin-2-yl-1H-benzimidazol-4-yl)methyl]-1H-imidazole-2-carbonitrile Using the alcohol compound obtained in Example 150 (step 1), the entitled compound was obtained in the same method as in Example 82 or in accordance with the method or by combining it with an ordinary method.
$^1$HNMR (CDCl$_3$) δ: 1.28 (3H, t, J=7.4 Hz), 3.36 (2H, q, J=7.4 Hz), 5.72 (2H, s), 6.95 (1H, s), 7.14 (1H, s), 7.18 (1H, s), 7.34 (1H, dd, J=8.6, 2.7 Hz), 7.40-7.38 (1H, m), 7.46 (1H, s), 7.89 (1H, t, J=7.8 Hz), 8.00 (1H, d, J=8.6 Hz), 8.44-8.43 (2H, m), 8.61-8.60 (1H, m), 11.09 (1H, brs).
ESI-MASS (m/e): 486(M+H).

Example 160

6-{[6-(Ethylsulfonyl)pyridin-3-yl]oxy}-4-[(2-fluoropyridin-3-yl)methyl]-2-pyridin-2-yl-1H-benzimidazole (Step 1) 6-{[6-(Ethylsulfonyl)pyridin-3-yl]oxy}-2-pyridin-2-yl-1-{[2-(trimethylsilyl)ethoxy]methyl}-1H-benzimidazole-4-carbaldehyde and 5-{[6-(ethylsulfonyl)pyridin-3-yl]oxy}-2-(2-pyridyl)-1-{[2-(trimethylsilyl)ethoxy]methyl}-1H-benzimidazole-7-carbaldehyde Using the alcohol compound obtained in Example 150 (step 1), the entitled compound was obtained in the same method as in Example 64 (step 1) or in accordance with the method or by combining it with an ordinary method.

(Step 2) Production of (6-{[6-(ethylsulfonyl)pyridin-3-yl]oxy}-2-pyridin-2-yl-1-{[2-(trimethylsilyl)ethoxy]methyl}-1H-benzimidazole-4-yl)(2-fluoropyridin-3-yl)methanol or (5-{[6-(ethylsulfonyl)pyridin-3-yl]oxy}-2-pyridin-2-yl-1-{[2-(trimethylsilyl)ethoxy]methyl}-1H-benzimidazole-7-yl)(2-fluoropyridin-3-yl)methanol At −78° C., 0.80 ml of normal-butyllithium (1.5 M hexane solution was added to a tetrahydrofuran (1 ml) solution of 169 μl of diisopropylamine, and with cooling with ice, stirred for 30 minutes to obtain lithiumdiisopropylamine. At −78° C., 103 μl of 2-fluoropyridine was added to it, and stirred for 3 hours at that temperature. At −78° C., a tetrahydrofuran (2 ml) solution of 130 mg of the aldehyde compound obtained in the step 1 was added to the above reaction liquid, and stirred for about 1 hour kept at that temperature. Aqueous saturated ammonium chloride solution was added to the reaction liquid, and extracted with ethyl acetate. The organic layer was dried, the solvent was evaporated away under reduced pressure, and the residue was purified through silica gel column chromatography (developing solvent: hexane/ethyl acetate=2/1) to obtain 106 mg of (6-{[6-(ethylsulfonyl)pyridin-3-yl]oxy}-2-pyridin-2-yl-1-{[2-(trimethylsilyl)ethoxy]methyl}-1H-benzimidazole-4-yl)(2-fluoropyridin-3-yl)methanol as an orange oil.

(Step 3) Production of 6-{[6-(ethylsulfonyl)pyridin-3-yl]oxy}-4-[(2-fluoropyridin-3-yl)methyl]-2-pyridin-2-yl-1H-benzimidazole At room temperature, 8.2 μl of thionyl chloride was added to a chloroform (0.5 ml) solution of 24 mg of the alcohol compound obtained in the step 2, and stirred for 30 minutes. The solvent was evaporated away under reduced pressure to obtain a crude product. 12 mg of zinc was added to a trifluoroacetic acid (0.7 ml) solution of this crude product, and stirred at 100° C. for 30 minutes. After restored to room temperature, this was filtered through Celite (elution solvent: chloroform, methanol), the solvent was evaporated away under reduced pressure, the residue was washed with aqueous saturated sodium hydrogencarbonate solution, dried, the solvent was evaporated away under reduced pressure, and the residue was purified through thin-layer column chromatography (developing solvent: chloroform/methanol=9/1) to obtain 3.5 g of the entitled compound as a white solid.
$^1$HNMR (CDCl$_3$) δ: 1.28 (3H, t, J=7.6 Hz), 3.35 (2H, q, J=7.6 Hz), 4.25 (1H, s), 4.46 (1H, s), 6.86-6.82 (1H, m), 7.10-7.08 (2H, m), 7.35-7.32 (2H, m), 7.87-7.85 (2H, m), 7.98 (1H, d, J=8.6 Hz), 8.10-8.04 (1H, m), 8.43-8.40 (2H, m), 8.62-8.60 (1H, m), 10.53 (1H, brs).
ESI-MASS (m/e): 490(M+H).

Example 161

1-[(6-{[6-(Ethylsulfonyl)pyridin-3-yl]oxy}-2-pyrazin-2-yl-1H-benzimidazol-4-yl)methyl]pyrrolidin-2-one (Step 1) Production of methyl 2-amino-5-[{[6-(ethylsulfonyl)pyridin-2-yl]oxy}benzoate Using 6-(ethylsulfonyl)-3-pyridinol obtained in Reference Example 4, the entitled compound was obtained in the same method as in Example 70 (steps 2, 3) or in accordance with the method or by combining it with an ordinary method.

(Step 2) Production of methyl 5-{[6-(ethylsulfonyl)
pyridin-3-yl]oxy}-3-nitro-2-[(pyrazin-2-ylcarbonyl)
aminobenzoate 4.7 of 1-(3-dimethylaminopropyl)-3-ethylcarbodiimide hydrochloride was added to a pyridine (150 ml) solution of 5.5 g of methyl 2-amino-5-[{[6-(ethylsulfonyl)pyridin-3-yl] oxy}benzoate and 2.4 g of pyridine-2-carboxylic acid, and stirred at room temperature for 6 hours. The solvent was evaporated away under reduced pressure, chloroform was added to the residue, and the organic layer was washed with aqueous 0.25 N hydrochloric acid solution, aqueous 0.25 N sodium hydroxide solution and saturated saline water. After dried, this was concentrated under reduced pressure, crystallized from toluene, and the resulting crystal was taken out through filtration. This was dried under reduced pressure to obtain 5.6 g of the entitled compound as a brown crystal.

Using 5.6 g of the obtained solid, 5.44 g of the entitled compound was obtained as a brown amorphous substance in the same method as in Example 70 (step 5) or in accordance with the method or by combining it with an ordinary method.

(Step 3) Production of methyl 6-{[6-(ethylsulfonyl)
pyridin-3-yl]oxy}-2-pyrazin-2-yl-1-{[2-(trimethyl
silyl)ethoxy]methyl}-1H-benzimidazole-4-carboxylate and methyl 5-{[6-(ethylsulfonyl)pyridin-3-yl]
oxy}-2-pyrazin-2-yl-1-{[2-(trimethyl silyl)ethoxy]
methyl}-1H-benzimidazole-7-carboxylate 3.1 g of iron was added to an acetic acid (60 ml) solution of 5.44 g of the obtained amorphous substance, and stirred at 80° C. for 40 minutes. After filtered, the solvent was evaporated away under reduced pressure, water was added to the residue, extracted with chloroform, and the organic layer was washed with saturated saline water. After dried, this was evaporated under reduced pressure, crystallized from toluene, and the resulting crystal was taken out through filtration. This was dried under reduced pressure to obtain 4.0 g of the entitled compound as a gray crystal.

80 ml of dimethylformamide and 80 ml of tetrahydrofuran were added to 4.0 g of the obtained crystal, and heated and dissolved. With cooling with water, 2.4 ml of 2-(trimethylsilyl)ethoxymethyl chloride and 476 mg of sodium hydride (with 30% liquid paraffin added thereto) were added to it, and stirred at room temperature for 1 hour. With cooling with ice, aqueous saturated ammonium chloride solution was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate=9/1 to 1/9) to obtain 5.22 g of the entitled compound as a yellow amorphous substance.

(Step 4) Production of (6-{[6-(ethylsulfonyl)pyridin-
3-yl]oxy}-2-pyrazin-2-yl-1-{[2-(trimethylsilyl)
ethoxy]methyl}-1H-benzimidazol-4-yl)methanol and
(5-{[6-(ethylsulfonyl)pyridin-3-yl]oxy}-2-pyrazin-2-
yl-1-{[2-(trimethylsilyl)ethoxy]methyl}-1H-benz-
imidazol-7-yl)methanol Using 5.22 g of the obtained methyl ester compound, 1.57 g of the entitled compound was obtained as a yellow amorphous substance in the same method as in Example 34 (step 3) or in accordance with the method or by combining it with an ordinary method.

(Step 5) Production of 1-[(6-{[6-(ethylsulfonyl)pyri-
din-3-yl]oxy}-2-pyrazin-2-yl-1H-benzimidazol-4-yl)
methyl]pyrrolidin-2-one Using the obtained alcohol compound, the entitled compound was obtained in the same method as in Example 2 or in accordance with the method or by combining it with an ordinary method.

$^1$HNMR (CDCl$_3$) δ: 1.29 (3H, t, J=7.4 Hz), 2.07-1.99 (2H, m), 2.48 (2H, t, J=8.2 Hz), 3.44-3.34 (4H, m), 4.62 (2H, s), 6.92 (1H, m), 8.36 (1H, m), 7.53 (1H, m), 8.00 (1H, d, J=8.6 Hz), 8.47-8.46 (1H, m), 8.63-8.62 (1H, m), 8.72-8.70 (1H, m), 9.57 (1H, d, J=1.2 Hz), 12.18 (1H, s).
ESI-MASS (m/e): 479(M+H).

Example 162

4-[(2-Chloropyridin-3-yl)methyl]-6-{[6-(ethylsulfo-
nyl)pyridin-3-yl]oxy}-2-pyridin-2-yl-1H-benzimida-
zole Using 2-chloropyridine, the entitled compound was obtained in the same method as in Example 160 (steps 2, 3) or in accordance with the method or by combining it with an ordinary method.

$^1$HNMR (CDCl$_3$) δ: 1.30-1.21 (3H, m), 3.35 (2H, q, J=7.4 Hz), 4.34 (1H, s), 4.57 (1H, s), 6.80-6.78 (1H, m), 7.15-7.13 (1H, m), 7.46-7.31 (3H, m), 7.75 (1H, d, J=7.8 Hz), 7.86-7.85 (1H, m), 7.97 (1H, d, J=8.6 Hz), 8.40-8.29 (3H, m), 8.61 (1H, s), 10.63 (1H, s).
ESI-MASS (m/e): 506(M+H).

Example 163

6-{[6-(Ethylsulfonyl)pyridin-3-yl]oxy}-4-[(3-fluoro-
pyridin-4-yl)methyl]-2-pyridin-2-yl-1H-benzimida-
zole (Step 1) Production of (6-{[6-(ethylsulfonyl)pyridin-
3-yl]oxy}-2-pyridin-2-yl-1-[{2-(trimethylsilyl)
ethoxy]methyl}-1H-benzimidazol-4-yl)(3-fluoropy-
ridin-4-yl)methanol or (5-{[6-(ethylsulfonyl)pyridin-
3-yl]oxy}-2-pyridin-2-yl-1-[{2-(trimethylsilyl)
ethoxy]methyl}-1H-benzimidazol-7-yl)(3-
fluoropyridin-4-yl)methanol At −20° C., 0.92 ml of normal-butyllithium (1.5 M hexane solution) was added to a diethyl ether (1.5 ml) solution of 154 mg of 4-diazabicyclo[2,2,2]octane, and stirred at that temperature for 1 hour. Then, 119 μl of 3-fluoropyridine was added to it at −78° C., and stirred at that temperature for 2 hours. At −60° C., a tetrahydrofuran (2 ml) solution of 149 mg of 6-{[6-(ethylsulfonyl)pyridin-3-yl]oxy}-2-pyridin-2-yl-1-[{2-(trimethylsilyl)ethoxy]methyl}-1H-benzimidazole-4-carbaldehyde was added to it, and stirred at that temperature for 1 hour. Then, aqueous saturated ammonium chloride solution was added to it, and extracted with ethyl acetate. The organic layer was dried, the solvent was evaporated away under reduced pressure, and the residue was purified through silica gel column chromatography (developing solvent: hexane/ethyl acetate=2/1 to 0/1) to obtain 32 mg of the entitled compound as a yellow oil.

(Step 2) Production of 6-{[6-(ethylsulfonyl)pyridin-
3-yl]oxy}-4-[(3-fluoropyridin-4-yl)methyl]-2-pyri-
din-2-yl-1H-benzimidazole The entitled compound was obtained in the same method as in Example 160 (step 3) or in accordance with the method or by combining it with an ordinary method.

¹HNMR (CDCl₃) δ: 1.30-1.21 (3H, m), 3.35 (2H, q, J=7.4 Hz), 4.49 (2H, s), 6.80 (1H, s), 7.10 (1H, s), 7.38-7.32 (3H, m), 7.86 (1H, t, J=7.2 Hz), 7.98 (1H, t, J=8.6 Hz), 8.28-8.26 (1H, m), 8.45-8.41 (3H, m), 8.61-8.60 (1H, m), 10.56 (1H, s).
ESI-MASS (m/e): 490(M+H).

Example 164

1-[(6-{[6-(Ethylsulfonyl)pyridin-3-yl]oxy}-2-pyridin-2-yl-1H-benzimidazol-4-yl)methyl]-1H-pyrrole-2-carbonitrile Using 2-cyanopyrrole, the entitled compound was obtained in the same method as in Example 150 or in accordance with the method or by combining it with an ordinary method.
¹HNMR (CDCl₃) δ: 1.28 (3H, t, J=7.4 Hz), 3.36 (2H, q, J=7.4 Hz), 5.68 (2H, s), 6.16 (1H, s), 6.79-6.75 (2H, m), 7.17-7.12 (2H, m), 7.32 (1H, dd, J=8.8, 2.5 Hz), 7.39-7.37 (1H, m), 7.89-7.87 (1H, m), 7.97 (1H, d, J=8.6 Hz), 8.44-8.41 (2H, m), 8.61-8.60 (1H, m), 10.92 (1H, brs).
ESI-MASS (m/e): 485(M+H).

Example 165

(6-{[6-(Ethylsulfonyl)pyridin-3-yl]oxy}-2-pyridin-2-yl-1H-benzimidazol-4-yl)(3-fluoropyridin-2-yl)methanol Using 3-fluoropyridine, the entitled compound was obtained in the same method as in Example 160 (steps 2, 3) or in accordance with the method or by combining it with an ordinary method.
¹HNMR (CDCl₃) δ: 1.28 (3H, t, J=7.6 Hz), 3.36 (2H, q, J=7.6 Hz), 6.67 (1H, s), 6.80 (1H, s), 7.33-7.29 (3H, m), 7.53-7.51 (1H, m), 7.77-7.74 (1H, m), 7.99 (2H, d, J=9.0 Hz), 8.41-8.39 (2H, m), 8.48-8.45 (1H, m), 8.68-8.66 (1H, m).
ESI-MASS (m/e): 506(M+H).

Example 166

1-{1-[(6-{[6-(Ethylsulfonyl)pyridin-3-yl]oxy}-2-pyridin-2-yl-1H-benzimidazol-4-yl)methyl]-1H-imidazol-2-yl}ethanone Using 2-acetylimidazole produced in Example 92 (step 1), the entitled compound was obtained in the same method as in Example 150 or in accordance with the method or by combining it with an ordinary method.
¹HNMR (CDCl₃) δ: 1.42 (3H, t, J=7.4 Hz), 2.78 (2H, s), 2.91 (1H, s), 3.50 (2H, q, J=7.4 Hz), 5.99 (2/3H, s), 6.24 (4/3H, s), 7.03 (2/3H, s), 7.12 (1/3H, s), 7.25 (1H, d, J=7.8 Hz), 7.53-7.40 (3H, m), 7.64 (2/3H, s), 7.70 (1/3H, s), 8.03-8.01 (1H, m), 8.12-8.10 (1H, m), 8.57-8.48 (2H, m), 8.75-8.74 (2/3H, m), 8.85-8.82 (1/3H, m), 11.08 (2/3H, s), 11.70 (1/3H, s).
ESI-MASS (m/e): 503(M+H).

Example 167

4-[(3,5-Difluoropyridin-4-yl)methyl]-6-{[6-(ethylsulfonyl)pyridin-3-yl]oxy}-2-pyridin-2-yl-1H-benzimidazole Using 3,5-difluoropyridine, the entitled compound was obtained in the same method as in Example 160 (steps 2, 3) or in accordance with the method or by combining it with an ordinary method.

¹HNMR (CDCl₃) δ: 1.26 (3H, t, J=7.6 Hz), 3.36 (2H, q, J=7.6 Hz), 4.46 (2H, s), 6.81 (1H, s), 7.30 (2H, m), 7.40-7.39 (1H, m), 7.88 (1H, t, J=7.0 Hz), 7.97 (1H, d, J=8.6 Hz), 8.33 (2H, s), 8.42-8.39 (2H, m), 8.64-8.63 (1H, m).
ESI-MASS (m/e): 508(M+H).

Example 168

1-{1-[(6-{[6-(Ethylsulfonyl)pyridin-3-yl]oxy}-2-pyridin-2-yl-1H-benzimidazol-4-yl)methyl]-1H-pyrrol-2-yl}-2,2,2-trifluoroethanone Using 2,2,2-trifluoro-1-(1H-pyrrol-2-yl)-1-ethanone, the entitled compound was obtained in the same method as in Example 150 or in accordance with the method or by combining it with an ordinary method.
¹HNMR (CDCl₃) δ: 1.27 (3H, t, J=7.4 Hz), 3.35 (2H, q, J=7.4 Hz), 6.05 (2H, s), 6.29 (1H, s), 6.73 (1H, s), 7.09 (1H, s), 7.39-7.37 (1H, m), 7.58 (1H, s), 7.89-7.86 (1H, m), 7.94 (1H, d, J=8.2 Hz), 8.41-8.38 (3H, m), 8.62-8.60 (2H, m), 10.90 (1H, s).
ESI-MASS (m/e): 556(M+H).

Example 169

4-(2,6-Difluorobenzyl)-6-{[6-(ethylsulfonyl)pyridin-3-yl]oxy}-2-pyridin-2-yl-1H-benzimidazole ¹HNMR (CDCl₃) δ: 1.27 (3H, t, J=7.4 Hz), 3.35 (2H, q, J=7.4 Hz), 4.24 (1H, s), 4.57 (1H, s), 6.89-6.91 (3H, m), 7.19-7.17 (1H, m), 7.29-7.27 (1H, m), 7.39-7.37 (2H, m), 7.85-7.84 (1H, m), 7.95 (1H, d, J=8.6 Hz), 8.45-8.35 (2H, m), 8.69-8.66 (1H, m), 10.74 (1H, s).
Using 1,3-difluorobenzene, the entitled compound was obtained in the same method as in Example 160 (steps 2, 3) or in accordance with the method or by combining it with an ordinary method.
ESI-MASS (m/e): 507(M+H).

Example 170

1-{1-[(6-{[6-(Ethylsulfonyl)pyridin-3-yl]oxy}-2-pyridin-2-yl-1H-benzimidazol-4-yl)methyl]-11H-pyrazol-3-yl}ethanone Using 5-acetylpyrazole hydrochloride, the entitled compound was obtained in the same method as in Example 150 or in accordance with the method or by combining it with an ordinary method.
¹HNMR (CDCl₃) δ: 1.30-1.24 (3H, m), 2.54 (1H, s), 2.88 (2H, s), 3.39-3.33 (2H, m), 5.59 (1H, s), 5.85 (1H, s), 6.84-6.75 (1H, m), 7.02 (1H, s), 7.38-7.33 (2H, m), 7.51-7.50 (1H, m), 7.90-7.82 (1H, m), 7.99-7.97 (1H, m), 8.33 (1H, d, J=7.8 Hz), 8.43-8.41 (1H, m), 8.47-8.46 (1H, m), 8.62-8.61 (1H, m), 10.81 (1/3H, s), 11.79 (2/3H, s).
ESI-MASS (m/e): 503(M+H).

Example 171

1-[(6-{[6-(5-methyl-1,2,4-oxadiazol-3-yl) pyridin-3-yl]oxy}-2-pyridin-2-yl-1H-benzimidazol-4-yl)methyl]pyrrolidin-2-one 1.54 g of 6-(5-methyl-1,2,4-oxadiazol-3-yl)pyridin-3-ol and 1.86 g of potassium carbonate were added to a dimethylformamide (10 ml) solution of 955 mg of methyl 5-fluoro-2-nitrobenzoate, and stirred at 80° C. for 1 hour. This was restored to room temperature, then aqueous saturated ammonium chloride solution was added to it, extracted with ethyl acetate, and the organic layer was dried, and the solvent was evaporated away under reduced pressure to obtain 1.38 g of methyl 5-{[6-(5-methyl-1,2,4-oxadiazol-3-yl)pyridin-3-yl]oxy}-2-nitrobenzoate as a yellow solid.

1.96 ml of aqueous 5 N sodium hydroxide solution was added to a solution of 700 mg of methyl 5-{[6-(5-methyl-1,2,4-oxadiazol-3-yl)pyridin-3-yl]oxy}-2-nitrobenzoate in 5 ml of methanol and 5 ml of tetrahydrofuran, and stirred at room temperature for 2.5 hours. Aqueous 10% citric acid solution was added to neutralize it, then extracted with ethyl acetate, and the organic layer was dried, and the solvent was evaporated away under reduced pressure to obtain 399 mg of 5-{[6-(5-methyl-1,2,4-oxadiazol-3-yl)pyridin-3-yl]oxy}-2-nitrobenzoic acid as a pale yellow solid.

282 mg of N,N'-carboxydiimidazole was added to a tetrahydrofuran (5 ml) solution of 399 mg of the above carboxylic acid, and stirred at room temperature for 30 minutes. With cooling with ice, the above reaction liquid was added to an aqueous 5 ml solution of 219 mg of sodium borohydride, and stirred for 20 minutes. This was neutralized with aqueous 10% citric acid solution added thereto, then extracted with ethyl acetate, the organic layer was dried, and the solvent was evaporated away under reduced pressure to obtain 367 mg of (5-{[6-(5-methyl-1,2,4-oxadiazol-3-yl)pyridin-3-yl]oxy}-2-nitrophenyl)methanol as a pale yellow solid.

0.92 ml of triethylamine and 530 mg of sulfur trioxide/pyridine complex were added to a dimethylsulfoxide (5 ml) solution of 367 mg of (5-{[6-(5-methyl-1,2,4-oxadiazol-3-yl)pyridin-3-yl]oxy}-2-nitrophenyl)methanol, and stirred at room temperature for 30 minutes. Aqueous saturated ammonium chloride solution was added to it, extracted with ethyl acetate, the organic layer was dried, the solvent was evaporated away under reduced pressure, and the residue was purified through silica gel column chromatography (developing solvent: hexane/ethyl acetate=9/1 to 3/7) to obtain 174 mg of 5-{[6-(5-methyl-1,2,4-oxadiazol-3-yl)pyridin-3-yl]oxy}-2-nitrobenzylaldehyde as a yellow solid.

123 mg of 4-aminobutanoic acid hydrochloride and 0.11 ml of triethylamine were added to a chloroform (4 ml) solution of 174 mg of the above compound, and stirred at room temperature for 30 minutes. Then 339 mg of sodium triacetoxyborohydride was added to it, and stirred overnight. Saturated saline water was added to it, extracted with chloroform, the organic layer was dried, and the solvent was evaporated away under reduced pressure to obtain 210 mg of 1-(5-{[6-(5-methyl-1,2,4-oxadiazol-3-yl)pyridin-3-yl]oxy}-2-nitrobenzyl)pyrrolidin-2-one as a pale yellow solid.

599 mg of tin chloride dihydrate was added to a solution of 210 mg of the above compound in 2 ml of dimethylformamide and 2 ml of methanol, and stirred under heat at 80° C. for 90 minutes. This was restored to room temperature, then neutralized with aqueous saturated sodium hydrogencarbonate solution added thereto, and the formed salt was removed through filtration. The organic layer of the filtrate was washed with water and saturated saline water. After dried, the solvent was evaporated away to obtain 144 mg of a crude product, 1-(2-amino-5-{[6-(5-methyl-1,2,4-oxadiazol-3-yl)pyridin-3-yl]oxy}benzyl)pyrrolidin-2-one as a yellow oil.

With cooling with ice, 0.33 ml of triethylamine and 210 mg of picolinic acid chloride were added to a chloroform (2 ml) solution of 144 mg of 1-(2-amino-5-{[6-(5-methyl-1,2,4-oxadiazol-3-yl)pyridin-3-yl]oxy}benzyl)pyrrolidin-2-one, and stirred at room temperature for 1 hour. Water was added to it, extracted with chloroform, the organic layer was dried, the solvent was removed, and the residue was purified through silica gel column chromatography (developing solvent: hexane/ethyl acetate=9/1 to 2/8) to obtain 117 mg of N-{4-{[6-(5-methyl-1,2,4-oxadiazol-3-yl)pyridin-3-yl]oxy}-2-[(2-oxopyrrolidin-1-yl)methyl]phenyl}pyridine-2-carboxamide as a pale yellow solid.

126 mg of potassium nitrate was added to a trifluoroacetic acid (3 ml) solution of 117 mg of N-{4-{[6-(5-methyl-1,2,4-oxadiazol-3-yl)pyridin-3-yl]oxy}-2-[(2-oxopyrrolidin-1-yl)methyl]phenyl}pyridine-2-carboxamide, and stirred under heat at 80° C. for 7 hours. Trifluoroacetic acid was evaporated away under reduced pressure, then chloroform was added to the residue, and washed with aqueous saturated sodium hydrogencarbonate solution. The organic layer was dried, and the solvent was evaporated away under reduced pressure to obtain 122 mg of N-{4-{[6-(5-methyl-1,2,4-oxadiazol-3-yl)pyridin-3-yl]oxy}-2-nitro-6-[(2-oxopyrrolidin-1-yl)methyl]phenyl}pyridine-2-carboxamide as a brown oil.

266 mg of tin chloride dihydrate was added to a solution of 122 mg of the above compound in 1 ml of dimethylformamide and 1 ml methanol, and stirred overnight under heat at 80° C. This was restored to room temperature, then aqueous saturated sodium hydrogencarbonate solution was added to it, and the formed salt was removed through filtration. The organic layer of the filtrate was washed with water and saturated saline water. After dried, the solvent was evaporated away, and the residue was purified through thin-layer column chromatography (developing solvent: chloroform/methanol=9/1) to obtain 20 mg of 1-[(6-{[6-(5-methyl-1,2,4-oxadiazol-3-yl)pyridin-3-yl]oxy}-2-pyridin-2-yl-1H-benzimidazol-4-yl)methyl]pyrrolidin-2-one as a brown solid.

$^1$HNMR (CDCl$_3$) δ: 2.03-1.98 (2H, m), 2.48-2.46 (2H, m), 2.66 (3H, s), 3.39 (2H, t, J=7.2 Hz), 4.62 (2H, s), 6.90 (1H, d, J=2.3 Hz), 7.34-7.31 (2H, m), 7.50 (1H, s), 7.82-7.80 (1H, m), 8.01-7.99 (1H, m), 8.33 (1H, d, J=7.4 Hz), 8.53 (1H, d, J=2.7 Hz), 8.76-8.75 (1H, m), 11.99 (1H, s).

ESI-MASS (m/e): 468 (M+H).

Example 172

4-[(2,4-Dichloropyridin-3-yl)methyl]-6-{[6-(ethylsulfonyl)pyridin-3-yl]oxy}-2-pyridin-2-yl-1H-benzimidazole Using 3,5-dichloropyridine, the entitled compound was obtained in the same method as in Example 160 (steps 2, 3) or in accordance with the method or by combining it with an ordinary method.

$^1$HNMR (CDCl$_3$) δ: 1.28-1.20 (3H, m), 3.34 (2H, q, J=7.4 Hz), 4.54 (1H, s), 4.84 (1H, s), 6.37 (1H, s), 7.03 (1H, d, J=2.0 Hz), 7.27-7.23 (1H, m), 7.41-7.31 (2H, m), 7.87-7.85 (1H, m), 7.94 (1H, q, J=9.0 Hz), 8.23-8.22 (1H, m), 8.44-8.36 (2H, m), 8.65-8.60 (1H, m), 11.00 (1H, s).

ESI-MASS (m/e): 540(M+H).

Example 173

4-(2,6-Difluorobenzyl)-6-{[6-(ethylsulfonyl)pyridin-3-yl]oxy}-2-pyrazin-2-yl-1H-benzimidazole With cooling with ice, 44 μl of triethylamine and 16 μl of methanesulfonyl chloride were added to a tetrahydrofuran (1.0 ml) solution of 57 mg of the alcohol compound obtained in Example 161 (step 4), and stirred at that temperature for 30 minutes. Saturated saline water was added to the reaction liquid, extracted with ethyl acetate, the organic layer was dried, and the solvent was evaporated away under reduced pressure to obtain 67 mg of a crude product as a yellow oil.

27 mg of lithium bromide was added to a dimethylformamide (1 ml) solution of 67 mg of the above crude product, and stirred at room temperature for 40 minutes. Water was added to the reaction liquid, extracted with ethyl acetate, the organic layer was dried, the solvent was evaporated away under reduced pressure, and the residue was purified through silica gel column chromatography (developing solvent: hexane/ethyl acetate=9/1 to 2/8) to obtain 32 mg of 4-(bromomethyl)-6-{[6-(ethylsulfonyl)pyridin-3-yl]oxy}-2-pyrazin-2-yl-1-{[2-(trimethylsilyl)ethoxy]methyl}-1H-benzimidazole as a yellow oil.

5.9 g of tetrakistriphenylphosphine/palladium was added to a dimethoxyethane (1.0 ml) solution of 31 mg of the obtained bromide compound, and stirred at 50° C. for 10 minutes. 12 mg of (2,6-difluorophenyl)boronic acid, 0.5 ml of ethanol, and 0.1 ml of aqueous (2 M) sodium carbonate solution were added to it, and refluxed under heat for 1.5 hours. This was restored to room temperature, extracted with chloroform, the organic layer was dried, and the solvent was evaporated away under reduced pressure to obtain 39 mg of a crude product as a yellow oil.

0.7 ml of trifluoroacetic acid was added to 39 mg of the above crude product and stirred for 1 hour. The excess trifluoroacetic acid was evaporated away under reduced pressure, the residue was dissolved in chloroform, and washed with aqueous saturated sodium hydrogencarbonate solution. The organic layer was dried, the solvent was removed, and the residue was purified through thin-layer column chromatography (developing solvent: chloroform/methanol=9/1) to obtain 13 mg of the entitled compound as a yellow solid.

$^1$HNMR (CDCl$_3$) δ: 1.26 (3H, t, J=7.4 Hz), 3.36 (2H, q, J=7.4 Hz), 4.25 (4/3H, s), 4.56 (2/3H, s), 6.93-6.91 (2H, m), 7.06-7.04 (1H, m), 7.20-7.18 (1H, m), 7.32-7.30 (1H, m), 7.43 (1H, s), 7.97 (1H, d, J=9.0 Hz), 8.44 (1H, d, J=16.0 Hz), 8.66-8.64 (2H, m), 9.66-9.58 (1H, m), 10.39 (1/3H, s), 10.61 (2/3H, s).

ESI-MASS (m/e): 508(M+H).

Example 174

Methyl 6-(4-(ethylsulfonyl)phenoxy)-2-pyridin-2-yl-1H-benzimidazole-5-carboxylate Methyl 6-[4-(ethylsulfonyl)phenoxy]-2-(2-pyridinyl)-1-{[2-(trimethylsilyl)ethoxy]methyl}-1H-benzimidazole-5-carboxylate was reacted with trifluoroacetic acid to obtain the entitled compound.

Example 175

6-(4-(Ethylsulfonyl)phenoxy)-2-pyridin-2-yl-1H-benzimidazole-5-carboxylic acid 10 ml of aqueous 1 N sodium hydroxide solution was added to 2.3 g of the methyl ester compound obtained in Example 174, and the reaction liquid was stirred overnight at 50° C. 4 ml of 3 N hydrochloric acid was added to the reaction liquid, and the precipitated deposit was taken out through filtration to obtain the entitled compound.

Example 176

(6-(4-Ethylsulfonyl)phenoxy)-2-pyridin-2-yl-1H-benzimidazol-5-yl)methanol 700 mg of 1,1'-carbonyldiimidazole was added to a dimethylformamide (5 ml) solution of 1.5 g of the carboxylic acid obtained in Example 175, and the reaction liquid was stirred at room temperature for 15 minutes. The reaction liquid was added to 5 ml of an aqueous solution of 1.5 g of sodium borohydride, and the reaction liquid was stirred at room temperature for 5 minutes, then diluted with ethyl acetate, washed with water and saturated saline water in that order, and dried with anhydrous sodium sulfate. The solvent was evaporated away under reduced pressure to obtain the entitled compound as an orange solid.

Example 177

6-(4-(Ethylsulfonyl)phenoxy)-2-pyridin-2-yl-1H-benzimidazole-5-carbaldehyde 5 ml of triethylamine and 750 mg of pyridine-sulfur trioxide were added to a dimethylsulfoxide (10 ml) solution of 1.0 g of the alcohol compound obtained in Example 176, and the reaction liquid was stirred at room temperature for 15 minutes. The reaction liquid was diluted with ethyl acetate, washed with water and saturated saline water in that order, and dried with anhydrous sodium sulfate. The solvent was evaporated away under reduced pressure to obtain the entitled compound as an orange solid.

Starting from phenols obtained in Reference Examples, the following compounds of Example 178 to Example 209 were produced in the same method as in Examples 174 to 177 or by combining it with an ordinary method.

Example 178

Methyl 6-(4-(methylsulfonyl)phenoxy)-2-pyridin-2-yl-1H-benzimidazole-5-carboxylate

Example 179

6-(4-(Methylsulfonyl)phenoxy)-2-pyridin-2-yl-1H-benzimidazole-5-carboxylic acid

Example 180

(6-(4-Methylsulfonyl)phenoxy)-2-pyridin-2-yl-1H-benzimidazol-5-yl)methanol

Example 181

6-(4-(Methylsulfonyl)phenoxy)-2-pyridin-2-yl-1H-benzimidazole-5-carbaldehyde

Example 182

Methyl 6-((6-(ethylsulfonyl)pyridin-3-yl)oxy)-2-pyridin-2-yl-1H-benzimidazole-5-carboxylate

Example 183

6-((6-(Ethylsulfonyl)pyridin-3-yl)oxy)-2-pyridin-2-yl-1H-benzimidazole-5-carboxylic acid

Example 184

(6-((6-(Ethylsulfonyl)pyridin-3-yl)oxy)-2-pyridin-2-yl-1H-benzimidazol-5-yl)methanol

Example 185

6-((6-(Ethylsulfonyl)pyridin-3-yl)oxy)-2-pyridin-2-yl-1H-benzimidazole-5-carbaldehyde

Example 186

Methyl 6-((6-(methylsulfonyl)pyridin-3-yl)oxy)-2-pyridin-2-yl-1H-benzimidazole-5-carboxylate

Example 187

6-((6-(Methylsulfonyl)pyridin-3-yl)oxy)-2-pyridin-2-yl-1H-benzimidazole-5-carboxylic acid

Example 188

(6-((6-Methylsulfonyl)pyridin-3-yl)oxy)-2-pyridin-2-yl-1H-benzimidazol-5-yl)methanol

Example 189

6-((6-Methylsulfonyl)pyridin-3-yl)oxy)-2-pyridin-2-yl-1H-benzimidazole-5-carbaldehyde

Example 190

Methyl 6-(6-(5-methyl-(1,2,4)oxadiazol-3-yl)-pyridin-3-yloxy)-2-pyridin-2-yl1H-benzimidazole-5-carboxylate

Example 191

6-(6-(5-Methyl-(1,2,4)oxadiazol-3-yl)-pyridin-3-yloxy)-2-pyridin-2-yl-1H-benzimidazole-5-carboxylic acid Example 192

(6-(6-(5-Methyl-(1,2,4)oxadiazol-3-yl)-pyridin-3-yloxy)-2-pyridin-2-yl-1H-benzimidazol-5-yl)methanol Example 193

6-(6-(5-Methyl-(1,2,4)oxadiazol-3-yl)-pyridin-3-yloxy)-2-pyridin-2-yl-1H-benzimidazole-5-carbaldehyde Example 194

Methyl 6-((6-(methoxymethyl)pyridin-3-yl)oxy)-2-pyridin-2-yl-1H-benzimidazole-5-carboxylate Example 195

6-((6-(Methoxymethyl)pyridin-3-yl)oxy)-2-pyridin-2-yl-1H-benzimidazole-5-carboxylic acid Example 196

(6-((6-(Methoxymethyl)pyridin-3-yl)oxy)-2-pyridin-2-yl-1H-benzimidazol-5-yl)methanol Example 197

6-((6-(Methoxymethyl)pyridin-3-yl)oxy)-2-pyridin-2-yl-1H-benzimidazole-5-carbaldehyde Example 198

Methyl 6-(4-ethylsulfonyl)phenoxy)-2-pyrazin-2-yl-1H-benzimidazole-5-carboxylate Example 199

6-(4-Ethylsulfonyl)phenoxy)-2-pyrazin-2-yl-1H-benzimidazole-5-carboxylic acid

Example 200

(6-(4-Ethylsulfonyl)phenoxy)-2-pyrazin-2-yl-1H-benzimidazol-5-yl)methanol

Example 201

6-(4-Ethylsulfonyl)phenoxy)-2-pyrazin-2-yl-1H-benzimidazole-5-carbaldehyde

Example 202

Methyl 6-((6-(ethylsulfonyl)pyridin-3-yl)oxy)-2-pyrazin-2-yl-1H-benzimidazole-5-carboxylate Example 203

6-((6-(Ethylsulfonyl)pyridin-3-yl)oxy)-2-pyrazin-2-yl-1H-benzimidazole-5-carboxylic acid Example 204

(6-((6-Ethylsulfonyl)pyridin-3-yl)oxy)-2-pyrazin-2-yl-1H-benzimidazol-5-yl)methanol Example 205

6-((6-Ethylsulfonyl)pyridin-3-yl)oxy)-2-pyrazin-2-yl-1H-benzimidazole-5-carbaldehyde Example 206

Methyl 6-((6-cyanopyridin-3-yl)oxy)-2-pyridin-2-yl-1H-benzimidazole-5-carboxylate Example 207

6-((6-Cyanopyridin-3-yl)oxy)-2-pyrazin-2-yl-1H-benzimidazole-5-carboxylic acid

Example 208

(6-((6-Cyanopyridin-3-yl)oxy)-2-pyrazin-2-yl-1H-benzimidazol-5-yl)methanol

Example 209

6-((6-Cyanopyridin-3-yl)oxy)-2-pyrazin-2-yl-1H-benzimidazole-5-carbaldehyde

Example 210

1-({5-[4-(2-Methyl-2H-tetrazol-5-yl)phenoxy]-2-pyridin-2-yl-1H-benzimidazol-6-yl}methyl)pyrrolidin-2-one Using 4-(2-methyl-2H-tetrazol-5-yl)phenol obtained in Reference Example 17, the entitled compound was obtained in the same method as in Example 102 (step 5) or in accordance with the method or by combining it with an ordinary method.

$^1$HNMR (CDCl$_3$) δ: 1.95 (2H, m), 2.37 (2H, m), 3.33 (2H, m), 4.39 (3H, s), 4.61 (2H, s), 7.05 (2H, d, J=8.8 Hz), 7.20-7.60 (1H, br), 7.38 (1H, m), 7.65 (1H, br), 7.87 (1H, m), 8.08 (2H, d, J=8.8 Hz), 8.39 (1H, d, J=8.0 Hz), 8.64 (1H, d, J=4.5 Hz).

ESI-MASS (m/e): 467(M+H).

Example 211

1-[(2-(5-Fluoropyridin-2-yl)-5-{[6-(5-methyl-1,2,4-oxadiazol-3-yl)pyridin-3-yl]oxy}-1H-benzimidazol-6-yl)methyl]pyrrolidin-2-one Using 5-fluoropyridine-2-carboxylic acid obtained in Reference Example 18, the entitled compound was obtained in the same method as in Example 53 or in accordance with the method or by combining it with an ordinary method.

$^1$HNMR (CDCl$_3$) δ: 1.97 (2H, m), 2.35 (2H, m), 2.69 (3H, s), 3.33 (2H, m), 4.60 (2H, s), 7.17 (1/2H, s), 7.33 (1H, m), 7.46 (1/2H, s), 7.58 (2H+1/2H, m), 7.76 (1/2H, s), 8.03 (1H, m), 8.40-8.60 (3H, m), 10.5 (1/2H, br), 10.8 (1/2H, br).

ESI-MASS (m/e): 486(M+H).

Example 212

(3S)-1-({6-[4-(ethylsulfonyl)phenoxy]-2-pyridin-2-yl-1H-benzimidazol-5-yl}methyl)-3-hydroxypyrrolidin-2-one (Step 1) Production of (3S)-3-{[t-butyldimethylsilyl]oxy}pyrrolidin-2-one In an ice bath, 3.1 ml of trimethylsilyldiazomethane (2.0 M, hexane solution) was added to a solution of 500 mg of (2S)-4-amino-2-hydroxybutyric acid in 5 ml of methanol and 4 ml of chloroform, and stirred overnight. The solvent was evaporated away under reduced pressure to obtain 503 mg of (3S)-3-hydroxypyrrolidin-2-one as a white solid.

In an ice bath, 570 mg of imidazole and 947 mg of t-butyldimethylsilyl chloride were added to a dimethylformamide (5 ml) solution of 503 mg of (3S)-3-hydroxypyrrolidin-2-one, and stirred at room temperature for 1 hour. Water was added to the reaction liquid, extracted with ethyl acetate, the organic layer was washed with water and saturated saline water, and dried. The solvent was evaporated away under reduced pressure to obtain 452 mg of the entitled compound as a pale yellow oil.

(Step 2) Production of (3S)-1-({6-[4-(ethylsulfonyl)phenoxy]-2-pyridin-2-yl-1H-benzimidazol-5-yl}methyl)-3-hydroxypyrrolidin-3-one Using the alcohol compound obtained in Example 19 (step 7) and (3S)-3-{[t-butyldimethylsilyl]oxy}pyrrolidin-2-one obtained in the step 1, the entitled compound was obtained in the same method as in Example 2 or in accordance with the method or by combining it with an ordinary method.

$^1$HNMR (CDCl$_3$) δ: 1.25 (3H, t, J=7.4 Hz), 1.95 (1H, s), 2.43 (1H, s), 3.09 (2H, q, J=7.4 Hz), 3.37-3.47 (2H, m), 4.45-4.49 (2H, m), 4.68 (1H, m), 7.07 (2H, d, J=8.0 Hz), 7.37-7.39 (1H, m), 7.43 (1H, s), 7.81-7.89 (3H, m), 7.99 (1H, s), 8.44 (1H, d, J=8.0 Hz), 8.60 (1H, d, J=4.1 Hz).

ESI-MASS (m/e): 493(M+H).

Example 213

1-[(2-(5-Methoxypyridin-2-yl)-5-{[6-(5-methyl-1,2,4-oxadiazol-3-yl)pyridin-3-yl]oxy}-1H-benzimidazol-6-yl)methyl]pyrrolidin-2-one Using 5-methoxypyridine-2-carboxylic acid obtained in Reference Example 19, the entitled compound was obtained in the same method as in Example 53 or in accordance with the method or by combining it with an ordinary method.

$^1$HNMR (CDCl$_3$) δ: 1.94 (2H, m), 2.35 (2H, m), 2.68 (3H, s), 3.30 (2H, m), 3.94 (3H, s), 4.58 (2H, m), 7.14 (1/2H, s), 7.25-7.38 (2H, m), 7.45 (1/2H, s), 7.55 (1/2H, s), 7.74 (1/2H, s), 8.03 (1H, m), 8.28-8.38 (2H, m), 8.47 (1/2H, m), 8.54 (1/2H, m), 10.7 (1/2H, m), 10.8 (1/2H, br).

ESI-MASS (m/e): 498(M+H).

Example 214

(6-{[6-(Ethylsulfonyl)pyridin-3-yl]oxy}-2-pyridin-2-yl-1H-benzimidazol-4-yl)acetonitrile Using the alcohol compound obtained in Example 150 (step 1), the entitled compound was obtained in the same method as in Example 127 or in accordance with the method or by combining it with an ordinary method.

$^1$HNMR (CDCl$_3$) δ: 1.29 (3H, m), 3.37 (2H, q, J=7.4 Hz), 4.27 (2H, s), 7.16 (2H, d, J=13.3 Hz), 7.35-7.39 (2H, m), 7.87 (1H, t, J=7.8 Hz), 8.01 (1H, s), 8.39 (1H, d, J=7.8 Hz), 8.46 (1H, d, J=2.7 Hz), 8.62 (1H, s), 10.83 (1H, brs).

ESI-MASS (m/e): 420(M+H).

Example 215

6-{[6-(Ethylsulfonyl)pyridin-3-yl]oxy}-4-[(5-methyl-1,2,4-oxadiazol-3-yl)methyl]-2-pyridin-2-yl-1H-benzimidazole Using the alcohol compound obtained in Example 150 (step 1), the entitled compound was obtained in the same method as in Example 140 or in accordance with the method or by combining it with an ordinary method.

$^1$HNMR (CDCl$_3$) δ: 1.26 (3H, m), 2.56 (3H, s), 3.33-3.38 (2H, m), 4.28 (1H, s), 4.59 (1H, s), 6.91-7.00 (1H, m), 7.31-7.37 (2H, m), 7.45 (1H, s), 7.85 (1H, t, J=8.6 Hz), 7.97-8.01 (1H, m), 8.37-8.44 (2H, m), 8.59-8.61 (1/2H, m), 8.68 (1/2H, d, J=4.7 Hz).

ESI-MASS (m/e): 477(M+H).

Example 216

1-{2-[(6-{[6-(Ethylsulfonyl)pyridin-3-yl]oxy}-2-pyridin-2-yl-1H-benzimidazol-4-yl)methyl]phenyl}ethanone Using the alcohol compound obtained in Example 150 (step 1), the entitled compound was obtained in the same method as in Example 173 or in accordance with the method or by combining it with an ordinary method.

$^1$HNMR (CDCl$_3$) δ: 1.28 (3H, q, J=7.4 Hz), 2.53 (11H, s), 2.71 (2H, s), 3.36 (2H, q, J=7.4 Hz), 4.36 (4/3H, s), 4.76 (2/3H, s), 6.96 (11H, d, J=2.2 Hz), 7.51 (2H, dd, J=10.3, 4.6 Hz), 7.61-7.68 (5H, m), 7.79 (1H, t, J=8.6 Hz), 7.98 (1H, d, J=8.6 Hz), 8.30 (1H, d, J=8.6 Hz), 8.48 (1H, d, J=2.9 Hz), 8.66 (1H, d, J=4.9 Hz), 12.11 (1H, brs).

ESI-MASS (m/e): 513(M+H).

Example 217

2-[(6-{6-(Ethylsulfonyl)pyridin-3-yl]oxy}-2-pyridin-2-yl-1H-benzimidazol-4-yl)methyl]benzonitrile Using the alcohol compound obtained in Example 150 (step 1), the entitled compound was obtained in the same method as in Example 173 or in accordance with the method or by combining it with an ordinary method.

$^1$HNMR (CDCl$_3$) δ: 1.22-1.29 (3H, m), 3.30-3.37 (2H, m), 4.45 (2/3H, s), 4.68 (4/3H, s), 6.79-6.81 (1H, m), 7.03 (1H, d, J=2.0 Hz), 7.28-7.34 (2H, m), 7.57 (1H, d, J=7.8 Hz), 7.61-7.66 (3H, m), 7.85 (1H, t, J=7.6 Hz), 7.95 (1H, d, J=8.6 Hz), 8.37-8.44 (2H, m), 8.56 (1H, d, J=4.7 Hz), 11.08 (1/3H, brs), 11.26 (2/3H, brs).

ESI-MASS (m/e): 496(M+H).

Example 218

6-{[6-(Ethylsulfonyl)pyridin-3-yl]oxy}-2-pyridin-2-yl-4-(2H-tetrazol-5-ylmethyl)-1H-benzimidazole 41 mg of sodium azide and 87 mg of triethylamine hydrochloride were added to a toluene (2 ml) solution of 116 mg of (6-{[6-(ethylsulfonyl) pyridin-3-yl]oxy}-2-pyridin-2-yl-1-{ [2-(trimethylsilyl)ethoxy]methyl}-1H-benzimidazol-4-yl) acetonitrile, and stirred overnight at 100° C. The reaction liquid was restored to room temperature, then hydrochloric acid (1 N) was added to it, extracted with ethyl acetate, and the organic layer was washed with saturated saline water. The solvent was evaporated away under reduced pressure to obtain 121 mg of a crude product as a yellow oil.

0.7 ml of trifluoroacetic acid was added to 121 mg of the above crude oil, and stirred at room temperature for 1 hour. The excess trifluoroacetic acid was evaporated away under reduced pressure, and the residue was purified through reversed-phase high-performance liquid column chromatography (water/acetonitrile=90/10 to 10/90) to obtain 14 mg of the entitled compound as a white solid.

$^1$HNMR (CDCl$_3$) δ: 1.29 (3H, m), 3.37 (2H, q, J=7.4 Hz), 4.68 (2H, s), 7.07 (1H, s), 7.33-7.36 (2H, m), 7.48-7.50 (1H, m), 7.98-8.00 (2H, m), 8.44 (2H, m), 8.69 (1H, m).

ESI-MASS (m/e): 463(M+H).

Example 219

2-[(6-{6-Ethylsulfonyl)pyridin-3-yl]oxy}-2-pyridin-2-yl-1H-benzimidazol-4-yl)methyl]benzamide Using the alcohol compound obtained in Example 150 (step 1), the entitled compound was obtained in the same method as in Example 173 or in accordance with the method or by combining it with an ordinary method.

$^1$HNMR (CDCl$_3$) δ: 1.32-1.56 (3H, m), 3.33-3.40 (2H, m), 4.40 (2H, s), 7.06 (1H, d, J=8.6 Hz), 7.27-7.42 (5H, m), 7.48-7.50 (2H, m), 7.76-7.80 (2H, m), 7.97-8.01 (1H, m), 8.47-8.48 (1H, m), 8.63 (1H, m).

ESI-MASS (m/e): 514(M+H).

Example 220

1-[Hydroxy(5-{[6-(5-methyl-1,2,4-oxadiazol-3-yl) pyridin-3-yl]oxy}-2-pyridin-2-yl-1H-benzimidazol-6-yl)methyl]pyrrolidin-2-one (Step 1) Production of (5-{[6-(5-methyl-1,2,4-oxadiazol-3-yl)pyridin-3-yl]oxy}-2-pyridin-2-yl-1H-benzimidazol-6-yl)methanol Using 6-(5-methyl-1,2,4-oxadiazol-3-yl)-3-pyridinol obtained from Reference Example 6, the entitled compound was obtained in the same method as in Example 19 (step 5) and Example 34 (step 3) or in accordance with the method or by combining it with an ordinary method.

(Step 2) Production of 5-{[6-(5-methyl-1,2,4-oxadiazol-3-yl)pyridin-3-yl]oxy}-2-pyridin-2-yl-1H-benzimidazole-6-carbaldehyde 1.5 ml of triethylamine and 796 mg of sulfur trioxide/ pyridine complex were added to a dimethyl sulfoxide (5 ml) solution of 400 mg of the alcohol compound obtained in the step 1, and stirred at room temperature for 30 minutes. Water was added to it, extracted with chloroform, and the organic layer was washed with saturated saline water. After dried, the solvent was evaporated away under reduced pressure, the residue was crystallized in diethyl ether/methanol to obtain 183 mg of the entitled compound as a pale yellow amorphous substance.

(Step 3) Production of 1-[hydroxy(5-{[6-(5-methyl-1,2,4-oxadiazol-3-yl)pyridin-3-yl]oxy}-2-pyridin-2-yl-1H-benzimidazol-6-yl)methyl]pyrrolidin-2-one 7 mg of sodium carbonate was added to an N,N-dimethylformamide (500 µl) solution of 8.7 µl of 2-pyrrolidone. With stirring at 80° C., 10 mg of the aldehyde compound obtained in the step 2 was added to it, and stirred overnight at 80° C. The solvent was evaporated away under reduced pressure, and the residue was purified through partitioning thin-layer chromatography (Kieselgel™ 60F$_{254}$, Art 5744 (by Merck), chloroform/methanol=5/1) to obtain 1.0 mg of the entitled compound as a pale yellow amorphous substance.

$^1$HNMR (CDCl$_3$) δ: 0.79-0.94 (1H, m), 1.77-1.91 (1H, m), 1.97-2.09 (1H, m), 2.14-2.34 (1H, m), 2.68 (3H, s), 2.83-2.94 (1H, m), 3.37-3.52 (1H, m), 6.87-6.95 (1H, m), 7.18 (1H×1/2, s), 7.33-7.46 (2H, m), 7.50 (1H×1/2, s), 7.86-7.94 (1H, m), 7.99-8.08 (1H, m, 1H×1/2, s), 8.31 (1H×1/2, s), 8.36-8.46 (2H, m), 8.60-8.72 (1H, m), 10.58 (1H×1/2, brs), 10.86 (1H× 1/2, brs).

ESI-MASS (m/e): 484(M+H).

Example 221

1-[(2-(5-Fluoropyridin-2-yl)-5-{[6-(5-methyl-1,2,4-oxadiazol-3-yl)pyridin-3-yl]oxy}-1H-benzimidazol-6-yl)methyl]pyrrolidin-2-one Using 5-fluoropyridine-2-carboxylic acid obtained in Reference Example 18, the entitled compound was obtained in the same method as in Example 53 (step 2, step 3) or in accordance with the method or by combining it with an ordinary method.

$^1$HNMR (CDCl$_3$) δ: 1.97 (2H, m), 2.35 (2H, m), 2.69 (3H, s), 3.33 (2H, m), 4.60 (2H, s), 7.17 (1/2H, s), 7.33 (1H, m), 7.46 (1/2H, s), 7.58 (2H+1/2H, m), 7.76 (1/2H, s), 8.03 (1H, m), 8.40-8.60 (3H, m), 10.5 (1/2H, br), 10.8 (1/2H, br).

ESI-MASS (m/e): 486(M+H).

Example 222

1-[(2-(5-Methoxypyridin-2-yl)-5-{[6-(5-methyl-1,2, 4-oxadiazol-3-yl)pyridin-3-yl]oxy}-1H-benzimidazol-6-yl)methyl]pyrrolidin-2-one Using 5-methoxypyridin-2-carboxylic acid obtained in Reference Example 19, the entitled compound was obtained in the same method as in Example 53 (step 2, step 3) or in accordance with the method or by combining it with an ordinary method.

$^1$HNMR (CDCl$_3$) δ: 1.94 (2H, m), 2.35 (2H, m), 2.68 (3H, s), 3.30 (2H, m), 3.94 (3H, s), 4.58 (2H, m), 7.14 (1/2H, s), 7.25-7.38 (2H, m), 7.45 (1/2H, s), 7.55 (1/2H, s), 7.74 (1/2H, s), 8.03 (1H, m), 8.28-8.38 (2H, m), 8.47 (1/2H, m), 8.54 (1/2H, m), 10.7 (1/2H, m), 10.8 (1/2H, br).

ESI-MASS (m/e): 498(M+H).

Example 223

1-[(2-(5-Methylpyridin-2-yl)-5-{[6-(5-methyl-1,2,4-oxadiazol-3-yl)pyridin-3-yl]oxy}-1H-benzimidazol-6-yl)methyl]pyrrolidin-2-one Using 6-methylpyridin-2-carboxylic acid, the entitled compound was obtained in the same method as in Example 53 (step 2, step 3) or in accordance with the method or by combining it with an ordinary method.

¹HNMR (CDCl₃) δ: 1.95 (2H, m), 2.33 (2H, m), 2.60 (3H, s), 2.68 (3H, s), 3.32 (2H, m), 4.58 (2H, s), 7.10-7.35 (2H+1/2H, m), 7.47 (1/2H, s), 7.56 (1/2H, s), 7.75 (1H+1/2H, m), 8.03 (1H, m), 8.19 (1H, m), 8.47 (1/2H, s), 8.54 (1/2H, s), 10.9 (1H, br).
ESI-MASS (m/e): 482(M+H).

Example 224

1-[(2-(6-Methoxypyridin-2-yl)-5-{[6-(5-methyl-1,2,4-oxadiazol-3-yl)pyridin-3-yl]oxy}-1H-benzimidazol-6-yl)methyl]pyrrolidin-2-one Using 6-methylpyridin-2-carboxylic acid, the entitled compound was obtained in the same method as in Example 53 (step 2, step 3) or in accordance with the method or by combining it with an ordinary method.
¹HNMR (CDCl₃) δ: 1.96 (2H, m), 2.34 (2H, m), 2.69 (3H, s), 3.34 (2H, m), 4.03 (3/2H, s), 4.07 (3/2H, s), 4.58 (2/2H, s), 4.59 (2/2H, s), 6.86 (1H, d, J=8.2 Hz), 7.16 (1/2H, s), 7.32 (1H, m), 7.46 (1/2H, s), 7.61 (1/2H, s), 7.78 (1H+1/2H, m), 7.96-8.06 (2H, m), 8.46 (1/2H, d, J=2.9 Hz), 8.54 (1/2H, d, J=2.5 Hz), 10.5 (1/2H, br), 10.6 (1/2H, br).
ESI-MASS (m/e): 498(M+H).

Example 225

Methyl 6-{5-{[6-(5-methyl-1,2,4-oxadiazol-3-yl)pyridin-3-yl]oxy}-6-[(2-oxopyrrolidin-1-yl)methyl]-1H-benzimidazol-2-yl}nicotinate Using 5-(methoxycarbonyl)pyridine-2-carboxylic acid, the entitled compound was obtained in the same method as in Example 53 (step 2, step 3) or in accordance with the method or by combining it with an ordinary method.
¹HNMR (CDCl₃) δ: 1.99 (2H, m), 2.40 (2H, m), 2.69 (3H, s), 3.35 (2H, m), 4.00 (3H, s), 4.61 (2H, s), 7.19 (1/2H, s), 7.35 (1H, m), 7.53 (1/2H, s), 7.65 (1/2H, s), 7.80 (1/2H, s), 8.05 (1H, m), 8.45 (2H, m), 8.48 (1/2H, d, J=3.0 Hz), 8.55 (1/2H, d, J=2.6 Hz), 9.22 (1H, m), 10.8 (1/2H, br), 11.1 (1/2H, br).
ESI-MASS (m/e): 526(M+H).

Example 226

1-[(2-(4-Methylpyridin-2-yl)-5-{[6-(5-methyl-1,2,4-oxadiazol-3-yl)pyridin-3-yl]oxy}-1H-benzimidazol-6-yl)methyl]pyrrolidin-2-one Using 4-methylpyridine-2-carboxylic acid, the entitled compound was obtained in the same method as in Example 53 (step 2, step 3) or in accordance with the method or by combining it with an ordinary method.
¹HNMR (CDCl₃) δ: 1.94 (2H, m), 2.34 (2H, m), 2.46 (3/2H, s), 2.47 (3/2H, s), 2.68 (3H, s), 3.32 (2H, m), 4.58 (2/2H, s), 4.61 (2/2H, s), 7.16 (1/2H, s), 7.72 (1H, d, J=4.7 Hz), 7.33 (1H, m), 7.48 (1/2H, s), 7.57 (1/2H, s), 7.77 (1/2H, s), 8.05 (1H, m), 8.23 (1/2H, s), 8.26 (1/2H, s), 8.49 (1H+1/2H, m), 8.55 (1/2H, d, J=2.7 Hz), 10.8 (1H, br).
ESI-MASS (m/e): 482(M+H).

Example 227

3-Hydroxy-1-[(5-{[6-(5-methyl-1,2,4-oxadiazol-3-yl]pyridin-3-yl]oxy}-2-pyridin-2-yl-1H-benzimidazol-6-yl)methyl]pyrrolidin-2-one trifluoroacetate (Step 1) Production of 3-{[tert-butyl(dimethyl)silyl]oxy}pyrrolidin-2-one 5 g of dl-maleic acid was dissolved in 20 ml of acetyl chloride, and stirred under heat at 45° C. for 3 hours. Acetyl chloride was evaporated away under reduced pressure, the resulting crude product was dissolved in 30 ml of methanol, and stirred overnight. The solvent was evaporated away under reduced pressure to obtain 5.3 g of 3-(acetyloxy)-4-methoxy-4-oxobutanoic acid as a pale yellow oil. In an ice bath, 10 ml of borane-dimethylsulfide complex (10 M) was added to a tetrahydrofuran (25 ml) solution of 5.3 g of 3-(acetyloxy)-4-methoxy-4-oxobutanoic acid, and stirred at room temperature for 24 hours. Aqueous 10% citric acid was added to the reaction liquid, extracted with chloroform, and the organic layer was washed with saturated saline water. After dried, the solvent was evaporated away under reduced pressure to obtain 5.1 g of methyl 2-(acetyloxy)-4-hydroxybutanoate as a colorless transparent oil.

In an ice bath, 6.1 ml of triethylamine and 2.3 ml of methanesulfonyl chloride were added to a chloroform (15 ml) solution of 2.59 g of methyl 2-(acetyloxy)-4-hydroxybutanoate, and stirred for 30 minutes. Saturated saline water was added to the reaction liquid, extracted with chloroform, and the organic layer was dried. The solvent was evaporated away under reduced pressure to obtain 2.54 g of methyl 2-(acetyloxy)-4-[(methylsulfonyl)oxy]butanoate as a brown liquid.

1.91 g of sodium azide was added to a dimethylformamide (10 ml) solution of 2.54 g of methyl 2-(acetyloxy)-4-[(methylsulfonyl)oxy]butanoate, and stirred under heat at 70° C. for 8 hours. The reaction liquid was restored to room temperature and extracted with ethyl acetate. The organic layer was washed with saturated saline water and dried, and the solvent was evaporated away under reduced pressure to obtain 2.70 g of methyl 2-(acetyloxy)-4-azidobutanoate as a brown oil.

2.53 g of potassium carbonate and 1 ml of water were added to a methanol (15 ml) solution of 2.47 g of methyl 2-(acetyloxy)-4-azidobutanoate, and stirred at room temperature for 30 minutes. Aqueous saturated ammonium chloride solution was added to the reaction liquid, and extracted with ethyl acetate. The organic layer was washed with saturated saline water and dried. The solvent was evaporated away under reduced pressure to obtain 591 mg of methyl 4-azido-2-hydroxybutanoate as an orange oil.

692 mg of triphenyl phosphine and 8 µl of water were added to a tetrahydrofuran (3 ml) solution of 351 mg of methyl 4-azido-2-hydroxybutanoate, stirred at room temperature for 24 hours, then stirred overnight under heat at 50° C. Tetrahydrofuran was evaporated away under reduced pressure, and the residue was extracted with ethyl acetate to obtain 255 mg of 3-hydroxypyrrolidin-2-one as a pale brown oil.

In an ice bath, 300 mg of imidazole and 497 mg of tert-butyldimethylchlorosilane were added to a dimethylformamide (2 ml) solution of 255 mg of 3-hydroxypyrrolidin-2-one, and stirred for 1 hour. Water was added to the reaction liquid, extracted with ethyl acetate, and washed with hydrochloric acid (1 N) and saturated saline water. The organic layer was dried to obtain 370 mg of a crude product. 208 g of the product was purified through silica gel column chromatography (developing solvent: hexane/ethyl acetate=9/1 to 2/8) to obtain 62 mg of the entitled compound as a white solid.

(Step 2) Production of 3-hydroxy-1-[(5-{[6-(5-methyl-1,24-oxadiazol-3-yl)pyridin-3-yl]oxy}-2-pyridin-2-yl-1H-benzimidazol-6-yl)methyl]pyrrolidin-2-one trifluoroacetate In an ice bath, 36 µl of triethylamine and 14 µl of methanesulfonyl chloride were added to a tetrahydrofuran (1 ml) solution of 47 mg of the alcohol obtained in Example 52 (step 2), and stirred for 30 minutes. Saturated saline water was added to the reaction liquid, extracted with ethyl acetate, and the organic layer was washed with saturated saline water and dried. The solvent was evaporated away under reduced pressure to obtain 48 mg of a crude product as a pale yellow oil.

In an ice bath, 62 mg of 3-{[tert-butyl(dimethyl)silyl]oxy}pyrrolidin-2-one obtained in the step 1 and 11 mg of sodium hydride (60%) were added to a dimethylformamide (2 ml) solution of the above crude product, and stirred at room temperature for 90 minutes. Aqueous saturated ammonium chloride solution was added to the reaction liquid, extracted with ethyl acetate, and the organic layer was washed with water and saturated saline water and dried. The solvent was evaporated away under reduced pressure and the residue was purified through thin-layer silica gel column chromatography (developing solvent: chloroform/methanol=9/1) to obtain 38 mg of a crude product as a yellow oil.

83 μl of tetrabutylammonium fluoride (1.0 M, tetrahydrofuran solution) was added to a tetrahydrofuran (0.2 ml) solution of 20 mg of the above crude product, and stirred overnight at room temperature. The solvent was evaporated away, and 0.7 ml of trifluoroacetic acid was added to the residue and stirred for 1 hour. The excess trifluoroacetic acid was evaporated away under reduced pressure, and the residue was purified through reversed-phase high-performance liquid column chromatography (developing solvent: water/acetonitrile=9/1 to 1/9) to obtain 6 mg of the entitled compound as a colorless transparent oil.

$^1$HNMR (CD$_3$OD) δ: 1.79-1.85 (1H, m), 2.36 (1H, m), 2.69 (3H, s), 3.26-3.31 (1H, m), 3.39 (1H, d, J=6.5 Hz), 4.19 (1H, t, J=8.2 Hz), 4.72-4.66 (2H, m), 7.49 (1H, s), 7.60-7.62 (1H, m), 7.66-7.68 (1H, m), 7.85 (1H, s), 8.11-8.16 (2H, m), 8.29 (1H, d, J=8.0 Hz), 8.48 (1H, d, J=2.3 Hz), 8.86 (1H, d, J=4.7 Hz).

ESI-MASS (m/e): 484(M+H).

Reference Example 1

Production of 4-(methylsulfonyl)phenol

In a water bath, 18.5 ml of methyl iodide and 28.7 g of potassium carbonate were added to an acetone (250 ml) solution of 25 g of 4-hydroxythiophenol, and stirred at room temperature for 5 hours. The salt was removed through filtration, the solvent was evaporated away under reduced pressure, diethyl ether was added to the residue, and extracted with aqueous 2 N sodium hydroxide solution. The obtained aqueous layer was acidified with aqueous 6 N hydrochloric acid solution, extracted with diethyl ether, and the organic layer was washed with aqueous saturated sodium chloride solution. After dried, the solvent was evaporated away under reduced pressure to obtain 27.3 g of 4-(methylsulfanyl)phenol as a pale yellow solid. In a water bath, 67 ml of aqueous 30% hydrogen peroxide solution was gradually and dropwise added to an acetic acid (130 ml) solution of 27.3 g of 4-(methylsulfanyl)phenol. After the addition, this was gradually heated up to 100° C., and stirred for 1 hour. The reaction liquid was restored to room temperature, and neutralized with aqueous saturated sodium bicarbonate. This was extracted with ethyl acetate, washed with aqueous saturated sodium bicarbonate and saturated saline water. After dried, the solvent was evaporated away to obtain 31.6 g of the entitled compound as a pale yellow solid.

Reference Example 2

Production of 4-(ethylsulfonyl)phenol

Using ethyl iodide, the entitled compound was obtained in the same method as in Reference Example 1 or in accordance with the method or by combining it with an ordinary method.

Reference Example 3

Production of 6-(methylsulfonyl)-3-pyridinol 6.6 g of bis(pinacolate)diboron, 5.9 g of potassium acetate and 980 mg of (1,1'-bis(diphenylphosphino)ferrocene)dichloropalladium(II)dichloromethane complex were added to a dimethylsulfoxide (80 ml) solution of 4.72 g of 3-bromo-6-(methylsulfonyl)pyridine, and the reaction liquid was stirred at 80° C. for 2 hours. Ethyl acetate and water were added to the reaction liquid, the insoluble matter was removed through filtration through Celite, and the organic layer was separated. The organic layer was washed with water and saturated saline water, then dried with anhydrous magnesium sulfate, and the solvent was evaporated away under reduced pressure.

At 0° C., 60 ml of aqueous 5 N sodium hydroxide solution and 30 ml of aqueous 30% hydrogen peroxide were added to a tetrahydrofuran (200 ml) solution of the obtained residue, and the reaction liquid was stirred overnight at room temperature. The reaction liquid was diluted with diethyl ether, and washed with water. The aqueous layer was acidified with 5 N hydrochloric acid, and extracted with ethyl acetate. The organic layer was dried with anhydrous magnesium sulfate, and the solvent was evaporated away under reduced pressure. The obtained residue was washed with a mixed solvent of chloroform and hexane to obtain 1.17 g of the entitled compound as a brown solid.

Reference Example 4

Production of 6-(ethylsulfonyl)-3-pyridinol

Using 3-chloro-6-(ethylsulfonyl)pyridine, the entitled compound was obtained in the same method as in Reference Example 3 or in accordance with the method or by combining it with an ordinary method.

Reference Example 5

Production of 3-chloro-4-(methylsulfonyl)phenol 48.3 ml of thionyl chloride was added to 108 ml of methanesulfonic acid, and heated under reflux for 1 hour. This was restored to room temperature, 1,3-dichlorobenzene and 2.9 ml of trifluorosulfonic acid were added to it, and stirred under heat at 120° C. for 4 hours. Restored to room temperature, the reaction liquid was poured into water with ice, and extracted with ethyl acetate. The organic layer was washed with water, aqueous saturated sodium bicarbonate and saturated saline water. After dried, the solvent was evaporated away under reduced pressure. The residue was recrystallized in a mixed solvent of hexane/ethyl acetate to obtain 48.3 g of 2,4-dichlorophenylmethyl sulfone.

An aqueous (1 ml) solution of 360 mg of potassium hydroxide was added to a dimethylsulfoxide (3 ml) solution of 1 g of 2,4-dichlorophenylmethyl sulfone, and stirred at 100° C. for 4 hours. This was acidified with aqueous 1 N hydrochloric acid solution, extracted with ethyl acetate, and the organic layer was washed with saturated saline water. After dried, the solvent was evaporated away under reduced pressure, and the residue was purified through silica gel column chromatography (developing solvent: hexane/ethyl acetate=9/1 to 2/1) to obtain 300 mg of 3-chloro-4-(methylsulfonyl)phenol.

Reference Example 6

Production of 6-(5-methyl-1,2,4-oxadiazol-3-yl)-3-pyridinol trifluoroacetate (Step 1) Production of 6-bromo-3-pyridinol With cooling with ice, 435 ml of isopropylmagnesium chloride (2 M tetrahydrofuran solution) was added to a tetrahydrofuran (800 ml) solution of 200 g of 2,5-dibromopyridine, and stirred at room temperature for 1.5 hours. With cooling with ice, a tetrahydrofuran (200 ml) solution of 214 ml of triisopropyl borate was added to it, and stirred overnight at room temperature. With cooling with ice, the reaction liquid was gradually added to an aqueous (2.5 L) solution of 160 g of sodium hydroxide. One L of water and 1 L of hexane were added to it, and the aqueous layer was extracted out. With cooling with ice, 150 ml of aqueous hydrogen peroxide (30%) was gradually added to the aqueous layer, taking 1 hour, and then this was stirred overnight at room temperature. With cooling with ice, the reaction liquid was neutralized with concentrated hydrochloric acid, extracted with ethyl acetate, and the organic layer was washed with saturated saline water. After dried, the solvent was evaporated away under reduced pressure to obtain 130 g of the entitled compound.

(Step 2) Production of 2-bromo-5-(methoxymethoxy)pyridine 73 ml of methoxymethyl chloride was added to a tetrahydrofuran (1.3 L) solution of 129 g of the obtained 6-bromo-3-pyridinol, and 32 g of sodium hydride (with 30% liquid paraffin added thereto) was added to it under so control that the inner temperature could not exceed −110° C. Water was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate=9.1 to 8/1) to obtain 105 g of the entitled compound as a colorless oil.

(Step 3) Production of 5-(methoxymethoxy)-2-pyridinecarbonitrile 88.9 g of zinc cyanide and 29.1 g of tetrakis(triphenylphosphine)palladium(0) were added to a dimethylformamide (1100 ml) solution of 105 g of the obtained oil, and stirred under heat at 105° C. for 1 hour. This was restored to room temperature, 1.5 L of ethyl acetate and 1.2 L of water were added to it, and extracted with ethyl acetate. The organic layer was washed with saturated saline water, and dried, the solvent was evaporated away under reduced pressure, and the residue was purified through silica gel column chromatography (developing solvent: hexane/ethyl acetate=8/1 to 7/1 to 2/1) to obtain 53.4 g of the entitled compound.

(Step 4) Production of 6-(5-methyl-1,2,4-oxadiazol-3-yl)-3-pyridinol

With cooling with ice, 35.4 ml of hydroxylamine (50% aqueous solution) was added to an ethanol (400 ml) solution of 41 g of the obtained product, and stirred at room temperature for 30 minutes. With cooling with ice, 1 L of water was added to it, and stirred for 1 hour. The formed crystal was taken out through filtration to obtain 39.5 g of a product.

200 ml of acetic acid was added to 39.5 g of the obtained crystal, and with cooling with ice, 20.8 ml of acetic anhydride was added to it and stirred at room temperature for 1 hour. This was heated at 70° C. as such, and stirred overnight. The reaction solvent was evaporated away under reduced pressure, and 100 ml of trifluoroacetic acid was added to the obtained brown solid, and stirred at room temperature for 3 hours. The solvent was evaporated away under reduced pressure, and a mixed solvent of hexane/ethyl acetate=20/1 was added to the residue and stirred. The formed solid was taken out through filtration and dried to obtain 57.1 g of the entitled compound as its trifluoroacetate.

Reference Example 7

Production of 4-(5-methyl-1,2,4-oxadiazol-3-yl)phenol (Step 1) Production of 4-(methoxymethoxy)benzonitrile Using 4-cyanophenol, the entitled compound was obtained in the same method as in Reference Example 6 (step 2) or in accordance with the method or by combining it with an ordinary method.

(Step 2) 4-(5-Methyl-1,2,4-oxadiazol-3-yl)phenol

Using 4-(methoxymethoxy)benzonitrile, the entitled compound was obtained in the same method as in Reference Example 6 (step 4) or in accordance with the method or by combining it with an ordinary method.

Reference Example 8

1-(4-Hydroxyphenyl)pyrrolidin-2-one (Step 1) Production of 1-iodo-4-(methoxymethoxy)benzene 2.33 ml of N,N-diisopropylethylamine and 900 µl of methoxymethyl chloride were added to a chloroform (20 ml) solution of 2 g of 4-iodophenol, and stirred overnight at room temperature. With cooling with ice, aqueous saturated ammonium chloride solution was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate) to obtain 1.08 g of the entitled compound as a colorless oil.

(Step 2) Production of 1-(4-hydroxyphenyl)pyrrolidin-2-one

5 µl of ethylenediamine, 14.5 mg of copper(I) iodide and 321 mg of potassium phosphate were added to a 1,4-dioxane (2 ml) solution of 200 mg of the compound obtained from the step 1 and 70 µl of 2-pyrrolidone, and stirred overnight in a nitrogen atmosphere at 110° C. With cooling with ice, aqueous saturated ammonium chloride solution was added to it, diluted with ethyl acetate, and the insoluble matter was removed through Celite filtration. This was extracted with ethyl acetate, and the organic layer was washed with saturated saline water. After dried, the solvent was evaporated away under reduced pressure, and the residue was purified through silica gel column chromatography (developing solvent: chloroform/methanol) to obtain 174 mg of an intermediate.

250 µl of 4 N hydrochloric acid/dioxane solution and 10 µl of water were added to a 1,4-dioxane (1.0 ml) solution of 80 mg of the obtained intermediate, and stirred at room temperature for 2.5 hours. After concentrated, this was azeotroped with chloroform, and the residue was solidified with diethyl ether to obtain 60.1 mg of the entitled compound as a white solid.

Reference Example 9

Production of
1-(4-hydroxyphenyl)pyridin-2(1H)-one

A toluene (1 ml) solution of 200 mg of the compound obtained from Reference Example 11 (step 11), 72 mg of 2-hydroxypyridine, 29 mg of copper(I) iodide, 210 mg of potassium carbonate and 22 mg of (1R,2R)-(−)-N,N'-dimethylcyclohexane-1,2-diamine was stirred overnight in a nitrogen atmosphere at 115° C. This was diluted with chloroform, the insoluble matter was removed through Celite filtration, and the organic layer was washed with water and saturated saline water. After dried, the solvent was evaporated away under reduced pressure, and the residue was purified through silica gel column chromatography (developing solvent: chloroform/methanol) to obtain 163 mg of an intermediate.

80 mg of the obtained intermediate was dissolved in 1.5 ml of water and 500 µl of chloroform, and 500 µl of 4 N hydrochloric acid/dioxane solution and 10 µl of water were added to it, and stirred at room temperature for 40 minutes. After concentrated, this was azeotroped with chloroform, and the residue was solidified with ether to obtain 65.6 mg of the entitled compound as a white solid.

Reference Example 10

5-Hydroxypyridine-2-carbonitrile

This was produced through by combining the step 3 and the step 4 of Reference Example 6.

Reference Example 11

6-(Methoxymethyl)pyridin-3-ol (Step 1) Production of
5-benzyloxy-2-methylpyridine 140 g of 3-hydroxy-6-methylpyridine was dissolved in 1.4 L of dimethylformamide, and with cooling with ice, 178 ml of benzyl chloride was added to it and stirred overnight at room temperature. The reaction liquid was poured into water with ice, extracted with ethyl acetate, and the organic layer was washed with saturated saline water. After dried, the solvent was evaporated away under reduced pressure, and the residue was purified through silica gel column chromatography (developing solvent: hexane/ethyl acetate=40/1 to 2/1) to obtain 246.7 g of the entitled compound as an orange oil.

(Step 2) Production of
[5-(benzyloxy)pyridin-2-yl]methanol

With cooling with ice, 335.8 g of m-chloroperbenzoic acid was added to a chloroform (2.8 L) solution of 246.7 g of the obtained oil, and stirred for 1 hour. The reaction liquid was washed with aqueous 10% sodium carbonate solution and saturated saline water. After dried, the solvent was evaporated away under reduced pressure, and the residue was recrystallized (hexane/ethyl acetate) to obtain 256.2 g of a pale yellow crystal.

600 ml of acetic anhydride was added to 266 g of the obtained crystal, gradually heated, and stirred at 120° C. for 20 minutes. The solvent was evaporated away under reduced pressure, aqueous saturate sodium bicarbonate was added to the residue and extracted with ethyl acetate. The organic layer was washed with saturated saline water, and dried with anhydrous magnesium sulfate. The solvent was evaporated away under reduced pressure, and the residue was purified through silica gel column chromatography (developing solvent: hexane/ethyl acetate=50/1 to 2/1) to obtain 259 g of a brown oil.

259 g of the obtained oil was dissolved in 2 L of ethanol and 500 ml of water, and 80 g of sodium hydroxide was added to it and heated under reflux for 30 minutes. The solvent was evaporated away under reduced pressure, 300 ml of water was added to the residue, and extracted with ethyl acetate. The organic layer was washed with aqueous saturated ammonium chloride solution and saturated saline water, and dried with anhydrous magnesium sulfate. After dried, the solvent was evaporated away under reduced pressure, and the residue was recrystallized (diethyl ether) to obtain 142.2 g of the entitled compound as a brown crystal.

(Step 3) Production of
6-(methoxymethyl)pyridin-3-ol 169 g of the obtained brown crystal was dissolved in 1.6 L of tetrahydrofuran, and with cooling with ice, 37.7 g of sodium hydride (with 30% liquid paraffin added thereto) was added to it, and stirred at room temperature for 1 hour. With cooling with ice, 53.7 ml of iodomethane was gradually dropwise added to it, and stirred overnight at room temperature. With cooling with ice, water was added to it, extracted with ethyl acetate, and the organic layer was washed with saturated saline water. After dried, the solvent was evaporated away under reduced pressure, and the residue was purified through silica gel column chromatography developing solvent: hexane/ethyl acetate=60/1 to 2/1) to obtain 162.7 g of an orange oil. 91.4 g of the obtained oil was dissolved in 900 ml of ethanol, and 13 g of 10% palladium-carbon was added to it and stirred in a hydrogen atmosphere for 2 hours. After filtered, the solvent was evaporated away under reduced pressure, and the residue was recrystallized (ethyl acetate/hexane) to obtain 53.0 g of the entitled compound as a pale yellow crystal.

Reference Example 12

6-(5-Methyl-1,3,4-oxadiazol-2-yl)pyridin-3-ol

This was produced according to the method described in European Journal of Pharmaceutical Science, Vol. 15, No. 4, pp. 367-378.

Reference Example 13

6-(3-Methyl-1,2,4-oxadiazol-5-yl)pyridin-3-ol

This was produced according to the method described in European Journal of Pharmaceutical Science, Vol. 15, No. 4, pp. 367-378.

Reference Example 14

6-(1-Methyl-1H-tetrazol-5-yl)pyridin-3-ol (Step 1) Production of 4-(benzyloxy)-N-methylbenzamide 1.77 g of methylamine hydrochloride was added to a pyridine (60 ml) solution of 3 g of 4-benzyloxybenzoic acid, and 5.04 g of 1-(3-dimethylaminopropyl)-3-ethylcarbodiimide hydrochloride was added to it, and stirred at room temperature. After the reaction, the solvent was evaporated away under reduced pressure, and the residue was diluted with ethyl acetate and washed with saturated saline water. After dried, the solvent was evaporated away under reduced pressure, and the residue was crystallized from chloroform/hexane and taken out through filtration to obtain 2.272 g of the entitled compound.

(Step 2) Production of 6-(1-methyl-1H-tetrazol-5-yl)pyridin-3-ol

One g of the obtained crystal was dissolved in 20 ml of toluene, and 0.36 ml of thionyl chloride was added to it and stirred overnight at 90° C. The solvent was evaporated away under reduced pressure, and 10 ml of acetonitrile, 0.54 g of sodium azide and 1.1 ml of chlorotrimethylsilane were added to it, and stirred overnight at room temperature. The reaction liquid was diluted with ethyl acetate, and washed with aqueous saturated sodium bicarbonate and saturated saline water. After dried, the solvent was evaporated away under reduced pressure, and the residue was purified through silica gel column chromatography developing solvent: hexane to hexane/ethyl acetate=1/1) to obtain 0.75 g of an intermediate.

0.75 g of the obtained intermediate was dissolved in 10 ml of ethanol, and 30 mg of palladium-carbon was added to it, and stirred in a hydrogen atmosphere at room temperature. After filtered, the solvent was evaporated away under reduced pressure, and the residue was purified through silica gel column chromatography (developing solvent: chloroform to chloroform/methanol=5/1) to obtain 0.24 g of the entitled compound as a crystal.

Reference Example 15

6-(1,3-Oxazol-4-yl)pyridin-3-ol (Step 1) Production of 4-(4-methoxyphenyl)-1,3-oxazole 10 ml of formamide was added to 2 g of 2-bromo-4'-methoxyacetophenone, and stirred at 180° C. for 20 minutes. This was restored to room temperature, diluted with ethyl acetate, and washed with water and saturated saline water. After dried, the solvent was evaporated away under reduced pressure, and the residue was purified through silica gel column chromatography (developing solvent: hexane to hexane/ethyl acetate=7/3) to obtain 0.76 g of the entitled compound.

(Step 2) Production of 6-(1,3-oxazol-4-yl)pyridin-3-ol

With cooling with ice, 12 ml of 1 M boron trifluoride/dichloromethane solution was added to a chloroform (8 ml) solution of 0.76 g of the obtained compound, and stirred for 4 hours. Water was added to it, extracted with ethyl acetate, and the organic layer was washed with saturated saline water. After dried, the solvent was evaporated away under reduced pressure, and the residue was purified through silica gel column chromatography (developing solvent: hexane/ethyl acetate=9/1 to 1/1) to obtain 0.36 g of the entitled compound.

Reference Example 16

Production of 6-(2-fluorophenyl)pyridin-3-ol

An aqueous (1 ml) solution of 127 mg of 2-fluorophenylboronic acid and 240 g of sodium carbonate, and 53.4 mg of dichlorobis(triphenylphosphine)palladium were added to a tetrahydrofuran (4 ml) solution of 200 mg of 1-iodo-4-(methoxymethoxy)benzene obtained in Reference Example 11 (step 1), and stirred overnight in a nitrogen atmosphere with heating under reflux. With cooling with ice, aqueous saturated ammonium chloride solution was added to it, and diluted with ethyl acetate, and the insoluble matter was removed through Celite filtration. This was extracted with ethyl acetate, and the organic layer was washed with aqueous saturated ammonium chloride solution and saturated saline water. After dried, the solvent was evaporated away under reduced pressure, and the residue was purified through silica gel column chromatography (developing solvent: hexane/ethyl acetate) to obtain 135 mg of a colorless oil.

750 μl of 4 N hydrochloric acid/dioxane solution and 10 μl of water were added to a 1,4-dioxane (3 ml) solution of 67 mg of the obtained colorless oil, and stirred at room temperature for 3 hours. After concentrated, this was azeotroped with chloroform to obtain 53.7 mg of the entitled compound as a white solid.

Reference Example 17

Production of 4-(2-methyl-2H-tetrazol-5-yl)phenol

This was produced according to the method described in European Journal of Pharmaceutical Science, Vol. 15, No. 4, pp. 367-378,

Reference Example 18

Production of 5-fluoropyridine-2-carboxylic acid (Step 1) Production of 2-chloro-5-fluoropyridine With cooling with ice, 16.3 ml of 42% tetrafluoroboric acid was added to an ethanol (50 ml) solution of 5 g of 5-amino-2-chloropyridine, and then an aqueous (10 ml) solution of 2.95 g of sodium nitrite was gradually dropwise added to it, and stirred for 10 minutes. The formed solid was taken out through filtration to obtain 9.9 g of a yellow solid. 100 ml of heptane was added to it, and heated under reflux. After the reaction, aqueous sodium bicarbonate was added to it, and extracted with diethyl ether, and the organic layer was washed with saturated saline water. After dried, the solvent was evaporated away under reduced pressure, and the residue was purified through silica gel column chromatography (developing solvent: hexane/chloroform) to obtain 1.32 g of the entitled compound as a pale yellow oil.

(Step 2) Production of ethyl 5-fluoropyridine-2-carboxylate 1.57 g of potassium carbonate, 0.34 g of 1,3-bis(diphenylphosphino)propane and 0.17 g of palladium acetate were added to a solution of 1 g of 2-chloro-5-fluoropyridine in 8 ml of dimethylformamide and 8 ml of ethanol, and stirred in a carbon monoxide atmosphere under heat at 90° C. for 2 hours. The reaction liquid was filtered, the filtrate was extracted with chloroform, and the organic layer was washed with saturated saline water. After dried, the solvent was evaporated away under reduced pressure, and the residue was purified through silica gel column chromatography (developing solvent: hexane/ethyl acetate) to obtain 0.97 g of the entitled compound as a white crystal.

(Step 3) Production of 5-fluoropyridine-2-carboxylic acid 2.4 ml of aqueous 2.5 N sodium hydroxide solution was added to a solution of 0.44 g of ethyl 5-fluoropyridine-2-carboxylate in 5 ml of tetrahydrofuran and 2 ml of methanol, and stirred at room temperature for 15 minutes. This was neutralized with aqueous 10% citric acid solution, extracted with ethyl acetate, and the organic layer was washed with saturated saline water. After dried, the solvent was evaporated away under reduced pressure to obtain 0.41 g of the entitled compound as a white crystal.

Reference Example 19

Production of 5-methoxypyridine-2-carboxylic acid 100 mg of ethyl 5-fluoropyridine-2-carboxylate obtained from Reference Example 18 (step 2) was dissolved in 1 ml of dimethylformamide and 1 ml of methanol, and 163 mg of potassium carbonate was added to it and stirred under heat at 90° C. for 40 minutes. This was neutralized with aqueous 10% citric acid solution, extracted with chloroform, and the organic layer was washed with saturated saline water. After dried, the solvent was evaporated away under reduced pressure, and the residue was purified through silica gel column chromatography (developing solvent: hexane/ethyl acetate) to obtain 46.5 mg of methyl 5-methoxypyridine-2-carboxylate as a white crystal.

The obtained ester compound was dissolved in 0.5 ml of methanol and 0.5 ml of tetrahydrofuran, and 0.52 ml of aqueous 1 N sodium hydroxide solution was added to it, and stirred at room temperature for 2 hours. This was neutralized with aqueous 10% citric acid solution, extracted with chloroform, and the organic layer was washed with saturated saline water. After dried, the solvent was evaporated away under reduced pressure to obtain 17.2 mg of the entitled compound as a white crystal.

INDUSTRIAL APPLICABILITY

Aryloxy-substituted benzimidazole derivatives of formula (I) and their pharmaceutically-acceptable salts of the invention have an excellent effect of glucokinase activation, and are useful in the field of medicines for treatment and/or prevention of diabetes, complications of diabetes or obesity.

The invention claimed is:
1. A compound of a formula (I):

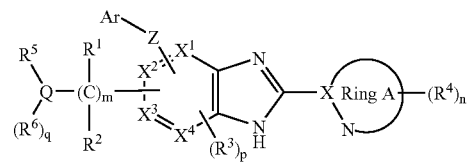

or a pharmaceutically acceptable salt thereof, wherein:
$R^1$ and $R^2$ each independently represent a hydrogen atom, a halogen atom, a lower alkyl group, a hydroxyl group, a cyano group or a lower alkoxy group;
$R^3$ independently represents a hydrogen atom, a halogen atom, a lower alkyl group, a lower alkoxy group, a hydroxyalkyl group, a trifluoromethyl group, a lower alkenyl group or a cyano group;
$R^4$ independently represents a hydrogen atom, a lower alkyl group, a lower alkoxy group, a halogen atom, a trifluoromethyl group, a hydroxyalkyl group optionally substituted with a lower alkyl group, an aminoalkyl group optionally substituted with a lower alkyl group, an alkanoyl group, a carboxyl group, a lower alkoxycarbonyl group or a cyano group;
Q represents a carbon atom, a nitrogen atom or a sulfur atom optionally substituted with one or two oxo groups;
$R^5$ and $R^6$ each independently represent a hydrogen atom, a lower alkyl group, a halogen atom, a lower alkyl group, a lower alkylsulfonyl group, a lower alkylsulfinyl group, an alkanoyl group, a formyl group, an aryl group, a mono- or di-lower alkylcarbamoyl group or a mono- or di-lower alkylsulfamoyl group; or taken together, Q, $R^5$ and $R^6$ may form the following:
(A) a 5- or 6-membered aliphatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms;
said heterocyclid group may have one or two double bonds;
(B) a 5- or 6-membered aromatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms, or
(C) a phenyl group,
and the aliphatic nitrogen-containing heterocyclic group, the aromatic nitrogen-containing heterocyclic group or the phenyl group may have from 1 to 3 groups selected from the following substituent group a, and/or may have, as the substituent thereof, a 3- to 6-membered ring formed through bonding to each other of the bondable groups selected from the substituent group α, and/or may be condensed with a group of a formula (A):

wherein ═══ represents a single bond or a double bond;
$X^1$, $X^2$, $X^3$ and $X^4$ each independently represent a carbon atom or a nitrogen atom;
Z represents an oxygen atom;

Ar represents a pyridyl group optionally substituted with from 1 to 3 groups selected from the following substituent group β;

ring A represents a pyridyl ring of a formula (III):

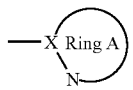

(III)

wherein X represents a carbon atom;

m indicates an integer of from 1 to 6;

n indicates an integer of from 0 to 3;

p indicates an integer of from 0 to 2; provided that at least two of $X^1$ to $X^4$ are hydrogen atoms;

q indicates 0 or 1;

Substituent group α:

an oxo group, a thioxo group, a lower alkyl group, a lower alkoxy group, an alkanoyl group, a formyl group, a hydroxy group, a carboxyl group, a trifluoromethyl group, a hydroxyalkyl group optionally substituted with a lower alkyl group, a cyano group, a mono- or di-lower alkylcarbamoyl group, a lower alkylsulfinyl group, a lower alkylsulfonyl group and a halogen atom;

Substituent group β:

a lower alkyl group, a lower alkoxy group, a halogen atom, a trifluoromethyl group, a hydroxyalkyl group optionally substituted with a lower alkyl group, a lower alkylsulfonyl group, a lower alkylsulfanyl group, a lower alkylsulfinyl group, an aminoalkyl group optionally substituted with a lower alkyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, and a heteroaryl group, having in the ring thereof, from 1 to 3 hetero atoms selected from the group consisting of a nitrogen atom, an oxygen atom and a sulfur atom;

said aryl group and heteroaryl group may have one or two groups selected from the following substituent group γ;

Substituent group γ:

a lower alkyl group, a lower alkoxy group, a halogen atom, a hydroxyl group, a lower alkylsulfonyl group, a lower alkylsulfinyl group, an alkanoyl group, a cyano group, a mono- or di-lower alkylcarbamoyl group.

2. The compound or a pharmaceutically acceptable salt according to claim 1, wherein m is from 1 to 4.

3. The compound or a pharmaceutically acceptable salt according to claim 1, wherein $R^5$ and $R^6$ each independently represent a hydrogen atom, a lower alkyl group, a halogen atom, a lower alkyl group, a lower alkylsulfonyl group, a lower alkylsulfonyl group, an alkanoyl group or a formyl group.

4. The compound or a pharmaceutically acceptable salt according to claim 1, wherein Q is a nitrogen atom.

5. The compound or a pharmaceutically acceptable salt according to claim 1, wherein Q is a carbon atom.

6. The compound or a pharmaceutically acceptable salt according to claim 1, wherein the group of a formula (I-A):

(I-A)

in the formula (I-1) is a group of the following formula:

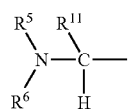

wherein: $R^{11}$ represents a hydrogen atom or a lower alkyl group; and the other symbols have the same meanings as above.

7. The compound or a pharmaceutically acceptable salt according to claim 1, wherein:

Q is a nitrogen atom;

$R^5$ and $R^6$, taken together with the nitrogen atom, form a 5- or 6-membered aliphatic nitrogen-containing heterocyclic group optionally having, in the ring thereof, from 1 to 3 hetero atoms selected from the group consisting of a nitrogen atom, a sulfur atom and an oxygen atom, and having at least one nitrogen atom in addition to the hetero atoms;

said 5- or 6- membered aliphatic nitrogen-containing heterocyclic group may have one or two double bonds, an may be mono- or di-substituted with the same or different groups selected from the following substituent group α1;

m is 1;

Z is an oxygen atom;

Ar is a pyridyl group optionally mono- or di-substituted with the same or different groups selected from the following substituent group β1;

$R^1$ and $R^2$ are independently a hydrogen atom or a lower alkyl group, Substituent group α1:

an oxo group, a thioxo group, a lower alkyl group, a lower alkoxy group, an alkanoyl group, a halogen atom, a cyano group, a mono- or di-lower alkylcarbamoyl group;

Substituent group β1:

a lower alkyl group, a lower alkoxy group, a halogen atom, a trifluoromethyl group, a hydroxyalkyl group optionally substituted with a lower alkyl group, a lower alkylsulfonyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, or a heteroaryl group having, in the ring thereof, 2 or 3 hetero atoms selected from the group consisting of a nitrogen atom, an oxygen atom and a sulfur atom;

said aryl group and the heteroaryl group may have one or two groups selected from the substituent group γ.

8. The compound or its pharmaceutically-acceptable salt according to claim 1, wherein: Q, $R^5$ and $R^6$, taken together, form a 5- or 6-membered aromatic nitrogen-containing heterocyclic group having at least one nitrogen atom, optionally having in the ring from 1 to 3 hetero atoms selected from the group consisting of a nitrogen atom, an oxygen atom and a sulfur atom in addition to that nitrogen atom, or a phenyl group;

said aromatic heterocyclic group or the phenyl group may have from 1 to 3 groups selected from the following substituent group α2;

Z is an oxygen atom;

Ar is a pyridyl group optionally mono- or di-substituted with the same or different groups selected from the following substituent group β1;

$R^1$ and $R^2$ are independently a hydrogen atom or a lower alkyl group;

Substituent group α2:

a hydroxyl group, a lower alkyl group, a lower alkoxy group, an alkanoyl group, a halogen atom, a cyano group and a mono- or di-lower alkylcarbamoyl group;

Substituent group β1:

a lower alkyl group, a lower alkoxy group, a halogen atom, a trifluoromethyl group, a hydroxyalkyl group optionally substituted with a lower alkyl group, a lower alkylsulfonyl group, an alkanoyl group, a carboxyl group, a mono- or di-lower alkylcarbamoyl group, a mono- or di-lower alkylsulfamoyl group, a lower alkoxycarbonyl group, a cyano group, an aryl group, or a heteroaryl group having, in the ring thereof, 2 or 3 hetero atoms selected from the group consisting of a nitrogen atom, an oxygen atom and a sulfur atom;

said aryl group and the heteroaryl group may have one or two groups selected from the substituent group γ.

9. The compound or a pharmaceutically acceptable salt thereof according to claim 1, wherein: the formula (I) is selected from the group consisting of:

1-{[5-{[6-(ethylsulfonyl)-3-pyridinyl]oxy}-2-(2-pyridinyl)-1H-benzimidazol-6-yl]methyl}pyrrolidine-2,5-dione, 1-[(5-{[6-(5-methyl-1,2,4-oxadiazol-3-yl)-3-pyridinyl]oxy}-2-(2-pyridinyl)-1H-benzimidazol-6-yl)methyl]-2-pyrrolidinone, and 1-[(6-{[6-(ethylsulfonyl)pyridin-3-yl]oxy}-2-pyridin-2-yl-1H-benzimidazol-4-yl)methyl]pyrrolidin-2-one.

10. The compound or a pharmaceutically acceptable salt thereof according to claim 1, wherein the formula (I) is 1-{[5-{[6-(ethylsulfonyl)-3-pyridinyl]oxy}-2-(2-pyridinyl)-1H-benzimidazol-6-yl]methyl}pyrrolidine-2,5-dione.

11. The compound or a pharmaceutically acceptable salt thereof according to claim 1, wherein the formula (I) is 1-[(5-{[6-(5-methyl-1,2,4-oxadiazol-3-yl)-3-pyridinyl]oxy}-2-(2-pyridinyl)-1H-benzimidazol-6-yl)methyl]-2-pyrrolidinone.

12. The compound or a pharmaceutically acceptable salt thereof according to claim 1, wherein the formula (I) is 1-[(6-{[6-(ethylsulfonyl)pyridin-3-yl]oxy}-2-pyridin-2-yl-1H-benzimidazol-4-yl)methyl]pyrrolidin-2-one.

13. A pharmaceutical composition comprised of a compound in accordance with claim 1 in combination with a phamaceutically acceptable carrier.

14. A method of treating type 2 diabetes in a mammialian patient, comprising administering to said patient a compound in accordance with claim 1 in an amount effective to treating type 2 diabetes.

* * * * *

UNITED STATES PATENT AND TRADEMARK OFFICE
CERTIFICATE OF CORRECTION

| | | |
|---|---|---|
| PATENT NO. | : 7,932,394 B2 | Page 1 of 1 |
| APPLICATION NO. | : 11/666555 | |
| DATED | : April 26, 2011 | |
| INVENTOR(S) | : Noriaki Hashimoto et al. | |

It is certified that error appears in the above-identified patent and that said Letters Patent is hereby corrected as shown below:

Claim 1 at column 173, line 18, delete "two of $X^1$ to $X^4$ are hydrogen atoms;" and replace with --two of $X^1$ to $X^4$ are carbon atoms;--.

Signed and Sealed this

Thirteenth Day of December, 2011

David J. Kappos
*Director of the United States Patent and Trademark Office*